US012262937B2

United States Patent
Messerly et al.

(10) Patent No.: US 12,262,937 B2
(45) Date of Patent: Apr. 1, 2025

(54) USER INTERFACE FOR SURGICAL INSTRUMENT WITH COMBINATION ENERGY MODALITY END-EFFECTOR

(71) Applicant: Cilag GmbH International, Zug (CH)

(72) Inventors: Jeffrey D. Messerly, Cincinnati, OH (US); Craig N. Faller, Batavia, OH (US); Justin S. Cramer, Loveland, OH (US); Steven M. Boronyak, Cincinnati, OH (US); Ellen E. Burkart, Liberty Township, OH (US); Monica L. Z. Rivard, Cincinnati, OH (US); Gregory J. Bakos, Mason, OH (US)

(73) Assignee: Cilag GmbH International, Zug (CH)

( * ) Notice: Subject to any disclaimer, the term of this patent is extended or adjusted under 35 U.S.C. 154(b) by 836 days.

(21) Appl. No.: 16/887,499

(22) Filed: May 29, 2020

(65) Prior Publication Data

US 2021/0196345 A1    Jul. 1, 2021

Related U.S. Application Data

(60) Provisional application No. 62/955,294, filed on Dec. 30, 2019.

(51) Int. Cl.
  *A61B 18/12*    (2006.01)
  *A61B 18/14*    (2006.01)
  *A61B 18/00*    (2006.01)

(52) U.S. Cl.
  CPC .......... *A61B 18/14* (2013.01); *A61B 18/1206* (2013.01); *A61B 2018/0019* (2013.01);
  (Continued)

(58) Field of Classification Search
  CPC ................ A61B 18/14; A61B 18/1206; A61B 2018/0019; A61B 2018/00607;
  (Continued)

(56) References Cited

U.S. PATENT DOCUMENTS

| 969,528 A | 9/1910 | Disbrow |
| 1,570,025 A | 1/1926 | Young |

(Continued)

FOREIGN PATENT DOCUMENTS

| CA | 2535467 A1 | 4/1993 |
| CN | 2460047 Y | 11/2001 |

(Continued)

OTHER PUBLICATIONS

Covidien Brochure, [Value Analysis Brief], LigaSure Advance ™ Pistol Grip, dated Rev. Apr. 2010 (7 pages).

(Continued)

*Primary Examiner* — Sean W Collins

(57) ABSTRACT

Disclosed is a surgical instrument having a housing, an end-effector, and a user interface. The end-effector includes a clamp arm and an ultrasonic blade configured to couple to an ultrasonic transducer and to a pole of an electrical generator. The clamp arm includes a clamp jaw pivotally movable about a pivot point, an electrode defining a surface configured to contact tissue and apply electrical energy to the tissue in contact therewith and configured to couple to an opposite pole of the electrical generator. The user interface includes a first activation button switch to activate a first energy source and a second button switch to select an energy mode for the activation button switch.

24 Claims, 24 Drawing Sheets

(52) U.S. Cl.
CPC ............... *A61B 2018/00607* (2013.01); *A61B 2018/0063* (2013.01); *A61B 2018/0072* (2013.01); *A61B 2018/00732* (2013.01); *A61B 2018/00767* (2013.01); *A61B 2018/00916* (2013.01); *A61B 2018/00922* (2013.01); *A61B 2018/00958* (2013.01); *A61B 2018/00994* (2013.01); *A61B 2018/1253* (2013.01); *A61B 2018/126* (2013.01); *A61B 2018/1412* (2013.01)

(58) Field of Classification Search
CPC .... A61B 2018/0063; A61B 2018/0072; A61B 2018/00732; A61B 2018/0076; A61B 2018/00916; A61B 2018/00922; A61B 2018/00958; A61B 2018/00994; A61B 2018/1253; A61B 2018/126; A61B 2018/1412
See application file for complete search history.

(56) References Cited

U.S. PATENT DOCUMENTS

| | | |
|---|---|---|
| 1,813,902 A | 7/1931 | Bovie |
| 2,188,497 A | 1/1940 | Calva |
| 2,366,274 A | 1/1945 | Luth et al. |
| 2,425,245 A | 8/1947 | Johnson |
| 2,442,966 A | 6/1948 | Wallace |
| 2,458,152 A | 1/1949 | Eakins |
| 2,510,693 A | 6/1950 | Green |
| 2,597,564 A | 5/1952 | Bugg |
| 2,704,333 A | 3/1955 | Calosi et al. |
| 2,736,960 A | 3/1956 | Armstrong |
| 2,748,967 A | 6/1956 | Roach |
| 2,845,072 A | 7/1958 | Shafer |
| 2,849,788 A | 9/1958 | Creek |
| 2,867,039 A | 1/1959 | Zach |
| 2,874,470 A | 2/1959 | Richards |
| 2,990,616 A | 7/1961 | Balamuth et al. |
| RE25,033 E | 8/1961 | Balamuth et al. |
| 3,015,961 A | 1/1962 | Roney |
| 3,033,407 A | 5/1962 | Alfons |
| 3,053,124 A | 9/1962 | Balamuth et al. |
| 3,082,805 A | 3/1963 | Royce |
| 3,166,971 A | 1/1965 | Stoecker |
| 3,322,403 A | 5/1967 | Murphy |
| 3,432,691 A | 3/1969 | Shoh |
| 3,433,226 A | 3/1969 | Boyd |
| 3,489,930 A | 1/1970 | Shoh |
| 3,513,848 A | 5/1970 | Winston et al. |
| 3,514,856 A | 6/1970 | Camp et al. |
| 3,525,912 A | 8/1970 | Wallin |
| 3,526,219 A | 9/1970 | Balamuth |
| 3,554,198 A | 1/1971 | Tatoian et al. |
| 3,580,841 A | 5/1971 | Cadotte et al. |
| 3,606,682 A | 9/1971 | Camp et al. |
| 3,614,484 A | 10/1971 | Shoh |
| 3,616,375 A | 10/1971 | Inoue |
| 3,629,726 A | 12/1971 | Popescu |
| 3,636,943 A | 1/1972 | Balamuth |
| 3,668,486 A | 6/1972 | Silver |
| 3,702,948 A | 11/1972 | Balamuth |
| 3,703,651 A | 11/1972 | Blowers |
| 3,776,238 A | 12/1973 | Peyman et al. |
| 3,777,760 A | 12/1973 | Essner |
| 3,805,787 A | 4/1974 | Banko |
| 3,809,977 A | 5/1974 | Balamuth et al. |
| 3,830,098 A | 8/1974 | Antonevich |
| 3,854,737 A | 12/1974 | Gilliam, Sr. |
| 3,862,630 A | 1/1975 | Balamuth |
| 3,875,945 A | 4/1975 | Friedman |
| 3,885,438 A | 5/1975 | Harris, Sr. et al. |
| 3,900,823 A | 8/1975 | Sokal et al. |
| 3,918,442 A | 11/1975 | Nikolaev et al. |
| 3,924,335 A | 12/1975 | Balamuth et al. |
| 3,946,738 A | 3/1976 | Newton et al. |
| 3,955,859 A | 5/1976 | Stella et al. |
| 3,956,826 A | 5/1976 | Perdreaux, Jr. |
| 3,989,952 A | 11/1976 | Hohmann |
| 4,005,714 A | 2/1977 | Hiltebrandt |
| 4,012,647 A | 3/1977 | Balamuth et al. |
| 4,034,762 A | 7/1977 | Cosens et al. |
| 4,058,126 A | 11/1977 | Leveen |
| 4,074,719 A | 2/1978 | Semm |
| 4,156,187 A | 5/1979 | Murry et al. |
| 4,167,944 A | 9/1979 | Banko |
| 4,188,927 A | 2/1980 | Harris |
| 4,200,106 A | 4/1980 | Douvas et al. |
| 4,203,430 A | 5/1980 | Takahashi |
| 4,203,444 A | 5/1980 | Bonnell et al. |
| 4,220,154 A | 9/1980 | Semm |
| 4,237,441 A | 12/1980 | van Konynenburg et al. |
| 4,244,371 A | 1/1981 | Farin |
| 4,281,785 A | 8/1981 | Brooks |
| 4,300,083 A | 11/1981 | Heiges |
| 4,302,728 A | 11/1981 | Nakamura |
| 4,304,987 A | 12/1981 | van Konynenburg |
| 4,306,570 A | 12/1981 | Matthews |
| 4,314,559 A | 2/1982 | Allen |
| 4,353,371 A | 10/1982 | Cosman |
| 4,409,981 A | 10/1983 | Lundberg |
| 4,445,063 A | 4/1984 | Smith |
| 4,461,304 A | 7/1984 | Kuperstein |
| 4,463,759 A | 8/1984 | Garito et al. |
| 4,491,132 A | 1/1985 | Aikins |
| 4,492,231 A | 1/1985 | Auth |
| 4,494,759 A | 1/1985 | Kieffer |
| 4,504,264 A | 3/1985 | Kelman |
| 4,512,344 A | 4/1985 | Barber |
| 4,526,571 A | 7/1985 | Wuchinich |
| 4,535,773 A | 8/1985 | Yoon |
| 4,541,638 A | 9/1985 | Ogawa et al. |
| 4,545,374 A | 10/1985 | Jacobson |
| 4,545,926 A | 10/1985 | Fouts, Jr. et al. |
| 4,549,147 A | 10/1985 | Kondo |
| 4,550,870 A | 11/1985 | Krumme et al. |
| 4,553,544 A | 11/1985 | Nomoto et al. |
| 4,562,838 A | 1/1986 | Walker |
| 4,574,615 A | 3/1986 | Bower et al. |
| 4,582,236 A | 4/1986 | Hirose |
| 4,593,691 A | 6/1986 | Lindstrom et al. |
| 4,608,981 A | 9/1986 | Rothfuss et al. |
| 4,617,927 A | 10/1986 | Manes |
| 4,633,119 A | 12/1986 | Thompson |
| 4,633,874 A | 1/1987 | Chow et al. |
| 4,634,420 A | 1/1987 | Spinosa et al. |
| 4,640,279 A | 2/1987 | Beard |
| 4,641,053 A | 2/1987 | Takeda |
| 4,646,738 A | 3/1987 | Trott |
| 4,646,756 A | 3/1987 | Watmough et al. |
| 4,649,919 A | 3/1987 | Thimsen et al. |
| 4,662,068 A | 5/1987 | Polonsky |
| 4,674,502 A | 6/1987 | Imonti |
| 4,694,835 A | 9/1987 | Strand |
| 4,708,127 A | 11/1987 | Abdelghani |
| 4,712,722 A | 12/1987 | Hood et al. |
| 4,735,603 A | 4/1988 | Goodson et al. |
| 4,739,759 A | 4/1988 | Rexroth et al. |
| 4,761,871 A | 8/1988 | O'Connor et al. |
| 4,808,154 A | 2/1989 | Freeman |
| 4,819,635 A | 4/1989 | Shapiro |
| 4,827,911 A | 5/1989 | Broadwin et al. |
| 4,830,462 A | 5/1989 | Karny et al. |
| 4,832,683 A | 5/1989 | Idemoto et al. |
| 4,836,186 A | 6/1989 | Scholz |
| 4,838,853 A | 6/1989 | Parisi |
| 4,844,064 A | 7/1989 | Thimsen et al. |
| 4,849,133 A | 7/1989 | Yoshida et al. |
| 4,850,354 A | 7/1989 | McGurk-Burleson et al. |
| 4,852,578 A | 8/1989 | Companion et al. |
| 4,860,745 A | 8/1989 | Farin et al. |
| 4,862,890 A | 9/1989 | Stasz et al. |
| 4,865,159 A | 9/1989 | Jamison |
| 4,867,157 A | 9/1989 | McGurk-Burleson et al. |

(56) References Cited

U.S. PATENT DOCUMENTS

| | | |
|---|---|---|
| 4,878,493 A | 11/1989 | Pasternak et al. |
| 4,880,015 A | 11/1989 | Nierman |
| 4,881,550 A | 11/1989 | Kothe |
| 4,896,009 A | 1/1990 | Pawlowski |
| 4,903,696 A | 2/1990 | Stasz et al. |
| 4,910,389 A | 3/1990 | Sherman et al. |
| 4,915,643 A | 4/1990 | Samejima et al. |
| 4,920,978 A | 5/1990 | Colvin |
| 4,922,902 A | 5/1990 | Wuchinich et al. |
| 4,926,860 A | 5/1990 | Stice et al. |
| 4,936,842 A | 6/1990 | D'Amelio et al. |
| 4,954,960 A | 9/1990 | Lo et al. |
| 4,965,532 A | 10/1990 | Sakurai |
| 4,979,952 A | 12/1990 | Kubota et al. |
| 4,981,756 A | 1/1991 | Rhandhawa |
| 5,001,649 A | 3/1991 | Lo et al. |
| 5,003,693 A | 4/1991 | Atkinson et al. |
| 5,009,661 A | 4/1991 | Michelson |
| 5,013,956 A | 5/1991 | Kurozumi et al. |
| 5,015,227 A | 5/1991 | Broadwin et al. |
| 5,020,514 A | 6/1991 | Heckele |
| 5,026,370 A | 6/1991 | Lottick |
| 5,026,387 A | 6/1991 | Thomas |
| 5,035,695 A | 7/1991 | Weber, Jr. et al. |
| 5,042,461 A | 8/1991 | Inoue et al. |
| 5,042,707 A | 8/1991 | Taheri |
| 5,052,145 A | 10/1991 | Wang |
| 5,061,269 A | 10/1991 | Muller |
| 5,075,839 A | 12/1991 | Fisher et al. |
| 5,084,052 A | 1/1992 | Jacobs |
| 5,099,840 A | 3/1992 | Goble et al. |
| 5,104,025 A | 4/1992 | Main et al. |
| 5,105,117 A | 4/1992 | Yamaguchi |
| 5,106,538 A | 4/1992 | Barma et al. |
| 5,108,383 A | 4/1992 | White |
| 5,109,819 A | 5/1992 | Custer et al. |
| 5,112,300 A | 5/1992 | Ureche |
| 5,113,139 A | 5/1992 | Furukawa |
| 5,123,903 A | 6/1992 | Quaid et al. |
| 5,126,618 A | 6/1992 | Takahashi et al. |
| D327,872 S | 7/1992 | McMills et al. |
| 5,152,762 A | 10/1992 | McElhenney |
| 5,156,633 A | 10/1992 | Smith |
| 5,160,334 A | 11/1992 | Billings et al. |
| 5,162,044 A | 11/1992 | Gahn et al. |
| 5,163,421 A | 11/1992 | Bernstein et al. |
| 5,163,537 A | 11/1992 | Radev |
| 5,163,945 A | 11/1992 | Ortiz et al. |
| 5,167,619 A | 12/1992 | Wuchinich |
| 5,167,725 A | 12/1992 | Clark et al. |
| 5,172,344 A | 12/1992 | Ehrlich |
| 5,174,276 A | 12/1992 | Crockard |
| D332,660 S | 1/1993 | Rawson et al. |
| 5,176,677 A | 1/1993 | Wuchinich |
| 5,176,695 A | 1/1993 | Dulebohn |
| 5,184,605 A | 2/1993 | Grzeszykowski |
| 5,188,102 A | 2/1993 | Idemoto et al. |
| D334,173 S | 3/1993 | Liu et al. |
| 5,190,517 A | 3/1993 | Zieve et al. |
| 5,190,518 A | 3/1993 | Takasu |
| 5,190,541 A | 3/1993 | Abele et al. |
| 5,196,007 A | 3/1993 | Ellman et al. |
| 5,203,380 A | 4/1993 | Chikama |
| 5,205,459 A | 4/1993 | Brinkerhoff et al. |
| 5,205,817 A | 4/1993 | Idemoto et al. |
| 5,209,719 A | 5/1993 | Baruch et al. |
| 5,213,569 A | 5/1993 | Davis |
| 5,214,339 A | 5/1993 | Naito |
| 5,217,460 A | 6/1993 | Knoepfler |
| 5,218,529 A | 6/1993 | Meyer et al. |
| 5,221,282 A | 6/1993 | Wuchinich |
| 5,222,937 A | 6/1993 | Kagawa |
| 5,226,909 A | 7/1993 | Evans et al. |
| 5,226,910 A | 7/1993 | Kajiyama et al. |
| 5,231,989 A | 8/1993 | Middleman et al. |
| 5,234,428 A | 8/1993 | Kaufman |
| 5,241,236 A | 8/1993 | Sasaki et al. |
| 5,241,968 A | 9/1993 | Slater |
| 5,242,339 A | 9/1993 | Thornton |
| 5,242,460 A | 9/1993 | Klein et al. |
| 5,246,003 A | 9/1993 | DeLonzor |
| 5,254,129 A | 10/1993 | Alexander |
| 5,257,988 A | 11/1993 | L'Esperance, Jr. |
| 5,258,004 A | 11/1993 | Bales et al. |
| 5,258,006 A | 11/1993 | Rydell et al. |
| 5,261,922 A | 11/1993 | Hood |
| 5,263,957 A | 11/1993 | Davison |
| 5,264,925 A | 11/1993 | Shipp et al. |
| 5,269,297 A | 12/1993 | Weng et al. |
| 5,275,166 A | 1/1994 | Vaitekunas et al. |
| 5,275,607 A | 1/1994 | Lo et al. |
| 5,275,609 A | 1/1994 | Pingleton et al. |
| 5,282,800 A | 2/1994 | Foshee et al. |
| 5,282,817 A | 2/1994 | Hoogeboom et al. |
| 5,285,795 A | 2/1994 | Ryan et al. |
| 5,285,945 A | 2/1994 | Brinkerhoff et al. |
| 5,290,286 A | 3/1994 | Parins |
| 5,293,863 A | 3/1994 | Zhu et al. |
| 5,300,068 A | 4/1994 | Rosar et al. |
| 5,304,115 A | 4/1994 | Pflueger et al. |
| D347,474 S | 5/1994 | Olson |
| 5,307,976 A | 5/1994 | Olson et al. |
| 5,309,927 A | 5/1994 | Welch |
| 5,312,023 A | 5/1994 | Green et al. |
| 5,312,425 A | 5/1994 | Evans et al. |
| 5,318,525 A | 6/1994 | West et al. |
| 5,318,563 A | 6/1994 | Malis et al. |
| 5,318,564 A | 6/1994 | Eggers |
| 5,318,570 A | 6/1994 | Hood et al. |
| 5,318,589 A | 6/1994 | Lichtman |
| 5,322,055 A | 6/1994 | Davison et al. |
| 5,324,299 A | 6/1994 | Davison et al. |
| 5,326,013 A | 7/1994 | Green et al. |
| 5,326,342 A | 7/1994 | Pflueger et al. |
| 5,330,471 A | 7/1994 | Eggers |
| 5,330,502 A | 7/1994 | Hassler et al. |
| 5,334,183 A | 8/1994 | Wuchinich |
| 5,339,723 A | 8/1994 | Huitema |
| 5,342,356 A | 8/1994 | Ellman et al. |
| 5,342,359 A | 8/1994 | Rydell |
| 5,344,420 A | 9/1994 | Hilal et al. |
| 5,345,937 A | 9/1994 | Middleman et al. |
| 5,346,502 A | 9/1994 | Estabrook et al. |
| 5,353,474 A | 10/1994 | Good et al. |
| 5,357,164 A | 10/1994 | Imabayashi et al. |
| 5,357,423 A | 10/1994 | Weaver et al. |
| 5,359,994 A | 11/1994 | Krauter et al. |
| 5,361,583 A | 11/1994 | Huitema |
| 5,366,466 A | 11/1994 | Christian et al. |
| 5,368,557 A | 11/1994 | Nita et al. |
| 5,370,645 A | 12/1994 | Klicek et al. |
| 5,371,429 A | 12/1994 | Manna |
| 5,374,813 A | 12/1994 | Shipp |
| D354,564 S | 1/1995 | Medema |
| 5,381,067 A | 1/1995 | Greenstein et al. |
| 5,383,874 A | 1/1995 | Jackson et al. |
| 5,383,917 A | 1/1995 | Desai et al. |
| 5,387,207 A | 2/1995 | Dyer et al. |
| 5,387,215 A | 2/1995 | Fisher |
| 5,389,098 A | 2/1995 | Tsuruta et al. |
| 5,394,187 A | 2/1995 | Shipp |
| 5,395,033 A | 3/1995 | Byrne et al. |
| 5,395,312 A | 3/1995 | Desai |
| 5,395,363 A | 3/1995 | Billings et al. |
| 5,395,364 A | 3/1995 | Anderhub et al. |
| 5,396,266 A | 3/1995 | Brimhall |
| 5,396,900 A | 3/1995 | Slater et al. |
| 5,400,267 A | 3/1995 | Denen et al. |
| 5,403,312 A | 4/1995 | Yates et al. |
| 5,403,334 A | 4/1995 | Evans et al. |
| 5,406,503 A | 4/1995 | Williams, Jr. et al. |
| 5,408,268 A | 4/1995 | Shipp |
| D358,887 S | 5/1995 | Feinberg |
| 5,411,481 A | 5/1995 | Allen et al. |

(56) References Cited

U.S. PATENT DOCUMENTS

| | | |
|---|---|---|
| 5,417,709 A | 5/1995 | Slater |
| 5,419,761 A | 5/1995 | Narayanan et al. |
| 5,421,829 A | 6/1995 | Olichney et al. |
| 5,423,844 A | 6/1995 | Miller |
| 5,428,504 A | 6/1995 | Bhatla |
| 5,429,131 A | 7/1995 | Scheinman et al. |
| 5,438,997 A | 8/1995 | Sieben et al. |
| 5,441,499 A | 8/1995 | Fritzsch |
| 5,443,463 A | 8/1995 | Stern et al. |
| 5,445,638 A | 8/1995 | Rydell et al. |
| 5,445,639 A | 8/1995 | Kuslich et al. |
| 5,447,509 A | 9/1995 | Mills et al. |
| 5,449,370 A | 9/1995 | Vaitekunas |
| 5,451,053 A | 9/1995 | Garrido |
| 5,451,161 A | 9/1995 | Sharp |
| 5,451,220 A | 9/1995 | Ciervo |
| 5,451,227 A | 9/1995 | Michaelson |
| 5,456,684 A | 10/1995 | Schmidt et al. |
| 5,458,598 A | 10/1995 | Feinberg et al. |
| 5,462,604 A | 10/1995 | Shibano et al. |
| 5,465,895 A | 11/1995 | Knodel et al. |
| 5,471,988 A | 12/1995 | Fujio et al. |
| 5,472,443 A | 12/1995 | Cordis et al. |
| 5,476,479 A | 12/1995 | Green et al. |
| 5,478,003 A | 12/1995 | Green et al. |
| 5,480,409 A | 1/1996 | Riza |
| 5,483,501 A | 1/1996 | Park et al. |
| 5,484,436 A | 1/1996 | Eggers et al. |
| 5,486,162 A | 1/1996 | Brumbach |
| 5,486,189 A | 1/1996 | Mudry et al. |
| 5,490,860 A | 2/1996 | Middle et al. |
| 5,496,317 A | 3/1996 | Goble et al. |
| 5,499,992 A | 3/1996 | Meade et al. |
| 5,500,216 A | 3/1996 | Julian et al. |
| 5,501,654 A | 3/1996 | Failla et al. |
| 5,504,650 A | 4/1996 | Katsui et al. |
| 5,505,693 A | 4/1996 | Mackool |
| 5,507,297 A | 4/1996 | Slater et al. |
| 5,507,738 A | 4/1996 | Ciervo |
| 5,509,922 A | 4/1996 | Aranyi et al. |
| 5,511,556 A | 4/1996 | DeSantis |
| 5,520,704 A | 5/1996 | Castro et al. |
| 5,522,832 A | 6/1996 | Kugo et al. |
| 5,522,839 A | 6/1996 | Pilling |
| 5,527,331 A | 6/1996 | Kresch et al. |
| 5,531,744 A | 7/1996 | Nardella et al. |
| 5,536,267 A | 7/1996 | Edwards et al. |
| 5,540,681 A | 7/1996 | Strul et al. |
| 5,540,684 A | 7/1996 | Hassler, Jr. |
| 5,540,693 A | 7/1996 | Fisher |
| 5,542,916 A | 8/1996 | Hirsch et al. |
| 5,548,286 A | 8/1996 | Craven |
| 5,549,637 A | 8/1996 | Crainich |
| 5,553,675 A | 9/1996 | Pitzen et al. |
| 5,558,671 A | 9/1996 | Yates |
| 5,562,609 A | 10/1996 | Brumbach |
| 5,562,610 A | 10/1996 | Brumbach |
| 5,562,659 A | 10/1996 | Morris |
| 5,562,703 A | 10/1996 | Desai |
| 5,563,179 A | 10/1996 | Stone et al. |
| 5,569,164 A | 10/1996 | Lurz |
| 5,571,121 A | 11/1996 | Heifetz |
| 5,573,424 A | 11/1996 | Poppe |
| 5,573,533 A | 11/1996 | Strul |
| 5,573,534 A | 11/1996 | Stone |
| 5,577,654 A | 11/1996 | Bishop |
| 5,584,830 A | 12/1996 | Ladd et al. |
| 5,591,187 A | 1/1997 | Dekel |
| 5,593,414 A | 1/1997 | Shipp et al. |
| 5,599,350 A | 2/1997 | Schulze et al. |
| 5,600,526 A | 2/1997 | Russell et al. |
| 5,601,601 A | 2/1997 | Tal et al. |
| 5,603,773 A | 2/1997 | Campbell |
| 5,607,436 A | 3/1997 | Pratt et al. |
| 5,607,450 A | 3/1997 | Zvenyatsky et al. |
| 5,609,573 A | 3/1997 | Sandock |
| 5,611,813 A | 3/1997 | Lichtman |
| 5,618,304 A | 4/1997 | Hart et al. |
| 5,618,307 A | 4/1997 | Donlon et al. |
| 5,618,492 A | 4/1997 | Auten et al. |
| 5,620,447 A | 4/1997 | Smith et al. |
| 5,624,452 A | 4/1997 | Yates |
| 5,626,587 A | 5/1997 | Bishop et al. |
| 5,626,595 A | 5/1997 | Sklar et al. |
| 5,626,608 A | 5/1997 | Cuny et al. |
| 5,628,760 A | 5/1997 | Knoepfler |
| 5,630,420 A | 5/1997 | Vaitekunas |
| 5,632,432 A | 5/1997 | Schulze et al. |
| 5,632,717 A | 5/1997 | Yoon |
| 5,638,827 A | 6/1997 | Palmer et al. |
| 5,640,741 A | 6/1997 | Yano |
| D381,077 S | 7/1997 | Hunt |
| 5,647,871 A | 7/1997 | Levine et al. |
| 5,649,937 A | 7/1997 | Bito et al. |
| 5,649,955 A | 7/1997 | Hashimoto et al. |
| 5,651,780 A | 7/1997 | Jackson et al. |
| 5,653,713 A | 8/1997 | Michelson |
| 5,655,100 A | 8/1997 | Ebrahim et al. |
| 5,658,281 A | 8/1997 | Heard |
| 5,662,662 A | 9/1997 | Bishop et al. |
| 5,662,667 A | 9/1997 | Knodel |
| 5,665,085 A | 9/1997 | Nardella |
| 5,665,100 A | 9/1997 | Yoon |
| 5,669,922 A | 9/1997 | Hood |
| 5,674,219 A | 10/1997 | Monson et al. |
| 5,674,220 A | 10/1997 | Fox et al. |
| 5,674,235 A | 10/1997 | Parisi |
| 5,678,568 A | 10/1997 | Uchikubo et al. |
| 5,688,270 A | 11/1997 | Yates et al. |
| 5,690,269 A | 11/1997 | Bolanos et al. |
| 5,693,042 A | 12/1997 | Boiarski et al. |
| 5,693,051 A | 12/1997 | Schulze et al. |
| 5,694,936 A | 12/1997 | Fujimoto et al. |
| 5,695,510 A | 12/1997 | Hood |
| 5,700,261 A | 12/1997 | Brinkerhoff |
| 5,704,534 A | 1/1998 | Huitema et al. |
| 5,704,791 A | 1/1998 | Gillio |
| 5,707,369 A | 1/1998 | Vaitekunas et al. |
| 5,709,680 A | 1/1998 | Yates et al. |
| 5,711,472 A | 1/1998 | Bryan |
| 5,713,896 A | 2/1998 | Nardella |
| 5,715,817 A | 2/1998 | Stevens-Wright et al. |
| 5,716,366 A | 2/1998 | Yates |
| 5,717,306 A | 2/1998 | Shipp |
| 5,720,742 A | 2/1998 | Zacharias |
| 5,720,744 A | 2/1998 | Eggleston et al. |
| 5,722,980 A | 3/1998 | Schulz et al. |
| 5,723,970 A | 3/1998 | Bell |
| 5,728,130 A | 3/1998 | Ishikawa et al. |
| 5,730,752 A | 3/1998 | Alden et al. |
| 5,733,074 A | 3/1998 | Stock et al. |
| 5,735,848 A | 4/1998 | Yates et al. |
| 5,741,226 A | 4/1998 | Strukel et al. |
| 5,743,906 A | 4/1998 | Parins et al. |
| 5,752,973 A | 5/1998 | Kieturakis |
| 5,755,717 A | 5/1998 | Yates et al. |
| 5,759,183 A | 6/1998 | VanDusseldorp |
| 5,762,255 A | 6/1998 | Chrisman et al. |
| 5,766,164 A | 6/1998 | Mueller et al. |
| 5,772,659 A | 6/1998 | Becker et al. |
| 5,776,130 A | 7/1998 | Buysse et al. |
| 5,776,155 A | 7/1998 | Beaupre et al. |
| 5,779,130 A | 7/1998 | Alesi et al. |
| 5,779,701 A | 7/1998 | McBrayer et al. |
| 5,782,834 A | 7/1998 | Lucey et al. |
| 5,792,135 A | 8/1998 | Madhani et al. |
| 5,792,138 A | 8/1998 | Shipp |
| 5,792,165 A | 8/1998 | Klieman et al. |
| 5,796,188 A | 8/1998 | Bays |
| 5,797,941 A | 8/1998 | Schulze et al. |
| 5,797,958 A | 8/1998 | Yoon |
| 5,797,959 A | 8/1998 | Castro et al. |
| 5,800,432 A | 9/1998 | Swanson |
| 5,800,448 A | 9/1998 | Banko |

(56) References Cited

U.S. PATENT DOCUMENTS

| | | |
|---|---|---|
| 5,800,449 A | 9/1998 | Wales |
| 5,805,140 A | 9/1998 | Rosenberg et al. |
| 5,807,393 A | 9/1998 | Williamson, IV et al. |
| 5,808,396 A | 9/1998 | Boukhny |
| 5,810,811 A | 9/1998 | Yates et al. |
| 5,810,828 A | 9/1998 | Lightman et al. |
| 5,810,859 A | 9/1998 | DiMatteo et al. |
| 5,817,033 A | 10/1998 | DeSantis et al. |
| 5,817,084 A | 10/1998 | Jensen |
| 5,817,093 A | 10/1998 | Williamson, IV et al. |
| 5,817,119 A | 10/1998 | Klieman et al. |
| 5,823,197 A | 10/1998 | Edwards |
| 5,827,271 A | 10/1998 | Buysse et al. |
| 5,827,323 A | 10/1998 | Klieman et al. |
| 5,828,160 A | 10/1998 | Sugishita |
| 5,833,696 A | 11/1998 | Whitfield et al. |
| 5,836,897 A | 11/1998 | Sakurai et al. |
| 5,836,909 A | 11/1998 | Cosmescu |
| 5,836,943 A | 11/1998 | Miller, III |
| 5,836,957 A | 11/1998 | Schulz et al. |
| 5,836,990 A | 11/1998 | Li |
| 5,843,109 A | 12/1998 | Mehta et al. |
| 5,851,212 A | 12/1998 | Zirps et al. |
| 5,853,412 A | 12/1998 | Mayenberger |
| 5,854,590 A | 12/1998 | Dalstein |
| 5,858,018 A | 1/1999 | Shipp et al. |
| 5,865,361 A | 2/1999 | Milliman et al. |
| 5,873,873 A | 2/1999 | Smith et al. |
| 5,873,882 A | 2/1999 | Straub et al. |
| 5,876,401 A | 3/1999 | Schulze et al. |
| 5,878,193 A | 3/1999 | Wang et al. |
| 5,879,364 A | 3/1999 | Bromfield et al. |
| 5,880,668 A | 3/1999 | Hall |
| 5,883,615 A | 3/1999 | Fago et al. |
| 5,891,142 A | 4/1999 | Eggers et al. |
| 5,893,835 A | 4/1999 | Witt et al. |
| 5,897,523 A | 4/1999 | Wright et al. |
| 5,897,569 A | 4/1999 | Kellogg et al. |
| 5,903,607 A | 5/1999 | Tailliet |
| 5,904,681 A | 5/1999 | West, Jr. |
| 5,906,625 A | 5/1999 | Bito et al. |
| 5,906,627 A | 5/1999 | Spaulding |
| 5,906,628 A | 5/1999 | Miyawaki et al. |
| 5,910,129 A | 6/1999 | Koblish et al. |
| 5,911,699 A | 6/1999 | Anis et al. |
| 5,913,823 A | 6/1999 | Hedberg et al. |
| 5,916,229 A | 6/1999 | Evans |
| 5,921,956 A | 7/1999 | Grinberg et al. |
| 5,929,846 A | 7/1999 | Rosenberg et al. |
| 5,935,143 A | 8/1999 | Hood |
| 5,935,144 A | 8/1999 | Estabrook |
| 5,938,633 A | 8/1999 | Beaupre |
| 5,944,718 A | 8/1999 | Austin et al. |
| 5,944,737 A | 8/1999 | Tsonton et al. |
| 5,947,984 A | 9/1999 | Whipple |
| 5,954,717 A | 9/1999 | Behl et al. |
| 5,954,736 A | 9/1999 | Bishop et al. |
| 5,954,746 A | 9/1999 | Holthaus et al. |
| 5,957,882 A | 9/1999 | Nita et al. |
| 5,957,943 A | 9/1999 | Vaitekunas |
| 5,968,007 A | 10/1999 | Simon et al. |
| 5,968,060 A | 10/1999 | Kellogg |
| 5,974,342 A | 10/1999 | Petrofsky |
| D416,089 S | 11/1999 | Barton et al. |
| 5,980,510 A | 11/1999 | Tsonton et al. |
| 5,980,546 A | 11/1999 | Hood |
| 5,984,938 A | 11/1999 | Yoon |
| 5,987,344 A | 11/1999 | West |
| 5,989,274 A | 11/1999 | Davison et al. |
| 5,989,275 A | 11/1999 | Estabrook et al. |
| 5,993,465 A | 11/1999 | Shipp et al. |
| 5,993,972 A | 11/1999 | Reich et al. |
| 5,994,855 A | 11/1999 | Lundell et al. |
| 6,003,517 A | 12/1999 | Sheffield et al. |
| 6,004,335 A | 12/1999 | Vaitekunas et al. |
| 6,013,052 A | 1/2000 | Durman et al. |
| 6,024,741 A | 2/2000 | Williamson, IV et al. |
| 6,024,744 A | 2/2000 | Kese et al. |
| 6,024,750 A | 2/2000 | Mastri et al. |
| 6,027,515 A | 2/2000 | Cimino |
| 6,031,526 A | 2/2000 | Shipp |
| 6,033,375 A | 3/2000 | Brumbach |
| 6,033,399 A | 3/2000 | Gines |
| 6,036,667 A | 3/2000 | Manna et al. |
| 6,036,707 A | 3/2000 | Spaulding |
| 6,039,734 A | 3/2000 | Goble |
| 6,048,224 A | 4/2000 | Kay |
| 6,050,943 A | 4/2000 | Slayton et al. |
| 6,050,996 A | 4/2000 | Schmaltz et al. |
| 6,051,010 A | 4/2000 | DiMatteo et al. |
| 6,056,735 A | 5/2000 | Okada et al. |
| 6,063,098 A | 5/2000 | Houser et al. |
| 6,066,132 A | 5/2000 | Chen et al. |
| 6,066,151 A | 5/2000 | Miyawaki et al. |
| 6,068,627 A | 5/2000 | Orszulak et al. |
| 6,068,629 A | 5/2000 | Haissaguerre et al. |
| 6,068,647 A | 5/2000 | Witt et al. |
| 6,074,389 A | 6/2000 | Levine et al. |
| 6,077,285 A | 6/2000 | Boukhny |
| 6,080,149 A | 6/2000 | Huang et al. |
| 6,083,191 A | 7/2000 | Rose |
| 6,086,584 A | 7/2000 | Miller |
| 6,090,120 A | 7/2000 | Wright et al. |
| 6,091,995 A | 7/2000 | Ingle et al. |
| 6,096,033 A | 8/2000 | Tu et al. |
| 6,099,483 A | 8/2000 | Palmer et al. |
| 6,099,542 A | 8/2000 | Cohn et al. |
| 6,099,550 A | 8/2000 | Yoon |
| 6,102,909 A | 8/2000 | Chen et al. |
| 6,109,500 A | 8/2000 | Alli et al. |
| 6,110,127 A | 8/2000 | Suzuki |
| 6,113,594 A | 9/2000 | Savage |
| 6,113,598 A | 9/2000 | Baker |
| 6,117,152 A | 9/2000 | Huitema |
| H1904 H | 10/2000 | Yates et al. |
| 6,126,629 A | 10/2000 | Perkins |
| 6,126,658 A | 10/2000 | Baker |
| 6,129,735 A | 10/2000 | Okada et al. |
| 6,129,740 A | 10/2000 | Michelson |
| 6,132,368 A | 10/2000 | Cooper |
| 6,132,427 A | 10/2000 | Jones et al. |
| 6,132,429 A | 10/2000 | Baker |
| 6,132,448 A | 10/2000 | Perez et al. |
| 6,139,320 A | 10/2000 | Hahn |
| 6,139,561 A | 10/2000 | Shibata et al. |
| 6,142,615 A | 11/2000 | Qiu et al. |
| 6,142,994 A | 11/2000 | Swanson et al. |
| 6,144,402 A | 11/2000 | Norsworthy et al. |
| 6,147,560 A | 11/2000 | Erhage et al. |
| 6,152,902 A | 11/2000 | Christian et al. |
| 6,152,923 A | 11/2000 | Ryan |
| 6,154,198 A | 11/2000 | Rosenberg |
| 6,156,029 A | 12/2000 | Mueller |
| 6,159,160 A | 12/2000 | Hsei et al. |
| 6,159,175 A | 12/2000 | Strukel et al. |
| 6,162,194 A | 12/2000 | Shipp |
| 6,162,208 A | 12/2000 | Hipps |
| 6,165,150 A | 12/2000 | Banko |
| 6,174,309 B1 | 1/2001 | Wrublewski et al. |
| 6,174,310 B1 | 1/2001 | Kirwan, Jr. |
| 6,176,857 B1 | 1/2001 | Ashley |
| 6,179,853 B1 | 1/2001 | Sachse et al. |
| 6,183,426 B1 | 2/2001 | Akisada et al. |
| 6,187,003 B1 | 2/2001 | Buysse et al. |
| 6,190,386 B1 | 2/2001 | Rydell |
| 6,193,709 B1 | 2/2001 | Miyawaki et al. |
| 6,204,592 B1 | 3/2001 | Hur |
| 6,205,383 B1 | 3/2001 | Hermann |
| 6,205,855 B1 | 3/2001 | Pfeiffer |
| 6,206,844 B1 | 3/2001 | Reichel et al. |
| 6,206,876 B1 | 3/2001 | Levine et al. |
| 6,210,337 B1 | 4/2001 | Dunham et al. |
| 6,210,402 B1 | 4/2001 | Olsen et al. |
| 6,210,403 B1 | 4/2001 | Klicek |

(56) References Cited

U.S. PATENT DOCUMENTS

| | | |
|---|---|---|
| 6,214,023 B1 | 4/2001 | Whipple et al. |
| 6,228,080 B1 | 5/2001 | Gines |
| 6,231,565 B1 | 5/2001 | Tovey et al. |
| 6,232,899 B1 | 5/2001 | Craven |
| 6,233,476 B1 | 5/2001 | Strommer et al. |
| 6,238,366 B1 | 5/2001 | Savage et al. |
| 6,238,384 B1 | 5/2001 | Peer |
| 6,241,724 B1 | 6/2001 | Fleischman et al. |
| 6,245,065 B1 | 6/2001 | Panescu et al. |
| 6,251,110 B1 | 6/2001 | Wampler |
| 6,252,110 B1 | 6/2001 | Uemura et al. |
| D444,365 S | 7/2001 | Bass et al. |
| D445,092 S | 7/2001 | Lee |
| D445,764 S | 7/2001 | Lee |
| 6,254,623 B1 | 7/2001 | Haibel, Jr. et al. |
| 6,257,241 B1 | 7/2001 | Wampler |
| 6,258,034 B1 | 7/2001 | Hanafy |
| 6,259,230 B1 | 7/2001 | Chou |
| 6,261,286 B1 | 7/2001 | Goble et al. |
| 6,267,761 B1 | 7/2001 | Ryan |
| 6,270,831 B2 | 8/2001 | Kumar et al. |
| 6,273,852 B1 | 8/2001 | Lehe et al. |
| 6,274,963 B1 | 8/2001 | Estabrook et al. |
| 6,277,115 B1 | 8/2001 | Saadat |
| 6,277,117 B1 | 8/2001 | Tetzlaff et al. |
| 6,278,218 B1 | 8/2001 | Madan et al. |
| 6,280,407 B1 | 8/2001 | Manna et al. |
| 6,283,981 B1 | 9/2001 | Beaupre |
| 6,287,344 B1 | 9/2001 | Wampler et al. |
| 6,290,575 B1 | 9/2001 | Shipp |
| 6,292,700 B1 | 9/2001 | Morrison et al. |
| 6,299,591 B1 | 10/2001 | Banko |
| 6,306,131 B1 | 10/2001 | Hareyama et al. |
| 6,306,157 B1 | 10/2001 | Shchervinsky |
| 6,309,400 B2 | 10/2001 | Beaupre |
| 6,311,783 B1 | 11/2001 | Harpell |
| 6,319,221 B1 | 11/2001 | Savage et al. |
| 6,325,795 B1 | 12/2001 | Lindemann et al. |
| 6,325,799 B1 | 12/2001 | Goble |
| 6,325,811 B1 | 12/2001 | Messerly |
| 6,328,751 B1 | 12/2001 | Beaupre |
| 6,332,891 B1 | 12/2001 | Himes |
| 6,338,657 B1 | 1/2002 | Harper et al. |
| 6,340,352 B1 | 1/2002 | Okada et al. |
| 6,340,878 B1 | 1/2002 | Oglesbee |
| 6,350,269 B1 | 2/2002 | Shipp et al. |
| 6,352,532 B1 | 3/2002 | Kramer et al. |
| 6,356,224 B1 | 3/2002 | Wohlfarth |
| 6,358,246 B1 | 3/2002 | Behl et al. |
| 6,358,264 B2 | 3/2002 | Banko |
| 6,364,888 B1 | 4/2002 | Niemeyer et al. |
| 6,379,320 B1 | 4/2002 | Lafon et al. |
| D457,958 S | 5/2002 | Dycus et al. |
| 6,383,194 B1 | 5/2002 | Pothula |
| 6,384,690 B1 | 5/2002 | Wilhelmsson et al. |
| 6,387,094 B1 | 5/2002 | Eitenmuller |
| 6,387,109 B1 | 5/2002 | Davison et al. |
| 6,388,657 B1 | 5/2002 | Natoli |
| 6,390,973 B1 | 5/2002 | Ouchi |
| 6,391,026 B1 | 5/2002 | Hung et al. |
| 6,391,042 B1 | 5/2002 | Cimino |
| 6,398,779 B1 | 6/2002 | Buysse et al. |
| 6,402,743 B1 | 6/2002 | Orszulak et al. |
| 6,402,748 B1 | 6/2002 | Schoenman et al. |
| 6,405,184 B1 | 6/2002 | Bohme et al. |
| 6,405,733 B1 | 6/2002 | Fogarty et al. |
| 6,409,722 B1 | 6/2002 | Hoey et al. |
| H2037 H | 7/2002 | Yates et al. |
| 6,416,469 B1 | 7/2002 | Phung et al. |
| 6,416,486 B1 | 7/2002 | Wampler |
| 6,417,969 B1 | 7/2002 | DeLuca et al. |
| 6,419,675 B1 | 7/2002 | Gallo, Sr. |
| 6,423,073 B2 | 7/2002 | Bowman |
| 6,423,082 B1 | 7/2002 | Houser et al. |
| 6,425,906 B1 | 7/2002 | Young et al. |
| 6,428,538 B1 | 8/2002 | Blewett et al. |
| 6,428,539 B1 | 8/2002 | Baxter et al. |
| 6,430,446 B1 | 8/2002 | Knowlton |
| 6,432,118 B1 | 8/2002 | Messerly |
| 6,436,114 B1 | 8/2002 | Novak et al. |
| 6,436,115 B1 | 8/2002 | Beaupre |
| 6,436,129 B1 | 8/2002 | Sharkey et al. |
| 6,440,062 B1 | 8/2002 | Ouchi |
| 6,443,968 B1 | 9/2002 | Holthaus et al. |
| 6,443,969 B1 | 9/2002 | Novak et al. |
| 6,449,006 B1 | 9/2002 | Shipp |
| 6,454,781 B1 | 9/2002 | Witt et al. |
| 6,454,782 B1 | 9/2002 | Schwemberger |
| 6,458,128 B1 | 10/2002 | Schulze |
| 6,458,130 B1 | 10/2002 | Frazier et al. |
| 6,458,142 B1 | 10/2002 | Faller et al. |
| 6,459,363 B1 | 10/2002 | Walker et al. |
| 6,461,363 B1 | 10/2002 | Gadberry et al. |
| 6,464,689 B1 | 10/2002 | Qin et al. |
| 6,464,702 B2 | 10/2002 | Schulze et al. |
| 6,468,270 B1 | 10/2002 | Hovda et al. |
| 6,475,211 B2 | 11/2002 | Chess et al. |
| 6,475,215 B1 | 11/2002 | Tanrisever |
| 6,480,796 B2 | 11/2002 | Wiener |
| 6,485,490 B2 | 11/2002 | Wampler et al. |
| 6,491,690 B1 | 12/2002 | Goble et al. |
| 6,491,701 B2 | 12/2002 | Tierney et al. |
| 6,491,708 B2 | 12/2002 | Madan et al. |
| 6,497,715 B2 | 12/2002 | Satou |
| 6,500,112 B1 | 12/2002 | Khouri |
| 6,500,176 B1 | 12/2002 | Truckai et al. |
| 6,500,188 B2 | 12/2002 | Harper et al. |
| 6,500,312 B2 | 12/2002 | Wedekamp |
| 6,503,248 B1 | 1/2003 | Levine |
| 6,506,208 B2 | 1/2003 | Hunt et al. |
| 6,511,478 B1 | 1/2003 | Burnside et al. |
| 6,511,480 B1 | 1/2003 | Tetzlaff et al. |
| 6,511,493 B1 | 1/2003 | Moutafis et al. |
| 6,514,252 B2 | 2/2003 | Nezhat et al. |
| 6,514,267 B2 | 2/2003 | Jewett |
| 6,517,565 B1 | 2/2003 | Whitman et al. |
| 6,524,251 B2 | 2/2003 | Rabiner et al. |
| 6,524,316 B1 | 2/2003 | Nicholson et al. |
| 6,527,736 B1 | 3/2003 | Attinger et al. |
| 6,531,846 B1 | 3/2003 | Smith |
| 6,533,784 B2 | 3/2003 | Truckai et al. |
| 6,537,272 B2 | 3/2003 | Christopherson et al. |
| 6,537,291 B2 | 3/2003 | Friedman et al. |
| 6,543,452 B1 | 4/2003 | Lavigne |
| 6,543,456 B1 | 4/2003 | Freeman |
| 6,544,260 B1 | 4/2003 | Markel et al. |
| 6,551,309 B1 | 4/2003 | LePivert |
| 6,554,829 B2 | 4/2003 | Schulze et al. |
| 6,558,376 B2 | 5/2003 | Bishop |
| 6,558,380 B2 | 5/2003 | Lingenfelder et al. |
| 6,561,983 B2 | 5/2003 | Cronin et al. |
| 6,562,035 B1 | 5/2003 | Levin |
| 6,562,037 B2 | 5/2003 | Paton et al. |
| 6,565,558 B1 | 5/2003 | Lindenmeier et al. |
| 6,572,563 B2 | 6/2003 | Ouchi |
| 6,572,632 B2 | 6/2003 | Zisterer et al. |
| 6,572,639 B1 | 6/2003 | Ingle et al. |
| 6,575,969 B1 | 6/2003 | Rittman, III et al. |
| 6,582,427 B1 | 6/2003 | Goble et al. |
| 6,582,451 B1 | 6/2003 | Marucci et al. |
| 6,584,360 B2 | 6/2003 | Francischelli et al. |
| D477,408 S | 7/2003 | Bromley |
| 6,585,735 B1 | 7/2003 | Frazier et al. |
| 6,588,277 B2 | 7/2003 | Giordano et al. |
| 6,589,200 B1 | 7/2003 | Schwemberger et al. |
| 6,589,239 B2 | 7/2003 | Khandkar et al. |
| 6,590,733 B1 | 7/2003 | Wilson et al. |
| 6,599,288 B2 | 7/2003 | Maguire et al. |
| 6,602,252 B2 | 8/2003 | Mollenauer |
| 6,602,262 B2 | 8/2003 | Griego et al. |
| 6,607,540 B1 | 8/2003 | Shipp |
| 6,610,059 B1 | 8/2003 | West, Jr. |
| 6,610,060 B2 | 8/2003 | Mulier et al. |
| 6,611,793 B1 | 8/2003 | Burnside et al. |

(56) References Cited

U.S. PATENT DOCUMENTS

| | | |
|---|---|---|
| 6,616,450 B2 | 9/2003 | Mossle et al. |
| 6,619,529 B2 | 9/2003 | Green et al. |
| 6,620,161 B2 | 9/2003 | Schulze et al. |
| 6,622,731 B2 | 9/2003 | Daniel et al. |
| 6,623,482 B2 | 9/2003 | Pendekanti et al. |
| 6,623,500 B1 | 9/2003 | Cook et al. |
| 6,623,501 B2 | 9/2003 | Heller et al. |
| 6,626,848 B2 | 9/2003 | Neuenfeldt |
| 6,626,926 B2 | 9/2003 | Friedman et al. |
| 6,629,974 B2 | 10/2003 | Penny et al. |
| 6,632,221 B1 | 10/2003 | Edwards et al. |
| 6,633,234 B2 | 10/2003 | Wiener et al. |
| 6,635,057 B2 | 10/2003 | Harano et al. |
| 6,644,532 B2 | 11/2003 | Green et al. |
| 6,651,669 B1 | 11/2003 | Burnside |
| 6,652,513 B2 | 11/2003 | Panescu et al. |
| 6,652,539 B2 | 11/2003 | Shipp et al. |
| 6,652,545 B2 | 11/2003 | Shipp et al. |
| 6,656,132 B1 | 12/2003 | Ouchi |
| 6,656,177 B2 | 12/2003 | Truckai et al. |
| 6,656,198 B2 | 12/2003 | Tsonton et al. |
| 6,660,017 B2 | 12/2003 | Beaupre |
| 6,662,127 B2 | 12/2003 | Wiener et al. |
| 6,663,941 B2 | 12/2003 | Brown et al. |
| 6,666,860 B1 | 12/2003 | Takahashi |
| 6,666,875 B1 | 12/2003 | Sakurai et al. |
| 6,669,690 B1 | 12/2003 | Okada et al. |
| 6,669,710 B2 | 12/2003 | Moutafis et al. |
| 6,673,248 B2 | 1/2004 | Chowdhury |
| 6,676,660 B2 | 1/2004 | Wampler et al. |
| 6,678,621 B2 | 1/2004 | Wiener et al. |
| 6,679,875 B2 | 1/2004 | Honda et al. |
| 6,679,882 B1 | 1/2004 | Kornerup |
| 6,679,899 B2 | 1/2004 | Wiener et al. |
| 6,682,501 B1 | 1/2004 | Nelson et al. |
| 6,682,544 B2 | 1/2004 | Mastri et al. |
| 6,685,700 B2 | 2/2004 | Behl et al. |
| 6,685,701 B2 | 2/2004 | Orszulak et al. |
| 6,685,703 B2 | 2/2004 | Pearson et al. |
| 6,689,145 B2 | 2/2004 | Lee et al. |
| 6,689,146 B1 | 2/2004 | Himes |
| 6,690,960 B2 | 2/2004 | Chen et al. |
| 6,695,840 B2 | 2/2004 | Schulze |
| 6,702,821 B2 | 3/2004 | Bonutti |
| 6,716,215 B1 | 4/2004 | David et al. |
| 6,719,692 B2 | 4/2004 | Kleffner et al. |
| 6,719,765 B2 | 4/2004 | Bonutti |
| 6,719,776 B2 | 4/2004 | Baxter et al. |
| 6,722,552 B2 | 4/2004 | Fenton, Jr. |
| 6,723,091 B2 | 4/2004 | Goble et al. |
| D490,059 S | 5/2004 | Conway et al. |
| 6,730,080 B2 | 5/2004 | Harano et al. |
| 6,731,047 B2 | 5/2004 | Kauf et al. |
| 6,733,498 B2 | 5/2004 | Paton et al. |
| 6,733,506 B1 | 5/2004 | McDevitt et al. |
| 6,736,813 B2 | 5/2004 | Yamauchi et al. |
| 6,739,872 B1 | 5/2004 | Turri |
| 6,740,079 B1 | 5/2004 | Eggers et al. |
| D491,666 S | 6/2004 | Kimmell et al. |
| 6,743,245 B2 | 6/2004 | Lobdell |
| 6,746,284 B1 | 6/2004 | Spink, Jr. |
| 6,746,443 B1 | 6/2004 | Morley et al. |
| 6,752,815 B2 | 6/2004 | Beaupre |
| 6,755,825 B2 | 6/2004 | Shoenman et al. |
| 6,761,698 B2 | 7/2004 | Shibata et al. |
| 6,762,535 B2 | 7/2004 | Take et al. |
| 6,766,202 B2 | 7/2004 | Underwood et al. |
| 6,770,072 B2 | 8/2004 | Truckai et al. |
| 6,773,409 B2 | 8/2004 | Truckai et al. |
| 6,773,434 B2 | 8/2004 | Ciarrocca |
| 6,773,435 B2 | 8/2004 | Schulze et al. |
| 6,773,443 B2 | 8/2004 | Truwit et al. |
| 6,773,444 B2 | 8/2004 | Messerly |
| 6,775,575 B2 | 8/2004 | Bommannan et al. |
| 6,778,023 B2 | 8/2004 | Christensen |
| 6,783,524 B2 | 8/2004 | Anderson et al. |
| 6,786,382 B1 | 9/2004 | Hoffman |
| 6,786,383 B2 | 9/2004 | Stegelmann |
| 6,789,939 B2 | 9/2004 | Schrodinger et al. |
| 6,790,173 B2 | 9/2004 | Saadat et al. |
| 6,790,216 B1 | 9/2004 | Ishikawa |
| 6,794,027 B1 | 9/2004 | Araki et al. |
| 6,796,981 B2 | 9/2004 | Wham et al. |
| D496,997 S | 10/2004 | Dycus et al. |
| 6,800,085 B2 | 10/2004 | Selmon et al. |
| 6,802,843 B2 | 10/2004 | Truckai et al. |
| 6,808,525 B2 | 10/2004 | Latterell et al. |
| 6,809,508 B2 | 10/2004 | Donofrio |
| 6,810,281 B2 | 10/2004 | Brock et al. |
| 6,811,842 B1 | 11/2004 | Ehrnsperger et al. |
| 6,814,731 B2 | 11/2004 | Swanson |
| 6,819,027 B2 | 11/2004 | Saraf |
| 6,821,273 B2 | 11/2004 | Mollenauer |
| 6,827,712 B2 | 12/2004 | Tovey et al. |
| 6,828,712 B2 | 12/2004 | Battaglin et al. |
| 6,835,082 B2 | 12/2004 | Gonnering |
| 6,835,199 B2 | 12/2004 | McGuckin, Jr. et al. |
| 6,840,938 B1 | 1/2005 | Morley et al. |
| 6,843,789 B2 | 1/2005 | Goble |
| 6,849,073 B2 | 2/2005 | Hoey et al. |
| 6,860,878 B2 | 3/2005 | Brock |
| 6,860,880 B2 | 3/2005 | Treat et al. |
| 6,863,676 B2 | 3/2005 | Lee et al. |
| 6,866,671 B2 | 3/2005 | Tierney et al. |
| 6,869,439 B2 | 3/2005 | White et al. |
| 6,875,220 B2 | 4/2005 | Du et al. |
| 6,877,647 B2 | 4/2005 | Green et al. |
| 6,882,439 B2 | 4/2005 | Ishijima |
| 6,887,209 B2 | 5/2005 | Kadziauskas et al. |
| 6,887,252 B1 | 5/2005 | Okada et al. |
| 6,893,435 B2 | 5/2005 | Goble |
| 6,898,536 B2 | 5/2005 | Wiener et al. |
| 6,899,685 B2 | 5/2005 | Kermode et al. |
| 6,905,497 B2 | 6/2005 | Truckai et al. |
| 6,908,463 B2 | 6/2005 | Treat et al. |
| 6,908,472 B2 | 6/2005 | Wiener et al. |
| 6,913,579 B2 | 7/2005 | Truckai et al. |
| 6,915,623 B2 | 7/2005 | Dey et al. |
| 6,923,804 B2 | 8/2005 | Eggers et al. |
| 6,923,806 B2 | 8/2005 | Hooven et al. |
| 6,926,712 B2 | 8/2005 | Phan |
| 6,926,716 B2 | 8/2005 | Baker et al. |
| 6,926,717 B1 | 8/2005 | Garito et al. |
| 6,929,602 B2 | 8/2005 | Hirakui et al. |
| 6,929,622 B2 | 8/2005 | Chian |
| 6,929,632 B2 | 8/2005 | Nita et al. |
| 6,929,644 B2 | 8/2005 | Truckai et al. |
| 6,933,656 B2 | 8/2005 | Matsushita et al. |
| D509,589 S | 9/2005 | Wells |
| 6,942,660 B2 | 9/2005 | Pantera et al. |
| 6,942,677 B2 | 9/2005 | Nita et al. |
| 6,945,981 B2 | 9/2005 | Donofrio et al. |
| 6,946,779 B2 | 9/2005 | Birgel |
| 6,948,503 B2 | 9/2005 | Refior et al. |
| 6,953,461 B2 | 10/2005 | McClurken et al. |
| 6,958,070 B2 | 10/2005 | Witt et al. |
| D511,145 S | 11/2005 | Donofrio et al. |
| 6,974,450 B2 | 12/2005 | Weber et al. |
| 6,976,844 B2 | 12/2005 | Hickok et al. |
| 6,976,969 B2 | 12/2005 | Messerly |
| 6,977,495 B2 | 12/2005 | Donofrio |
| 6,979,332 B2 | 12/2005 | Adams |
| 6,981,628 B2 | 1/2006 | Wales |
| 6,984,220 B2 | 1/2006 | Wuchinich |
| 6,984,231 B2 | 1/2006 | Goble et al. |
| 6,988,295 B2 | 1/2006 | Tillim |
| 6,988,649 B2 | 1/2006 | Shelton, IV et al. |
| 6,994,708 B2 | 2/2006 | Manzo |
| 6,994,709 B2 | 2/2006 | Iida |
| 7,000,818 B2 | 2/2006 | Shelton, IV et al. |
| 7,001,335 B2 | 2/2006 | Adachi et al. |
| 7,001,379 B2 | 2/2006 | Behl et al. |
| 7,001,382 B2 | 2/2006 | Gallo, Sr. |
| 7,004,951 B2 | 2/2006 | Gibbens, III |

(56) References Cited

U.S. PATENT DOCUMENTS

| | | |
|---|---|---|
| 7,011,657 B2 | 3/2006 | Truckai et al. |
| 7,014,638 B2 | 3/2006 | Michelson |
| 7,018,389 B2 | 3/2006 | Camerlengo |
| 7,025,732 B2 | 4/2006 | Thompson et al. |
| 7,033,356 B2 | 4/2006 | Latterell et al. |
| 7,033,357 B2 | 4/2006 | Baxter et al. |
| 7,037,306 B2 | 5/2006 | Podany et al. |
| 7,041,083 B2 | 5/2006 | Chu et al. |
| 7,041,088 B2 | 5/2006 | Nawrocki et al. |
| 7,041,102 B2 | 5/2006 | Truckai et al. |
| 7,044,949 B2 | 5/2006 | Orszulak et al. |
| 7,052,494 B2 | 5/2006 | Goble et al. |
| 7,052,496 B2 | 5/2006 | Yamauchi |
| 7,055,731 B2 | 6/2006 | Shelton, IV et al. |
| 7,063,699 B2 | 6/2006 | Hess et al. |
| 7,066,893 B2 | 6/2006 | Hibner et al. |
| 7,066,895 B2 | 6/2006 | Podany |
| 7,066,936 B2 | 6/2006 | Ryan |
| 7,070,597 B2 | 7/2006 | Truckai et al. |
| 7,074,218 B2 | 7/2006 | Washington et al. |
| 7,074,219 B2 | 7/2006 | Levine et al. |
| 7,077,039 B2 | 7/2006 | Gass et al. |
| 7,077,845 B2 | 7/2006 | Hacker et al. |
| 7,077,853 B2 | 7/2006 | Kramer et al. |
| 7,083,075 B2 | 8/2006 | Swayze et al. |
| 7,083,613 B2 | 8/2006 | Treat |
| 7,083,618 B2 | 8/2006 | Couture et al. |
| 7,083,619 B2 | 8/2006 | Truckai et al. |
| 7,087,054 B2 | 8/2006 | Truckai et al. |
| 7,090,637 B2 | 8/2006 | Danitz et al. |
| 7,090,672 B2 | 8/2006 | Underwood et al. |
| 7,094,235 B2 | 8/2006 | Francischelli |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,101,378 B2 | 9/2006 | Salameh et al. |
| 7,104,834 B2 | 9/2006 | Robinson et al. |
| 7,108,695 B2 | 9/2006 | Witt et al. |
| 7,111,769 B2 | 9/2006 | Wales et al. |
| 7,112,201 B2 | 9/2006 | Truckai et al. |
| 7,113,831 B2 | 9/2006 | Hooven |
| D531,311 S | 10/2006 | Guerra et al. |
| 7,117,034 B2 | 10/2006 | Kronberg |
| 7,118,564 B2 | 10/2006 | Ritchie et al. |
| 7,118,570 B2 | 10/2006 | Tetzlaff et al. |
| 7,118,587 B2 | 10/2006 | Dycus et al. |
| 7,119,516 B2 | 10/2006 | Denning |
| 7,124,932 B2 | 10/2006 | Isaacson et al. |
| 7,125,409 B2 | 10/2006 | Truckai et al. |
| 7,128,720 B2 | 10/2006 | Podany |
| 7,131,860 B2 | 11/2006 | Sartor et al. |
| 7,131,970 B2 | 11/2006 | Moses et al. |
| 7,135,018 B2 | 11/2006 | Ryan et al. |
| 7,135,030 B2 | 11/2006 | Schwemberger et al. |
| 7,137,980 B2 | 11/2006 | Buysse et al. |
| 7,143,925 B2 | 12/2006 | Shelton, IV et al. |
| 7,144,403 B2 | 12/2006 | Booth |
| 7,147,138 B2 | 12/2006 | Shelton, IV |
| 7,153,315 B2 | 12/2006 | Miller |
| D536,093 S | 1/2007 | Nakajima et al. |
| 7,156,189 B1 | 1/2007 | Bar-Cohen et al. |
| 7,156,846 B2 | 1/2007 | Dycus et al. |
| 7,156,853 B2 | 1/2007 | Muratsu |
| 7,157,058 B2 | 1/2007 | Marhasin et al. |
| 7,159,750 B2 | 1/2007 | Racenet et al. |
| 7,160,259 B2 | 1/2007 | Tardy et al. |
| 7,160,296 B2 | 1/2007 | Pearson et al. |
| 7,160,298 B2 | 1/2007 | Lawes et al. |
| 7,160,299 B2 | 1/2007 | Baily |
| 7,163,548 B2 | 1/2007 | Stulen et al. |
| 7,166,103 B2 | 1/2007 | Carmel et al. |
| 7,169,144 B2 | 1/2007 | Hoey et al. |
| 7,169,146 B2 | 1/2007 | Truckai et al. |
| 7,169,156 B2 | 1/2007 | Hart |
| 7,179,254 B2 | 2/2007 | Pendekanti et al. |
| 7,179,271 B2 | 2/2007 | Friedman et al. |
| 7,186,253 B2 | 3/2007 | Truckai et al. |
| 7,189,233 B2 | 3/2007 | Truckai et al. |
| 7,195,631 B2 | 3/2007 | Dumbauld |
| D541,418 S | 4/2007 | Schechter et al. |
| 7,198,635 B2 | 4/2007 | Danek et al. |
| 7,204,820 B2 | 4/2007 | Akahoshi |
| 7,207,471 B2 | 4/2007 | Heinrich et al. |
| 7,207,997 B2 | 4/2007 | Shipp et al. |
| 7,208,005 B2 | 4/2007 | Frecker et al. |
| 7,210,881 B2 | 5/2007 | Greenberg |
| 7,211,079 B2 | 5/2007 | Treat |
| 7,217,128 B2 | 5/2007 | Atkin et al. |
| 7,217,269 B2 | 5/2007 | El-Galley et al. |
| 7,220,951 B2 | 5/2007 | Truckai et al. |
| 7,223,229 B2 | 5/2007 | Inman et al. |
| 7,225,964 B2 | 6/2007 | Mastri et al. |
| 7,226,447 B2 | 6/2007 | Uchida et al. |
| 7,226,448 B2 | 6/2007 | Bertolero et al. |
| 7,229,455 B2 | 6/2007 | Sakurai et al. |
| 7,232,440 B2 | 6/2007 | Dumbauld et al. |
| 7,235,071 B2 | 6/2007 | Gonnering |
| 7,235,073 B2 | 6/2007 | Levine et al. |
| 7,241,294 B2 | 7/2007 | Reschke |
| 7,244,262 B2 | 7/2007 | Wiener et al. |
| 7,251,531 B2 | 7/2007 | Mosher et al. |
| 7,252,641 B2 | 8/2007 | Thompson et al. |
| 7,252,667 B2 | 8/2007 | Moses et al. |
| 7,258,688 B1 | 8/2007 | Shah et al. |
| 7,264,618 B2 | 9/2007 | Murakami et al. |
| 7,267,677 B2 | 9/2007 | Johnson et al. |
| 7,267,685 B2 | 9/2007 | Butaric et al. |
| 7,269,873 B2 | 9/2007 | Brewer et al. |
| 7,273,483 B2 | 9/2007 | Wiener et al. |
| D552,241 S | 10/2007 | Bromley et al. |
| 7,282,048 B2 | 10/2007 | Goble et al. |
| 7,285,895 B2 | 10/2007 | Beaupre |
| 7,287,682 B1 | 10/2007 | Ezzat et al. |
| 7,297,149 B2 | 11/2007 | Vitali et al. |
| 7,300,431 B2 | 11/2007 | Dubrovsky |
| 7,300,435 B2 | 11/2007 | Wham et al. |
| 7,300,446 B2 | 11/2007 | Beaupre |
| 7,300,450 B2 | 11/2007 | Vleugels et al. |
| 7,303,531 B2 | 12/2007 | Lee et al. |
| 7,303,557 B2 | 12/2007 | Wham et al. |
| 7,306,597 B2 | 12/2007 | Manzo |
| 7,307,313 B2 | 12/2007 | Ohyanagi et al. |
| 7,309,849 B2 | 12/2007 | Truckai et al. |
| 7,311,706 B2 | 12/2007 | Schoenman et al. |
| 7,311,709 B2 | 12/2007 | Truckai et al. |
| 7,317,955 B2 | 1/2008 | McGreevy |
| 7,318,831 B2 | 1/2008 | Alvarez et al. |
| 7,318,832 B2 | 1/2008 | Young et al. |
| 7,326,236 B2 | 2/2008 | Andreas et al. |
| 7,329,257 B2 | 2/2008 | Kanehira et al. |
| 7,331,410 B2 | 2/2008 | Yong et al. |
| 7,335,165 B2 | 2/2008 | Truwit et al. |
| 7,335,997 B2 | 2/2008 | Wiener |
| 7,337,010 B2 | 2/2008 | Howard et al. |
| 7,353,068 B2 | 4/2008 | Tanaka et al. |
| 7,354,440 B2 | 4/2008 | Truckal et al. |
| 7,357,287 B2 | 4/2008 | Shelton, IV et al. |
| 7,357,802 B2 | 4/2008 | Palanker et al. |
| 7,361,172 B2 | 4/2008 | Cimino |
| 7,364,577 B2 | 4/2008 | Wham et al. |
| 7,367,976 B2 | 5/2008 | Lawes et al. |
| 7,371,227 B2 | 5/2008 | Zeiner |
| RE40,388 E | 6/2008 | Gines |
| 7,380,695 B2 | 6/2008 | Doll et al. |
| 7,380,696 B2 | 6/2008 | Shelton, IV et al. |
| 7,381,209 B2 | 6/2008 | Truckai et al. |
| 7,384,420 B2 | 6/2008 | Dycus et al. |
| 7,390,317 B2 | 6/2008 | Taylor et al. |
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |
| 7,408,288 B2 | 8/2008 | Hara |
| 7,412,008 B2 | 8/2008 | Lliev |

(56) References Cited

U.S. PATENT DOCUMENTS

| | | |
|---|---|---|
| 7,416,101 B2 | 8/2008 | Shelton, IV et al. |
| 7,416,437 B2 | 8/2008 | Sartor et al. |
| D576,725 S | 9/2008 | Shumer et al. |
| 7,419,490 B2 | 9/2008 | Falkenstein et al. |
| 7,422,139 B2 | 9/2008 | Shelton, IV et al. |
| 7,422,463 B2 | 9/2008 | Kuo |
| 7,422,582 B2 | 9/2008 | Malackowski et al. |
| D578,643 S | 10/2008 | Shumer et al. |
| D578,644 S | 10/2008 | Shumer et al. |
| D578,645 S | 10/2008 | Shumer et al. |
| 7,431,694 B2 | 10/2008 | Stefanchik et al. |
| 7,431,704 B2 | 10/2008 | Babaev |
| 7,431,720 B2 | 10/2008 | Pendekanti et al. |
| 7,435,582 B2 | 10/2008 | Zimmermann et al. |
| 7,441,684 B2 | 10/2008 | Shelton, IV et al. |
| 7,442,193 B2 | 10/2008 | Shields et al. |
| 7,445,621 B2 | 11/2008 | Dumbauld et al. |
| 7,449,004 B2 | 11/2008 | Yamada et al. |
| 7,451,904 B2 | 11/2008 | Shelton, IV |
| 7,455,208 B2 | 11/2008 | Wales et al. |
| 7,455,641 B2 | 11/2008 | Yamada et al. |
| 7,462,181 B2 | 12/2008 | Kraft et al. |
| 7,464,846 B2 | 12/2008 | Shelton, IV et al. |
| 7,464,849 B2 | 12/2008 | Shelton, IV et al. |
| 7,472,815 B2 | 1/2009 | Shelton, IV et al. |
| 7,473,145 B2 | 1/2009 | Ehr et al. |
| 7,473,253 B2 | 1/2009 | Dycus et al. |
| 7,473,263 B2 | 1/2009 | Johnston et al. |
| 7,479,148 B2 | 1/2009 | Beaupre |
| 7,479,160 B2 | 1/2009 | Branch et al. |
| 7,481,775 B2 | 1/2009 | Weikel, Jr. et al. |
| 7,488,285 B2 | 2/2009 | Honda et al. |
| 7,488,319 B2 | 2/2009 | Yates |
| 7,491,201 B2 | 2/2009 | Shields et al. |
| 7,491,202 B2 | 2/2009 | Odom et al. |
| 7,494,468 B2 | 2/2009 | Rabiner et al. |
| 7,494,501 B2 | 2/2009 | Ahlberg et al. |
| 7,498,080 B2 | 3/2009 | Tung et al. |
| 7,502,234 B2 | 3/2009 | Goliszek et al. |
| 7,503,893 B2 | 3/2009 | Kucklick |
| 7,503,895 B2 | 3/2009 | Rabiner et al. |
| 7,506,790 B2 | 3/2009 | Shelton, IV |
| 7,506,791 B2 | 3/2009 | Omaits et al. |
| 7,507,239 B2 | 3/2009 | Shadduck |
| 7,510,107 B2 | 3/2009 | Timm et al. |
| 7,510,556 B2 | 3/2009 | Nguyen et al. |
| 7,513,025 B2 | 4/2009 | Fischer |
| 7,517,349 B2 | 4/2009 | Truckai et al. |
| 7,520,865 B2 | 4/2009 | Radley Young et al. |
| 7,524,320 B2 | 4/2009 | Tierney et al. |
| 7,525,309 B2 | 4/2009 | Sherman et al. |
| 7,530,986 B2 | 5/2009 | Beaupre et al. |
| 7,534,243 B1 | 5/2009 | Chin et al. |
| 7,535,233 B2 | 5/2009 | Kojovic et al. |
| D594,983 S | 6/2009 | Price et al. |
| 7,540,871 B2 | 6/2009 | Gonnering |
| 7,540,872 B2 | 6/2009 | Schechter et al. |
| 7,543,730 B1 | 6/2009 | Marczyk |
| 7,544,200 B2 | 6/2009 | Houser |
| 7,549,564 B2 | 6/2009 | Boudreaux |
| 7,550,216 B2 | 6/2009 | Ofer et al. |
| 7,553,309 B2 | 6/2009 | Buysse et al. |
| 7,554,343 B2 | 6/2009 | Bromfield |
| 7,559,450 B2 | 7/2009 | Wales et al. |
| 7,559,452 B2 | 7/2009 | Wales et al. |
| 7,563,259 B2 | 7/2009 | Takahashi |
| 7,566,318 B2 | 7/2009 | Haefner |
| 7,567,012 B2 | 7/2009 | Namikawa |
| 7,568,603 B2 | 8/2009 | Shelton, IV et al. |
| 7,569,057 B2 | 8/2009 | Liu et al. |
| 7,572,266 B2 | 8/2009 | Young et al. |
| 7,572,268 B2 | 8/2009 | Babaev |
| 7,578,820 B2 | 8/2009 | Moore et al. |
| 7,582,084 B2 | 9/2009 | Swanson et al. |
| 7,582,086 B2 | 9/2009 | Privitera et al. |
| 7,582,087 B2 | 9/2009 | Tetzlaff et al. |
| 7,582,095 B2 | 9/2009 | Shipp et al. |
| 7,585,181 B2 | 9/2009 | Olsen |
| 7,586,289 B2 | 9/2009 | Andruk et al. |
| 7,587,536 B2 | 9/2009 | McLeod |
| 7,588,176 B2 | 9/2009 | Timm et al. |
| 7,588,177 B2 | 9/2009 | Racenet |
| 7,594,925 B2 | 9/2009 | Danek et al. |
| 7,597,693 B2 | 10/2009 | Garrison |
| 7,601,119 B2 | 10/2009 | Shahinian |
| 7,601,136 B2 | 10/2009 | Akahoshi |
| 7,604,150 B2 | 10/2009 | Boudreaux |
| 7,607,557 B2 | 10/2009 | Shelton, IV et al. |
| 7,617,961 B2 | 11/2009 | Viola |
| 7,621,930 B2 | 11/2009 | Houser |
| 7,625,370 B2 | 12/2009 | Hart et al. |
| 7,628,791 B2 | 12/2009 | Garrison et al. |
| 7,628,792 B2 | 12/2009 | Guerra |
| 7,632,267 B2 | 12/2009 | Dahla |
| 7,632,269 B2 | 12/2009 | Truckai et al. |
| 7,637,410 B2 | 12/2009 | Marczyk |
| 7,641,653 B2 | 1/2010 | Dalla Betta et al. |
| 7,641,671 B2 | 1/2010 | Crainich |
| 7,644,848 B2 | 1/2010 | Swayze et al. |
| 7,645,240 B2 | 1/2010 | Thompson et al. |
| 7,645,277 B2 | 1/2010 | McClurken et al. |
| 7,645,278 B2 | 1/2010 | Ichihashi et al. |
| 7,648,499 B2 | 1/2010 | Orszulak et al. |
| 7,649,410 B2 | 1/2010 | Andersen et al. |
| 7,654,431 B2 | 2/2010 | Hueil et al. |
| 7,655,003 B2 | 2/2010 | Lorang et al. |
| 7,658,311 B2 | 2/2010 | Boudreaux |
| 7,659,833 B2 | 2/2010 | Warner et al. |
| 7,662,151 B2 | 2/2010 | Crompton, Jr. et al. |
| 7,665,647 B2 | 2/2010 | Shelton, IV et al. |
| 7,666,206 B2 | 2/2010 | Taniguchi et al. |
| 7,667,592 B2 | 2/2010 | Ohyama et al. |
| 7,670,334 B2 | 3/2010 | Hueil et al. |
| 7,670,338 B2 | 3/2010 | Albrecht et al. |
| 7,674,263 B2 | 3/2010 | Ryan |
| 7,678,069 B1 | 3/2010 | Baker et al. |
| 7,678,105 B2 | 3/2010 | McGreevy et al. |
| 7,678,125 B2 | 3/2010 | Shipp |
| 7,682,366 B2 | 3/2010 | Sakurai et al. |
| 7,686,770 B2 | 3/2010 | Cohen |
| 7,686,826 B2 | 3/2010 | Lee et al. |
| 7,688,028 B2 | 3/2010 | Phillips et al. |
| 7,691,095 B2 | 4/2010 | Bednarek et al. |
| 7,691,098 B2 | 4/2010 | Wallace et al. |
| 7,696,441 B2 | 4/2010 | Kataoka |
| 7,699,846 B2 | 4/2010 | Ryan |
| 7,703,459 B2 | 4/2010 | Saadat et al. |
| 7,703,653 B2 | 4/2010 | Shah et al. |
| 7,708,735 B2 | 5/2010 | Chapman et al. |
| 7,708,751 B2 | 5/2010 | Hughes et al. |
| 7,708,758 B2 | 5/2010 | Lee et al. |
| 7,708,768 B2 | 5/2010 | Danek et al. |
| 7,713,202 B2 | 5/2010 | Boukhny et al. |
| 7,713,267 B2 | 5/2010 | Pozzato |
| 7,714,481 B2 | 5/2010 | Sakai |
| 7,717,312 B2 | 5/2010 | Beetel |
| 7,717,914 B2 | 5/2010 | Kimura |
| 7,717,915 B2 | 5/2010 | Miyazawa |
| 7,721,935 B2 | 5/2010 | Racenet et al. |
| 7,722,527 B2 | 5/2010 | Bouchier et al. |
| 7,722,607 B2 | 5/2010 | Dumbauld et al. |
| D618,797 S | 6/2010 | Price et al. |
| 7,726,537 B2 | 6/2010 | Olson et al. |
| 7,727,177 B2 | 6/2010 | Bayat |
| 7,731,717 B2 | 6/2010 | Odom et al. |
| 7,738,969 B2 | 6/2010 | Bleich |
| 7,740,594 B2 | 6/2010 | Hibner |
| 7,744,615 B2 | 6/2010 | Couture |
| 7,749,240 B2 | 7/2010 | Takahashi et al. |
| 7,751,115 B2 | 7/2010 | Song |
| 7,753,245 B2 | 7/2010 | Boudreaux et al. |
| 7,753,904 B2 | 7/2010 | Shelton, IV et al. |
| 7,753,908 B2 | 7/2010 | Swanson |
| 7,762,445 B2 | 7/2010 | Heinrich et al. |

(56) References Cited

U.S. PATENT DOCUMENTS

| | | |
|---|---|---|
| D621,503 S | 8/2010 | Otten et al. |
| 7,766,210 B2 | 8/2010 | Shelton, IV et al. |
| 7,766,693 B2 | 8/2010 | Sartor et al. |
| 7,766,910 B2 | 8/2010 | Hixson et al. |
| 7,768,510 B2 | 8/2010 | Tsai et al. |
| 7,770,774 B2 | 8/2010 | Mastri et al. |
| 7,770,775 B2 | 8/2010 | Shelton, IV et al. |
| 7,771,425 B2 | 8/2010 | Dycus et al. |
| 7,771,444 B2 | 8/2010 | Patel et al. |
| 7,775,972 B2 | 8/2010 | Brock et al. |
| 7,776,036 B2 | 8/2010 | Schechter et al. |
| 7,776,037 B2 | 8/2010 | Odom |
| 7,778,733 B2 | 8/2010 | Nowlin et al. |
| 7,780,054 B2 | 8/2010 | Wales |
| 7,780,593 B2 | 8/2010 | Ueno et al. |
| 7,780,651 B2 | 8/2010 | Madhani et al. |
| 7,780,659 B2 | 8/2010 | Okada et al. |
| 7,780,663 B2 | 8/2010 | Yates et al. |
| 7,784,662 B2 | 8/2010 | Wales et al. |
| 7,784,663 B2 | 8/2010 | Shelton, IV |
| 7,789,883 B2 | 9/2010 | Takashino et al. |
| 7,793,814 B2 | 9/2010 | Racenet et al. |
| 7,794,475 B2 | 9/2010 | Hess et al. |
| 7,796,969 B2 | 9/2010 | Kelly et al. |
| 7,798,386 B2 | 9/2010 | Schall et al. |
| 7,799,020 B2 | 9/2010 | Shores et al. |
| 7,799,027 B2 | 9/2010 | Hafner |
| 7,799,045 B2 | 9/2010 | Masuda |
| 7,803,151 B2 | 9/2010 | Whitman |
| 7,803,152 B2 | 9/2010 | Honda et al. |
| 7,803,156 B2 | 9/2010 | Eder et al. |
| 7,803,168 B2 | 9/2010 | Gifford et al. |
| 7,806,891 B2 | 10/2010 | Nowlin et al. |
| 7,810,693 B2 | 10/2010 | Broehl et al. |
| 7,811,283 B2 | 10/2010 | Moses et al. |
| 7,815,238 B2 | 10/2010 | Cao |
| 7,815,641 B2 | 10/2010 | Dodde et al. |
| 7,819,298 B2 | 10/2010 | Hall et al. |
| 7,819,299 B2 | 10/2010 | Shelton, IV et al. |
| 7,819,819 B2 | 10/2010 | Quick et al. |
| 7,819,872 B2 | 10/2010 | Johnson et al. |
| 7,821,143 B2 | 10/2010 | Wiener |
| D627,066 S | 11/2010 | Romero |
| 7,824,401 B2 | 11/2010 | Manzo et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,834,484 B2 | 11/2010 | Sartor |
| 7,837,699 B2 | 11/2010 | Yamada et al. |
| 7,845,537 B2 | 12/2010 | Shelton, IV et al. |
| 7,846,155 B2 | 12/2010 | Houser et al. |
| 7,846,159 B2 | 12/2010 | Morrison et al. |
| 7,846,160 B2 | 12/2010 | Payne et al. |
| 7,846,161 B2 | 12/2010 | Dumbauld et al. |
| 7,854,735 B2 | 12/2010 | Houser et al. |
| D631,155 S | 1/2011 | Peine et al. |
| 7,861,906 B2 | 1/2011 | Doll et al. |
| 7,862,560 B2 | 1/2011 | Marion |
| 7,862,561 B2 | 1/2011 | Swanson et al. |
| 7,867,228 B2 | 1/2011 | Nobis et al. |
| 7,871,392 B2 | 1/2011 | Sartor |
| 7,871,423 B2 | 1/2011 | Livneh |
| 7,876,030 B2 | 1/2011 | Taki et al. |
| D631,965 S | 2/2011 | Price et al. |
| 7,877,852 B2 | 2/2011 | Unger et al. |
| 7,878,991 B2 | 2/2011 | Babaev |
| 7,879,029 B2 | 2/2011 | Jimenez |
| 7,879,033 B2 | 2/2011 | Sartor et al. |
| 7,879,035 B2 | 2/2011 | Garrison et al. |
| 7,879,070 B2 | 2/2011 | Ortiz et al. |
| 7,883,475 B2 | 2/2011 | Dupont et al. |
| 7,892,606 B2 | 2/2011 | Thies et al. |
| 7,896,875 B2 | 3/2011 | Heim et al. |
| 7,897,792 B2 | 3/2011 | Likura et al. |
| 7,901,400 B2 | 3/2011 | Wham et al. |
| 7,901,423 B2 | 3/2011 | Stulen et al. |
| 7,905,881 B2 | 3/2011 | Masuda et al. |
| 7,909,220 B2 | 3/2011 | Viola |
| 7,909,820 B2 | 3/2011 | Lipson et al. |
| 7,909,824 B2 | 3/2011 | Masuda et al. |
| 7,918,848 B2 | 4/2011 | Lau et al. |
| 7,919,184 B2 | 4/2011 | Mohapatra et al. |
| 7,922,061 B2 | 4/2011 | Shelton, IV et al. |
| 7,922,651 B2 | 4/2011 | Yamada et al. |
| 7,931,611 B2 | 4/2011 | Novak et al. |
| 7,931,649 B2 | 4/2011 | Couture et al. |
| D637,288 S | 5/2011 | Houghton |
| D638,540 S | 5/2011 | Ljiri et al. |
| 7,935,114 B2 | 5/2011 | Takashino et al. |
| 7,936,203 B2 | 5/2011 | Zimlich |
| 7,951,095 B2 | 5/2011 | Makin et al. |
| 7,951,165 B2 | 5/2011 | Golden et al. |
| 7,954,682 B2 | 6/2011 | Giordano et al. |
| 7,955,331 B2 | 6/2011 | Truckai et al. |
| 7,956,620 B2 | 6/2011 | Gilbert |
| 7,959,050 B2 | 6/2011 | Smith et al. |
| 7,959,626 B2 | 6/2011 | Hong et al. |
| 7,963,963 B2 | 6/2011 | Francischelli et al. |
| 7,967,602 B2 | 6/2011 | Lindquist |
| 7,972,328 B2 | 7/2011 | Wham et al. |
| 7,972,329 B2 | 7/2011 | Refior et al. |
| 7,975,895 B2 | 7/2011 | Milliman |
| 7,976,544 B2 | 7/2011 | McClurken et al. |
| 7,980,443 B2 | 7/2011 | Scheib et al. |
| 7,981,050 B2 | 7/2011 | Ritchart et al. |
| 7,981,113 B2 | 7/2011 | Truckai et al. |
| 7,997,278 B2 | 8/2011 | Utley et al. |
| 7,998,157 B2 | 8/2011 | Culp et al. |
| 8,002,732 B2 | 8/2011 | Visconti |
| 8,002,770 B2 | 8/2011 | Swanson et al. |
| 8,020,743 B2 | 9/2011 | Shelton, IV |
| 8,025,672 B2 | 9/2011 | Novak et al. |
| 8,028,885 B2 | 10/2011 | Smith et al. |
| 8,033,173 B2 | 10/2011 | Ehlert et al. |
| 8,034,049 B2 | 10/2011 | Odom et al. |
| 8,038,693 B2 | 10/2011 | Allen |
| 8,048,070 B2 | 11/2011 | O'Brien et al. |
| 8,048,074 B2 | 11/2011 | Masuda |
| 8,052,672 B2 | 11/2011 | Laufer et al. |
| 8,055,208 B2 | 11/2011 | Lilla et al. |
| 8,056,720 B2 | 11/2011 | Hawkes |
| 8,056,787 B2 | 11/2011 | Boudreaux et al. |
| 8,057,468 B2 | 11/2011 | Konesky |
| 8,057,498 B2 | 11/2011 | Robertson |
| 8,058,771 B2 | 11/2011 | Giordano et al. |
| 8,061,014 B2 | 11/2011 | Smith et al. |
| 8,066,167 B2 | 11/2011 | Measamer et al. |
| 8,070,036 B1 | 12/2011 | Knodel |
| 8,070,711 B2 | 12/2011 | Bassinger et al. |
| 8,070,762 B2 | 12/2011 | Escudero et al. |
| 8,075,555 B2 | 12/2011 | Truckai et al. |
| 8,075,558 B2 | 12/2011 | Truckai et al. |
| 8,089,197 B2 | 1/2012 | Rinner et al. |
| 8,092,475 B2 | 1/2012 | Cotter et al. |
| 8,096,459 B2 | 1/2012 | Ortiz et al. |
| 8,097,012 B2 | 1/2012 | Kagarise |
| 8,100,894 B2 | 1/2012 | Mucko et al. |
| 8,105,230 B2 | 1/2012 | Honda et al. |
| 8,105,323 B2 | 1/2012 | Buysse et al. |
| 8,105,324 B2 | 1/2012 | Palanker et al. |
| 8,114,104 B2 | 2/2012 | Young et al. |
| 8,118,276 B2 | 2/2012 | Sanders et al. |
| 8,128,624 B2 | 3/2012 | Couture et al. |
| 8,133,218 B2 | 3/2012 | Daw et al. |
| 8,136,712 B2 | 3/2012 | Zingman |
| 8,141,762 B2 | 3/2012 | Bedi et al. |
| 8,142,421 B2 | 3/2012 | Cooper et al. |
| 8,142,461 B2 | 3/2012 | Houser et al. |
| 8,147,485 B2 | 4/2012 | Wham et al. |
| 8,147,488 B2 | 4/2012 | Masuda |
| 8,147,508 B2 | 4/2012 | Madan et al. |
| 8,152,801 B2 | 4/2012 | Goldberg et al. |
| 8,152,825 B2 | 4/2012 | Madan et al. |
| 8,157,145 B2 | 4/2012 | Shelton, IV et al. |

(56) References Cited

U.S. PATENT DOCUMENTS

| | | |
|---|---|---|
| 8,161,977 B2 | 4/2012 | Shelton, IV et al. |
| 8,162,966 B2 | 4/2012 | Connor et al. |
| 8,170,717 B2 | 5/2012 | Sutherland et al. |
| 8,172,846 B2 | 5/2012 | Brunnett et al. |
| 8,172,870 B2 | 5/2012 | Shipp |
| 8,177,800 B2 | 5/2012 | Spitz et al. |
| 8,182,502 B2 | 5/2012 | Stulen et al. |
| 8,186,560 B2 | 5/2012 | Hess et al. |
| 8,186,877 B2 | 5/2012 | Klimovitch et al. |
| 8,187,267 B2 | 5/2012 | Pappone et al. |
| D661,801 S | 6/2012 | Price et al. |
| D661,802 S | 6/2012 | Price et al. |
| D661,803 S | 6/2012 | Price et al. |
| D661,804 S | 6/2012 | Price et al. |
| 8,197,472 B2 | 6/2012 | Lau et al. |
| 8,197,479 B2 | 6/2012 | Olson et al. |
| 8,197,502 B2 | 6/2012 | Smith et al. |
| 8,207,651 B2 | 6/2012 | Gilbert |
| 8,210,411 B2 | 7/2012 | Yates et al. |
| 8,211,100 B2 | 7/2012 | Podhajsky et al. |
| 8,216,223 B2 | 7/2012 | Wham et al. |
| 8,220,688 B2 | 7/2012 | Laurent et al. |
| 8,221,306 B2 | 7/2012 | Okada et al. |
| 8,221,415 B2 | 7/2012 | Francischelli |
| 8,221,418 B2 | 7/2012 | Prakash et al. |
| 8,226,580 B2 | 7/2012 | Govari et al. |
| 8,226,665 B2 | 7/2012 | Cohen |
| 8,226,675 B2 | 7/2012 | Houser et al. |
| 8,231,607 B2 | 7/2012 | Takuma |
| 8,235,917 B2 | 8/2012 | Joseph et al. |
| 8,236,018 B2 | 8/2012 | Yoshimine et al. |
| 8,236,019 B2 | 8/2012 | Houser |
| 8,236,020 B2 | 8/2012 | Smith et al. |
| 8,241,235 B2 | 8/2012 | Kahler et al. |
| 8,241,271 B2 | 8/2012 | Millman et al. |
| 8,241,282 B2 | 8/2012 | Unger et al. |
| 8,241,283 B2 | 8/2012 | Guerra et al. |
| 8,241,284 B2 | 8/2012 | Dycus et al. |
| 8,241,312 B2 | 8/2012 | Messerly |
| 8,246,575 B2 | 8/2012 | Viola |
| 8,246,615 B2 | 8/2012 | Behnke |
| 8,246,616 B2 | 8/2012 | Amoah et al. |
| 8,246,618 B2 | 8/2012 | Bucciaglia et al. |
| 8,246,642 B2 | 8/2012 | Houser et al. |
| 8,251,994 B2 | 8/2012 | McKenna et al. |
| 8,252,012 B2 | 8/2012 | Stulen |
| 8,253,303 B2 | 8/2012 | Giordano et al. |
| 8,257,377 B2 | 9/2012 | Wiener et al. |
| 8,257,387 B2 | 9/2012 | Cunningham |
| 8,262,563 B2 | 9/2012 | Bakos et al. |
| 8,267,300 B2 | 9/2012 | Boudreaux |
| 8,267,935 B2 | 9/2012 | Couture et al. |
| 8,273,087 B2 | 9/2012 | Kimura et al. |
| D669,992 S | 10/2012 | Schafer et al. |
| D669,993 S | 10/2012 | Merchant et al. |
| 8,277,446 B2 | 10/2012 | Heard |
| 8,277,447 B2 | 10/2012 | Garrison et al. |
| 8,277,471 B2 | 10/2012 | Wiener et al. |
| 8,282,581 B2 | 10/2012 | Zhao et al. |
| 8,282,669 B2 | 10/2012 | Gerber et al. |
| 8,286,846 B2 | 10/2012 | Smith et al. |
| 8,287,485 B2 | 10/2012 | Kimura et al. |
| 8,287,528 B2 | 10/2012 | Wham et al. |
| 8,287,532 B2 | 10/2012 | Carroll et al. |
| 8,292,886 B2 | 10/2012 | Kerr et al. |
| 8,292,888 B2 | 10/2012 | Whitman |
| 8,292,905 B2 | 10/2012 | Taylor et al. |
| 8,295,902 B2 | 10/2012 | Salahieh et al. |
| 8,298,223 B2 | 10/2012 | Wham et al. |
| 8,298,225 B2 | 10/2012 | Gilbert |
| 8,298,232 B2 | 10/2012 | Unger |
| 8,298,233 B2 | 10/2012 | Mueller |
| 8,303,576 B2 | 11/2012 | Brock |
| 8,303,579 B2 | 11/2012 | Shibata |
| 8,303,580 B2 | 11/2012 | Wham et al. |
| 8,303,583 B2 | 11/2012 | Hosier et al. |
| 8,303,613 B2 | 11/2012 | Crandall et al. |
| 8,306,629 B2 | 11/2012 | Mioduski et al. |
| 8,308,040 B2 | 11/2012 | Huang et al. |
| 8,308,721 B2 | 11/2012 | Shibata et al. |
| 8,319,400 B2 | 11/2012 | Houser et al. |
| 8,323,302 B2 | 12/2012 | Robertson et al. |
| 8,323,310 B2 | 12/2012 | Kingsley |
| 8,328,061 B2 | 12/2012 | Kasvikis |
| 8,328,761 B2 | 12/2012 | Widenhouse et al. |
| 8,328,802 B2 | 12/2012 | Deville et al. |
| 8,328,833 B2 | 12/2012 | Cuny |
| 8,328,834 B2 | 12/2012 | Isaacs et al. |
| 8,333,764 B2 | 12/2012 | Francischelli et al. |
| 8,333,778 B2 | 12/2012 | Smith et al. |
| 8,333,779 B2 | 12/2012 | Smith et al. |
| 8,334,468 B2 | 12/2012 | Palmer et al. |
| 8,334,635 B2 | 12/2012 | Voegele et al. |
| 8,337,407 B2 | 12/2012 | Quistgaard et al. |
| 8,338,726 B2 | 12/2012 | Palmer et al. |
| 8,343,146 B2 | 1/2013 | Godara et al. |
| 8,344,596 B2 | 1/2013 | Nield et al. |
| 8,348,880 B2 | 1/2013 | Messerly et al. |
| 8,348,947 B2 | 1/2013 | Takashino et al. |
| 8,348,967 B2 | 1/2013 | Stulen |
| 8,353,297 B2 | 1/2013 | Dacquay et al. |
| 8,357,103 B2 | 1/2013 | Mark et al. |
| 8,357,144 B2 | 1/2013 | Whitman et al. |
| 8,357,149 B2 | 1/2013 | Govari et al. |
| 8,357,158 B2 | 1/2013 | McKenna et al. |
| 8,360,299 B2 | 1/2013 | Zemlok et al. |
| 8,361,066 B2 | 1/2013 | Long et al. |
| 8,361,072 B2 | 1/2013 | Dumbauld et al. |
| 8,361,569 B2 | 1/2013 | Saito et al. |
| 8,366,727 B2 | 2/2013 | Witt et al. |
| 8,372,064 B2 | 2/2013 | Douglass et al. |
| 8,372,099 B2 | 2/2013 | Deville et al. |
| 8,372,101 B2 | 2/2013 | Smith et al. |
| 8,372,102 B2 | 2/2013 | Stulen et al. |
| 8,374,670 B2 | 2/2013 | Selkee |
| 8,377,044 B2 | 2/2013 | Coe et al. |
| 8,377,059 B2 | 2/2013 | Deville et al. |
| 8,377,085 B2 | 2/2013 | Smith et al. |
| 8,382,748 B2 | 2/2013 | Geisel |
| 8,382,775 B1 | 2/2013 | Bender et al. |
| 8,382,782 B2 | 2/2013 | Robertson et al. |
| 8,382,792 B2 | 2/2013 | Chojin |
| 8,388,646 B2 | 3/2013 | Chojin |
| 8,388,647 B2 | 3/2013 | Nau, Jr. et al. |
| 8,393,514 B2 | 3/2013 | Shelton, IV et al. |
| 8,394,115 B2 | 3/2013 | Houser et al. |
| 8,397,971 B2 | 3/2013 | Yates et al. |
| 8,398,394 B2 | 3/2013 | Sauter et al. |
| 8,398,674 B2 | 3/2013 | Prestel |
| 8,403,926 B2 | 3/2013 | Nobis et al. |
| 8,403,945 B2 | 3/2013 | Whitfield et al. |
| 8,403,948 B2 | 3/2013 | Deville et al. |
| 8,403,949 B2 | 3/2013 | Palmer et al. |
| 8,403,950 B2 | 3/2013 | Palmer et al. |
| 8,409,234 B2 | 4/2013 | Stahler et al. |
| 8,414,577 B2 | 4/2013 | Boudreaux et al. |
| 8,418,073 B2 | 4/2013 | Mohr et al. |
| 8,418,349 B2 | 4/2013 | Smith et al. |
| 8,419,757 B2 | 4/2013 | Smith et al. |
| 8,419,758 B2 | 4/2013 | Smith et al. |
| 8,419,759 B2 | 4/2013 | Dietz |
| 8,423,182 B2 | 4/2013 | Robinson et al. |
| 8,425,410 B2 | 4/2013 | Murray et al. |
| 8,425,545 B2 | 4/2013 | Smith et al. |
| 8,430,811 B2 | 4/2013 | Hess et al. |
| 8,430,874 B2 | 4/2013 | Newton et al. |
| 8,430,876 B2 | 4/2013 | Kappus et al. |
| 8,430,897 B2 | 4/2013 | Novak et al. |
| 8,430,898 B2 | 4/2013 | Wiener et al. |
| 8,435,257 B2 | 5/2013 | Smith et al. |
| 8,437,832 B2 | 5/2013 | Govari et al. |
| 8,439,912 B2 | 5/2013 | Cunningham et al. |
| 8,439,939 B2 | 5/2013 | Deville et al. |
| 8,444,036 B2 | 5/2013 | Shelton, IV |

(56) References Cited

U.S. PATENT DOCUMENTS

| | | |
|---|---|---|
| 8,444,637 B2 | 5/2013 | Podmore et al. |
| 8,444,662 B2 | 5/2013 | Palmer et al. |
| 8,444,663 B2 | 5/2013 | Houser et al. |
| 8,444,664 B2 | 5/2013 | Balanev et al. |
| 8,453,906 B2 | 6/2013 | Huang et al. |
| 8,454,599 B2 | 6/2013 | Inagaki et al. |
| 8,454,639 B2 | 6/2013 | Du et al. |
| 8,459,525 B2 | 6/2013 | Yates et al. |
| 8,460,284 B2 | 6/2013 | Aronow et al. |
| 8,460,288 B2 | 6/2013 | Tamai et al. |
| 8,460,292 B2 | 6/2013 | Truckai et al. |
| 8,461,744 B2 | 6/2013 | Wiener et al. |
| 8,469,981 B2 | 6/2013 | Robertson et al. |
| 8,471,685 B2 | 6/2013 | Shingai |
| 8,479,969 B2 | 7/2013 | Shelton, IV |
| 8,480,703 B2 | 7/2013 | Nicholas et al. |
| 8,484,833 B2 | 7/2013 | Cunningham et al. |
| 8,485,413 B2 | 7/2013 | Scheib et al. |
| 8,485,970 B2 | 7/2013 | Widenhouse et al. |
| 8,486,057 B2 | 7/2013 | Behnke, II |
| 8,486,096 B2 | 7/2013 | Robertson et al. |
| 8,491,578 B2 | 7/2013 | Manwaring et al. |
| 8,491,625 B2 | 7/2013 | Horner |
| 8,496,682 B2 | 7/2013 | Guerra et al. |
| D687,549 S | 8/2013 | Johnson et al. |
| 8,506,555 B2 | 8/2013 | Ruiz Morales |
| 8,509,318 B2 | 8/2013 | Tailliet |
| 8,512,336 B2 | 8/2013 | Couture |
| 8,512,337 B2 | 8/2013 | Francischelli et al. |
| 8,512,359 B2 | 8/2013 | Whitman et al. |
| 8,512,364 B2 | 8/2013 | Kowalski et al. |
| 8,512,365 B2 | 8/2013 | Wiener et al. |
| 8,517,239 B2 | 8/2013 | Scheib et al. |
| 8,518,067 B2 | 8/2013 | Masuda et al. |
| 8,521,331 B2 | 8/2013 | Itkowitz |
| 8,523,043 B2 | 9/2013 | Ullrich et al. |
| 8,523,882 B2 | 9/2013 | Huitema et al. |
| 8,523,889 B2 | 9/2013 | Stulen et al. |
| 8,528,563 B2 | 9/2013 | Gruber |
| 8,529,437 B2 | 9/2013 | Taylor et al. |
| 8,529,565 B2 | 9/2013 | Masuda et al. |
| 8,531,064 B2 | 9/2013 | Robertson et al. |
| 8,535,308 B2 | 9/2013 | Govari et al. |
| 8,535,311 B2 | 9/2013 | Schall |
| 8,535,340 B2 | 9/2013 | Allen |
| 8,535,341 B2 | 9/2013 | Allen |
| 8,540,128 B2 | 9/2013 | Shelton, IV et al. |
| 8,546,996 B2 | 10/2013 | Messerly et al. |
| 8,546,999 B2 | 10/2013 | Houser et al. |
| 8,551,077 B2 | 10/2013 | Main et al. |
| 8,551,086 B2 | 10/2013 | Kimura et al. |
| 8,556,929 B2 | 10/2013 | Harper et al. |
| 8,561,870 B2 | 10/2013 | Baxter, III et al. |
| 8,562,592 B2 | 10/2013 | Conlon et al. |
| 8,562,598 B2 | 10/2013 | Falkenstein et al. |
| 8,562,600 B2 | 10/2013 | Kirkpatrick et al. |
| 8,562,604 B2 | 10/2013 | Nishimura |
| 8,568,390 B2 | 10/2013 | Mueller |
| 8,568,397 B2 | 10/2013 | Horner et al. |
| 8,568,400 B2 | 10/2013 | Gilbert |
| 8,568,412 B2 | 10/2013 | Brandt et al. |
| 8,569,997 B2 | 10/2013 | Lee |
| 8,573,461 B2 | 11/2013 | Shelton, IV et al. |
| 8,573,465 B2 | 11/2013 | Shelton, IV |
| 8,574,231 B2 | 11/2013 | Boudreaux et al. |
| 8,574,253 B2 | 11/2013 | Gruber et al. |
| 8,579,176 B2 | 11/2013 | Smith et al. |
| 8,579,897 B2 | 11/2013 | Vakharia et al. |
| 8,579,928 B2 | 11/2013 | Robertson et al. |
| 8,579,937 B2 | 11/2013 | Gresham |
| 8,585,727 B2 | 11/2013 | Polo |
| 8,588,371 B2 | 11/2013 | Ogawa et al. |
| 8,591,459 B2 | 11/2013 | Clymer et al. |
| 8,591,506 B2 | 11/2013 | Wham et al. |
| 8,591,536 B2 | 11/2013 | Robertson |
| D695,407 S | 12/2013 | Price et al. |
| D696,631 S | 12/2013 | Price et al. |
| 8,596,513 B2 | 12/2013 | Olson et al. |
| 8,597,193 B2 | 12/2013 | Grunwald et al. |
| 8,597,287 B2 | 12/2013 | Benamou et al. |
| 8,602,031 B2 | 12/2013 | Reis et al. |
| 8,602,288 B2 | 12/2013 | Shelton, IV et al. |
| 8,603,085 B2 | 12/2013 | Jimenez |
| 8,603,089 B2 | 12/2013 | Viola |
| 8,608,044 B2 | 12/2013 | Hueil et al. |
| 8,608,045 B2 | 12/2013 | Smith et al. |
| 8,608,745 B2 | 12/2013 | Guzman et al. |
| 8,613,383 B2 | 12/2013 | Beckman et al. |
| 8,616,431 B2 | 12/2013 | Timm et al. |
| 8,617,152 B2 | 12/2013 | Werneth et al. |
| 8,617,194 B2 | 12/2013 | Beaupre |
| 8,622,274 B2 | 1/2014 | Yates et al. |
| 8,623,011 B2 | 1/2014 | Spivey |
| 8,623,016 B2 | 1/2014 | Fischer |
| 8,623,027 B2 | 1/2014 | Price et al. |
| 8,623,040 B2 | 1/2014 | Artsyukhovich et al. |
| 8,623,044 B2 | 1/2014 | Timm et al. |
| 8,628,529 B2 | 1/2014 | Aldridge et al. |
| 8,628,534 B2 | 1/2014 | Jones et al. |
| 8,632,461 B2 | 1/2014 | Glossop |
| 8,636,736 B2 | 1/2014 | Yates et al. |
| 8,638,428 B2 | 1/2014 | Brown |
| 8,640,788 B2 | 2/2014 | Dachs, II et al. |
| 8,641,663 B2 | 2/2014 | Kirschenman et al. |
| 8,647,350 B2 | 2/2014 | Mohan et al. |
| 8,650,728 B2 | 2/2014 | Wan et al. |
| 8,652,120 B2 | 2/2014 | Giordano et al. |
| 8,652,132 B2 | 2/2014 | Tsuchiya et al. |
| 8,652,155 B2 | 2/2014 | Houser et al. |
| 8,657,489 B2 | 2/2014 | Ladurner et al. |
| 8,659,208 B1 | 2/2014 | Rose et al. |
| 8,663,214 B2 | 3/2014 | Weinberg et al. |
| 8,663,220 B2 | 3/2014 | Wiener et al. |
| 8,663,222 B2 | 3/2014 | Anderson et al. |
| 8,663,223 B2 | 3/2014 | Masuda et al. |
| 8,663,262 B2 | 3/2014 | Smith et al. |
| 8,668,691 B2 | 3/2014 | Heard |
| 8,668,710 B2 | 3/2014 | Slipszenko et al. |
| 8,684,253 B2 | 4/2014 | Giordano et al. |
| 8,685,016 B2 | 4/2014 | Wham et al. |
| 8,685,020 B2 | 4/2014 | Weizman et al. |
| 8,690,582 B2 | 4/2014 | Rohrbach et al. |
| 8,695,866 B2 | 4/2014 | Leimbach et al. |
| 8,696,366 B2 | 4/2014 | Chen et al. |
| 8,696,665 B2 | 4/2014 | Hunt et al. |
| 8,696,666 B2 | 4/2014 | Sanai et al. |
| 8,696,917 B2 | 4/2014 | Petisce et al. |
| 8,702,609 B2 | 4/2014 | Hadjicostis |
| 8,702,702 B1 | 4/2014 | Edwards et al. |
| 8,702,704 B2 | 4/2014 | Shelton, IV et al. |
| 8,704,425 B2 | 4/2014 | Giordano et al. |
| 8,708,213 B2 | 4/2014 | Shelton, IV et al. |
| 8,709,008 B2 | 4/2014 | Willis et al. |
| 8,709,031 B2 | 4/2014 | Stulen |
| 8,709,035 B2 | 4/2014 | Johnson et al. |
| 8,715,270 B2 | 5/2014 | Weitzner et al. |
| 8,715,277 B2 | 5/2014 | Weizman |
| 8,721,640 B2 | 5/2014 | Taylor et al. |
| 8,721,657 B2 | 5/2014 | Kondoh et al. |
| 8,733,613 B2 | 5/2014 | Huitema et al. |
| 8,733,614 B2 | 5/2014 | Ross et al. |
| 8,734,443 B2 | 5/2014 | Hixson et al. |
| 8,738,110 B2 | 5/2014 | Tabada et al. |
| 8,747,238 B2 | 6/2014 | Shelton, IV et al. |
| 8,747,351 B2 | 6/2014 | Schultz |
| 8,747,404 B2 | 6/2014 | Boudreaux et al. |
| 8,749,116 B2 | 6/2014 | Messerly et al. |
| 8,752,264 B2 | 6/2014 | Ackley et al. |
| 8,752,749 B2 | 6/2014 | Moore et al. |
| 8,753,338 B2 | 6/2014 | Widenhouse et al. |
| 8,754,570 B2 | 6/2014 | Voegele et al. |
| 8,758,342 B2 | 6/2014 | Bales et al. |
| 8,758,352 B2 | 6/2014 | Cooper et al. |
| 8,758,391 B2 | 6/2014 | Swayze et al. |

(56) References Cited

U.S. PATENT DOCUMENTS

| | | |
|---|---|---|
| 8,764,735 B2 | 7/2014 | Coe et al. |
| 8,764,747 B2 | 7/2014 | Cummings et al. |
| 8,767,970 B2 | 7/2014 | Eppolito |
| 8,770,459 B2 | 7/2014 | Racenet et al. |
| 8,771,269 B2 | 7/2014 | Sherman et al. |
| 8,771,270 B2 | 7/2014 | Burbank |
| 8,771,293 B2 | 7/2014 | Surti et al. |
| 8,773,001 B2 | 7/2014 | Wiener et al. |
| 8,777,944 B2 | 7/2014 | Frankhouser et al. |
| 8,777,945 B2 | 7/2014 | Floume et al. |
| 8,779,648 B2 | 7/2014 | Giordano et al. |
| 8,783,541 B2 | 7/2014 | Shelton, IV et al. |
| 8,784,415 B2 | 7/2014 | Malackowski et al. |
| 8,784,418 B2 | 7/2014 | Romero |
| 8,790,342 B2 | 7/2014 | Stulen et al. |
| 8,795,274 B2 | 8/2014 | Hanna |
| 8,795,275 B2 | 8/2014 | Hafner |
| 8,795,276 B2 | 8/2014 | Dietz et al. |
| 8,795,327 B2 | 8/2014 | Dietz et al. |
| 8,800,838 B2 | 8/2014 | Shelton, IV |
| 8,801,710 B2 | 8/2014 | Ullrich et al. |
| 8,801,752 B2 | 8/2014 | Fortier et al. |
| 8,807,414 B2 | 8/2014 | Ross et al. |
| 8,808,204 B2 | 8/2014 | Irisawa et al. |
| 8,808,319 B2 | 8/2014 | Houser et al. |
| 8,814,856 B2 | 8/2014 | Elmouelhi et al. |
| 8,814,870 B2 | 8/2014 | Paraschiv et al. |
| 8,820,605 B2 | 9/2014 | Shelton, IV |
| 8,821,388 B2 | 9/2014 | Naito et al. |
| 8,827,992 B2 | 9/2014 | Koss et al. |
| 8,827,995 B2 | 9/2014 | Schaller et al. |
| 8,834,466 B2 | 9/2014 | Cummings et al. |
| 8,834,518 B2 | 9/2014 | Faller et al. |
| 8,844,789 B2 | 9/2014 | Shelton, IV et al. |
| 8,845,537 B2 | 9/2014 | Tanaka et al. |
| 8,845,630 B2 | 9/2014 | Mehta et al. |
| 8,848,808 B2 | 9/2014 | Dress |
| 8,851,354 B2 | 10/2014 | Swensgard et al. |
| 8,852,184 B2 | 10/2014 | Kucklick |
| 8,858,547 B2 | 10/2014 | Brogna |
| 8,862,955 B2 | 10/2014 | Cesari |
| 8,864,749 B2 | 10/2014 | Okada |
| 8,864,757 B2 | 10/2014 | Klimovitch et al. |
| 8,864,761 B2 | 10/2014 | Johnson et al. |
| 8,870,865 B2 | 10/2014 | Frankhouser et al. |
| 8,874,220 B2 | 10/2014 | Draghici et al. |
| 8,876,726 B2 | 11/2014 | Amit et al. |
| 8,876,858 B2 | 11/2014 | Braun |
| 8,882,766 B2 | 11/2014 | Couture et al. |
| 8,882,791 B2 | 11/2014 | Stulen |
| 8,888,776 B2 | 11/2014 | Dietz et al. |
| 8,888,783 B2 | 11/2014 | Young |
| 8,888,809 B2 | 11/2014 | Davison et al. |
| 8,899,462 B2 | 12/2014 | Kostrzewski et al. |
| 8,900,259 B2 | 12/2014 | Houser et al. |
| 8,906,016 B2 | 12/2014 | Boudreaux et al. |
| 8,906,017 B2 | 12/2014 | Rioux et al. |
| 8,911,438 B2 | 12/2014 | Swoyer et al. |
| 8,911,460 B2 | 12/2014 | Neurohr et al. |
| 8,920,412 B2 | 12/2014 | Fritz et al. |
| 8,920,414 B2 | 12/2014 | Stone et al. |
| 8,920,421 B2 | 12/2014 | Rupp |
| 8,926,607 B2 | 1/2015 | Norvell et al. |
| 8,926,608 B2 | 1/2015 | Bacher et al. |
| 8,926,620 B2 | 1/2015 | Chasmawala et al. |
| 8,931,682 B2 | 1/2015 | Timm et al. |
| 8,932,282 B2 | 1/2015 | Gilbert |
| 8,932,299 B2 | 1/2015 | Bono et al. |
| 8,936,614 B2 | 1/2015 | Allen, IV |
| 8,939,974 B2 | 1/2015 | Boudreaux et al. |
| 8,945,126 B2 | 2/2015 | Garrison et al. |
| 8,951,248 B2 | 2/2015 | Messerly et al. |
| 8,951,272 B2 | 2/2015 | Robertson et al. |
| 8,956,349 B2 | 2/2015 | Aldridge et al. |
| 8,960,520 B2 | 2/2015 | McCuen |
| 8,961,515 B2 | 2/2015 | Twomey et al. |
| 8,961,547 B2 | 2/2015 | Dietz et al. |
| 8,967,443 B2 | 3/2015 | McCuen |
| 8,968,283 B2 | 3/2015 | Kharin |
| 8,968,294 B2 | 3/2015 | Maass et al. |
| 8,968,296 B2 | 3/2015 | McPherson |
| 8,968,355 B2 | 3/2015 | Malkowski et al. |
| 8,974,447 B2 | 3/2015 | Kimball et al. |
| 8,974,477 B2 | 3/2015 | Yamada |
| 8,974,479 B2 | 3/2015 | Ross et al. |
| 8,974,932 B2 | 3/2015 | McGahan et al. |
| 8,979,843 B2 | 3/2015 | Timm et al. |
| 8,979,844 B2 | 3/2015 | White et al. |
| 8,979,890 B2 | 3/2015 | Boudreaux |
| 8,986,287 B2 | 3/2015 | Park et al. |
| 8,986,297 B2 | 3/2015 | Daniel et al. |
| 8,986,302 B2 | 3/2015 | Aldridge et al. |
| 8,989,855 B2 | 3/2015 | Murphy et al. |
| 8,989,903 B2 | 3/2015 | Weir et al. |
| 8,991,678 B2 | 3/2015 | Wellman et al. |
| 8,992,422 B2 | 3/2015 | Spivey et al. |
| 8,992,526 B2 | 3/2015 | Brodbeck et al. |
| 8,998,891 B2 | 4/2015 | Garito et al. |
| 9,005,199 B2 | 4/2015 | Beckman et al. |
| 9,011,437 B2 | 4/2015 | Woodruff et al. |
| 9,011,471 B2 | 4/2015 | Timm et al. |
| 9,017,326 B2 | 4/2015 | DiNardo et al. |
| 9,017,355 B2 | 4/2015 | Smith et al. |
| 9,017,370 B2 | 4/2015 | Reschke et al. |
| 9,017,372 B2 | 4/2015 | Artale et al. |
| 9,023,035 B2 | 5/2015 | Allen, IV et al. |
| 9,023,070 B2 | 5/2015 | Levine et al. |
| 9,023,071 B2 | 5/2015 | Miller et al. |
| 9,028,397 B2 | 5/2015 | Naito |
| 9,028,476 B2 | 5/2015 | Bonn |
| 9,028,478 B2 | 5/2015 | Mueller |
| 9,028,481 B2 | 5/2015 | Behnke, II |
| 9,028,494 B2 | 5/2015 | Shelton, IV et al. |
| 9,028,519 B2 | 5/2015 | Yates et al. |
| 9,031,667 B2 | 5/2015 | Williams |
| 9,033,973 B2 | 5/2015 | Krapohl et al. |
| 9,035,741 B2 | 5/2015 | Hamel et al. |
| 9,037,259 B2 | 5/2015 | Mathur |
| 9,039,690 B2 | 5/2015 | Kersten et al. |
| 9,039,691 B2 | 5/2015 | Moua et al. |
| 9,039,692 B2 | 5/2015 | Behnke, II et al. |
| 9,039,695 B2 | 5/2015 | Giordano et al. |
| 9,039,696 B2 | 5/2015 | Assmus et al. |
| 9,039,705 B2 | 5/2015 | Takashino |
| 9,039,731 B2 | 5/2015 | Joseph |
| 9,043,018 B2 | 5/2015 | Mohr |
| 9,044,227 B2 | 6/2015 | Shelton, IV et al. |
| 9,044,230 B2 | 6/2015 | Morgan et al. |
| 9,044,238 B2 | 6/2015 | Orszulak |
| 9,044,243 B2 | 6/2015 | Johnson et al. |
| 9,044,245 B2 | 6/2015 | Condie et al. |
| 9,044,256 B2 | 6/2015 | Cadeddu et al. |
| 9,044,261 B2 | 6/2015 | Houser |
| 9,050,083 B2 | 6/2015 | Yates et al. |
| 9,050,093 B2 | 6/2015 | Aldridge et al. |
| 9,050,098 B2 | 6/2015 | Deville et al. |
| 9,050,123 B2 | 6/2015 | Krause et al. |
| 9,050,124 B2 | 6/2015 | Houser |
| 9,055,961 B2 | 6/2015 | Manzo et al. |
| 9,059,547 B2 | 6/2015 | McLawhorn |
| 9,060,770 B2 | 6/2015 | Shelton, IV et al. |
| 9,060,775 B2 | 6/2015 | Wiener et al. |
| 9,060,776 B2 | 6/2015 | Yates et al. |
| 9,060,778 B2 | 6/2015 | Condie et al. |
| 9,066,720 B2 | 6/2015 | Ballakur et al. |
| 9,066,723 B2 | 6/2015 | Beller et al. |
| 9,066,747 B2 | 6/2015 | Robertson |
| 9,072,523 B2 | 7/2015 | Houser et al. |
| 9,072,535 B2 | 7/2015 | Shelton, IV et al. |
| 9,072,536 B2 | 7/2015 | Shelton, IV et al. |
| 9,072,538 B2 | 7/2015 | Suzuki et al. |
| 9,072,539 B2 | 7/2015 | Messerly et al. |
| 9,084,624 B2 | 7/2015 | Larkin et al. |
| 9,089,327 B2 | 7/2015 | Worrell et al. |

(56) References Cited

U.S. PATENT DOCUMENTS

| | | | |
|---|---|---|---|
| 9,089,360 B2 | 7/2015 | Messerly et al. |
| 9,095,333 B2 | 8/2015 | Konesky et al. |
| 9,095,362 B2 | 8/2015 | Dachs, II et al. |
| 9,095,367 B2 | 8/2015 | Olson et al. |
| 9,099,863 B2 | 8/2015 | Smith et al. |
| 9,101,358 B2 | 8/2015 | Kerr et al. |
| 9,101,385 B2 | 8/2015 | Shelton, IV et al. |
| 9,107,684 B2 | 8/2015 | Ma |
| 9,107,689 B2 | 8/2015 | Robertson et al. |
| 9,107,690 B2 | 8/2015 | Bales, Jr. et al. |
| 9,113,900 B2 | 8/2015 | Buysse et al. |
| 9,113,907 B2 | 8/2015 | Allen, IV et al. |
| 9,113,940 B2 | 8/2015 | Twomey |
| 9,119,657 B2 | 9/2015 | Shelton, IV et al. |
| 9,119,957 B2 | 9/2015 | Gantz et al. |
| 9,125,662 B2 | 9/2015 | Shelton, IV |
| 9,125,667 B2 | 9/2015 | Stone et al. |
| 9,144,453 B2 | 9/2015 | Rencher et al. |
| 9,147,965 B2 | 9/2015 | Lee |
| 9,149,324 B2 | 10/2015 | Huang et al. |
| 9,149,325 B2 | 10/2015 | Worrell et al. |
| 9,161,803 B2 | 10/2015 | Yates et al. |
| 9,165,114 B2 | 10/2015 | Jain et al. |
| 9,168,054 B2 | 10/2015 | Turner et al. |
| 9,168,085 B2 | 10/2015 | Juzkiw et al. |
| 9,168,089 B2 | 10/2015 | Buysse et al. |
| 9,173,656 B2 | 11/2015 | Schurr et al. |
| 9,179,912 B2 | 11/2015 | Yates et al. |
| 9,186,199 B2 | 11/2015 | Strauss et al. |
| 9,186,204 B2 | 11/2015 | Nishimura et al. |
| 9,186,796 B2 | 11/2015 | Ogawa |
| 9,192,380 B2 | 11/2015 | (Tarinelli) Racenet et al. |
| 9,192,421 B2 | 11/2015 | Garrison |
| 9,192,428 B2 | 11/2015 | Houser et al. |
| 9,192,431 B2 | 11/2015 | Woodruff et al. |
| 9,198,714 B2 | 12/2015 | Worrell et al. |
| 9,198,715 B2 | 12/2015 | Livneh |
| 9,198,718 B2 | 12/2015 | Marczyk et al. |
| 9,198,776 B2 | 12/2015 | Young |
| 9,204,879 B2 | 12/2015 | Shelton, IV |
| 9,204,891 B2 | 12/2015 | Weitzman |
| 9,204,918 B2 | 12/2015 | Germain et al. |
| 9,204,923 B2 | 12/2015 | Manzo et al. |
| 9,216,050 B2 | 12/2015 | Condie et al. |
| 9,216,051 B2 | 12/2015 | Fischer et al. |
| 9,216,062 B2 | 12/2015 | Duque et al. |
| 9,220,483 B2 | 12/2015 | Frankhouser et al. |
| 9,220,527 B2 | 12/2015 | Houser et al. |
| 9,220,559 B2 | 12/2015 | Worrell et al. |
| 9,226,750 B2 | 1/2016 | Weir et al. |
| 9,226,751 B2 | 1/2016 | Shelton, IV et al. |
| 9,226,766 B2 | 1/2016 | Aldridge et al. |
| 9,226,767 B2 | 1/2016 | Stulen et al. |
| 9,232,979 B2 | 1/2016 | Parihar et al. |
| 9,237,891 B2 | 1/2016 | Shelton, IV |
| 9,237,921 B2 | 1/2016 | Messerly et al. |
| 9,241,060 B1 | 1/2016 | Fujisaki |
| 9,241,692 B2 | 1/2016 | Gunday et al. |
| 9,241,728 B2 | 1/2016 | Price et al. |
| 9,241,730 B2 | 1/2016 | Babaev |
| 9,241,731 B2 | 1/2016 | Boudreaux et al. |
| 9,241,768 B2 | 1/2016 | Sandhu et al. |
| 9,247,953 B2 | 2/2016 | Palmer et al. |
| 9,254,165 B2 | 2/2016 | Aronow et al. |
| 9,259,234 B2 | 2/2016 | Robertson et al. |
| 9,259,265 B2 | 2/2016 | Harris et al. |
| 9,265,567 B2 | 2/2016 | Orban, III et al. |
| 9,265,926 B2 | 2/2016 | Strobl et al. |
| 9,265,973 B2 | 2/2016 | Akagane |
| 9,266,310 B2 | 2/2016 | Krogdahl et al. |
| 9,277,962 B2 | 3/2016 | Koss et al. |
| 9,282,974 B2 | 3/2016 | Shelton, IV |
| 9,283,027 B2 | 3/2016 | Monson et al. |
| 9,283,045 B2 | 3/2016 | Rhee et al. |
| 9,283,054 B2 | 3/2016 | Morgan et al. |
| 9,289,256 B2 | 3/2016 | Shelton, IV et al. |
| 9,295,514 B2 | 3/2016 | Shelton, IV et al. |
| 9,301,759 B2 | 4/2016 | Spivey et al. |
| 9,305,497 B2 | 4/2016 | Seo et al. |
| 9,307,388 B2 | 4/2016 | Liang et al. |
| 9,307,986 B2 | 4/2016 | Hall et al. |
| 9,308,009 B2 | 4/2016 | Madan et al. |
| 9,308,014 B2 | 4/2016 | Fischer |
| 9,314,261 B2 | 4/2016 | Bales, Jr. et al. |
| 9,314,292 B2 | 4/2016 | Trees et al. |
| 9,314,301 B2 | 4/2016 | Ben-Haim et al. |
| 9,326,754 B2 | 5/2016 | Polster |
| 9,326,767 B2 | 5/2016 | Koch, Jr. et al. |
| 9,326,787 B2 | 5/2016 | Sanai et al. |
| 9,326,788 B2 | 5/2016 | Batross et al. |
| 9,332,987 B2 | 5/2016 | Leimbach et al. |
| 9,333,025 B2 | 5/2016 | Monson et al. |
| 9,333,034 B2 | 5/2016 | Hancock |
| 9,339,289 B2 | 5/2016 | Robertson |
| 9,339,323 B2 | 5/2016 | Eder et al. |
| 9,339,326 B2 | 5/2016 | McCullagh et al. |
| 9,345,481 B2 | 5/2016 | Hall et al. |
| 9,345,534 B2 | 5/2016 | Artale et al. |
| 9,345,900 B2 | 5/2016 | Wu et al. |
| 9,351,642 B2 | 5/2016 | Nadkarni et al. |
| 9,351,726 B2 | 5/2016 | Leimbach et al. |
| 9,351,727 B2 | 5/2016 | Leimbach et al. |
| 9,351,754 B2 | 5/2016 | Vakharia et al. |
| 9,352,173 B2 | 5/2016 | Yamada et al. |
| 9,358,003 B2 | 6/2016 | Hall et al. |
| 9,358,065 B2 | 6/2016 | Ladtkow et al. |
| 9,364,171 B2 | 6/2016 | Harris et al. |
| 9,364,230 B2 | 6/2016 | Shelton, IV et al. |
| 9,364,279 B2 | 6/2016 | Houser et al. |
| 9,370,364 B2 | 6/2016 | Smith et al. |
| 9,370,400 B2 | 6/2016 | Parihar |
| 9,370,611 B2 | 6/2016 | Ross et al. |
| 9,375,206 B2 | 6/2016 | Vidal et al. |
| 9,375,230 B2 | 6/2016 | Ross et al. |
| 9,375,232 B2 | 6/2016 | Hunt et al. |
| 9,375,256 B2 | 6/2016 | Cunningham et al. |
| 9,375,264 B2 | 6/2016 | Horner et al. |
| 9,375,267 B2 | 6/2016 | Kerr et al. |
| 9,385,831 B2 | 7/2016 | Marr et al. |
| 9,386,983 B2 | 7/2016 | Swensgard et al. |
| 9,393,037 B2 | 7/2016 | Olson et al. |
| 9,393,070 B2 | 7/2016 | Gelfand et al. |
| 9,398,911 B2 | 7/2016 | Auld |
| 9,402,680 B2 | 8/2016 | Ginnebaugh et al. |
| 9,402,682 B2 | 8/2016 | Worrell et al. |
| 9,408,606 B2 | 8/2016 | Shelton, IV |
| 9,408,622 B2 | 8/2016 | Stulen et al. |
| 9,408,660 B2 | 8/2016 | Strobl et al. |
| 9,414,853 B2 | 8/2016 | Stulen et al. |
| 9,414,880 B2 | 8/2016 | Monson et al. |
| 9,421,014 B2 | 8/2016 | Ingmanson et al. |
| 9,421,060 B2 | 8/2016 | Monson et al. |
| 9,427,249 B2 | 8/2016 | Robertson et al. |
| 9,427,279 B2 | 8/2016 | Muniz-Medina et al. |
| 9,439,668 B2 | 9/2016 | Timm et al. |
| 9,439,669 B2 | 9/2016 | Wiener et al. |
| 9,439,671 B2 | 9/2016 | Akagane |
| 9,442,288 B2 | 9/2016 | Tanimura |
| 9,445,784 B2 | 9/2016 | O'Keeffe |
| 9,445,832 B2 | 9/2016 | Wiener et al. |
| 9,451,967 B2 | 9/2016 | Jordan et al. |
| 9,456,863 B2 | 10/2016 | Moua |
| 9,456,864 B2 | 10/2016 | Witt et al. |
| 9,468,438 B2 | 10/2016 | Baber et al. |
| 9,468,498 B2 | 10/2016 | Sigmon, Jr. |
| 9,474,542 B2 | 10/2016 | Slipszenko et al. |
| 9,474,568 B2 | 10/2016 | Akagane |
| 9,486,236 B2 | 11/2016 | Price et al. |
| 9,492,146 B2 | 11/2016 | Kostrzewski et al. |
| 9,492,224 B2 | 11/2016 | Boudreaux et al. |
| 9,498,245 B2 | 11/2016 | Voegele et al. |
| 9,498,275 B2 | 11/2016 | Wham et al. |
| 9,504,483 B2 | 11/2016 | Houser et al. |
| 9,504,520 B2 | 11/2016 | Worrell et al. |

(56) References Cited

U.S. PATENT DOCUMENTS

| | | |
|---|---|---|
| 9,504,524 B2 | 11/2016 | Behnke, II |
| 9,504,855 B2 | 11/2016 | Messerly et al. |
| 9,510,850 B2 | 12/2016 | Robertson et al. |
| 9,510,906 B2 | 12/2016 | Boudreaux et al. |
| 9,522,029 B2 | 12/2016 | Yates et al. |
| 9,522,032 B2 | 12/2016 | Behnke |
| 9,526,564 B2 | 12/2016 | Rusin |
| 9,526,565 B2 | 12/2016 | Strobl |
| 9,545,253 B2 | 1/2017 | Worrell et al. |
| 9,545,497 B2 | 1/2017 | Wenderow et al. |
| 9,554,465 B1 | 1/2017 | Liu et al. |
| 9,554,794 B2 | 1/2017 | Baber et al. |
| 9,554,846 B2 | 1/2017 | Boudreaux |
| 9,554,854 B2 | 1/2017 | Yates et al. |
| 9,560,995 B2 | 2/2017 | Addison et al. |
| 9,561,038 B2 | 2/2017 | Shelton, IV et al. |
| 9,572,592 B2 | 2/2017 | Price et al. |
| 9,574,644 B2 | 2/2017 | Parihar |
| 9,585,714 B2 | 3/2017 | Livneh |
| 9,592,056 B2 | 3/2017 | Mozdzierz et al. |
| 9,592,072 B2 | 3/2017 | Akagane |
| 9,597,143 B2 | 3/2017 | Madan et al. |
| 9,603,669 B2 | 3/2017 | Govari et al. |
| 9,610,091 B2 | 4/2017 | Johnson et al. |
| 9,610,114 B2 | 4/2017 | Baxter, III et al. |
| 9,615,877 B2 | 4/2017 | Tyrrell et al. |
| 9,623,237 B2 | 4/2017 | Turner et al. |
| 9,629,623 B2 | 4/2017 | Lytle, IV et al. |
| 9,629,629 B2 | 4/2017 | Leimbach et al. |
| 9,632,573 B2 | 4/2017 | Ogawa et al. |
| 9,636,135 B2 | 5/2017 | Stulen |
| 9,636,165 B2 | 5/2017 | Larson et al. |
| 9,636,167 B2 | 5/2017 | Gregg |
| 9,638,770 B2 | 5/2017 | Dietz et al. |
| 9,642,644 B2 | 5/2017 | Houser et al. |
| 9,642,669 B2 | 5/2017 | Takashino et al. |
| 9,643,052 B2 | 5/2017 | Tchao et al. |
| 9,649,110 B2 | 5/2017 | Parihar et al. |
| 9,649,111 B2 | 5/2017 | Shelton, IV et al. |
| 9,649,126 B2 | 5/2017 | Robertson et al. |
| 9,649,173 B2 | 5/2017 | Choi et al. |
| 9,655,670 B2 | 5/2017 | Larson et al. |
| 9,662,131 B2 | 5/2017 | Omori et al. |
| 9,668,806 B2 | 6/2017 | Unger et al. |
| 9,671,860 B2 | 6/2017 | Ogawa et al. |
| 9,674,949 B1 | 6/2017 | Liu et al. |
| 9,675,374 B2 | 6/2017 | Stulen et al. |
| 9,675,375 B2 | 6/2017 | Houser et al. |
| 9,681,884 B2 | 6/2017 | Clem et al. |
| 9,687,230 B2 | 6/2017 | Leimbach et al. |
| 9,687,290 B2 | 6/2017 | Keller |
| 9,690,362 B2 | 6/2017 | Leimbach et al. |
| 9,693,817 B2 | 7/2017 | Mehta et al. |
| 9,700,309 B2 | 7/2017 | Jaworek et al. |
| 9,700,339 B2 | 7/2017 | Nield |
| 9,700,343 B2 | 7/2017 | Messerly et al. |
| 9,705,456 B2 | 7/2017 | Gilbert |
| 9,707,004 B2 | 7/2017 | Houser et al. |
| 9,707,027 B2 | 7/2017 | Ruddenklau et al. |
| 9,707,030 B2 | 7/2017 | Davison et al. |
| 9,713,507 B2 | 7/2017 | Stulen et al. |
| 9,717,548 B2 | 8/2017 | Couture |
| 9,717,552 B2 | 8/2017 | Cosman et al. |
| 9,724,094 B2 | 8/2017 | Baber et al. |
| 9,724,118 B2 | 8/2017 | Schulte et al. |
| 9,724,120 B2 | 8/2017 | Faller et al. |
| 9,724,152 B2 | 8/2017 | Horlle et al. |
| 9,730,695 B2 | 8/2017 | Leimbach et al. |
| 9,733,663 B2 | 8/2017 | Leimbach et al. |
| 9,737,301 B2 | 8/2017 | Baber et al. |
| 9,737,326 B2 | 8/2017 | Worrell et al. |
| 9,737,355 B2 | 8/2017 | Yates et al. |
| 9,737,358 B2 | 8/2017 | Beckman et al. |
| 9,743,929 B2 | 8/2017 | Leimbach et al. |
| 9,743,946 B2 | 8/2017 | Faller et al. |
| 9,743,947 B2 | 8/2017 | Price et al. |
| 9,750,499 B2 | 9/2017 | Leimbach et al. |
| 9,757,142 B2 | 9/2017 | Shimizu |
| 9,757,150 B2 | 9/2017 | Alexander et al. |
| 9,757,186 B2 | 9/2017 | Boudreaux et al. |
| 9,764,164 B2 | 9/2017 | Wiener et al. |
| 9,770,285 B2 | 9/2017 | Zoran et al. |
| 9,782,169 B2 | 10/2017 | Kimsey et al. |
| 9,782,214 B2 | 10/2017 | Houser et al. |
| 9,788,836 B2 | 10/2017 | Overmyer et al. |
| 9,788,851 B2 | 10/2017 | Dannaher et al. |
| 9,795,405 B2 | 10/2017 | Price et al. |
| 9,795,436 B2 | 10/2017 | Yates et al. |
| 9,795,808 B2 | 10/2017 | Messerly et al. |
| 9,801,626 B2 | 10/2017 | Parihar et al. |
| 9,801,648 B2 | 10/2017 | Houser et al. |
| 9,802,033 B2 | 10/2017 | Hibner et al. |
| 9,804,618 B2 | 10/2017 | Leimbach et al. |
| 9,808,244 B2 | 11/2017 | Leimbach et al. |
| 9,808,246 B2 | 11/2017 | Shelton, IV et al. |
| 9,808,308 B2 | 11/2017 | Faller et al. |
| 9,814,460 B2 | 11/2017 | Kimsey et al. |
| 9,814,514 B2 | 11/2017 | Shelton, IV et al. |
| 9,815,211 B2 | 11/2017 | Cao et al. |
| 9,820,738 B2 | 11/2017 | Lytle, IV et al. |
| 9,820,768 B2 | 11/2017 | Gee et al. |
| 9,820,771 B2 | 11/2017 | Norton et al. |
| 9,820,806 B2 | 11/2017 | Lee et al. |
| 9,826,976 B2 | 11/2017 | Parihar et al. |
| 9,839,443 B2 | 12/2017 | Brockman et al. |
| 9,844,368 B2 | 12/2017 | Boudreaux et al. |
| 9,844,374 B2 | 12/2017 | Lytle, IV et al. |
| 9,844,375 B2 | 12/2017 | Overmyer et al. |
| 9,848,901 B2 | 12/2017 | Robertson et al. |
| 9,848,902 B2 | 12/2017 | Price et al. |
| 9,848,937 B2 | 12/2017 | Trees et al. |
| 9,861,381 B2 | 1/2018 | Johnson |
| 9,861,428 B2 | 1/2018 | Trees et al. |
| 9,867,612 B2 | 1/2018 | Parihar et al. |
| 9,867,651 B2 | 1/2018 | Wham |
| 9,867,670 B2 | 1/2018 | Brannan et al. |
| 9,872,722 B2 | 1/2018 | Lech |
| 9,872,725 B2 | 1/2018 | Worrell et al. |
| 9,872,726 B2 | 1/2018 | Morisaki |
| 9,877,720 B2 | 1/2018 | Worrell et al. |
| 9,877,776 B2 | 1/2018 | Boudreaux |
| 9,877,782 B2 | 1/2018 | Voegele et al. |
| 9,878,184 B2 | 1/2018 | Beaupre |
| 9,883,860 B2 | 2/2018 | Leimbach et al. |
| 9,883,884 B2 | 2/2018 | Neurohr et al. |
| 9,888,919 B2 | 2/2018 | Leimbach et al. |
| 9,888,958 B2 | 2/2018 | Evans et al. |
| 9,895,148 B2 | 2/2018 | Shelton, IV et al. |
| 9,895,160 B2 | 2/2018 | Fan et al. |
| 9,901,321 B2 | 2/2018 | Harks et al. |
| 9,901,342 B2 | 2/2018 | Shelton, IV et al. |
| 9,901,383 B2 | 2/2018 | Hassler, Jr. |
| 9,901,754 B2 | 2/2018 | Yamada |
| 9,907,563 B2 | 3/2018 | Germain et al. |
| 9,913,642 B2 | 3/2018 | Leimbach et al. |
| 9,913,656 B2 | 3/2018 | Stulen |
| 9,913,680 B2 | 3/2018 | Voegele et al. |
| 9,918,730 B2 | 3/2018 | Trees et al. |
| 9,924,961 B2 | 3/2018 | Shelton, IV et al. |
| 9,925,003 B2 | 3/2018 | Parihar et al. |
| 9,931,118 B2 | 4/2018 | Shelton, IV et al. |
| 9,937,001 B2 | 4/2018 | Nakamura |
| 9,943,309 B2 | 4/2018 | Shelton, IV et al. |
| 9,949,785 B2 | 4/2018 | Price et al. |
| 9,949,788 B2 | 4/2018 | Boudreaux |
| 9,962,182 B2 | 5/2018 | Dietz et al. |
| 9,968,355 B2 | 5/2018 | Shelton, IV et al. |
| 9,974,539 B2 | 5/2018 | Yates et al. |
| 9,987,000 B2 | 6/2018 | Shelton, IV et al. |
| 9,987,033 B2 | 6/2018 | Neurohr et al. |
| 9,993,248 B2 | 6/2018 | Shelton, IV et al. |
| 9,993,258 B2 | 6/2018 | Shelton, IV et al. |
| 9,993,289 B2 | 6/2018 | Sobajima et al. |
| 10,004,497 B2 | 6/2018 | Overmyer et al. |

(56) References Cited

U.S. PATENT DOCUMENTS

| | | |
|---|---|---|
| 10,004,501 B2 | 6/2018 | Shelton, IV et al. |
| 10,004,526 B2 | 6/2018 | Dycus et al. |
| 10,004,527 B2 | 6/2018 | Gee et al. |
| D822,206 S | 7/2018 | Shelton, IV et al. |
| 10,010,339 B2 | 7/2018 | Witt et al. |
| 10,010,341 B2 | 7/2018 | Houser et al. |
| 10,013,049 B2 | 7/2018 | Leimbach et al. |
| 10,016,199 B2 | 7/2018 | Baber et al. |
| 10,016,207 B2 | 7/2018 | Suzuki et al. |
| 10,022,142 B2 | 7/2018 | Aranyi et al. |
| 10,022,567 B2 | 7/2018 | Messerly et al. |
| 10,022,568 B2 | 7/2018 | Messerly et al. |
| 10,028,761 B2 | 7/2018 | Leimbach et al. |
| 10,028,786 B2 | 7/2018 | Mucilli et al. |
| 10,034,684 B2 | 7/2018 | Weisenburgh, II et al. |
| 10,034,704 B2 | 7/2018 | Asher et al. |
| D826,405 S | 8/2018 | Shelton, IV et al. |
| 10,039,588 B2 | 8/2018 | Harper et al. |
| 10,041,822 B2 | 8/2018 | Zemlok |
| 10,045,776 B2 | 8/2018 | Shelton, IV et al. |
| 10,045,779 B2 | 8/2018 | Savage et al. |
| 10,045,794 B2 | 8/2018 | Witt et al. |
| 10,045,810 B2 | 8/2018 | Schall et al. |
| 10,045,819 B2 | 8/2018 | Jensen et al. |
| 10,052,044 B2 | 8/2018 | Shelton, IV et al. |
| 10,052,102 B2 | 8/2018 | Baxter et al. |
| 10,070,916 B2 | 9/2018 | Artale |
| 10,080,609 B2 | 9/2018 | Hancock et al. |
| 10,085,748 B2 | 10/2018 | Morgan et al. |
| 10,085,762 B2 | 10/2018 | Timm et al. |
| 10,085,792 B2 | 10/2018 | Johnson et al. |
| 10,092,310 B2 | 10/2018 | Boudreaux et al. |
| 10,092,344 B2 | 10/2018 | Mohr et al. |
| 10,092,347 B2 | 10/2018 | Weisshaupt et al. |
| 10,092,348 B2 | 10/2018 | Boudreaux |
| 10,092,350 B2 | 10/2018 | Rothweiler et al. |
| 10,105,140 B2 | 10/2018 | Malinouskas et al. |
| 10,111,679 B2 | 10/2018 | Baber et al. |
| 10,111,699 B2 | 10/2018 | Boudreaux |
| 10,111,703 B2 | 10/2018 | Cosman, Jr. et al. |
| 10,117,649 B2 | 11/2018 | Baxter, III et al. |
| 10,117,667 B2 | 11/2018 | Robertson et al. |
| 10,117,702 B2 | 11/2018 | Danziger et al. |
| 10,123,835 B2 | 11/2018 | Keller et al. |
| 10,130,367 B2 | 11/2018 | Cappola et al. |
| 10,130,410 B2 | 11/2018 | Strobl et al. |
| 10,130,412 B2 | 11/2018 | Wham |
| 10,135,242 B2 | 11/2018 | Baber et al. |
| 10,136,887 B2 | 11/2018 | Shelton, IV et al. |
| 10,149,680 B2 | 12/2018 | Parihar et al. |
| 10,154,848 B2 | 12/2018 | Chernov et al. |
| 10,154,852 B2 | 12/2018 | Conlon et al. |
| 10,159,483 B2 | 12/2018 | Beckman et al. |
| 10,159,524 B2 | 12/2018 | Yates et al. |
| 10,166,060 B2 | 1/2019 | Johnson et al. |
| 10,172,665 B2 | 1/2019 | Heckel et al. |
| 10,172,669 B2 | 1/2019 | Felder et al. |
| 10,178,992 B2 | 1/2019 | Wise et al. |
| 10,179,022 B2 | 1/2019 | Yates et al. |
| 10,180,463 B2 | 1/2019 | Beckman et al. |
| 10,182,816 B2 | 1/2019 | Shelton, IV et al. |
| 10,182,818 B2 | 1/2019 | Hensel et al. |
| 10,188,385 B2 | 1/2019 | Kerr et al. |
| 10,188,455 B2 | 1/2019 | Hancock et al. |
| 10,194,907 B2 | 2/2019 | Marczyk et al. |
| 10,194,972 B2 | 2/2019 | Yates et al. |
| 10,194,973 B2 | 2/2019 | Wiener et al. |
| 10,194,976 B2 | 2/2019 | Boudreaux |
| 10,194,977 B2 | 2/2019 | Yang |
| 10,194,999 B2 | 2/2019 | Bacher et al. |
| 10,201,364 B2 | 2/2019 | Leimbach et al. |
| 10,201,365 B2 | 2/2019 | Boudreaux et al. |
| 10,201,382 B2 | 2/2019 | Wiener et al. |
| 10,206,676 B2 | 2/2019 | Shelton, IV |
| 10,226,250 B2 | 3/2019 | Beckman et al. |
| 10,226,273 B2 | 3/2019 | Messerly et al. |
| 10,231,747 B2 | 3/2019 | Stulen et al. |
| 10,238,385 B2 | 3/2019 | Yates et al. |
| 10,238,391 B2 | 3/2019 | Leimbach et al. |
| 10,245,027 B2 | 4/2019 | Shelton, IV et al. |
| 10,245,028 B2 | 4/2019 | Shelton, IV et al. |
| 10,245,029 B2 | 4/2019 | Hunter et al. |
| 10,245,030 B2 | 4/2019 | Hunter et al. |
| 10,245,033 B2 | 4/2019 | Overmyer et al. |
| 10,245,095 B2 | 4/2019 | Boudreaux |
| 10,245,097 B2 | 4/2019 | Honda et al. |
| 10,245,104 B2 | 4/2019 | McKenna et al. |
| 10,251,664 B2 | 4/2019 | Shelton, IV et al. |
| 10,258,331 B2 | 4/2019 | Shelton, IV et al. |
| 10,258,505 B2 | 4/2019 | Ovchinnikov |
| 10,263,171 B2 | 4/2019 | Wiener et al. |
| 10,265,068 B2 | 4/2019 | Harris et al. |
| 10,265,117 B2 | 4/2019 | Wiener et al. |
| 10,265,118 B2 | 4/2019 | Gerhardt |
| 10,271,840 B2 | 4/2019 | Sapre |
| 10,271,851 B2 | 4/2019 | Shelton, IV et al. |
| D847,989 S | 5/2019 | Shelton, IV et al. |
| 10,278,721 B2 | 5/2019 | Dietz et al. |
| 10,285,705 B2 | 5/2019 | Shelton, IV et al. |
| 10,285,724 B2 | 5/2019 | Faller et al. |
| 10,285,750 B2 | 5/2019 | Coulson et al. |
| 10,292,704 B2 | 5/2019 | Harris et al. |
| 10,299,810 B2 | 5/2019 | Robertson et al. |
| 10,299,821 B2 | 5/2019 | Shelton, IV et al. |
| D850,617 S | 6/2019 | Shelton, IV et al. |
| D851,762 S | 6/2019 | Shelton, IV et al. |
| 10,307,159 B2 | 6/2019 | Harris et al. |
| 10,314,579 B2 | 6/2019 | Chowaniec et al. |
| 10,314,582 B2 | 6/2019 | Shelton, IV et al. |
| 10,314,638 B2 | 6/2019 | Gee et al. |
| 10,321,907 B2 | 6/2019 | Shelton, IV et al. |
| 10,321,950 B2 | 6/2019 | Yates et al. |
| D854,151 S | 7/2019 | Shelton, IV et al. |
| 10,335,149 B2 | 7/2019 | Baxter, III et al. |
| 10,335,182 B2 | 7/2019 | Stulen et al. |
| 10,335,183 B2 | 7/2019 | Worrell et al. |
| 10,335,614 B2 | 7/2019 | Messerly et al. |
| 10,342,543 B2 | 7/2019 | Shelton, IV et al. |
| 10,342,602 B2 | 7/2019 | Strobl et al. |
| 10,342,606 B2 | 7/2019 | Cosman et al. |
| 10,342,623 B2 | 7/2019 | Huelman et al. |
| 10,348,941 B2 | 7/2019 | Elliot, Jr. et al. |
| 10,349,999 B2 | 7/2019 | Yates et al. |
| 10,350,016 B2 | 7/2019 | Burbank et al. |
| 10,350,025 B1 | 7/2019 | Loyd et al. |
| 10,357,246 B2 | 7/2019 | Shelton, IV et al. |
| 10,357,247 B2 | 7/2019 | Shelton, IV et al. |
| 10,357,303 B2 | 7/2019 | Conlon et al. |
| 10,363,084 B2 | 7/2019 | Friedrichs |
| 10,368,861 B2 | 8/2019 | Baxter, III et al. |
| 10,368,865 B2 | 8/2019 | Harris et al. |
| 10,376,263 B2 | 8/2019 | Morgan et al. |
| 10,376,305 B2 | 8/2019 | Yates et al. |
| 10,390,841 B2 | 8/2019 | Shelton, IV et al. |
| 10,398,439 B2 | 9/2019 | Cabrera et al. |
| 10,398,466 B2 | 9/2019 | Stulen et al. |
| 10,398,497 B2 | 9/2019 | Batross et al. |
| 10,405,857 B2 | 9/2019 | Shelton, IV et al. |
| 10,405,863 B2 | 9/2019 | Wise et al. |
| 10,413,291 B2 | 9/2019 | Worthington et al. |
| 10,413,293 B2 | 9/2019 | Shelton, IV et al. |
| 10,413,297 B2 | 9/2019 | Harris et al. |
| 10,413,352 B2 | 9/2019 | Thomas et al. |
| 10,413,353 B2 | 9/2019 | Kerr et al. |
| 10,420,552 B2 | 9/2019 | Shelton, IV et al. |
| 10,420,579 B2 | 9/2019 | Wiener et al. |
| 10,420,607 B2 | 9/2019 | Woloszko et al. |
| D865,175 S | 10/2019 | Widenhouse et al. |
| 10,426,471 B2 | 10/2019 | Shelton, IV et al. |
| 10,426,507 B2 | 10/2019 | Wiener et al. |
| 10,426,546 B2 | 10/2019 | Graham et al. |
| 10,426,978 B2 | 10/2019 | Akagane |
| 10,433,837 B2 | 10/2019 | Worthington et al. |
| 10,433,849 B2 | 10/2019 | Shelton, IV et al. |

(56) References Cited

U.S. PATENT DOCUMENTS

| | | |
|---|---|---|
| 10,433,865 B2 | 10/2019 | Witt et al. |
| 10,433,866 B2 | 10/2019 | Witt et al. |
| 10,433,900 B2 | 10/2019 | Harris et al. |
| 10,441,279 B2 | 10/2019 | Shelton, IV et al. |
| 10,441,308 B2 | 10/2019 | Robertson |
| 10,441,310 B2 | 10/2019 | Olson et al. |
| 10,441,345 B2 | 10/2019 | Aldridge et al. |
| 10,448,948 B2 | 10/2019 | Shelton, IV et al. |
| 10,448,950 B2 | 10/2019 | Shelton, IV et al. |
| 10,448,986 B2 | 10/2019 | Zikorus et al. |
| 10,456,140 B2 | 10/2019 | Shelton, IV et al. |
| 10,456,193 B2 | 10/2019 | Yates et al. |
| 10,463,421 B2 | 11/2019 | Boudreaux et al. |
| 10,463,887 B2 | 11/2019 | Witt et al. |
| 10,470,762 B2 | 11/2019 | Leimbach et al. |
| 10,470,764 B2 | 11/2019 | Baxter, III et al. |
| 10,478,182 B2 | 11/2019 | Taylor |
| 10,478,190 B2 | 11/2019 | Miller et al. |
| 10,485,542 B2 | 11/2019 | Shelton, IV et al. |
| 10,485,543 B2 | 11/2019 | Shelton, IV et al. |
| 10,485,607 B2 | 11/2019 | Strobl et al. |
| D869,655 S | 12/2019 | Shelton, IV et al. |
| 10,492,785 B2 | 12/2019 | Overmyer et al. |
| 10,492,849 B2 | 12/2019 | Juergens et al. |
| 10,499,914 B2 | 12/2019 | Huang et al. |
| 10,507,033 B2 | 12/2019 | Dickerson et al. |
| 10,512,795 B2 | 12/2019 | Voegele et al. |
| 10,517,595 B2 | 12/2019 | Hunter et al. |
| 10,517,596 B2 | 12/2019 | Hunter et al. |
| 10,517,627 B2 | 12/2019 | Timm et al. |
| 10,524,787 B2 | 1/2020 | Shelton, IV et al. |
| 10,524,789 B2 | 1/2020 | Swayze et al. |
| 10,524,854 B2 | 1/2020 | Woodruff et al. |
| 10,524,872 B2 | 1/2020 | Stewart et al. |
| 10,531,874 B2 | 1/2020 | Morgan et al. |
| 10,537,324 B2 | 1/2020 | Shelton, IV et al. |
| 10,537,325 B2 | 1/2020 | Bakos et al. |
| 10,537,351 B2 | 1/2020 | Shelton, IV et al. |
| 10,542,979 B2 | 1/2020 | Shelton, IV et al. |
| 10,542,982 B2 | 1/2020 | Beckman et al. |
| 10,542,991 B2 | 1/2020 | Shelton, IV et al. |
| 10,543,008 B2 | 1/2020 | Vakharia et al. |
| 10,548,504 B2 | 2/2020 | Shelton, IV et al. |
| 10,548,655 B2 | 2/2020 | Scheib et al. |
| 10,555,769 B2 | 2/2020 | Worrell et al. |
| 10,561,560 B2 | 2/2020 | Boutoussov et al. |
| 10,568,624 B2 | 2/2020 | Shelton, IV et al. |
| 10,568,625 B2 | 2/2020 | Harris et al. |
| 10,568,626 B2 | 2/2020 | Shelton, IV et al. |
| 10,568,632 B2 | 2/2020 | Miller et al. |
| 10,575,892 B2 | 3/2020 | Danziger et al. |
| 10,582,928 B2 | 3/2020 | Hunter et al. |
| 10,588,625 B2 | 3/2020 | Weaner et al. |
| 10,588,630 B2 | 3/2020 | Shelton, IV et al. |
| 10,588,631 B2 | 3/2020 | Shelton, IV et al. |
| 10,588,632 B2 | 3/2020 | Shelton, IV et al. |
| 10,588,633 B2 | 3/2020 | Shelton, IV et al. |
| 10,595,929 B2 | 3/2020 | Boudreaux et al. |
| 10,595,930 B2 | 3/2020 | Scheib et al. |
| 10,603,036 B2 | 3/2020 | Hunter et al. |
| 10,610,224 B2 | 4/2020 | Shelton, IV et al. |
| 10,610,286 B2 | 4/2020 | Wiener et al. |
| 10,610,313 B2 | 4/2020 | Bailey et al. |
| 10,617,412 B2 | 4/2020 | Shelton, IV et al. |
| 10,617,420 B2 | 4/2020 | Shelton, IV et al. |
| 10,617,464 B2 | 4/2020 | Duppuis |
| 10,624,635 B2 | 4/2020 | Harris et al. |
| 10,624,691 B2 | 4/2020 | Wiener et al. |
| 10,631,858 B2 | 4/2020 | Burbank |
| 10,631,859 B2 | 4/2020 | Shelton, IV et al. |
| 10,631,928 B2 | 4/2020 | Basu et al. |
| 10,632,630 B2 | 4/2020 | Cao et al. |
| RE47,996 E | 5/2020 | Turner et al. |
| 10,639,034 B2 | 5/2020 | Harris et al. |
| 10,639,035 B2 | 5/2020 | Shelton, IV et al. |
| 10,639,037 B2 | 5/2020 | Shelton, IV et al. |
| 10,639,092 B2 | 5/2020 | Corbett et al. |
| 10,639,098 B2 | 5/2020 | Cosman et al. |
| 10,646,269 B2 | 5/2020 | Worrell et al. |
| 10,646,292 B2 | 5/2020 | Solomon et al. |
| 10,653,413 B2 | 5/2020 | Worthington et al. |
| 10,660,692 B2 | 5/2020 | Lesko et al. |
| 10,667,809 B2 | 6/2020 | Bakos et al. |
| 10,667,810 B2 | 6/2020 | Shelton, IV et al. |
| 10,667,811 B2 | 6/2020 | Harris et al. |
| 10,675,021 B2 | 6/2020 | Harris et al. |
| 10,675,024 B2 | 6/2020 | Shelton, IV et al. |
| 10,675,025 B2 | 6/2020 | Swayze et al. |
| 10,675,026 B2 | 6/2020 | Harris et al. |
| 10,677,764 B2 | 6/2020 | Ross et al. |
| 10,682,136 B2 | 6/2020 | Harris et al. |
| 10,682,138 B2 | 6/2020 | Shelton, IV et al. |
| 10,687,806 B2 | 6/2020 | Shelton, IV et al. |
| 10,687,809 B2 | 6/2020 | Shelton, IV et al. |
| 10,687,810 B2 | 6/2020 | Shelton, IV et al. |
| 10,687,884 B2 | 6/2020 | Wiener et al. |
| 10,688,321 B2 | 6/2020 | Wiener et al. |
| 10,695,055 B2 | 6/2020 | Shelton, IV et al. |
| 10,695,057 B2 | 6/2020 | Shelton, IV et al. |
| 10,695,058 B2 | 6/2020 | Lytle, IV et al. |
| 10,695,119 B2 | 6/2020 | Smith |
| 10,702,270 B2 | 7/2020 | Shelton, IV et al. |
| 10,702,329 B2 | 7/2020 | Strobl et al. |
| 10,709,446 B2 | 7/2020 | Harris et al. |
| 10,709,469 B2 | 7/2020 | Shelton, IV et al. |
| 10,709,906 B2 | 7/2020 | Nield |
| 10,716,615 B2 | 7/2020 | Shelton, IV et al. |
| 10,722,233 B2 | 7/2020 | Wellman |
| D893,717 S | 8/2020 | Messerly et al. |
| 10,729,458 B2 | 8/2020 | Stoddard et al. |
| 10,729,494 B2 | 8/2020 | Parihar et al. |
| 10,736,629 B2 | 8/2020 | Shelton, IV et al. |
| 10,736,685 B2 | 8/2020 | Wiener et al. |
| 10,751,108 B2 | 8/2020 | Yates et al. |
| 10,751,138 B2 | 8/2020 | Giordano et al. |
| 10,758,229 B2 | 9/2020 | Shelton, IV et al. |
| 10,758,230 B2 | 9/2020 | Shelton, IV et al. |
| 10,758,232 B2 | 9/2020 | Shelton, IV et al. |
| 10,758,294 B2 | 9/2020 | Jones |
| 10,765,427 B2 | 9/2020 | Shelton, IV et al. |
| 10,765,470 B2 | 9/2020 | Yates et al. |
| 10,772,629 B2 | 9/2020 | Shelton, IV et al. |
| 10,772,630 B2 | 9/2020 | Wixey |
| 10,779,821 B2 | 9/2020 | Harris et al. |
| 10,779,823 B2 | 9/2020 | Shelton, IV et al. |
| 10,779,824 B2 | 9/2020 | Shelton, IV et al. |
| 10,779,825 B2 | 9/2020 | Shelton, IV et al. |
| 10,779,845 B2 | 9/2020 | Timm et al. |
| 10,779,849 B2 | 9/2020 | Shelton, IV et al. |
| 10,779,879 B2 | 9/2020 | Yates et al. |
| 10,786,253 B2 | 9/2020 | Shelton, IV et al. |
| 10,786,276 B2 | 9/2020 | Hirai et al. |
| 10,806,454 B2 | 10/2020 | Kopp |
| 10,813,638 B2 | 10/2020 | Shelton, IV et al. |
| 10,820,938 B2 | 11/2020 | Fischer et al. |
| 10,828,058 B2 | 11/2020 | Shelton, IV et al. |
| 10,835,245 B2 | 11/2020 | Swayze et al. |
| 10,835,246 B2 | 11/2020 | Shelton, IV et al. |
| 10,835,247 B2 | 11/2020 | Shelton, IV et al. |
| 10,835,307 B2 | 11/2020 | Shelton, IV et al. |
| 10,842,492 B2 | 11/2020 | Shelton, IV et al. |
| 10,842,523 B2 | 11/2020 | Shelton, IV et al. |
| 10,842,563 B2 | 11/2020 | Gilbert et al. |
| D906,355 S | 12/2020 | Messerly et al. |
| 10,856,867 B2 | 12/2020 | Shelton, IV et al. |
| 10,856,868 B2 | 12/2020 | Shelton, IV et al. |
| 10,856,869 B2 | 12/2020 | Shelton, IV et al. |
| 10,856,870 B2 | 12/2020 | Harris et al. |
| 10,856,896 B2 | 12/2020 | Eichmann et al. |
| 10,856,929 B2 | 12/2020 | Yates et al. |
| 10,856,934 B2 | 12/2020 | Trees et al. |
| 10,874,465 B2 | 12/2020 | Weir et al. |
| D908,216 S | 1/2021 | Messerly et al. |
| 10,881,399 B2 | 1/2021 | Shelton, IV et al. |

(56) References Cited

U.S. PATENT DOCUMENTS

| | | |
|---|---|---|
| 10,881,401 B2 | 1/2021 | Baber et al. |
| 10,881,409 B2 | 1/2021 | Cabrera |
| 10,881,449 B2 | 1/2021 | Boudreaux et al. |
| 10,888,322 B2 | 1/2021 | Morgan et al. |
| 10,888,347 B2 | 1/2021 | Witt et al. |
| 10,893,863 B2 | 1/2021 | Shelton, IV et al. |
| 10,893,864 B2 | 1/2021 | Harris et al. |
| 10,893,883 B2 | 1/2021 | Dannaher |
| 10,898,186 B2 | 1/2021 | Bakos et al. |
| 10,898,256 B2 | 1/2021 | Yates et al. |
| 10,912,559 B2 | 2/2021 | Harris et al. |
| 10,912,580 B2 | 2/2021 | Green et al. |
| 10,912,603 B2 | 2/2021 | Boudreaux et al. |
| 10,918,385 B2 | 2/2021 | Overmyer et al. |
| 10,925,659 B2 | 2/2021 | Shelton, IV et al. |
| D914,878 S | 3/2021 | Shelton, IV et al. |
| 10,932,766 B2 | 3/2021 | Tesar et al. |
| 10,932,847 B2 | 3/2021 | Yates et al. |
| 10,945,727 B2 | 3/2021 | Shelton, IV et al. |
| 10,952,788 B2 | 3/2021 | Asher et al. |
| 10,959,727 B2 | 3/2021 | Hunter et al. |
| 10,966,741 B2 | 4/2021 | Illizaliturri-Sanchez et al. |
| 10,966,747 B2 | 4/2021 | Worrell et al. |
| 10,973,516 B2 | 4/2021 | Shelton, IV et al. |
| 10,973,517 B2 | 4/2021 | Wixey |
| 10,973,520 B2 | 4/2021 | Shelton, IV et al. |
| 10,980,536 B2 | 4/2021 | Weaner et al. |
| 10,987,105 B2 | 4/2021 | Cappola et al. |
| 10,987,123 B2 | 4/2021 | Weir et al. |
| 10,987,156 B2 | 4/2021 | Trees et al. |
| 10,993,715 B2 | 5/2021 | Shelton, IV et al. |
| 10,993,716 B2 | 5/2021 | Shelton, IV et al. |
| 10,993,763 B2 | 5/2021 | Batross et al. |
| 11,000,278 B2 | 5/2021 | Shelton, IV et al. |
| 11,000,279 B2 | 5/2021 | Shelton, IV et al. |
| 11,020,114 B2 | 6/2021 | Shelton, IV et al. |
| 11,020,140 B2 | 6/2021 | Gee et al. |
| 11,033,322 B2 | 6/2021 | Wiener et al. |
| 11,039,834 B2 | 6/2021 | Harris et al. |
| 11,045,191 B2 | 6/2021 | Shelton, IV et al. |
| 11,045,192 B2 | 6/2021 | Harris et al. |
| 11,045,275 B2 | 6/2021 | Boudreaux et al. |
| 11,051,840 B2 | 7/2021 | Shelton, IV et al. |
| 11,051,873 B2 | 7/2021 | Wiener et al. |
| 11,058,424 B2 | 7/2021 | Shelton, IV et al. |
| 11,058,447 B2 | 7/2021 | Houser |
| 11,058,448 B2 | 7/2021 | Shelton, IV et al. |
| 11,058,475 B2 | 7/2021 | Wiener et al. |
| 11,064,997 B2 | 7/2021 | Shelton, IV et al. |
| 11,065,048 B2 | 7/2021 | Messerly et al. |
| 11,083,455 B2 | 8/2021 | Shelton, IV et al. |
| 11,083,458 B2 | 8/2021 | Harris et al. |
| 11,090,048 B2 | 8/2021 | Fanelli et al. |
| 11,090,049 B2 | 8/2021 | Bakos et al. |
| 11,090,104 B2 | 8/2021 | Wiener et al. |
| 11,096,688 B2 | 8/2021 | Shelton, IV et al. |
| 11,096,752 B2 | 8/2021 | Stulen et al. |
| 11,109,866 B2 | 9/2021 | Shelton, IV et al. |
| 11,129,611 B2 | 9/2021 | Shelton, IV et al. |
| 11,129,666 B2 | 9/2021 | Messerly et al. |
| 11,129,669 B2 | 9/2021 | Stulen et al. |
| 11,129,670 B2 | 9/2021 | Shelton, IV et al. |
| 11,134,942 B2 | 10/2021 | Harris et al. |
| 11,134,978 B2 | 10/2021 | Shelton, IV et al. |
| 11,141,154 B2 | 10/2021 | Shelton, IV et al. |
| 11,141,213 B2 | 10/2021 | Yates et al. |
| 11,147,551 B2 | 10/2021 | Shelton, IV |
| 11,147,553 B2 | 10/2021 | Shelton, IV |
| 11,160,551 B2 | 11/2021 | Shelton, IV et al. |
| 11,166,716 B2 | 11/2021 | Shelton, IV et al. |
| 11,172,929 B2 | 11/2021 | Shelton, IV |
| 11,179,155 B2 | 11/2021 | Shelton, IV et al. |
| 11,191,539 B2 | 12/2021 | Overmyer et al. |
| 11,191,540 B2 | 12/2021 | Aronhalt et al. |
| 11,197,668 B2 | 12/2021 | Shelton, IV et al. |
| 11,202,670 B2 | 12/2021 | Worrell et al. |
| 11,207,065 B2 | 12/2021 | Harris et al. |
| 11,207,067 B2 | 12/2021 | Shelton, IV et al. |
| 11,213,293 B2 | 1/2022 | Worthington et al. |
| 11,213,294 B2 | 1/2022 | Shelton, IV et al. |
| 11,219,453 B2 | 1/2022 | Shelton, IV et al. |
| 11,224,426 B2 | 1/2022 | Shelton, IV et al. |
| 11,224,497 B2 | 1/2022 | Shelton, IV et al. |
| 11,229,437 B2 | 1/2022 | Shelton, IV et al. |
| 11,229,450 B2 | 1/2022 | Shelton, IV et al. |
| 11,229,471 B2 | 1/2022 | Shelton, IV et al. |
| 11,229,472 B2 | 1/2022 | Shelton, IV et al. |
| 11,234,698 B2 | 2/2022 | Shelton, IV et al. |
| 11,241,235 B2 | 2/2022 | Shelton, IV et al. |
| 11,246,592 B2 | 2/2022 | Shelton, IV et al. |
| 11,246,625 B2 | 2/2022 | Kane et al. |
| 11,246,678 B2 | 2/2022 | Shelton, IV et al. |
| 11,253,256 B2 | 2/2022 | Harris et al. |
| 11,259,803 B2 | 3/2022 | Shelton, IV et al. |
| 11,259,805 B2 | 3/2022 | Shelton, IV et al. |
| 11,259,806 B2 | 3/2022 | Shelton, IV et al. |
| 11,259,807 B2 | 3/2022 | Shelton, IV et al. |
| 11,266,405 B2 | 3/2022 | Shelton, IV et al. |
| 11,266,430 B2 | 3/2022 | Clauda et al. |
| 11,284,890 B2 | 3/2022 | Nalagatla et al. |
| 11,291,440 B2 | 4/2022 | Harris et al. |
| 11,304,695 B2 | 4/2022 | Shelton, IV et al. |
| 11,311,306 B2 | 4/2022 | Shelton, IV et al. |
| 11,311,342 B2 | 4/2022 | Parihar et al. |
| D950,728 S | 5/2022 | Bakos et al. |
| D952,144 S | 5/2022 | Boudreaux |
| 11,324,503 B2 | 5/2022 | Shelton, IV et al. |
| 11,324,557 B2 | 5/2022 | Shelton, IV et al. |
| 11,389,161 B2 | 7/2022 | Shelton, IV et al. |
| 11,419,606 B2 | 8/2022 | Overmyer et al. |
| 11,424,027 B2 | 8/2022 | Shelton, IV |
| D964,564 S | 9/2022 | Boudreaux |
| 11,471,155 B2 | 10/2022 | Shelton, IV et al. |
| 11,478,242 B2 | 10/2022 | Shelton, IV et al. |
| 11,484,310 B2 | 11/2022 | Shelton, IV et al. |
| 11,571,210 B2 | 2/2023 | Shelton, IV et al. |
| 11,653,920 B2 | 5/2023 | Shelton, IV et al. |
| 2001/0025173 A1 | 9/2001 | Ritchie et al. |
| 2001/0025183 A1 | 9/2001 | Shahidi |
| 2001/0025184 A1 | 9/2001 | Messerly |
| 2001/0031950 A1 | 10/2001 | Ryan |
| 2001/0039419 A1 | 11/2001 | Francischelli et al. |
| 2002/0002377 A1 | 1/2002 | Cimino |
| 2002/0002380 A1 | 1/2002 | Bishop |
| 2002/0019649 A1 | 2/2002 | Sikora et al. |
| 2002/0022836 A1 | 2/2002 | Goble et al. |
| 2002/0029036 A1 | 3/2002 | Goble et al. |
| 2002/0029055 A1 | 3/2002 | Bonutti |
| 2002/0032452 A1 | 3/2002 | Tierney et al. |
| 2002/0049551 A1 | 4/2002 | Friedman et al. |
| 2002/0052617 A1 | 5/2002 | Anis et al. |
| 2002/0077550 A1 | 6/2002 | Rabiner et al. |
| 2002/0107517 A1 | 8/2002 | Witt et al. |
| 2002/0123749 A1 | 9/2002 | Jain |
| 2002/0133152 A1 | 9/2002 | Strul |
| 2002/0151884 A1 | 10/2002 | Hoey et al. |
| 2002/0156466 A1 | 10/2002 | Sakurai et al. |
| 2002/0156493 A1 | 10/2002 | Houser et al. |
| 2002/0165577 A1 | 11/2002 | Witt et al. |
| 2002/0177373 A1 | 11/2002 | Shibata et al. |
| 2002/0177862 A1 | 11/2002 | Aranyi et al. |
| 2003/0009164 A1 | 1/2003 | Woloszko et al. |
| 2003/0014053 A1 | 1/2003 | Nguyen et al. |
| 2003/0014087 A1 | 1/2003 | Fang et al. |
| 2003/0036705 A1 | 2/2003 | Hare et al. |
| 2003/0040758 A1 | 2/2003 | Wang et al. |
| 2003/0050572 A1 | 3/2003 | Brautigam et al. |
| 2003/0055443 A1 | 3/2003 | Spotnitz |
| 2003/0073981 A1 | 4/2003 | Whitman et al. |
| 2003/0109778 A1 | 6/2003 | Rashidi |
| 2003/0109875 A1 | 6/2003 | Tetzlaff et al. |
| 2003/0114851 A1 | 6/2003 | Truckai et al. |
| 2003/0130693 A1 | 7/2003 | Levin et al. |
| 2003/0139741 A1 | 7/2003 | Goble et al. |

(56) References Cited

U.S. PATENT DOCUMENTS

| | | |
|---|---|---|
| 2003/0144680 A1 | 7/2003 | Kellogg et al. |
| 2003/0158548 A1 | 8/2003 | Phan et al. |
| 2003/0171747 A1 | 9/2003 | Kanehira et al. |
| 2003/0176778 A1 | 9/2003 | Messing et al. |
| 2003/0181898 A1 | 9/2003 | Bowers |
| 2003/0199794 A1 | 10/2003 | Sakurai et al. |
| 2003/0204199 A1 | 10/2003 | Novak et al. |
| 2003/0208186 A1 | 11/2003 | Moreyra |
| 2003/0212332 A1 | 11/2003 | Fenton et al. |
| 2003/0212363 A1 | 11/2003 | Shipp |
| 2003/0212392 A1 | 11/2003 | Fenton et al. |
| 2003/0212422 A1 | 11/2003 | Fenton et al. |
| 2003/0225332 A1 | 12/2003 | Okada et al. |
| 2003/0229344 A1 | 12/2003 | Dycus et al. |
| 2004/0030254 A1 | 2/2004 | Babaev |
| 2004/0030330 A1 | 2/2004 | Brassell et al. |
| 2004/0047485 A1 | 3/2004 | Sherrit et al. |
| 2004/0054364 A1 | 3/2004 | Aranyi et al. |
| 2004/0064151 A1 | 4/2004 | Mollenauer |
| 2004/0087943 A1 | 5/2004 | Dycus et al. |
| 2004/0092921 A1 | 5/2004 | Kadziauskas et al. |
| 2004/0092992 A1 | 5/2004 | Adams et al. |
| 2004/0094597 A1 | 5/2004 | Whitman et al. |
| 2004/0097911 A1 | 5/2004 | Murakami et al. |
| 2004/0097912 A1 | 5/2004 | Gonnering |
| 2004/0097919 A1 | 5/2004 | Wellman et al. |
| 2004/0097996 A1 | 5/2004 | Rabiner et al. |
| 2004/0116952 A1 | 6/2004 | Sakurai et al. |
| 2004/0122423 A1 | 6/2004 | Dycus et al. |
| 2004/0132383 A1 | 7/2004 | Langford et al. |
| 2004/0138621 A1 | 7/2004 | Jahns et al. |
| 2004/0142667 A1 | 7/2004 | Lochhead et al. |
| 2004/0143263 A1 | 7/2004 | Schechter et al. |
| 2004/0147934 A1 | 7/2004 | Kiester |
| 2004/0147945 A1 | 7/2004 | Fritzsch |
| 2004/0158237 A1 | 8/2004 | Abboud et al. |
| 2004/0167508 A1 | 8/2004 | Wham et al. |
| 2004/0176686 A1 | 9/2004 | Hare et al. |
| 2004/0176751 A1 | 9/2004 | Weitzner et al. |
| 2004/0181242 A1 | 9/2004 | Stack et al. |
| 2004/0193150 A1 | 9/2004 | Sharkey et al. |
| 2004/0193153 A1 | 9/2004 | Sartor et al. |
| 2004/0193212 A1 | 9/2004 | Taniguchi et al. |
| 2004/0199193 A1 | 10/2004 | Hayashi et al. |
| 2004/0215132 A1 | 10/2004 | Yoon |
| 2004/0243147 A1 | 12/2004 | Lipow |
| 2004/0249374 A1 | 12/2004 | Tetzlaff et al. |
| 2004/0260273 A1 | 12/2004 | Wan |
| 2004/0260300 A1 | 12/2004 | Gorensek et al. |
| 2004/0267311 A1 | 12/2004 | Viola et al. |
| 2005/0015125 A1 | 1/2005 | Mioduski et al. |
| 2005/0020967 A1 | 1/2005 | Ono |
| 2005/0021018 A1 | 1/2005 | Anderson et al. |
| 2005/0021065 A1 | 1/2005 | Yamada et al. |
| 2005/0021078 A1 | 1/2005 | Vleugels et al. |
| 2005/0033278 A1 | 2/2005 | McClurken et al. |
| 2005/0033337 A1 | 2/2005 | Muir et al. |
| 2005/0070800 A1 | 3/2005 | Takahashi |
| 2005/0080427 A1 | 4/2005 | Govari et al. |
| 2005/0088285 A1 | 4/2005 | Jei |
| 2005/0090817 A1 | 4/2005 | Phan |
| 2005/0096683 A1 | 5/2005 | Ellins et al. |
| 2005/0099824 A1 | 5/2005 | Dowling et al. |
| 2005/0107777 A1 | 5/2005 | West et al. |
| 2005/0131390 A1 | 6/2005 | Heinrich et al. |
| 2005/0143769 A1 | 6/2005 | White et al. |
| 2005/0149108 A1 | 7/2005 | Cox |
| 2005/0165429 A1 | 7/2005 | Douglas et al. |
| 2005/0171522 A1 | 8/2005 | Christopherson |
| 2005/0171533 A1 | 8/2005 | Latterell et al. |
| 2005/0177184 A1 | 8/2005 | Easley |
| 2005/0182339 A1 | 8/2005 | Lee et al. |
| 2005/0187576 A1 | 8/2005 | Whitman et al. |
| 2005/0188743 A1 | 9/2005 | Land |
| 2005/0192610 A1 | 9/2005 | Houser et al. |
| 2005/0192611 A1 | 9/2005 | Houser |
| 2005/0206583 A1 | 9/2005 | Lemelson et al. |
| 2005/0222598 A1 | 10/2005 | Ho et al. |
| 2005/0234484 A1 | 10/2005 | Houser et al. |
| 2005/0249667 A1 | 11/2005 | Tuszynski et al. |
| 2005/0256405 A1 | 11/2005 | Makin et al. |
| 2005/0261588 A1 | 11/2005 | Makin et al. |
| 2005/0262175 A1 | 11/2005 | Iino et al. |
| 2005/0267464 A1 | 12/2005 | Truckai et al. |
| 2005/0271807 A1 | 12/2005 | Iljima et al. |
| 2005/0273090 A1 | 12/2005 | Nieman et al. |
| 2005/0288659 A1 | 12/2005 | Kimura et al. |
| 2006/0025757 A1 | 2/2006 | Heim |
| 2006/0030797 A1 | 2/2006 | Zhou et al. |
| 2006/0030848 A1 | 2/2006 | Craig et al. |
| 2006/0058825 A1 | 3/2006 | Ogura et al. |
| 2006/0063130 A1 | 3/2006 | Hayman et al. |
| 2006/0064086 A1 | 3/2006 | Odom |
| 2006/0066181 A1 | 3/2006 | Bromfield et al. |
| 2006/0074442 A1 | 4/2006 | Noriega et al. |
| 2006/0079874 A1 | 4/2006 | Faller et al. |
| 2006/0079879 A1 | 4/2006 | Faller et al. |
| 2006/0095046 A1 | 5/2006 | Trieu et al. |
| 2006/0109061 A1 | 5/2006 | Dobson et al. |
| 2006/0142656 A1 | 6/2006 | Malackowski et al. |
| 2006/0159731 A1 | 7/2006 | Shoshan |
| 2006/0190034 A1 | 8/2006 | Nishizawa et al. |
| 2006/0206100 A1 | 9/2006 | Eskridge et al. |
| 2006/0206115 A1 | 9/2006 | Schomer et al. |
| 2006/0211943 A1 | 9/2006 | Beaupre |
| 2006/0217700 A1 | 9/2006 | Garito et al. |
| 2006/0217729 A1 | 9/2006 | Eskridge et al. |
| 2006/0224160 A1 | 10/2006 | Trieu et al. |
| 2006/0247558 A1 | 11/2006 | Yamada |
| 2006/0253050 A1 | 11/2006 | Yoshimine et al. |
| 2006/0259026 A1 | 11/2006 | Godara et al. |
| 2006/0259102 A1 | 11/2006 | Slatkine |
| 2006/0264809 A1 | 11/2006 | Hansmann et al. |
| 2006/0264995 A1 | 11/2006 | Fanton et al. |
| 2006/0265035 A1 | 11/2006 | Yachi et al. |
| 2006/0270916 A1 | 11/2006 | Skwarek et al. |
| 2006/0271030 A1 | 11/2006 | Francis et al. |
| 2006/0293656 A1 | 12/2006 | Shadduck et al. |
| 2007/0016235 A1 | 1/2007 | Tanaka et al. |
| 2007/0016236 A1 | 1/2007 | Beaupre |
| 2007/0021738 A1 | 1/2007 | Hasser et al. |
| 2007/0027468 A1 | 2/2007 | Wales et al. |
| 2007/0032704 A1 | 2/2007 | Gandini et al. |
| 2007/0055228 A1 | 3/2007 | Berg et al. |
| 2007/0056596 A1 | 3/2007 | Fanney et al. |
| 2007/0060935 A1 | 3/2007 | Schwardt et al. |
| 2007/0063618 A1 | 3/2007 | Bromfield |
| 2007/0066971 A1 | 3/2007 | Podhajsky |
| 2007/0067123 A1 | 3/2007 | Jungerman |
| 2007/0073185 A1 | 3/2007 | Nakao |
| 2007/0073341 A1 | 3/2007 | Smith et al. |
| 2007/0074584 A1 | 4/2007 | Talarico et al. |
| 2007/0106317 A1 | 5/2007 | Shelton et al. |
| 2007/0118115 A1 | 5/2007 | Artale et al. |
| 2007/0129726 A1 | 6/2007 | Eder et al. |
| 2007/0130771 A1 | 6/2007 | Ehlert et al. |
| 2007/0135803 A1 | 6/2007 | Belson |
| 2007/0149881 A1 | 6/2007 | Rabin |
| 2007/0156163 A1 | 7/2007 | Davison et al. |
| 2007/0166663 A1 | 7/2007 | Telles et al. |
| 2007/0173803 A1 | 7/2007 | Wham et al. |
| 2007/0173813 A1 | 7/2007 | Odom |
| 2007/0173872 A1 | 7/2007 | Neuenfeldt |
| 2007/0175955 A1 | 8/2007 | Shelton et al. |
| 2007/0185474 A1 | 8/2007 | Nahen |
| 2007/0191712 A1 | 8/2007 | Messerly et al. |
| 2007/0191713 A1 | 8/2007 | Eichmann et al. |
| 2007/0203483 A1 | 8/2007 | Kim et al. |
| 2007/0208336 A1 | 9/2007 | Kim et al. |
| 2007/0208340 A1 | 9/2007 | Ganz et al. |
| 2007/0219481 A1 | 9/2007 | Babaev |
| 2007/0232926 A1 | 10/2007 | Stulen et al. |
| 2007/0232928 A1 | 10/2007 | Wiener et al. |
| 2007/0236213 A1 | 10/2007 | Paden et al. |

(56) References Cited

U.S. PATENT DOCUMENTS

| | | |
|---|---|---|
| 2007/0239101 A1 | 10/2007 | Kellogg |
| 2007/0249941 A1 | 10/2007 | Salehi et al. |
| 2007/0260242 A1 | 11/2007 | Dycus et al. |
| 2007/0265560 A1 | 11/2007 | Soltani et al. |
| 2007/0265613 A1 | 11/2007 | Edelstein et al. |
| 2007/0265616 A1 | 11/2007 | Couture et al. |
| 2007/0265620 A1 | 11/2007 | Kraas et al. |
| 2007/0275348 A1 | 11/2007 | Lemon |
| 2007/0287933 A1 | 12/2007 | Phan et al. |
| 2007/0288055 A1 | 12/2007 | Lee |
| 2007/0299895 A1 | 12/2007 | Johnson et al. |
| 2008/0005213 A1 | 1/2008 | Holtzman |
| 2008/0013809 A1 | 1/2008 | Zhu et al. |
| 2008/0015473 A1 | 1/2008 | Shimizu |
| 2008/0015575 A1 | 1/2008 | Odom et al. |
| 2008/0033465 A1 | 2/2008 | Schmitz et al. |
| 2008/0039746 A1 | 2/2008 | Hissong et al. |
| 2008/0046122 A1 | 2/2008 | Manzo et al. |
| 2008/0051812 A1 | 2/2008 | Schmitz et al. |
| 2008/0058775 A1 | 3/2008 | Darian et al. |
| 2008/0058845 A1 | 3/2008 | Shimizu et al. |
| 2008/0071269 A1 | 3/2008 | Hilario et al. |
| 2008/0077145 A1 | 3/2008 | Boyden et al. |
| 2008/0082039 A1 | 4/2008 | Babaev |
| 2008/0082098 A1 | 4/2008 | Tanaka et al. |
| 2008/0097501 A1 | 4/2008 | Blier |
| 2008/0114355 A1 | 5/2008 | Whayne et al. |
| 2008/0114364 A1 | 5/2008 | Goldin et al. |
| 2008/0122496 A1 | 5/2008 | Wagner |
| 2008/0125768 A1 | 5/2008 | Tahara et al. |
| 2008/0147058 A1 | 6/2008 | Horrell et al. |
| 2008/0147062 A1 | 6/2008 | Truckai et al. |
| 2008/0147092 A1 | 6/2008 | Rogge et al. |
| 2008/0161809 A1 | 7/2008 | Schmitz et al. |
| 2008/0167670 A1 | 7/2008 | Shelton et al. |
| 2008/0171938 A1 | 7/2008 | Masuda et al. |
| 2008/0177268 A1 | 7/2008 | Daum et al. |
| 2008/0188755 A1 | 8/2008 | Hart |
| 2008/0200940 A1 | 8/2008 | Eichmann et al. |
| 2008/0208108 A1 | 8/2008 | Kimura |
| 2008/0208231 A1 | 8/2008 | Ota et al. |
| 2008/0214967 A1 | 9/2008 | Aranyi et al. |
| 2008/0234709 A1 | 9/2008 | Houser |
| 2008/0243162 A1 | 10/2008 | Shibata et al. |
| 2008/0255413 A1 | 10/2008 | Zemlok et al. |
| 2008/0275440 A1 | 11/2008 | Kratoska et al. |
| 2008/0281200 A1 | 11/2008 | Voic et al. |
| 2008/0281315 A1 | 11/2008 | Gines |
| 2008/0287944 A1 | 11/2008 | Pearson et al. |
| 2008/0287948 A1 | 11/2008 | Newton et al. |
| 2008/0296346 A1 | 12/2008 | Shelton, IV et al. |
| 2008/0300588 A1 | 12/2008 | Groth et al. |
| 2009/0012516 A1 | 1/2009 | Curtis et al. |
| 2009/0023985 A1 | 1/2009 | Ewers |
| 2009/0036913 A1 | 2/2009 | Wiener et al. |
| 2009/0043293 A1 | 2/2009 | Pankratov et al. |
| 2009/0048537 A1 | 2/2009 | Lydon et al. |
| 2009/0048589 A1 | 2/2009 | Takashino et al. |
| 2009/0054886 A1 | 2/2009 | Yachi et al. |
| 2009/0054889 A1 | 2/2009 | Newton et al. |
| 2009/0054894 A1 | 2/2009 | Yachi |
| 2009/0065565 A1 | 3/2009 | Cao |
| 2009/0076506 A1 | 3/2009 | Baker |
| 2009/0082716 A1 | 3/2009 | Akahoshi |
| 2009/0082766 A1 | 3/2009 | Unger et al. |
| 2009/0088745 A1 | 4/2009 | Hushka et al. |
| 2009/0088785 A1 | 4/2009 | Masuda |
| 2009/0090763 A1 | 4/2009 | Zemlok et al. |
| 2009/0101692 A1 | 4/2009 | Whitman et al. |
| 2009/0105750 A1 | 4/2009 | Price et al. |
| 2009/0112206 A1 | 4/2009 | Dumbauld et al. |
| 2009/0118751 A1 | 5/2009 | Wiener et al. |
| 2009/0131885 A1 | 5/2009 | Akahoshi |
| 2009/0131929 A1* | 5/2009 | Shimizu ............ A61B 18/1206 601/2 |
| 2009/0131934 A1 | 5/2009 | Odom et al. |
| 2009/0138025 A1 | 5/2009 | Stahler et al. |
| 2009/0143678 A1 | 6/2009 | Keast et al. |
| 2009/0143799 A1 | 6/2009 | Smith et al. |
| 2009/0143800 A1 | 6/2009 | Deville et al. |
| 2009/0157064 A1 | 6/2009 | Hodel |
| 2009/0163807 A1 | 6/2009 | Sliwa |
| 2009/0177119 A1 | 7/2009 | Heidner et al. |
| 2009/0179923 A1 | 7/2009 | Amundson et al. |
| 2009/0182322 A1 | 7/2009 | D'Amelio et al. |
| 2009/0182331 A1 | 7/2009 | D'Amelio et al. |
| 2009/0182332 A1 | 7/2009 | Long et al. |
| 2009/0182333 A1 | 7/2009 | Eder et al. |
| 2009/0192441 A1 | 7/2009 | Gelbart et al. |
| 2009/0198272 A1 | 8/2009 | Kerver et al. |
| 2009/0204114 A1 | 8/2009 | Odom |
| 2009/0216157 A1 | 8/2009 | Yamada |
| 2009/0223033 A1 | 9/2009 | Houser |
| 2009/0240244 A1 | 9/2009 | Malis et al. |
| 2009/0248021 A1 | 10/2009 | McKenna |
| 2009/0248022 A1 | 10/2009 | Falkenstein et al. |
| 2009/0254077 A1 | 10/2009 | Craig |
| 2009/0254080 A1 | 10/2009 | Honda |
| 2009/0259149 A1 | 10/2009 | Tahara et al. |
| 2009/0264909 A1 | 10/2009 | Beaupre |
| 2009/0270771 A1 | 10/2009 | Takahashi |
| 2009/0270812 A1 | 10/2009 | Litscher et al. |
| 2009/0270853 A1 | 10/2009 | Yachi et al. |
| 2009/0270891 A1 | 10/2009 | Beaupre |
| 2009/0270899 A1 | 10/2009 | Carusillo et al. |
| 2009/0287205 A1 | 11/2009 | Ingle |
| 2009/0292283 A1 | 11/2009 | Odom |
| 2009/0299141 A1 | 12/2009 | Downey et al. |
| 2009/0306639 A1 | 12/2009 | Nevo et al. |
| 2009/0327715 A1 | 12/2009 | Smith et al. |
| 2010/0004508 A1 | 1/2010 | Naito et al. |
| 2010/0022825 A1 | 1/2010 | Yoshie |
| 2010/0030233 A1 | 2/2010 | Whitman et al. |
| 2010/0034605 A1 | 2/2010 | Huckins et al. |
| 2010/0036370 A1 | 2/2010 | Mirel et al. |
| 2010/0036373 A1 | 2/2010 | Ward |
| 2010/0042093 A9 | 2/2010 | Wham et al. |
| 2010/0049180 A1 | 2/2010 | Wells et al. |
| 2010/0057081 A1 | 3/2010 | Hanna |
| 2010/0057118 A1 | 3/2010 | Dietz et al. |
| 2010/0063437 A1 | 3/2010 | Nelson et al. |
| 2010/0063525 A1 | 3/2010 | Beaupre et al. |
| 2010/0063528 A1 | 3/2010 | Beaupre |
| 2010/0081863 A1 | 4/2010 | Hess et al. |
| 2010/0081864 A1 | 4/2010 | Hess et al. |
| 2010/0081883 A1 | 4/2010 | Murray et al. |
| 2010/0094323 A1 | 4/2010 | Isaacs et al. |
| 2010/0106173 A1 | 4/2010 | Yoshimine |
| 2010/0109480 A1 | 5/2010 | Forslund et al. |
| 2010/0145335 A1 | 6/2010 | Johnson et al. |
| 2010/0158307 A1 | 6/2010 | Kubota et al. |
| 2010/0168741 A1 | 7/2010 | Sanai et al. |
| 2010/0181966 A1 | 7/2010 | Sakakibara |
| 2010/0187283 A1 | 7/2010 | Crainich et al. |
| 2010/0191233 A1* | 7/2010 | Wham ............... A61B 18/1206 606/33 |
| 2010/0193566 A1 | 8/2010 | Scheib et al. |
| 2010/0204721 A1 | 8/2010 | Young et al. |
| 2010/0222714 A1 | 9/2010 | Muir et al. |
| 2010/0222752 A1 | 9/2010 | Collins, Jr. et al. |
| 2010/0225209 A1 | 9/2010 | Goldberg et al. |
| 2010/0228249 A1 | 9/2010 | Mohr et al. |
| 2010/0228250 A1 | 9/2010 | Brogna |
| 2010/0234906 A1 | 9/2010 | Koh |
| 2010/0256635 A1 | 10/2010 | McKenna et al. |
| 2010/0274160 A1 | 10/2010 | Yachi et al. |
| 2010/0274278 A1 | 10/2010 | Fleenor et al. |
| 2010/0280368 A1 | 11/2010 | Can et al. |
| 2010/0298743 A1 | 11/2010 | Nield et al. |
| 2010/0305564 A1 | 12/2010 | Livneh |
| 2010/0331742 A1 | 12/2010 | Masuda |
| 2010/0331871 A1 | 12/2010 | Nield et al. |
| 2011/0004233 A1 | 1/2011 | Muir et al. |
| 2011/0015632 A1 | 1/2011 | Artale |

(56) References Cited

U.S. PATENT DOCUMENTS

| | | |
|---|---|---|
| 2011/0015650 A1 | 1/2011 | Choi et al. |
| 2011/0022032 A1 | 1/2011 | Zemlok et al. |
| 2011/0028964 A1 | 2/2011 | Edwards |
| 2011/0071523 A1 | 3/2011 | Dickhans |
| 2011/0082494 A1 | 4/2011 | Kerr et al. |
| 2011/0106141 A1 | 5/2011 | Nakamura |
| 2011/0112400 A1 | 5/2011 | Emery et al. |
| 2011/0125149 A1 | 5/2011 | El-Galley et al. |
| 2011/0125151 A1 | 5/2011 | Strauss et al. |
| 2011/0144640 A1 | 6/2011 | Heinrich et al. |
| 2011/0160725 A1 | 6/2011 | Kabaya et al. |
| 2011/0238010 A1 | 9/2011 | Kirschenman et al. |
| 2011/0238079 A1 | 9/2011 | Hannaford et al. |
| 2011/0273465 A1 | 11/2011 | Konishi et al. |
| 2011/0278343 A1 | 11/2011 | Knodel et al. |
| 2011/0279268 A1 | 11/2011 | Konishi et al. |
| 2011/0284014 A1 | 11/2011 | Cadeddu et al. |
| 2011/0290856 A1 | 12/2011 | Shelton, IV et al. |
| 2011/0295295 A1 | 12/2011 | Shelton, IV et al. |
| 2011/0306967 A1 | 12/2011 | Payne et al. |
| 2011/0313415 A1 | 12/2011 | Fernandez et al. |
| 2012/0004655 A1 | 1/2012 | Kim et al. |
| 2012/0016413 A1 | 1/2012 | Timm et al. |
| 2012/0022519 A1 | 1/2012 | Huang et al. |
| 2012/0022526 A1 | 1/2012 | Aldridge et al. |
| 2012/0022528 A1 | 1/2012 | White et al. |
| 2012/0022583 A1 | 1/2012 | Sugalski et al. |
| 2012/0041358 A1 | 2/2012 | Mann et al. |
| 2012/0053597 A1 | 3/2012 | Anvari et al. |
| 2012/0059286 A1 | 3/2012 | Hastings et al. |
| 2012/0059289 A1 | 3/2012 | Nield et al. |
| 2012/0071863 A1 | 3/2012 | Lee et al. |
| 2012/0078244 A1 | 3/2012 | Worrell et al. |
| 2012/0080344 A1 | 4/2012 | Shelton, IV |
| 2012/0101493 A1 | 4/2012 | Masuda et al. |
| 2012/0101495 A1 | 4/2012 | Young et al. |
| 2012/0109186 A1 | 5/2012 | Parrott et al. |
| 2012/0116222 A1 | 5/2012 | Sawada et al. |
| 2012/0116265 A1 | 5/2012 | Houser et al. |
| 2012/0116266 A1 | 5/2012 | Houser et al. |
| 2012/0116381 A1 | 5/2012 | Houser et al. |
| 2012/0136279 A1 | 5/2012 | Tanaka et al. |
| 2012/0136347 A1 | 5/2012 | Brustad et al. |
| 2012/0136386 A1 | 5/2012 | Kishida et al. |
| 2012/0143182 A1 | 6/2012 | Ullrich et al. |
| 2012/0143211 A1 | 6/2012 | Kishi |
| 2012/0150049 A1 | 6/2012 | Zielinski et al. |
| 2012/0150169 A1 | 6/2012 | Zielinksi et al. |
| 2012/0172904 A1 | 7/2012 | Muir et al. |
| 2012/0191091 A1 | 7/2012 | Allen |
| 2012/0193396 A1 | 8/2012 | Zemlok et al. |
| 2012/0211542 A1 | 8/2012 | Racenet |
| 2012/0226266 A1 | 9/2012 | Ghosal et al. |
| 2012/0234893 A1 | 9/2012 | Schuckmann et al. |
| 2012/0253328 A1 | 10/2012 | Cunningham et al. |
| 2012/0253329 A1 | 10/2012 | Zemlok et al. |
| 2012/0265241 A1 | 10/2012 | Hart et al. |
| 2012/0296239 A1 | 11/2012 | Chernov et al. |
| 2012/0296325 A1 | 11/2012 | Takashino |
| 2012/0296371 A1 | 11/2012 | Kappus et al. |
| 2013/0023925 A1 | 1/2013 | Mueller |
| 2013/0071282 A1 | 3/2013 | Fry |
| 2013/0085510 A1 | 4/2013 | Stefanchik et al. |
| 2013/0103031 A1* | 4/2013 | Garrison ............ A61B 18/1445 606/174 |
| 2013/0123776 A1 | 5/2013 | Monson et al. |
| 2013/0158659 A1 | 6/2013 | Bergs et al. |
| 2013/0158660 A1 | 6/2013 | Bergs et al. |
| 2013/0165929 A1 | 6/2013 | Muir et al. |
| 2013/0190760 A1 | 7/2013 | Allen, IV et al. |
| 2013/0214025 A1 | 8/2013 | Zemlok et al. |
| 2013/0253256 A1 | 9/2013 | Griffith et al. |
| 2013/0253480 A1 | 9/2013 | Kimball et al. |
| 2013/0264369 A1 | 10/2013 | Whitman |
| 2013/0267874 A1 | 10/2013 | Marcotte et al. |
| 2013/0277410 A1 | 10/2013 | Fernandez et al. |
| 2013/0296843 A1 | 11/2013 | Boudreaux et al. |
| 2013/0321425 A1 | 12/2013 | Greene et al. |
| 2013/0334989 A1 | 12/2013 | Kataoka |
| 2013/0345701 A1 | 12/2013 | Allen, IV et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0005663 A1 | 1/2014 | Heard et al. |
| 2014/0005678 A1 | 1/2014 | Shelton, IV et al. |
| 2014/0005702 A1 | 1/2014 | Timm et al. |
| 2014/0005705 A1 | 1/2014 | Weir et al. |
| 2014/0005718 A1 | 1/2014 | Shelton, IV et al. |
| 2014/0014544 A1 | 1/2014 | Bugnard et al. |
| 2014/0077426 A1 | 3/2014 | Park |
| 2014/0107538 A1 | 4/2014 | Wiener et al. |
| 2014/0121569 A1 | 5/2014 | Schafer et al. |
| 2014/0135804 A1 | 5/2014 | Weisenburgh et al. |
| 2014/0163541 A1 | 6/2014 | Shelton, IV et al. |
| 2014/0163549 A1 | 6/2014 | Yates et al. |
| 2014/0180274 A1 | 6/2014 | Kabaya et al. |
| 2014/0194868 A1 | 7/2014 | Sanai et al. |
| 2014/0194874 A1 | 7/2014 | Dietz et al. |
| 2014/0194875 A1 | 7/2014 | Reschke et al. |
| 2014/0207124 A1 | 7/2014 | Aldridge et al. |
| 2014/0207135 A1 | 7/2014 | Winter |
| 2014/0221994 A1 | 8/2014 | Reschke |
| 2014/0236152 A1 | 8/2014 | Walberg et al. |
| 2014/0246475 A1 | 9/2014 | Hall et al. |
| 2014/0249557 A1 | 9/2014 | Koch, Jr. et al. |
| 2014/0263541 A1 | 9/2014 | Leimbach et al. |
| 2014/0263552 A1 | 9/2014 | Hall et al. |
| 2014/0276794 A1 | 9/2014 | Batchelor et al. |
| 2014/0276797 A1 | 9/2014 | Batchelor et al. |
| 2014/0276798 A1 | 9/2014 | Batchelor et al. |
| 2014/0303605 A1 | 10/2014 | Boyden et al. |
| 2014/0303612 A1 | 10/2014 | Williams |
| 2014/0357984 A1 | 12/2014 | Wallace et al. |
| 2014/0373003 A1 | 12/2014 | Grez et al. |
| 2015/0014392 A1 | 1/2015 | Williams et al. |
| 2015/0025528 A1 | 1/2015 | Arts |
| 2015/0032150 A1 | 1/2015 | Ishida et al. |
| 2015/0048140 A1 | 2/2015 | Penna et al. |
| 2015/0066027 A1 | 3/2015 | Garrison et al. |
| 2015/0080876 A1 | 3/2015 | Worrell et al. |
| 2015/0080887 A1 | 3/2015 | Sobajima et al. |
| 2015/0080889 A1 | 3/2015 | Cunningham et al. |
| 2015/0088122 A1 | 3/2015 | Jensen |
| 2015/0100056 A1 | 4/2015 | Nakamura |
| 2015/0112335 A1 | 4/2015 | Boudreaux et al. |
| 2015/0119901 A1 | 4/2015 | Steege |
| 2015/0157356 A1 | 6/2015 | Gee |
| 2015/0164533 A1 | 6/2015 | Felder et al. |
| 2015/0164534 A1 | 6/2015 | Felder et al. |
| 2015/0164535 A1 | 6/2015 | Felder et al. |
| 2015/0164536 A1 | 6/2015 | Czarnecki et al. |
| 2015/0164537 A1 | 6/2015 | Cagle et al. |
| 2015/0164538 A1 | 6/2015 | Aldridge et al. |
| 2015/0230796 A1 | 8/2015 | Calderoni |
| 2015/0238260 A1 | 8/2015 | Nau, Jr. |
| 2015/0272557 A1 | 10/2015 | Overmyer et al. |
| 2015/0272571 A1 | 10/2015 | Leimbach et al. |
| 2015/0272580 A1 | 10/2015 | Leimbach et al. |
| 2015/0272581 A1 | 10/2015 | Leimbach et al. |
| 2015/0272582 A1 | 10/2015 | Leimbach et al. |
| 2015/0272657 A1 | 10/2015 | Yates et al. |
| 2015/0272659 A1 | 10/2015 | Boudreaux et al. |
| 2015/0282879 A1 | 10/2015 | Ruelas |
| 2015/0289364 A1 | 10/2015 | Ilkko et al. |
| 2015/0313667 A1 | 11/2015 | Allen, IV |
| 2015/0317899 A1 | 11/2015 | Dumbauld et al. |
| 2015/0351765 A1 | 12/2015 | Valentine et al. |
| 2015/0351857 A1 | 12/2015 | Vander Poorten et al. |
| 2015/0374430 A1 | 12/2015 | Weiler et al. |
| 2015/0374457 A1* | 12/2015 | Colby ............ A61C 1/082 433/215 |
| 2016/0000437 A1 | 1/2016 | Giordano et al. |
| 2016/0038228 A1 | 2/2016 | Daniel et al. |
| 2016/0044841 A1 | 2/2016 | Chamberlain |

(56) References Cited

U.S. PATENT DOCUMENTS

| | | |
|---|---|---|
| 2016/0045248 A1 | 2/2016 | Unger et al. |
| 2016/0051314 A1 | 2/2016 | Batchelor et al. |
| 2016/0051316 A1 | 2/2016 | Boudreaux |
| 2016/0066909 A1 | 3/2016 | Swayze et al. |
| 2016/0066913 A1 | 3/2016 | Swayze et al. |
| 2016/0120601 A1 | 5/2016 | Boudreaux et al. |
| 2016/0175025 A1 | 6/2016 | Strobl |
| 2016/0175029 A1 | 6/2016 | Witt et al. |
| 2016/0206342 A1 | 7/2016 | Robertson et al. |
| 2016/0228171 A1 | 8/2016 | Boudreaux |
| 2016/0249910 A1 | 9/2016 | Shelton, IV et al. |
| 2016/0256184 A1* | 9/2016 | Shelton, IV ......... A61B 17/068 |
| 2016/0262786 A1 | 9/2016 | Madan et al. |
| 2016/0270842 A1 | 9/2016 | Strobl et al. |
| 2016/0296251 A1 | 10/2016 | Olson et al. |
| 2016/0296252 A1 | 10/2016 | Olson et al. |
| 2016/0296270 A1 | 10/2016 | Strobl et al. |
| 2016/0317216 A1 | 11/2016 | Hermes et al. |
| 2016/0331455 A1 | 11/2016 | Hancock et al. |
| 2016/0358849 A1 | 12/2016 | Jur et al. |
| 2017/0020614 A1 | 1/2017 | Jackson et al. |
| 2017/0065331 A1 | 3/2017 | Mayer et al. |
| 2017/0086909 A1 | 3/2017 | Yates et al. |
| 2017/0119426 A1 | 5/2017 | Akagane |
| 2017/0135751 A1 | 5/2017 | Rothweiler et al. |
| 2017/0164972 A1 | 6/2017 | Johnson et al. |
| 2017/0164973 A1* | 6/2017 | Lesko ............ A61B 17/320092 |
| 2017/0164997 A1 | 6/2017 | Johnson et al. |
| 2017/0189095 A1 | 7/2017 | Danziger et al. |
| 2017/0202595 A1 | 7/2017 | Shelton, IV |
| 2017/0202607 A1* | 7/2017 | Shelton, IV ............ H02J 7/342 |
| 2017/0209145 A1 | 7/2017 | Swayze et al. |
| 2017/0224332 A1 | 8/2017 | Hunter et al. |
| 2017/0224405 A1 | 8/2017 | Takashino et al. |
| 2017/0231628 A1 | 8/2017 | Shelton, IV et al. |
| 2017/0281186 A1 | 10/2017 | Shelton, IV et al. |
| 2017/0296169 A1 | 10/2017 | Yates et al. |
| 2017/0296177 A1 | 10/2017 | Harris et al. |
| 2017/0296180 A1 | 10/2017 | Harris et al. |
| 2017/0303954 A1 | 10/2017 | Ishii |
| 2017/0312018 A1 | 11/2017 | Trees et al. |
| 2017/0325874 A1 | 11/2017 | Noack et al. |
| 2017/0333073 A1 | 11/2017 | Faller et al. |
| 2017/0348043 A1 | 12/2017 | Wang et al. |
| 2017/0348044 A1 | 12/2017 | Wang et al. |
| 2017/0367772 A1* | 12/2017 | Gunn ..................... A61B 5/489 |
| 2018/0014872 A1 | 1/2018 | Dickerson |
| 2018/0085157 A1 | 3/2018 | Batchelor et al. |
| 2018/0098785 A1 | 4/2018 | Price et al. |
| 2018/0132850 A1 | 5/2018 | Leimbach et al. |
| 2018/0168575 A1 | 6/2018 | Simms et al. |
| 2018/0168577 A1 | 6/2018 | Aronhalt et al. |
| 2018/0168579 A1 | 6/2018 | Aronhalt et al. |
| 2018/0168598 A1 | 6/2018 | Shelton, IV et al. |
| 2018/0168608 A1 | 6/2018 | Shelton, IV et al. |
| 2018/0168609 A1 | 6/2018 | Fanelli et al. |
| 2018/0168615 A1 | 6/2018 | Shelton, IV et al. |
| 2018/0168618 A1 | 6/2018 | Scott et al. |
| 2018/0168619 A1 | 6/2018 | Scott et al. |
| 2018/0168623 A1 | 6/2018 | Simms et al. |
| 2018/0168625 A1 | 6/2018 | Posada et al. |
| 2018/0168633 A1 | 6/2018 | Shelton, IV et al. |
| 2018/0168647 A1 | 6/2018 | Shelton, IV et al. |
| 2018/0168648 A1 | 6/2018 | Shelton, IV et al. |
| 2018/0168650 A1 | 6/2018 | Shelton, IV et al. |
| 2018/0188125 A1 | 7/2018 | Park et al. |
| 2018/0206904 A1 | 7/2018 | Felder et al. |
| 2018/0221045 A1 | 8/2018 | Zimmerman et al. |
| 2018/0235691 A1 | 8/2018 | Voegele et al. |
| 2018/0250066 A1 | 9/2018 | Ding et al. |
| 2018/0271578 A1 | 9/2018 | Coulombe |
| 2018/0289432 A1 | 10/2018 | Kostrzewski et al. |
| 2018/0303493 A1 | 10/2018 | Chapolini |
| 2018/0325517 A1 | 11/2018 | Wingardner et al. |
| 2018/0333179 A1 | 11/2018 | Weisenburgh, II et al. |
| 2018/0353245 A1 | 12/2018 | Mccloud et al. |
| 2018/0368844 A1 | 12/2018 | Bakos et al. |
| 2019/0000459 A1 | 1/2019 | Shelton, IV et al. |
| 2019/0000461 A1 | 1/2019 | Shelton, IV et al. |
| 2019/0000475 A1 | 1/2019 | Shelton, IV et al. |
| 2019/0000477 A1 | 1/2019 | Shelton, IV et al. |
| 2019/0029746 A1 | 1/2019 | Dudhedia et al. |
| 2019/0038283 A1 | 2/2019 | Shelton, IV et al. |
| 2019/0053818 A1 | 2/2019 | Nelson et al. |
| 2019/0104919 A1 | 4/2019 | Shelton, IV et al. |
| 2019/0105067 A1 | 4/2019 | Boudreaux et al. |
| 2019/0117293 A1 | 4/2019 | Kano et al. |
| 2019/0125361 A1 | 5/2019 | Shelton, IV et al. |
| 2019/0125384 A1 | 5/2019 | Scheib et al. |
| 2019/0125390 A1 | 5/2019 | Shelton, IV et al. |
| 2019/0175258 A1 | 6/2019 | Tsuruta |
| 2019/0183504 A1 | 6/2019 | Shelton, IV et al. |
| 2019/0200844 A1 | 7/2019 | Shelton, IV et al. |
| 2019/0200977 A1 | 7/2019 | Shelton, IV et al. |
| 2019/0200981 A1 | 7/2019 | Harris et al. |
| 2019/0200987 A1 | 7/2019 | Shelton, IV et al. |
| 2019/0201029 A1 | 7/2019 | Shelton, IV et al. |
| 2019/0201030 A1 | 7/2019 | Shelton, IV et al. |
| 2019/0201045 A1 | 7/2019 | Yates et al. |
| 2019/0201046 A1 | 7/2019 | Shelton, IV et al. |
| 2019/0201047 A1 | 7/2019 | Yates et al. |
| 2019/0201048 A1 | 7/2019 | Stulen et al. |
| 2019/0201104 A1 | 7/2019 | Shelton, IV et al. |
| 2019/0201136 A1 | 7/2019 | Shelton, IV et al. |
| 2019/0201137 A1 | 7/2019 | Shelton, IV et al. |
| 2019/0201594 A1 | 7/2019 | Shelton, IV et al. |
| 2019/0206562 A1 | 7/2019 | Shelton, IV et al. |
| 2019/0206563 A1 | 7/2019 | Shelton, IV et al. |
| 2019/0206564 A1 | 7/2019 | Shelton, IV et al. |
| 2019/0206569 A1 | 7/2019 | Shelton, IV et al. |
| 2019/0208641 A1 | 7/2019 | Yates et al. |
| 2019/0209201 A1 | 7/2019 | Boudreaux et al. |
| 2019/0223941 A1 | 7/2019 | Kitamura et al. |
| 2019/0262030 A1 | 8/2019 | Faller et al. |
| 2019/0269455 A1 | 9/2019 | Mensch et al. |
| 2019/0274700 A1 | 9/2019 | Robertson et al. |
| 2019/0282288 A1 | 9/2019 | Boudreaux |
| 2019/0290265 A1 | 9/2019 | Shelton, IV et al. |
| 2019/0298340 A1 | 10/2019 | Shelton, IV et al. |
| 2019/0298350 A1 | 10/2019 | Shelton, IV et al. |
| 2019/0298352 A1 | 10/2019 | Shelton, IV et al. |
| 2019/0298353 A1 | 10/2019 | Shelton, IV et al. |
| 2019/0298357 A1 | 10/2019 | Shelton, IV et al. |
| 2019/0366562 A1 | 12/2019 | Zhang et al. |
| 2019/0388091 A1 | 12/2019 | Eschbach et al. |
| 2020/0030021 A1 | 1/2020 | Yates et al. |
| 2020/0054321 A1 | 2/2020 | Harris et al. |
| 2020/0054382 A1 | 2/2020 | Yates et al. |
| 2020/0078076 A1 | 3/2020 | Henderson et al. |
| 2020/0078085 A1 | 3/2020 | Yates et al. |
| 2020/0078106 A1 | 3/2020 | Henderson et al. |
| 2020/0078609 A1 | 3/2020 | Messerly et al. |
| 2020/0085465 A1 | 3/2020 | Timm et al. |
| 2020/0100825 A1 | 4/2020 | Henderson et al. |
| 2020/0100830 A1 | 4/2020 | Henderson et al. |
| 2020/0113622 A1 | 4/2020 | Honegger |
| 2020/0129261 A1 | 4/2020 | Eschbach |
| 2020/0138473 A1 | 5/2020 | Shelton, IV et al. |
| 2020/0188047 A1 | 6/2020 | Itkowitz et al. |
| 2020/0222111 A1 | 7/2020 | Yates et al. |
| 2020/0222112 A1 | 7/2020 | Hancock et al. |
| 2020/0229833 A1 | 7/2020 | Vakharia et al. |
| 2020/0229834 A1 | 7/2020 | Olson et al. |
| 2020/0237434 A1 | 7/2020 | Scheib et al. |
| 2020/0261075 A1 | 8/2020 | Boudreaux et al. |
| 2020/0261076 A1 | 8/2020 | Boudreaux et al. |
| 2020/0261078 A1 | 8/2020 | Bakos et al. |
| 2020/0261080 A1 | 8/2020 | Bakos et al. |
| 2020/0261081 A1 | 8/2020 | Boudreaux et al. |
| 2020/0261082 A1 | 8/2020 | Boudreaux et al. |
| 2020/0261083 A1 | 8/2020 | Bakos et al. |
| 2020/0261084 A1 | 8/2020 | Bakos et al. |
| 2020/0261085 A1 | 8/2020 | Boudreaux et al. |
| 2020/0261086 A1 | 8/2020 | Zeiner et al. |

(56) References Cited

U.S. PATENT DOCUMENTS

| | | |
|---|---|---|
| 2020/0261087 A1 | 8/2020 | Timm et al. |
| 2020/0261088 A1 | 8/2020 | Harris et al. |
| 2020/0261089 A1 | 8/2020 | Shelton, IV et al. |
| 2020/0261141 A1 | 8/2020 | Wiener et al. |
| 2020/0268430 A1 | 8/2020 | Takei et al. |
| 2020/0268433 A1 | 8/2020 | Wiener et al. |
| 2020/0305870 A1 | 10/2020 | Shelton, IV |
| 2020/0315623 A1 | 10/2020 | Eisinger et al. |
| 2020/0315712 A1 | 10/2020 | Jasperson et al. |
| 2020/0338370 A1 | 10/2020 | Wiener et al. |
| 2020/0405296 A1 | 12/2020 | Shelton, IV et al. |
| 2020/0405302 A1 | 12/2020 | Shelton, IV et al. |
| 2020/0405303 A1 | 12/2020 | Shelton, IV |
| 2020/0405312 A1 | 12/2020 | Shelton, IV et al. |
| 2020/0405313 A1 | 12/2020 | Shelton, IV |
| 2020/0405314 A1 | 12/2020 | Shelton, IV et al. |
| 2020/0405316 A1 | 12/2020 | Shelton, IV et al. |
| 2020/0405409 A1 | 12/2020 | Shelton, IV et al. |
| 2020/0405410 A1 | 12/2020 | Shelton, IV |
| 2020/0405436 A1 | 12/2020 | Shelton, IV et al. |
| 2020/0405437 A1 | 12/2020 | Shelton, IV et al. |
| 2020/0405438 A1 | 12/2020 | Shelton, IV et al. |
| 2020/0405439 A1 | 12/2020 | Shelton, IV et al. |
| 2020/0410177 A1 | 12/2020 | Shelton, IV |
| 2020/0410180 A1 | 12/2020 | Shelton, IV et al. |
| 2021/0052313 A1 | 2/2021 | Shelton, IV et al. |
| 2021/0100578 A1 | 4/2021 | Weir et al. |
| 2021/0100579 A1 | 4/2021 | Shelton, IV et al. |
| 2021/0153927 A1 | 5/2021 | Ross et al. |
| 2021/0177481 A1 | 6/2021 | Shelton, IV et al. |
| 2021/0177494 A1 | 6/2021 | Houser et al. |
| 2021/0177496 A1 | 6/2021 | Shelton, IV et al. |
| 2021/0186492 A1 | 6/2021 | Shelton, IV et al. |
| 2021/0186493 A1 | 6/2021 | Shelton, IV et al. |
| 2021/0186494 A1 | 6/2021 | Shelton, IV et al. |
| 2021/0186495 A1 | 6/2021 | Shelton, IV et al. |
| 2021/0186497 A1 | 6/2021 | Shelton, IV et al. |
| 2021/0186498 A1 | 6/2021 | Boudreaux et al. |
| 2021/0186499 A1 | 6/2021 | Shelton, IV et al. |
| 2021/0186500 A1 | 6/2021 | Shelton, IV et al. |
| 2021/0186501 A1 | 6/2021 | Shelton, IV et al. |
| 2021/0186502 A1 | 6/2021 | Shelton, IV et al. |
| 2021/0186503 A1 | 6/2021 | Shelton, IV et al. |
| 2021/0186504 A1 | 6/2021 | Shelton, IV et al. |
| 2021/0186505 A1 | 6/2021 | Shelton, IV et al. |
| 2021/0186506 A1 | 6/2021 | Shelton, IV et al. |
| 2021/0186507 A1 | 6/2021 | Shelton, IV et al. |
| 2021/0186553 A1 | 6/2021 | Green et al. |
| 2021/0186554 A1 | 6/2021 | Green et al. |
| 2021/0196263 A1 | 7/2021 | Shelton, IV et al. |
| 2021/0196265 A1 | 7/2021 | Shelton, IV et al. |
| 2021/0196266 A1 | 7/2021 | Shelton, IV et al. |
| 2021/0196267 A1 | 7/2021 | Shelton, IV et al. |
| 2021/0196268 A1 | 7/2021 | Shelton, IV et al. |
| 2021/0196269 A1 | 7/2021 | Shelton, IV et al. |
| 2021/0196270 A1 | 7/2021 | Shelton, IV et al. |
| 2021/0196271 A1 | 7/2021 | Shelton, IV et al. |
| 2021/0196301 A1 | 7/2021 | Shelton, IV et al. |
| 2021/0196302 A1 | 7/2021 | Shelton, IV et al. |
| 2021/0196305 A1 | 7/2021 | Strobl |
| 2021/0196306 A1 | 7/2021 | Estera et al. |
| 2021/0196307 A1 | 7/2021 | Shelton, IV |
| 2021/0196334 A1 | 7/2021 | Sarley et al. |
| 2021/0196335 A1 | 7/2021 | Messerly et al. |
| 2021/0196336 A1 | 7/2021 | Faller et al. |
| 2021/0196343 A1 | 7/2021 | Shelton, IV et al. |
| 2021/0196344 A1 | 7/2021 | Shelton, IV et al. |
| 2021/0196346 A1 | 7/2021 | Leuck et al. |
| 2021/0196349 A1 | 7/2021 | Fiebig et al. |
| 2021/0196350 A1 | 7/2021 | Fiebig et al. |
| 2021/0196351 A1 | 7/2021 | Sarley et al. |
| 2021/0196352 A1 | 7/2021 | Messerly et al. |
| 2021/0196353 A1 | 7/2021 | Gee et al. |
| 2021/0196354 A1 | 7/2021 | Shelton, IV et al. |
| 2021/0196355 A1 | 7/2021 | Shelton, IV et al. |
| 2021/0196356 A1 | 7/2021 | Shelton, IV et al. |
| 2021/0196357 A1 | 7/2021 | Shelton, IV et al. |
| 2021/0196358 A1 | 7/2021 | Shelton, IV et al. |
| 2021/0196359 A1 | 7/2021 | Shelton, IV et al. |
| 2021/0196360 A1 | 7/2021 | Shelton, IV et al. |
| 2021/0196361 A1 | 7/2021 | Shelton, IV et al. |
| 2021/0196362 A1 | 7/2021 | Shelton, IV et al. |
| 2021/0196363 A1 | 7/2021 | Shelton, IV et al. |
| 2021/0196364 A1 | 7/2021 | Shelton, IV et al. |
| 2021/0196365 A1 | 7/2021 | Shelton, IV et al. |
| 2021/0196366 A1 | 7/2021 | Shelton, IV et al. |
| 2021/0196367 A1 | 7/2021 | Salguero et al. |
| 2021/0212744 A1 | 7/2021 | Shelton, IV et al. |
| 2021/0212754 A1 | 7/2021 | Olson |
| 2021/0220036 A1 | 7/2021 | Shelton, IV et al. |
| 2021/0236195 A1 | 8/2021 | Asher et al. |
| 2021/0282804 A1 | 9/2021 | Worrell et al. |
| 2021/0393288 A1 | 12/2021 | Shelton, IV et al. |
| 2021/0393314 A1 | 12/2021 | Wiener et al. |
| 2021/0393319 A1 | 12/2021 | Shelton, IV et al. |
| 2022/0039891 A1 | 2/2022 | Stulen et al. |
| 2022/0071655 A1 | 3/2022 | Price et al. |
| 2022/0167982 A1 | 6/2022 | Shelton, IV et al. |
| 2022/0168005 A1 | 6/2022 | Aldridge et al. |
| 2022/0168039 A1 | 6/2022 | Worrell et al. |
| 2022/0226014 A1 | 7/2022 | Clauda, IV et al. |
| 2022/0304736 A1 | 9/2022 | Boudreaux |
| 2022/0313297 A1 | 10/2022 | Aldridge et al. |
| 2022/0346863 A1 | 11/2022 | Yates et al. |
| 2022/0387067 A1 | 12/2022 | Faller et al. |
| 2022/0406452 A1 | 12/2022 | Shelton, IV |
| 2023/0038162 A1 | 2/2023 | Timm et al. |
| 2023/0048996 A1 | 2/2023 | Vakharia et al. |
| 2023/0270486 A1 | 8/2023 | Wiener et al. |
| 2023/0277205 A1 | 9/2023 | Olson et al. |

FOREIGN PATENT DOCUMENTS

| | | |
|---|---|---|
| CN | 1634601 A | 7/2005 |
| CN | 1775323 A | 5/2006 |
| CN | 1922563 A | 2/2007 |
| CN | 2868227 Y | 2/2007 |
| CN | 201029899 Y | 3/2008 |
| CN | 101474081 A | 7/2009 |
| CN | 101516285 A | 8/2009 |
| CN | 101522112 A | 9/2009 |
| CN | 102100582 A | 6/2011 |
| CN | 102149312 A | 8/2011 |
| CN | 202027624 U | 11/2011 |
| CN | 102792181 A | 11/2012 |
| CN | 103281982 A | 9/2013 |
| CN | 103379853 A | 10/2013 |
| CN | 203468630 U | 3/2014 |
| CN | 104001276 A | 8/2014 |
| CN | 104013444 A | 9/2014 |
| CN | 104434298 A | 3/2015 |
| CN | 107374752 A | 11/2017 |
| DE | 3904558 A1 | 8/1990 |
| DE | 9210327 U1 | 11/1992 |
| DE | 4300307 A1 | 7/1994 |
| DE | 29623113 U1 | 10/1997 |
| DE | 20004812 U1 | 9/2000 |
| DE | 20021619 U1 | 3/2001 |
| DE | 10042606 A1 | 8/2001 |
| DE | 10201569 A1 | 7/2003 |
| DE | 102012109037 A1 | 4/2014 |
| EP | 0171967 A2 | 2/1986 |
| EP | 0336742 A2 | 10/1989 |
| EP | 0136855 B1 | 11/1989 |
| EP | 0705571 A1 | 4/1996 |
| EP | 1698289 A2 | 9/2006 |
| EP | 1862133 A1 | 12/2007 |
| EP | 1972264 A1 | 9/2008 |
| EP | 2060238 A1 | 5/2009 |
| EP | 1747761 B1 | 10/2009 |
| EP | 2131760 A1 | 12/2009 |
| EP | 1214913 B1 | 7/2010 |
| EP | 1946708 B1 | 6/2011 |
| EP | 1767164 B1 | 1/2013 |

(56) References Cited

FOREIGN PATENT DOCUMENTS

| | | |
|---|---|---|
| EP | 2578172 A2 | 4/2013 |
| EP | 2668922 A1 | 12/2013 |
| EP | 2076195 B1 | 12/2015 |
| EP | 2510891 B1 | 6/2016 |
| EP | 3476302 A2 | 5/2019 |
| EP | 3476331 A1 | 5/2019 |
| EP | 3694298 A1 | 8/2020 |
| GB | 2032221 A | 4/1980 |
| GB | 2317566 A | 4/1998 |
| JP | S50100891 A | 8/1975 |
| JP | S5968513 U | 5/1984 |
| JP | S59141938 A | 8/1984 |
| JP | S62221343 A | 9/1987 |
| JP | S62227343 A | 10/1987 |
| JP | S62292153 A | 12/1987 |
| JP | S62292154 A | 12/1987 |
| JP | S63109386 A | 5/1988 |
| JP | S63315049 A | 12/1988 |
| JP | H01151452 A | 6/1989 |
| JP | H01198540 A | 8/1989 |
| JP | H0271510 U | 5/1990 |
| JP | H02286149 A | 11/1990 |
| JP | H02292193 A | 12/1990 |
| JP | H0337061 A | 2/1991 |
| JP | H0425707 U | 2/1992 |
| JP | H0464351 A | 2/1992 |
| JP | H0430508 U | 3/1992 |
| JP | H04152942 A | 5/1992 |
| JP | H 0541716 A | 2/1993 |
| JP | H0576482 A | 3/1993 |
| JP | H0595955 A | 4/1993 |
| JP | H05115490 A | 5/1993 |
| JP | H0670938 A | 3/1994 |
| JP | H06104503 A | 4/1994 |
| JP | H0824266 A | 1/1996 |
| JP | H08229050 A | 9/1996 |
| JP | H08275951 A | 10/1996 |
| JP | H08299351 A | 11/1996 |
| JP | H08336545 A | 12/1996 |
| JP | H09130655 A | 5/1997 |
| JP | H09135553 A | 5/1997 |
| JP | H09140722 A | 6/1997 |
| JP | H105237 A | 1/1998 |
| JP | 10127654 A | 5/1998 |
| JP | H10295700 A | 11/1998 |
| JP | H11128238 A | 5/1999 |
| JP | H11169381 A | 6/1999 |
| JP | 2000210299 A | 8/2000 |
| JP | 2000271142 A | 10/2000 |
| JP | 2000271145 A | 10/2000 |
| JP | 2000287987 A | 10/2000 |
| JP | 2001029353 A | 2/2001 |
| JP | 2002059380 A | 2/2002 |
| JP | 2002186901 A | 7/2002 |
| JP | 2002263579 A | 9/2002 |
| JP | 2002330977 A | 11/2002 |
| JP | 2003000612 A | 1/2003 |
| JP | 2003010201 A | 1/2003 |
| JP | 2003116870 A | 4/2003 |
| JP | 2003126104 A | 5/2003 |
| JP | 2003126110 A | 5/2003 |
| JP | 2003153919 A | 5/2003 |
| JP | 2003339730 A | 12/2003 |
| JP | 2004129871 A | 4/2004 |
| JP | 2004147701 A | 5/2004 |
| JP | 2005003496 A | 1/2005 |
| JP | 2005027026 A | 1/2005 |
| JP | 2005074088 A | 3/2005 |
| JP | 2005337119 A | 12/2005 |
| JP | 2006068396 A | 3/2006 |
| JP | 2006081664 A | 3/2006 |
| JP | 2006114072 A | 4/2006 |
| JP | 2006217716 A | 8/2006 |
| JP | 2006288431 A | 10/2006 |
| JP | 2007037568 A | 2/2007 |
| JP | 200801876 A | 1/2008 |
| JP | 200833644 A | 2/2008 |
| JP | 2008188160 A | 8/2008 |
| JP | D1339835 S | 8/2008 |
| JP | 2010009686 A | 1/2010 |
| JP | 2010121865 A | 6/2010 |
| JP | 2012071186 A | 4/2012 |
| JP | 2012223582 A | 11/2012 |
| JP | 2012235658 A | 11/2012 |
| JP | 2013126430 A | 6/2013 |
| KR | 100789356 B1 | 12/2007 |
| KR | 101298237 B1 | 8/2013 |
| RU | 2154437 C1 | 8/2000 |
| RU | 22035 U1 | 3/2002 |
| RU | 2201169 C2 | 3/2003 |
| RU | 2405603 C1 | 12/2010 |
| RU | 2013119977 A | 11/2014 |
| SU | 850068 A1 | 7/1981 |
| WO | WO-8103272 A1 | 11/1981 |
| WO | WO-9308757 A1 | 5/1993 |
| WO | WO-9314708 A1 | 8/1993 |
| WO | WO-9421183 A1 | 9/1994 |
| WO | WO-9424949 A1 | 11/1994 |
| WO | WO-9639086 A1 | 12/1996 |
| WO | WO-9712557 A1 | 4/1997 |
| WO | WO-9800069 A1 | 1/1998 |
| WO | WO-9840015 A2 | 9/1998 |
| WO | WO-9920213 A1 | 4/1999 |
| WO | WO-9923960 A1 | 5/1999 |
| WO | WO-0024330 A1 | 5/2000 |
| WO | WO-0064358 A2 | 11/2000 |
| WO | WO-0128444 A1 | 4/2001 |
| WO | WO-0167970 A1 | 9/2001 |
| WO | WO-0172251 A1 | 10/2001 |
| WO | WO-0195810 A2 | 12/2001 |
| WO | WO-02080793 A1 | 10/2002 |
| WO | WO-03095028 A1 | 11/2003 |
| WO | WO-2004037095 A2 | 5/2004 |
| WO | WO-2004078051 A2 | 9/2004 |
| WO | WO-2004098426 A1 | 11/2004 |
| WO | WO-2006091494 A1 | 8/2006 |
| WO | WO-2007008710 A2 | 1/2007 |
| WO | WO-2008118709 A1 | 10/2008 |
| WO | WO-2008130793 A1 | 10/2008 |
| WO | WO-2010027109 A1 | 3/2010 |
| WO | WO-2010104755 A1 | 9/2010 |
| WO | WO-2011008672 A2 | 1/2011 |
| WO | WO-2011044343 A2 | 4/2011 |
| WO | WO-2011052939 A2 | 5/2011 |
| WO | WO-2011060031 A1 | 5/2011 |
| WO | WO-2011092464 A1 | 8/2011 |
| WO | WO-2012044606 A2 | 4/2012 |
| WO | WO-2012061722 A2 | 5/2012 |
| WO | WO-2012088535 A1 | 6/2012 |
| WO | WO-2012150567 A1 | 11/2012 |
| WO | WO-2016130844 A1 | 8/2016 |
| WO | WO-2019130090 A1 | 7/2019 |
| WO | WO-2019130113 A1 | 7/2019 |

OTHER PUBLICATIONS

Wright, et al., "Time-Temperature Equivalence of Heat-Induced Changes in Cells and Proteins," Feb. 1998. ASME Journal of Biomechanical Engineering, vol. 120, pp. 22-26.

Covidien Brochure, LigaSure Impact™ Instrument LF4318, dated Feb. 2013 (3 pages).

Covidien Brochure, LigaSure Atlas ™ Hand Switching Instruments, dated Dec. 2008 (2 pages).

Covidien Brochure, The LigaSure ™ 5 mm Blunt Tip Sealer/Divider Family, dated Apr. 2013 (2 pages).

Jang, J. et al. "Neuro-fuzzy and Soft Computing." Prentice Hall, 1997, pp. 13-89, 199-293, 335-393, 453-496, 535-549.

Sullivan, "Optimal Choice for Number of Strands in a Litz-Wire Transformer Winding," IEEE Transactions on Power Electronics, vol. 14, No. 2, Mar. 1999, pp. 283-291.

Weir, C.E., "Rate of shrinkage of tendon collagen—heat, entropy and free energy of activation of the shrinkage of untreated tendon.

(56) References Cited

OTHER PUBLICATIONS

Effect of acid salt, pickle, and tannage on the activation of tendon collagen." Journal of the American Leather Chemists Association, 44, pp. 108-140 (1949).
Wall et al., "Thermal modification of collagen," J Shoulder Elbow Surg, No. 8, pp. 339-344 (Jul./Aug. 1999).
Chen et al., "Heat-Induced Changes in the Mechanics of a Collagenous Tissue: Isothermal Free Shrinkage," Transactions of the ASME, vol. 119, pp. 372-378 (Nov. 1997).
Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).
Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).
Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).
Lee et al., "A multi-sample denaturation temperature tester for collagenous biomaterials," Med. Eng. Phy., vol. 17, No. 2, pp. 115-121 (Mar. 1995).
Moran et al., "Thermally Induced Shrinkage of Joint Capsule," Clinical Orthopaedics and Related Research, No. 281, pp. 248-255 (Dec. 2000).
Wells et al., "Altered Mechanical Behavior of Epicardium Under Isothermal Biaxial Loading," Transactions of the ASME, Journal of Biomedical Engineering, vol. 126, pp. 492-497 (Aug. 2004).
Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).
Humphrey, J.D., "Continuum Thermomechanics and the Clinical Treatment of Disease and Injury," Appl. Mech. Rev., vol. 56, No. 2 pp. 231-260 (Mar. 2003).
National Semiconductors Temperature Sensor Handbook—http://www.national.com/appinfo/tempsensors/files/temphb.pdf; accessed online: Apr. 1, 2011.
Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=MI&sp=1 . . . , accessed Aug. 25, 2009.
Douglas, S.C. "Introduction to Adaptive Filter". Digital Signal Processing Handbook. Ed. Vijay K. Madisetti and Douglas B. Williams. Boca Raton: CRC Press LLC, 1999.
Chen et al., "Heat-induced changes in the mechanics of a collagenous tissue: pseudoelastic behavior at 37° C.," Journal of Biomechanics, 31, pp. 211-216 (1998).
Technology Overview, printed from www.harmonicscalpel.com, Internet site, website accessed on Jun. 13, 2007, (3 pages).
Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.
AST Products, Inc., "Principles of Video Contact Angle Analysis," 20 pages, (2006).
Lim et al., "A Review of Mechanism Used in Laparoscopic Surgical Instruments," Mechanism and Machine Theory, vol. 38, pp. 1133-1147, (2003).
Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).
Incropera et al., Fundamentals of Heat and Mass Transfer, Wiley, New York (1990). (Book—not attached).
F. A. Duck, "Optical Properties of Tissue Including Ultraviolet and Infrared Radiation," pp. 43-71 in Physical Properties of Tissue (1990).
http://www.apicalinstr.com/generators.htm.
http://www.dotmed.com/listing/electrosurical-unit/ethicon/ultracision-g110-/1466724.
http:/www.ethicon.com/gb-en/healthcare-professionals/products/energy-devices/capital//ge . . . .
http://www.medicalexpo.com/medical-manufacturer/electrosurgical-generator-6951.html.
http://www.megadyne.com/es_generator.php.
http://www.valleylab.com/product/es/generators/index.html.
Graff, K.F., "Elastic Wave Propagation in a Curved Sonic Transmission Line," IEEE Transactions on Sonics and Ultrasonics, SU-17(1), 1-6 (1970).
Makarov, S. N., Ochmann, M., Desinger, K., "The longitudinal vibration response of a curved fiber used for laser ultrasound surgical therapy," Journal of the Acoustical Society of America 102, 1191-1199 (1997).
Walsh, S. J., White, R. G., "Vibrational Power Transmission in Curved Beams," Journal of Sound and Vibration, 233(3), 455-488 (2000).
Covidien 501(k) Summary Sonicision, dated Feb. 24, 2011 (7 pages).
Morley, L. S. D., "Elastic Waves in a Naturally Curved Rod," Quarterly Journal of Mechanics and Applied Mathematics, 14: 155-172 (1961).
Gooch et al., "Recommended Infection-Control Practices for Dentistry, 1993," Published: May 28, 1993; [retrieved on Aug. 23, 2008]. Retrieved from the internet: URL: http//wonder.cdc.gov/wonder/prevguid/p0000191/p0000191.asp (15 pages).
Sullivan, "Cost-Constrained Selection of Strand Diameter and Number in a Litz-Wire Transformer Winding," IEEE Transactions on Power Electronics, vol. 16, No. 2, Mar. 2001, pp. 281-288.
Orr et al., "Overview of Bioheat Transfer," pp. 367-384 in Optical-Thermal Response of Laser-Irradiated Tissue, A. J. Welch and M. J. C. van Gemert, eds., Plenum, New York (1995).
Fowler, K.R., "A Programmable, Arbitrary Waveform Electrosurgical Device," IEEE Engineering in Medicine and Biology Society 10th Annual International Conference, pp. 1324, 1325 (1988).
Lacourse, J.R.; Vogt, M.C.; Miller, W.T., III; Selikowitz, S.M., "Spectral Analysis Interpretation of Electrosurgical Generator Nerve and Muscle Stimulation," IEEE Transactions on Biomedical Engineering, vol. 35, No. 7, pp. 505-509, Jul. 1988.
Campbell et al., "Thermal Imaging in Surgery," p. 19-3, in Medical Infrared Imaging, N. A. Diakides and J. D. Bronzino, Eds. (2008).
Gerhard, Glen C., "Surgical Electrotechnology: Quo Vadis?," IEEE Transactions on Biomedical Engineering, vol. BME-31, No. 12, pp. 787-792, Dec. 1984.
http://www.4-traders.com/Johnson-Johnson-4832/news/Johnson-Johnson-Ethicon-E . . . .
Henriques. F.C., "Studies in thermal injury V. The predictability and the significance of thermally induced rate processes leading to irreversible epidermal injury." Archives of Pathology, 434, pp. 489-502 (1947).
Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).
Chen et al., "Heat-Induced Changes in the Mechanics of a Collagenous Tissue: Isothermal, Isotonic Shrinkage," Transactions of the ASME, vol. 120, pp. 382-388 (Jun. 1998).
Kurt Gieck & Reiner Gieck, *Engineering Formulas* § Z.7 (7th ed. 1997).
https://www.kjmagnetics.com/fieldcalculator.asp, retrieved Jul. 11, 2016, backdated to Nov. 11, 2011 via https://web.archive.org/web/20111116164447/http://www.kjmagnetics.com/fieldcalculator.asp.
Leonard I. Malis, M.D., "The Value of Irrigation During Bipolar Coagulation," 1989.
Covidien Brochure, The LigaSure Precise™ Instrument, dated Mar. 2011 (2 pages).
Glaser and Subak-Sharpe, Integrated Circuit Engineering, Addison-Wesley Publishing, Reading, MA (1979). (book—not attached).
Erbe Electrosurgery VIO® 200 S, (2012), p. 7, 12 pages, accessed Mar. 31, 2014 at http://www.erbe-med.com/erbe/media/Marketing materialien/85140170 ERBE EN VIO 200 S D027541.
Hörmann et al., "Reversible and irreversible denaturation of collagen fibers." Biochemistry, 10, pp. 932-937 (1971).

(56) References Cited

OTHER PUBLICATIONS

Dean, D.A., "Electrical Impedance Spectroscopy Study of Biological Tissues," J. Electrostat, 66(3-4), Mar. 2008, pp. 165-177. Accessed Apr. 10, 2018: https://www.ncbi.nlm.nih.gov/pmc/articles/PMC2597841/.
Moraleda et al., A Temperature Sensor Based on a Polymer Optical Fiber Macro-Bend, Sensors 2013, 13, 13076-13089, doi: 10.3390/s131013076, ISSN 1424-8220.
IEEE Std 802.Mar. 2012 (Revision of IEEE Std 802.Mar. 2008, published Dec. 28, 2012.
"ATM-MPLS Network Interworking Version 2.0, af-aic-0178.001" ATM Standard, The ATM Forum Technical Committee, published Aug. 2003.
Missinne, et al. "Stretchable Optical Waveguides," vol. 22, No. 4, Feb. 18, 2014, pp. 4168-4179 (12 pages).

* cited by examiner

USER INTERFACE FOR SURGICAL INSTRUMENT WITH COMBINATION ENERGY MODALITY END-EFFECTOR

CROSS-REFERENCE TO RELATED APPLICATION

The present application claims priority under 35 U.S.C. § 119(e) to U.S. Provisional Patent Application Ser. No. 62/955,294, titled USER INTERFACE FOR SURGICAL INSTRUMENT WITH COMBINATION ENERGY MODALITY END-EFFECTOR, filed Dec. 30, 2019, the disclosure of which is herein incorporated by reference in its entirety.

TECHNICAL FIELD

The present disclosure generally relates to user interfaces for surgical instruments with end-effectors adapted and configured to operate with multiple energy modalities to enable tissue sealing and cutting employing simultaneously, independently, or sequentially applied energy modalities. More particularly, the present disclosure relates to user interfaces for surgical instruments with end-effectors adapted and configured to operate with surgical instruments that employ combined ultrasonic and electrosurgical systems, such as monopolar or bipolar radio frequency (RF), to enable tissue sealing and cutting employing simultaneously, independently, or sequentially applied ultrasonic and electrosurgical energy modalities. The energy modalities may be applied based on tissue parameters or other algorithms. The end-effectors may be adapted and configured to couple to hand held or robotic surgical systems.

BACKGROUND

Ultrasonic surgical instruments employing ultrasonic energy modalities are finding increasingly widespread applications in surgical procedures by virtue of the unique performance characteristics of such instruments. Depending upon specific instrument configurations and operational parameters, ultrasonic surgical instruments can provide substantially simultaneous cutting of tissue and hemostasis by coagulation, desirably minimizing patient trauma. The cutting action is typically realized by an end-effector, or blade tip, at the distal end of the instrument, which transmits ultrasonic energy to tissue brought into contact with the end-effector. An ultrasonic end-effector may comprise an ultrasonic blade, a clamp arm, and a pad, among other components. Ultrasonic instruments of this nature can be configured for open surgical use, minimally invasive procedures such as laparoscopic procedures, for example, or non-invasive procedures such as endoscopic surgical procedures, for example. The instruments may be controlled by a surgeon using a hand held instrument or a robot.

Some surgical instruments utilize ultrasonic energy for both precise cutting and controlled coagulation. Ultrasonic energy cuts and coagulates by vibrating a blade in contact with tissue. Vibrating at high frequencies (e.g., 55,500 times per second), the ultrasonic blade denatures protein in the tissue to form a sticky coagulum. Pressure exerted on tissue with the blade surface collapses blood vessels and allows the coagulum to form a hemostatic seal. The precision of cutting and coagulation is controlled by the surgeon's technique and adjusting the power level, blade edge, tissue traction, and blade pressure.

Electrosurgical devices for applying electrical energy modalities to tissue to treat, seal, cut, and/or destroy tissue also are finding increasingly widespread applications in surgical procedures. An electrosurgical device typically includes an instrument having a distally-mounted end-effector comprising one or more than one electrode. The end-effector can be positioned against the tissue such that electrical current is introduced into the tissue.

Electrosurgical devices can be configured for bipolar or monopolar operation. During bipolar operation, current is introduced though a first electrode (e.g., active electrode) into the tissue and returned from the tissue through a second electrode (e.g., return electrode). During monopolar operation, current is introduced into the tissue by an active electrode of the end-effector and returned through a return electrode such as a grounding pad, for example, separately coupled to the body of a patient. Heat generated by the current flowing through the tissue may form hemostatic seals within the tissue and/or between tissues and thus may be particularly useful for sealing blood vessels, for example. The end-effector of an electrosurgical device also may include a cutting member that is movable relative to the tissue and the electrodes to transect the tissue. Electrosurgical end-effectors may be adapted and configured to couple to hand held instruments as well as robotic instruments.

Electrical energy applied by an electrosurgical device can be transmitted to the instrument by a generator in communication with the hand piece. The electrical energy may be in the form of radio frequency ("RF") energy. RF energy is a form of electrical energy that may be in the frequency range of 200 kilohertz (kHz) to 1 megahertz (MHz). In application, an electrosurgical device can transmit low frequency RF energy through tissue, which causes ionic agitation, or friction, in effect resistive heating, thereby increasing the temperature of the tissue. Because a sharp boundary is created between the affected tissue and the surrounding tissue, surgeons can operate with a high level of precision and control, without sacrificing un-targeted adjacent tissue. The low operating temperatures of RF energy is useful for removing, shrinking, or sculpting soft tissue while simultaneously sealing blood vessels. RF energy works particularly well on connective tissue, which is primarily comprised of collagen and shrinks when contacted by heat.

The RF energy may be in a frequency range described in EN 60601-2-2:2009+A11:2011, Definition 201.3.218—HIGH FREQUENCY. For example, the frequency in monopolar RF applications may be typically restricted to less than 5 MHz. However, in bipolar RF energy applications, the frequency can be almost anything. Frequencies above 200 kHz can be typically used for monopolar applications in order to avoid the unwanted stimulation of nerves and muscles that would result from the use of low frequency current. Lower frequencies may be used for bipolar applications if the risk analysis shows the possibility of neuromuscular stimulation has been mitigated to an acceptable level. Normally, frequencies above 5 MHz are not used in order to minimize the problems associated with high frequency leakage currents. Higher frequencies may, however, be used in the case of bipolar applications. It is generally recognized that 10 mA is the lower threshold of thermal effects on tissue.

A challenge of utilizing these medical devices is the inability to control and customize single or multiple energy modalities depending on the type of tissue being treated. It would be desirable to provide end-effectors that overcome some of the deficiencies of current instruments and improve the quality of tissue treatment, sealing, or cutting or combinations thereof. The combination energy modality end-effectors described herein overcome those deficiencies and improve the quality of tissue treatment, sealing, or cutting or combinations thereof.

SUMMARY

In one aspect, an apparatus is provided for dissecting and coagulating tissue. The apparatus comprises a surgical instrument comprising an end-effector adapted and configured to deliver a plurality of energy modalities to tissue at a distal end thereof. The energy modalities may be applied simultaneously, independently, or sequentially. A generator is electrically coupled to the surgical instrument and is configured to supply a plurality of energy modalities to the end-effector. In one aspect, the generator is configured to supply electrosurgical energy (e.g., monopolar or bipolar radio frequency (RF) energy) and ultrasonic energy to the end-effector to allow the end-effector to interact with the tissue. The energy modalities may be supplied to the end-effector by a single generator or multiple generators.

In one aspect, the present disclosure provides a surgical instrument. The surgical instrument comprises a housing, an end-effector, and a user interface. The end-effector comprises a clamp arm and an ultrasonic blade configured to couple to an ultrasonic transducer and to a pole of an electrical generator. The clamp arm comprises a clamp jaw pivotally movable about a pivot point and an electrode defining a surface configured to contact tissue and apply electrical energy to the tissue in contact therewith. The electrode is configured to couple to an opposite pole of the electrical generator. The user interface comprises a first activation button switch to activate a first energy source and a second button switch to select an energy mode for the activation button switch.

In addition to the foregoing, various other method and/or system and/or program product aspects are set forth and described in the teachings such as text (e.g., claims and/or detailed description) and/or drawings of the present disclosure.

The foregoing is a summary and thus may contain simplifications, generalizations, inclusions, and/or omissions of detail; consequently, those skilled in the art will appreciate that the summary is illustrative only and is NOT intended to be in any way limiting. Other aspects, features, and advantages of the devices and/or processes and/or other subject matter described herein will become apparent in the teachings set forth herein.

In one or more various aspects, related systems include but are not limited to circuitry and/or programming for effecting herein-referenced method aspects; the circuitry and/or programming can be virtually any combination of hardware, software, and/or firmware configured to affect the herein-referenced method aspects depending upon the design choices of the system designer. In addition to the foregoing, various other method and/or system aspects are set forth and described in the teachings such as text (e.g., claims and/or detailed description) and/or drawings of the present disclosure.

Further, it is understood that any one or more of the following-described forms, expressions of forms, examples, can be combined with any one or more of the other following-described forms, expressions of forms, and examples.

The foregoing summary is illustrative only and is not intended to be in any way limiting. In addition to the illustrative aspects, embodiments, and features described above, further aspects, embodiments, and features will become apparent by reference to the drawings and the following detailed description.

FIGURES

The novel features of the described forms are set forth with particularity in the appended claims. The described forms, however, both as to organization and methods of operation, may be best understood by reference to the following description, taken in conjunction with the accompanying drawings in which:

FIG. 2A shows a first mode selection option;

Figure 2A:
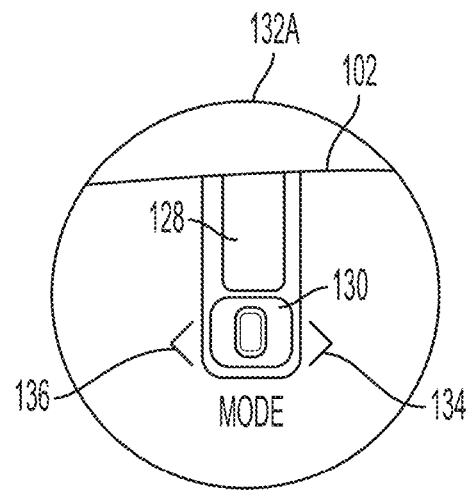
FIGS. 2A-2C illustrate three options for selecting the various operating modes of the surgical device 100, according to at least one aspect of the present disclosure, where.
Figure 2B:
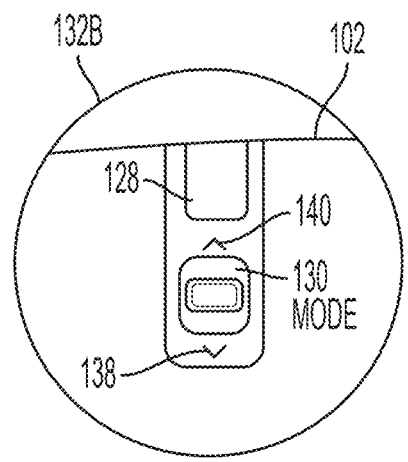

FIG. 2B sows a second mode selection option; and

Figure 2C:
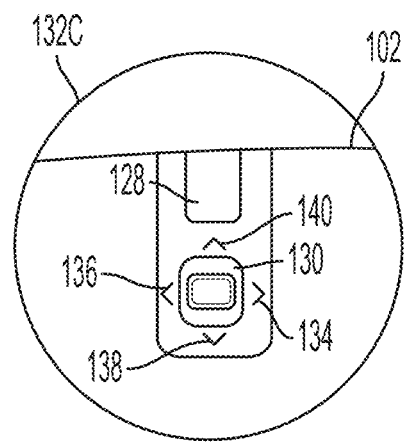

FIG. 2C shows a third mode selection option.

Figure 3:
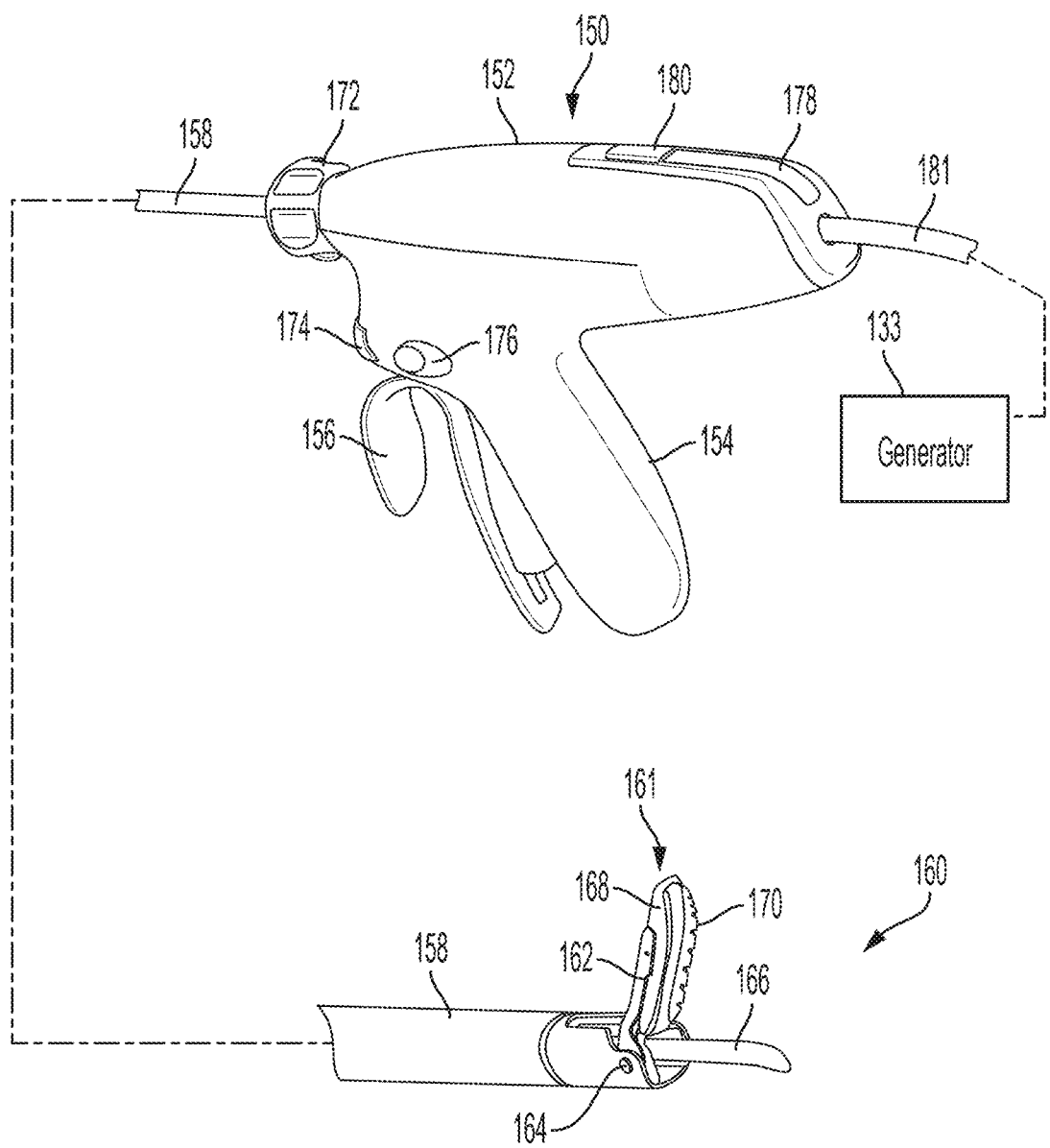

FIG. 3 illustrates a surgical device comprising a mode selection button switch on the back of the device, according to at least one aspect of the present disclosure.

Figure 4A:
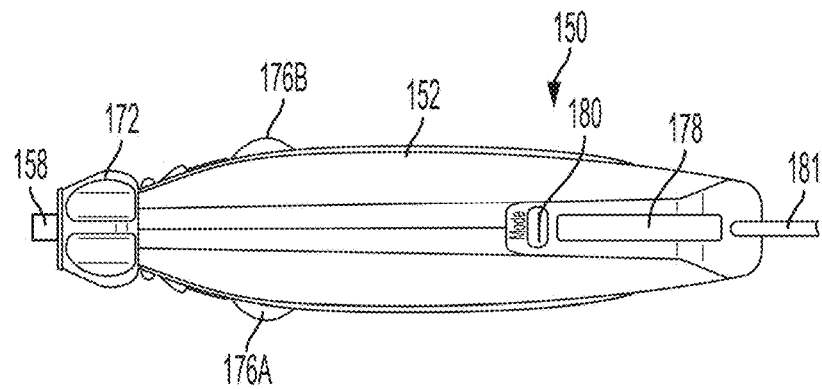

FIG. 4A shows a first mode selection option where as the mode button switch is pressed to toggle through various modes a visual indicator indicates the selected mode.

Figure 4B:
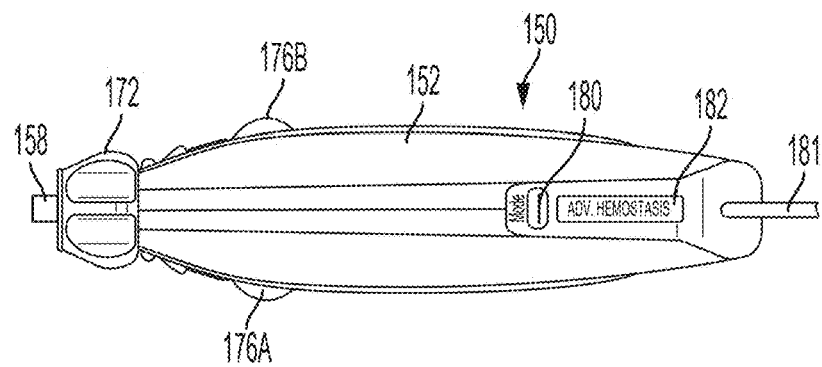

FIG. 4B shows a second mode selection option where as the mode button switch is pressed to toggle through various modes a visual indicator indicates the selected mode.

Figure 4C:
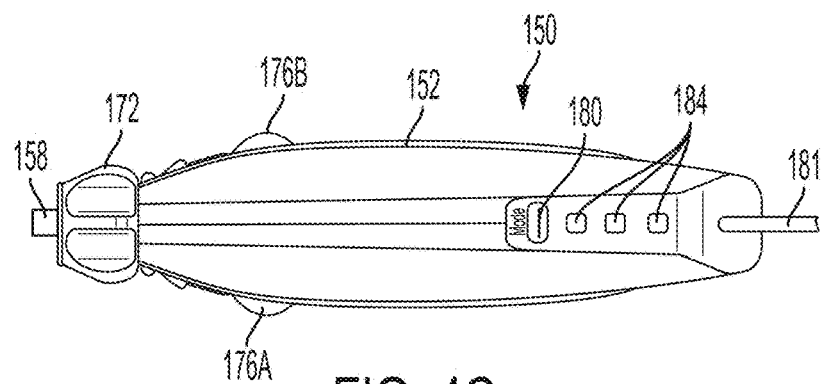

FIG. 4C shows a third mode selection option where as the mode button switch is pressed to toggle through various modes a visual indicator indicates the selected mode.

Figure 4D:
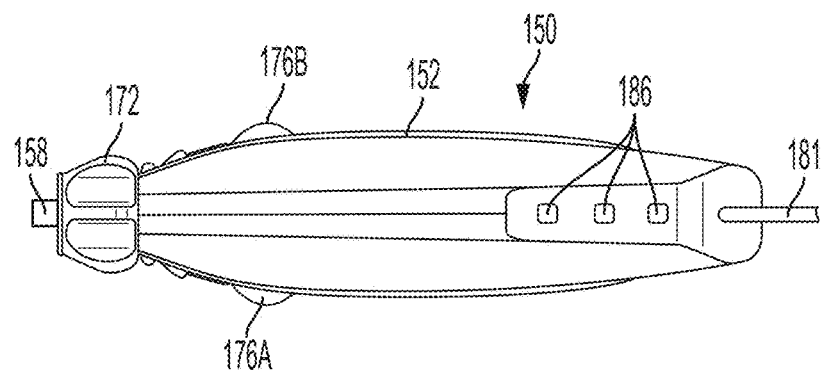

FIG. 4D shows a fourth mode selection option where as a visual indicator in the form of labeled button switches is pressed to select a mode, a visual indicator indicates the selected mode.

Figure 5:
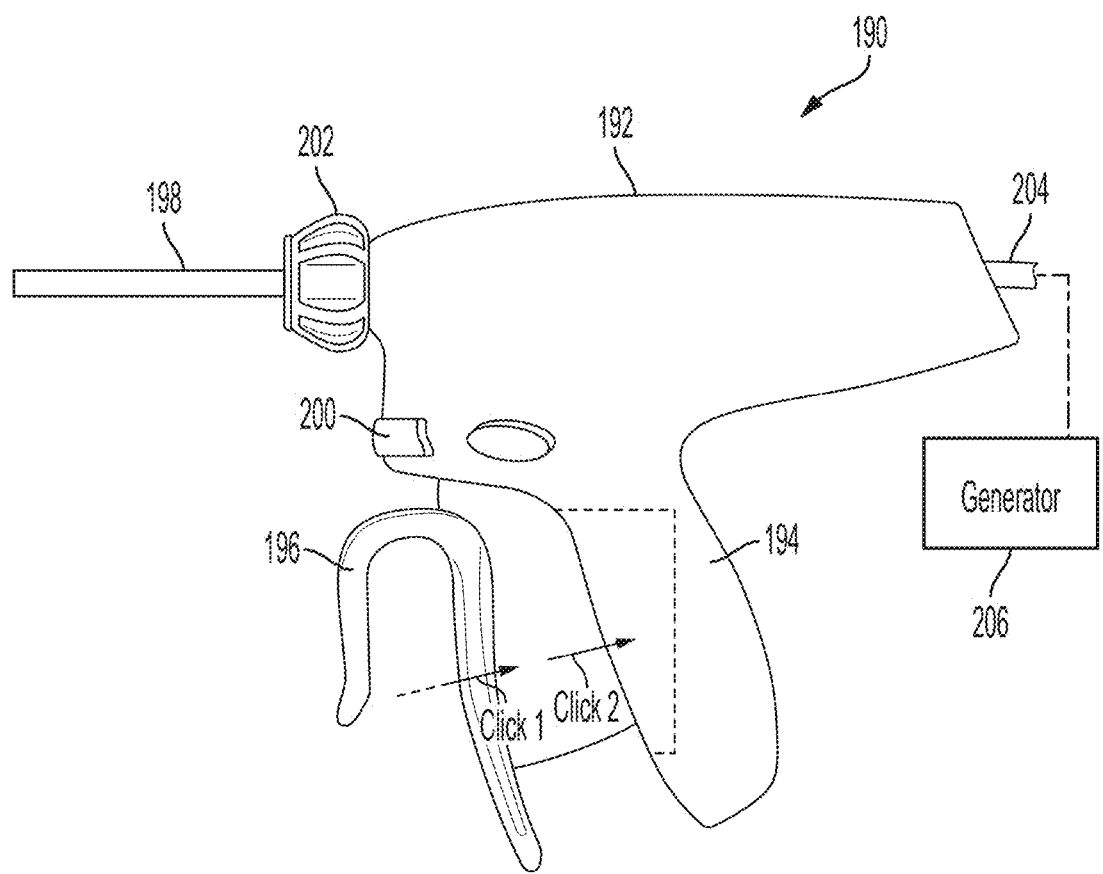

FIG. 5 illustrates a surgical device comprising a trigger activation mechanism, according to at least one aspect of the present disclosure.

Figure 6A:
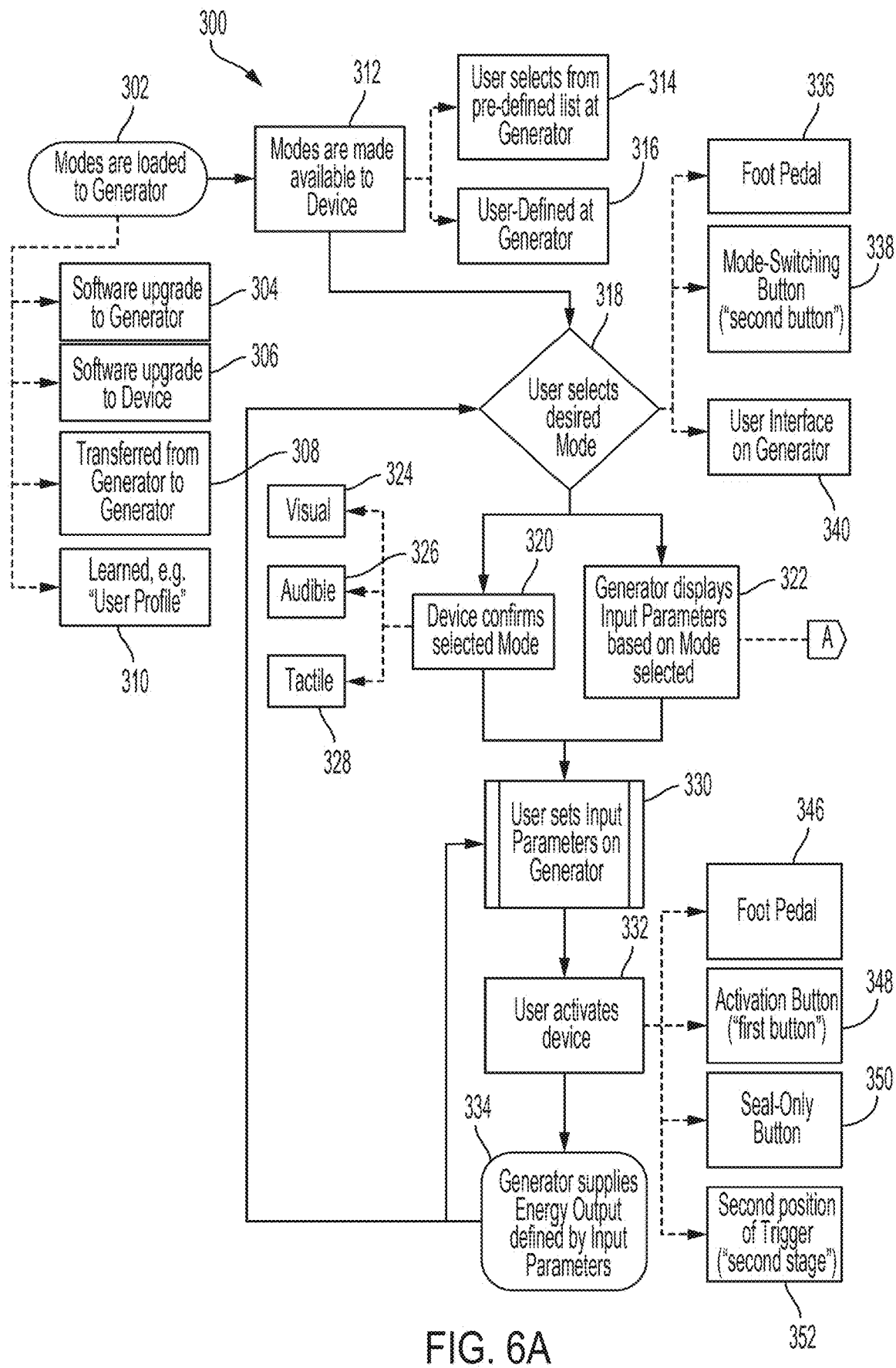
Figure 6B:
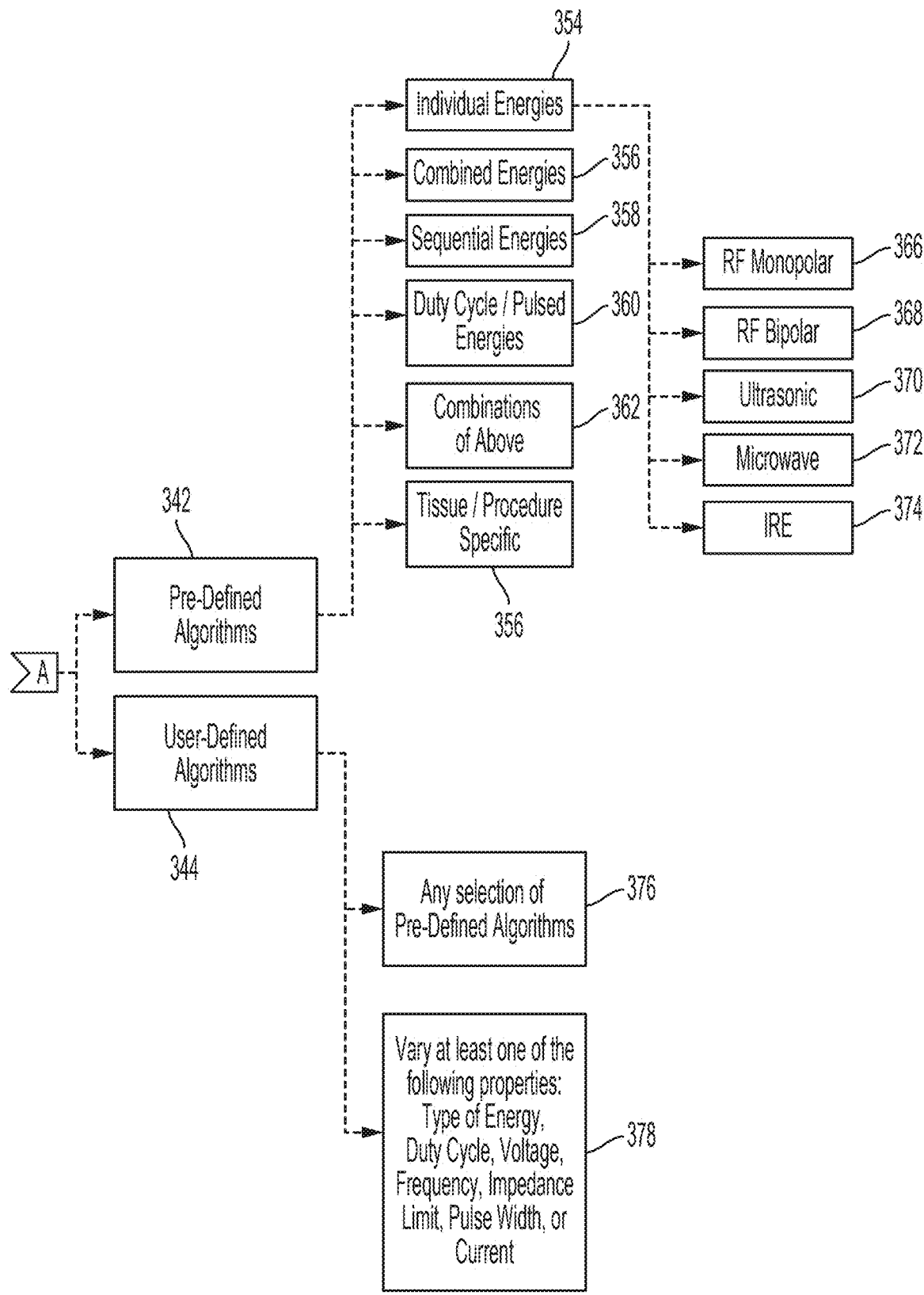

FIGS. 6A-6B illustrates a framework for energy mode selection and switching for a surgical device, according to at least one aspect of the present disclosure.

Figure 7:
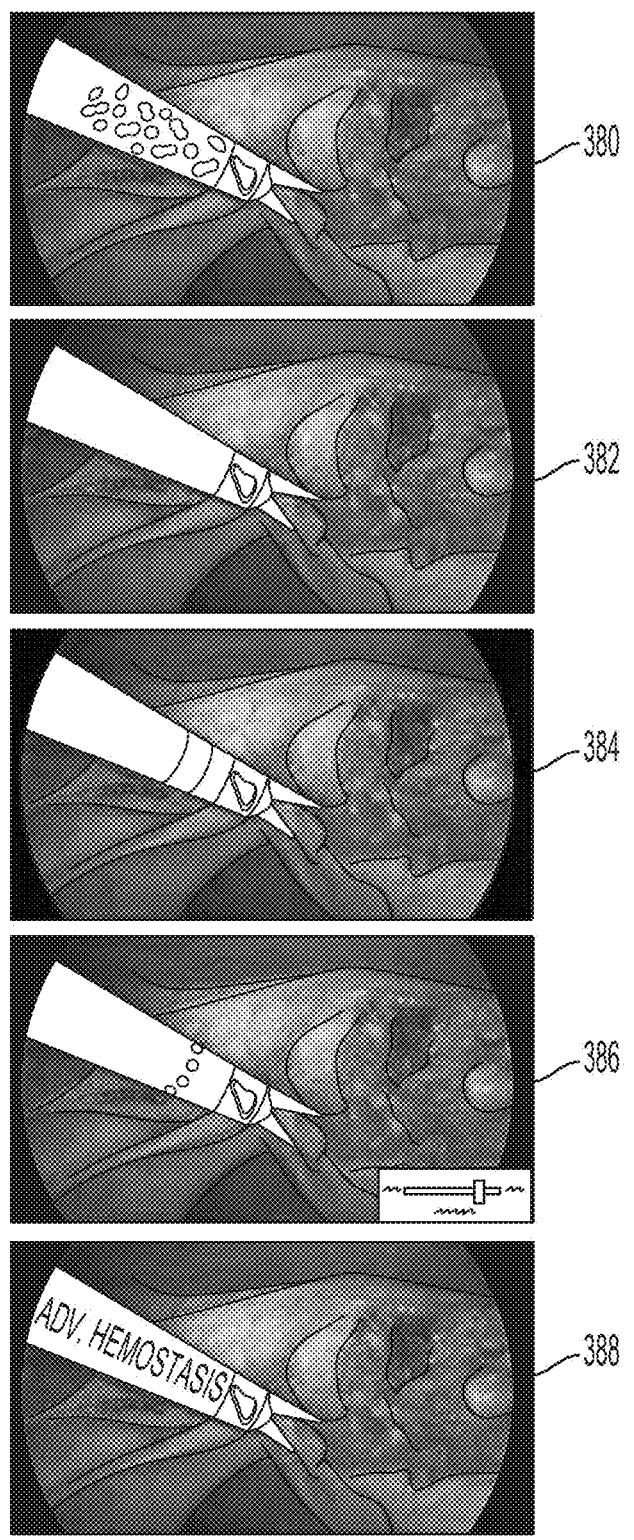

FIG. 7 illustrates various shaft light indicators with optional digital overlay disposed on a distal end of the shaft near the end-effector to indicate the operating mode the surgical device, according to at least one aspect of the present disclosure.

Figure 8:
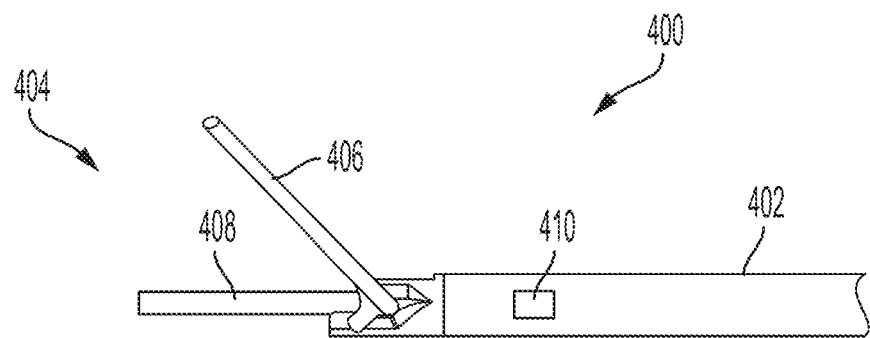

FIG. 8 illustrates a surgical device comprising a physical shaft light indicator (e.g., a visual indicator) disposed on a distal end of a shaft coupled to an end-effector, according to at least one aspect of the present disclosure.

Figure 9:
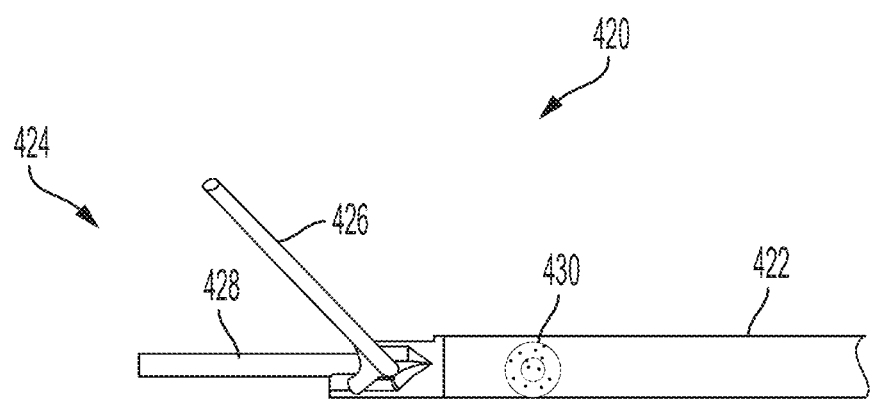

FIG. 9 illustrates a surgical device comprising a physical shaft light indicator (e.g., a visual indicator) disposed on a distal end of a shaft coupled to an end-effector, according to at least one aspect of the present disclosure.

Figure 10:
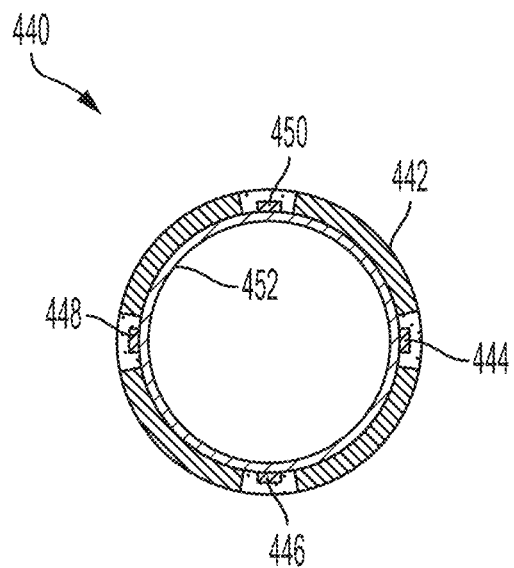

FIG. 10 is a cross sectional schematic layout view of four LED physical shaft light indicators (e.g., visual indicators) disposed at the distal end of a shaft of a surgical device, according to at least one aspect of the present disclosure.

Figure 11:
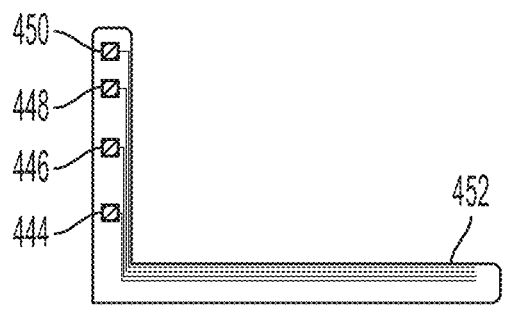

FIG. 11 is a flexible circuit with four embedded LED physical shaft light indicators (e.g., visual indicators) attached thereto, according to at least one aspect of the present disclosure.

Figure 12:
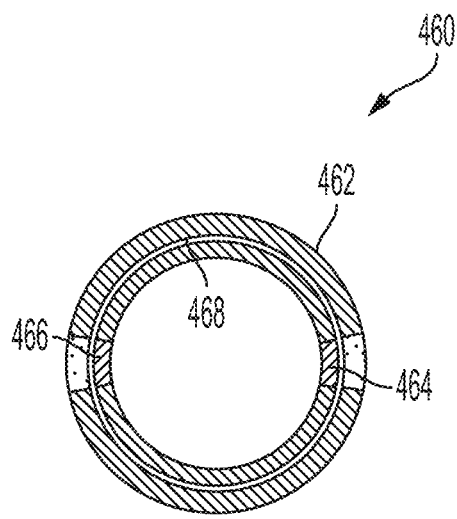

FIG. 12 is a cross sectional schematic layout view of two LEDs physical shaft light indicators with a light pipe (e.g., a visual indicator) or tube with a co-molded light pipe disposed at the distal end of a shaft of a surgical device, according to at least one aspect of the present disclosure.

Figure 13:
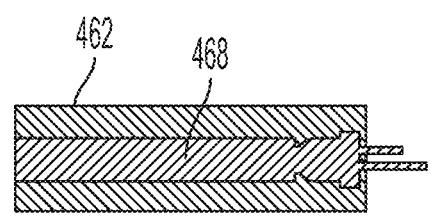

FIG. 13 is a light pipe or tube with co-molded light pipe (e.g., a visual indicator) for use with the surgical device shown in FIG. 12, according to at least one aspect of the present disclosure.

Figure 14:
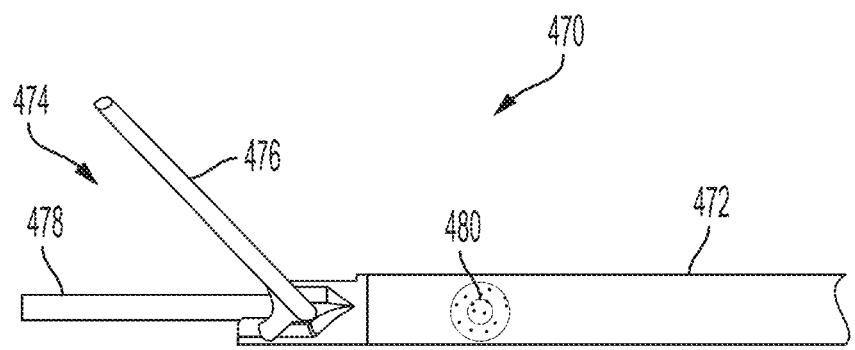
Figure 15:
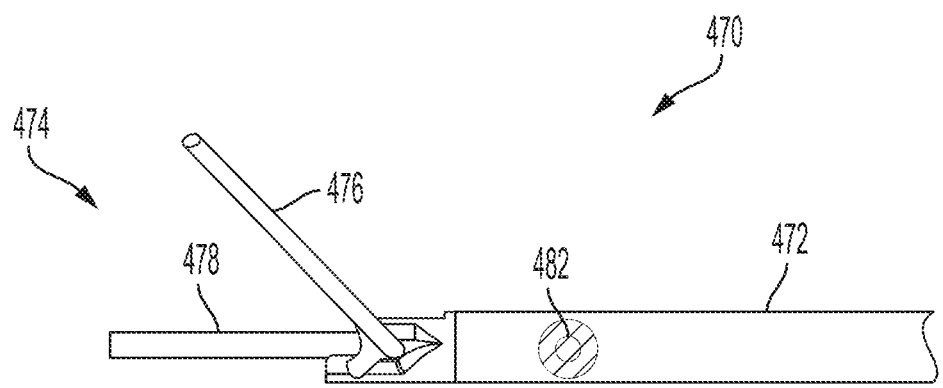

FIGS. 14-15 illustrate a surgical device comprising a single physical shaft light indicator (e.g., visual indicators) comprising multi-color LEDS disposed on a distal end of a shaft coupled to an end-effector, according to at least one aspect of the present disclosure.

Figure 16:
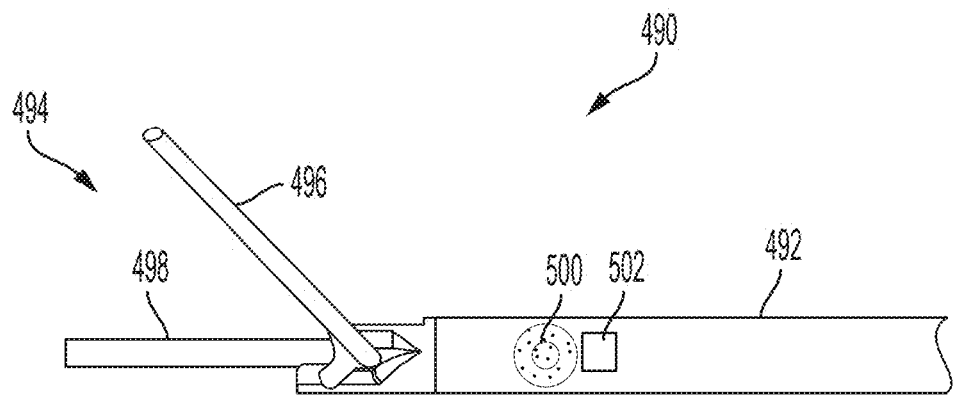
Figure 17:
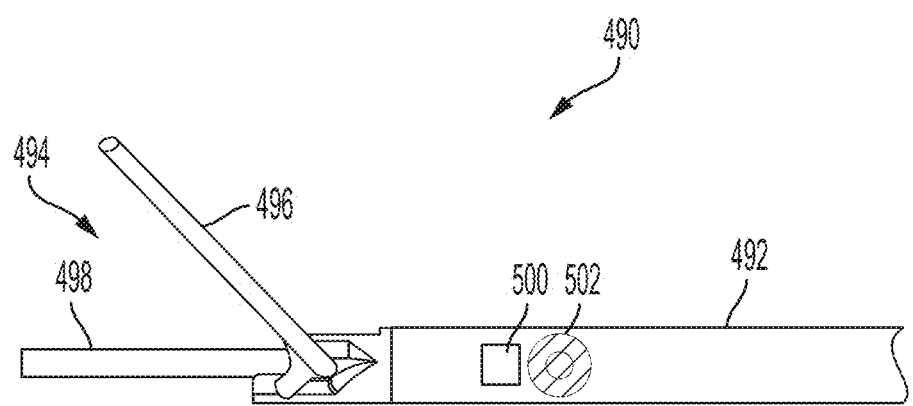

FIGS. 16-17 illustrate a surgical device comprising physical shaft light indicators (e.g., visual indicators) comprising multiple staggered single color LEDS disposed on a distal end of a shaft coupled to an end-effector, according to at least one aspect of the present disclosure.

Figure 18:
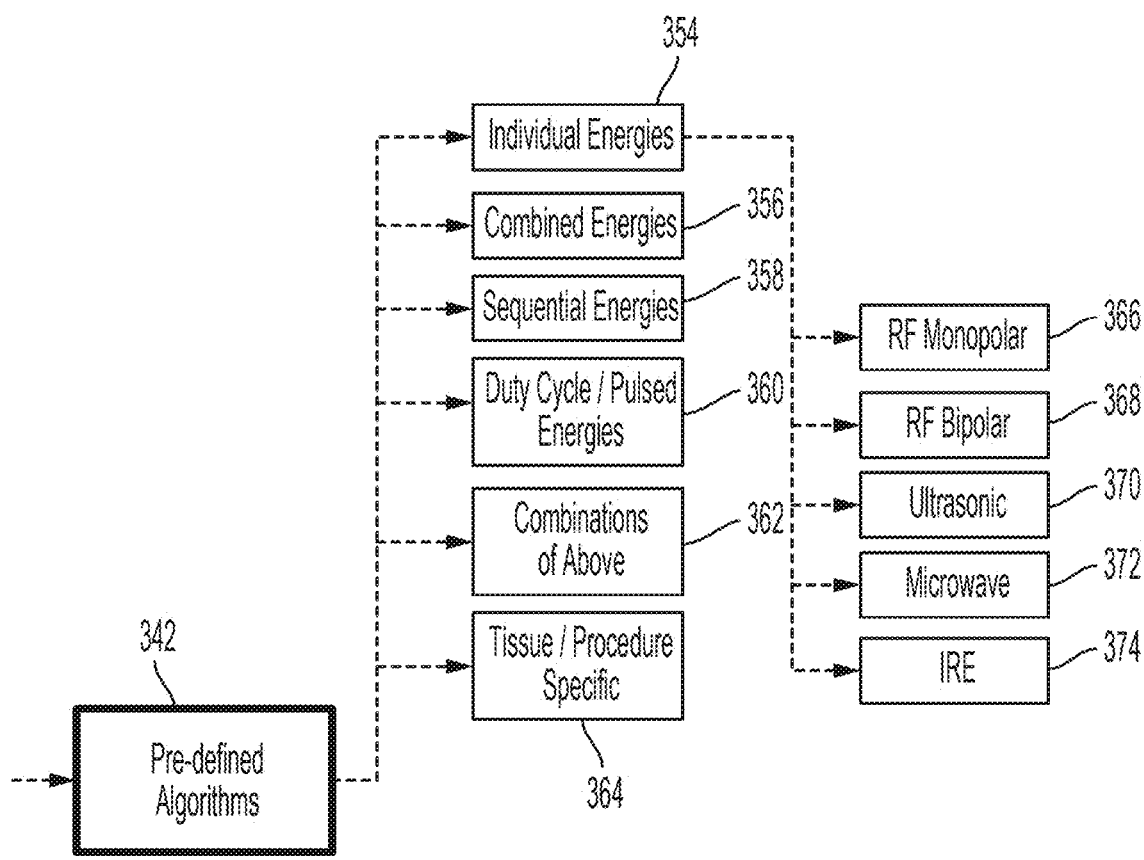

FIG. 18 is diagram of a pre-defined algorithm, according to at least one aspect of the present disclosure.

Figure 19:
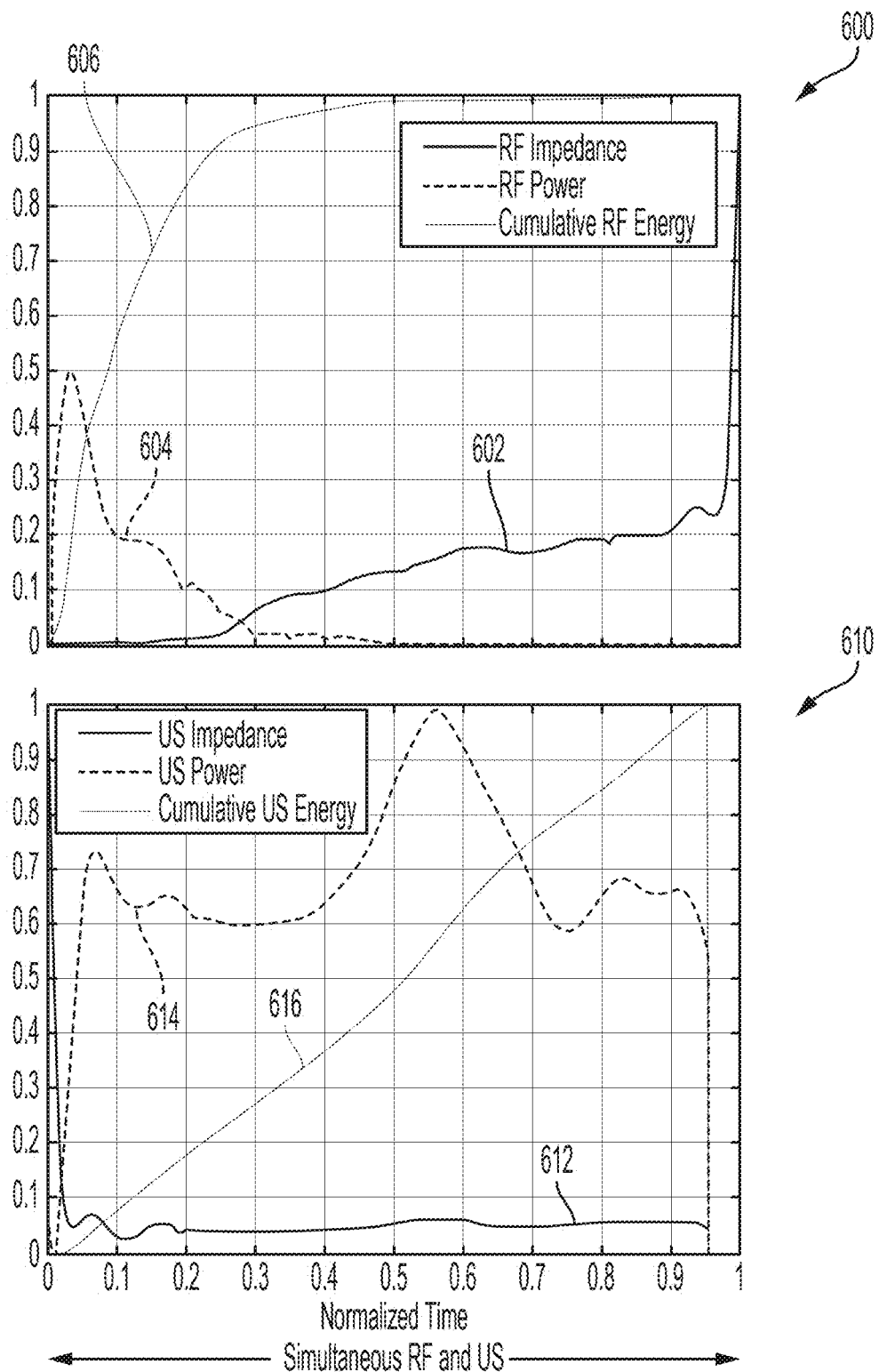

FIG. 19 is a graphical illustration of impedance, power, and cumulative energy for combined (simultaneous) application of ultrasonic and RF energy versus normalized time, according to at least one aspect of the present disclosure.

Figure 20:
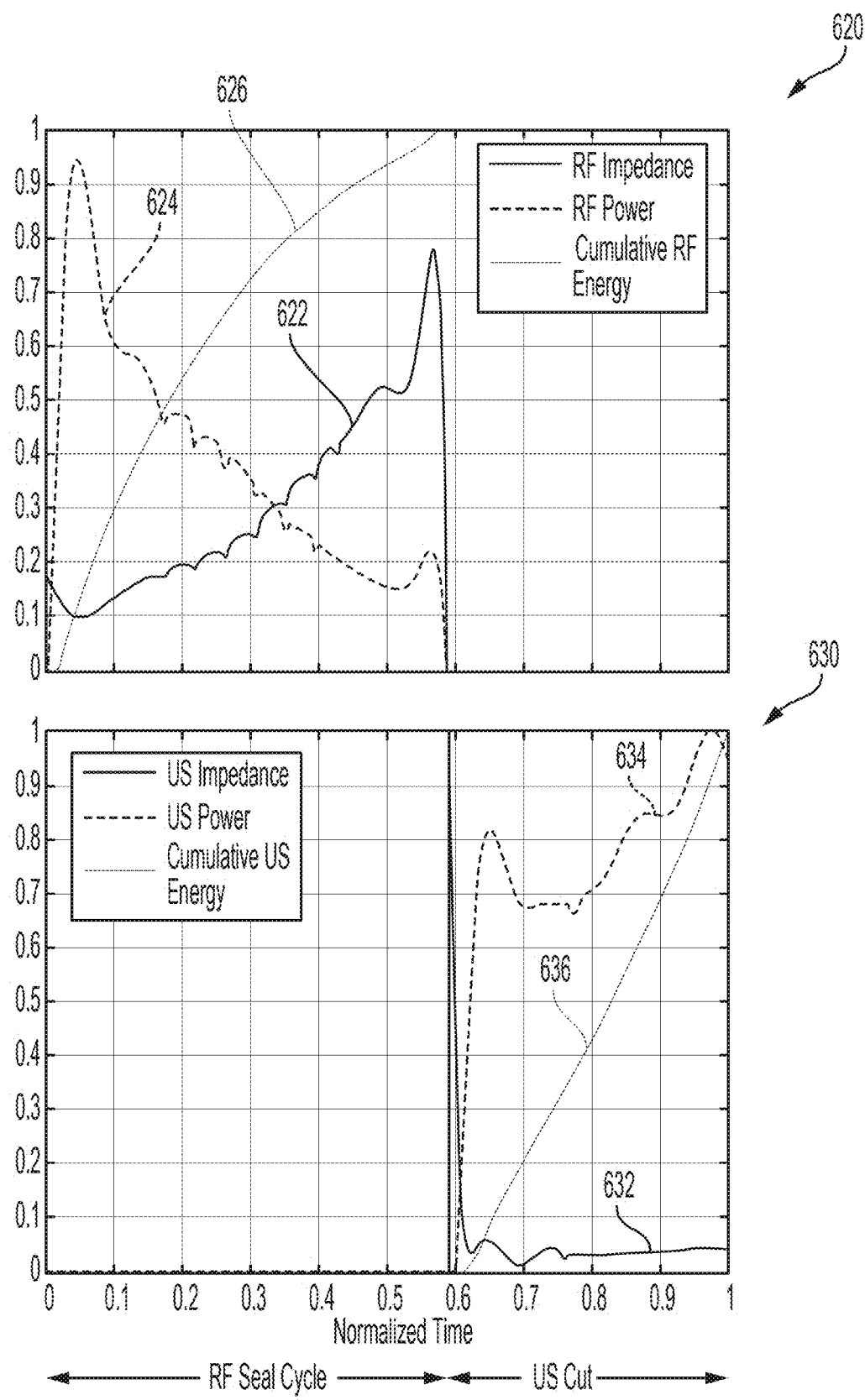

FIG. 20 is a graphical illustration of impedance, power, and cumulative energy for sequential application of ultrasonic and RF energy versus normalized time, according to at least one aspect of the present disclosure.

Figure 21:
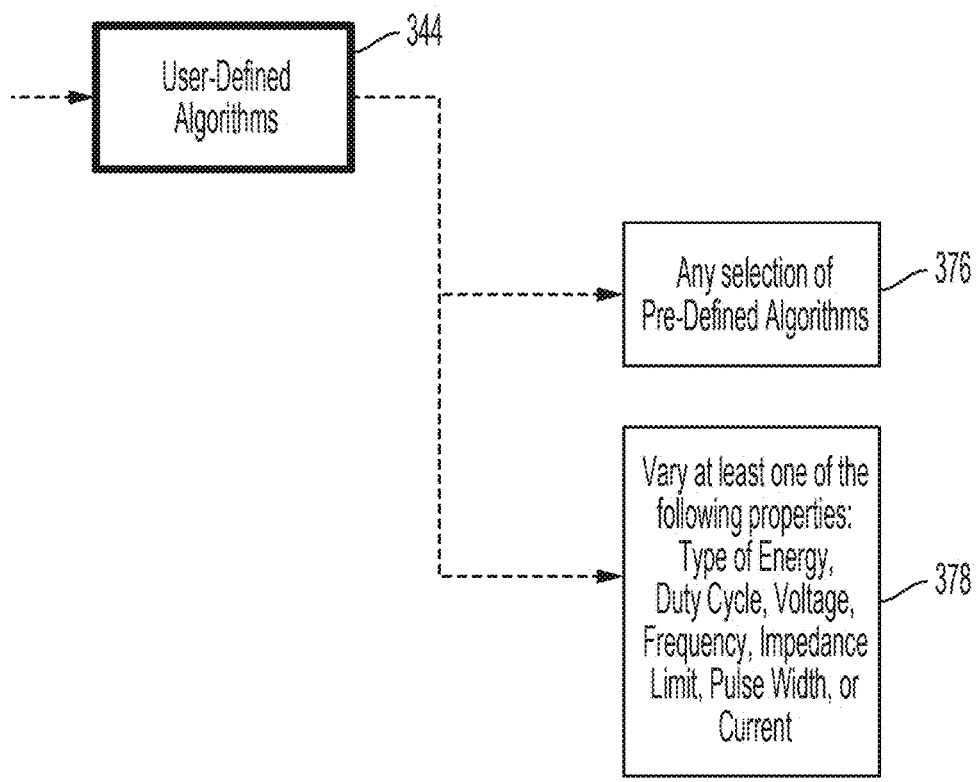

FIG. 21 is diagram of a user-defined algorithm, according to at least one aspect of the present disclosure.

Figure 22:
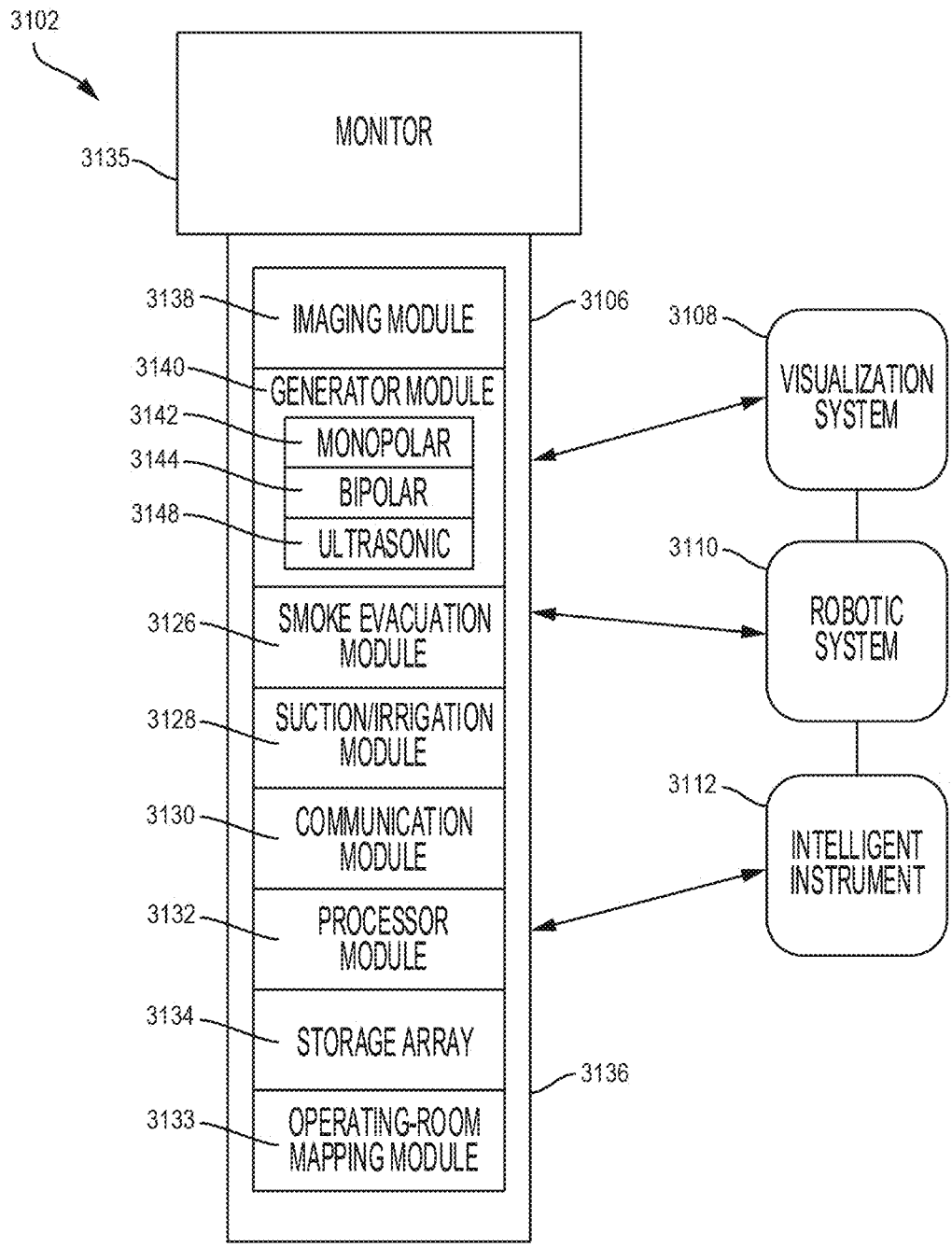

FIG. 22 is a surgical system comprising a surgical hub paired with a visualization system, a robotic system, and an intelligent instrument, in accordance with at least one aspect of the present disclosure.

Figure 23:
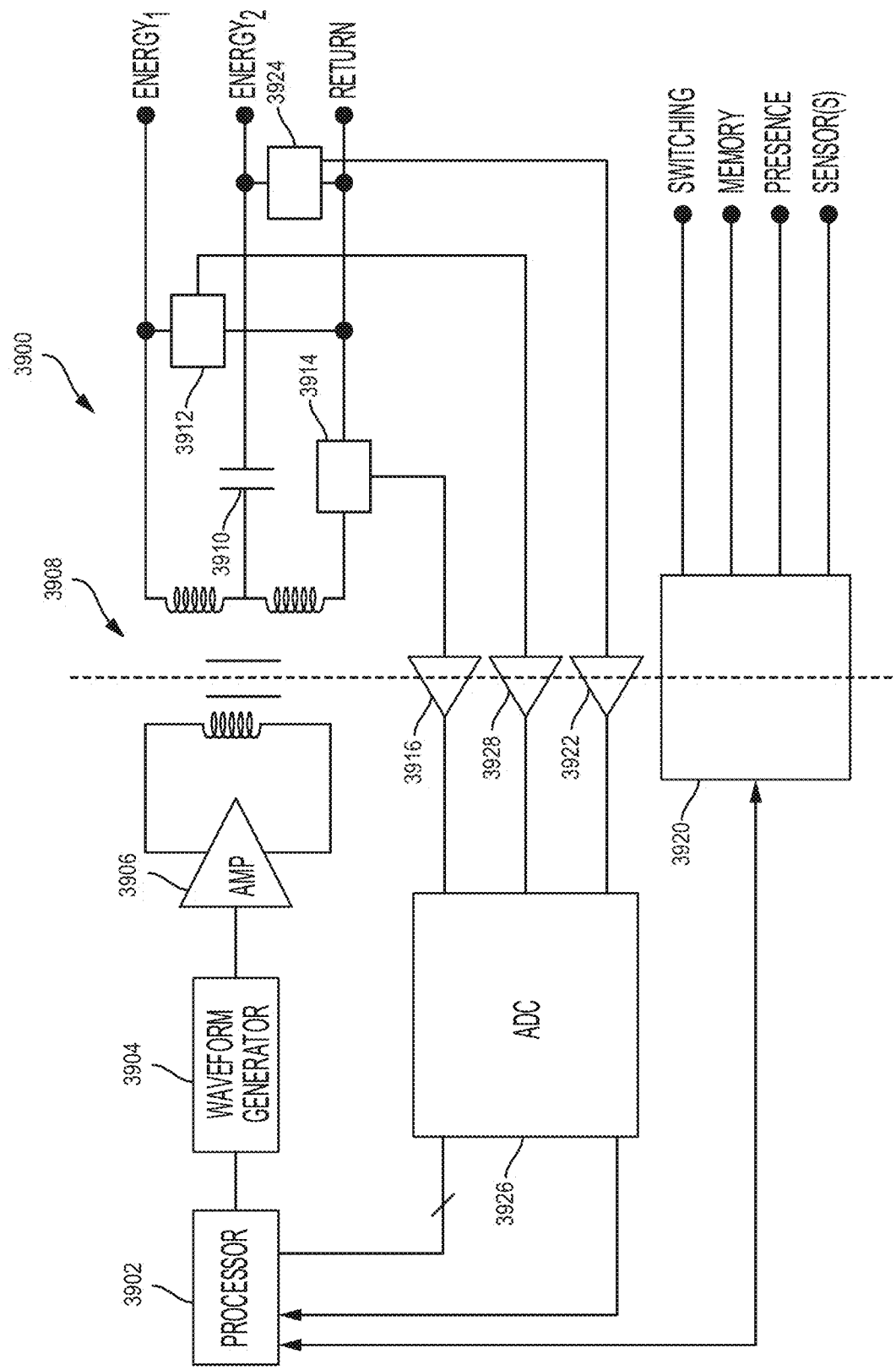

FIG. 23 illustrates an example of a generator, in accordance with at least one aspect of the present disclosure.

Figure 24:
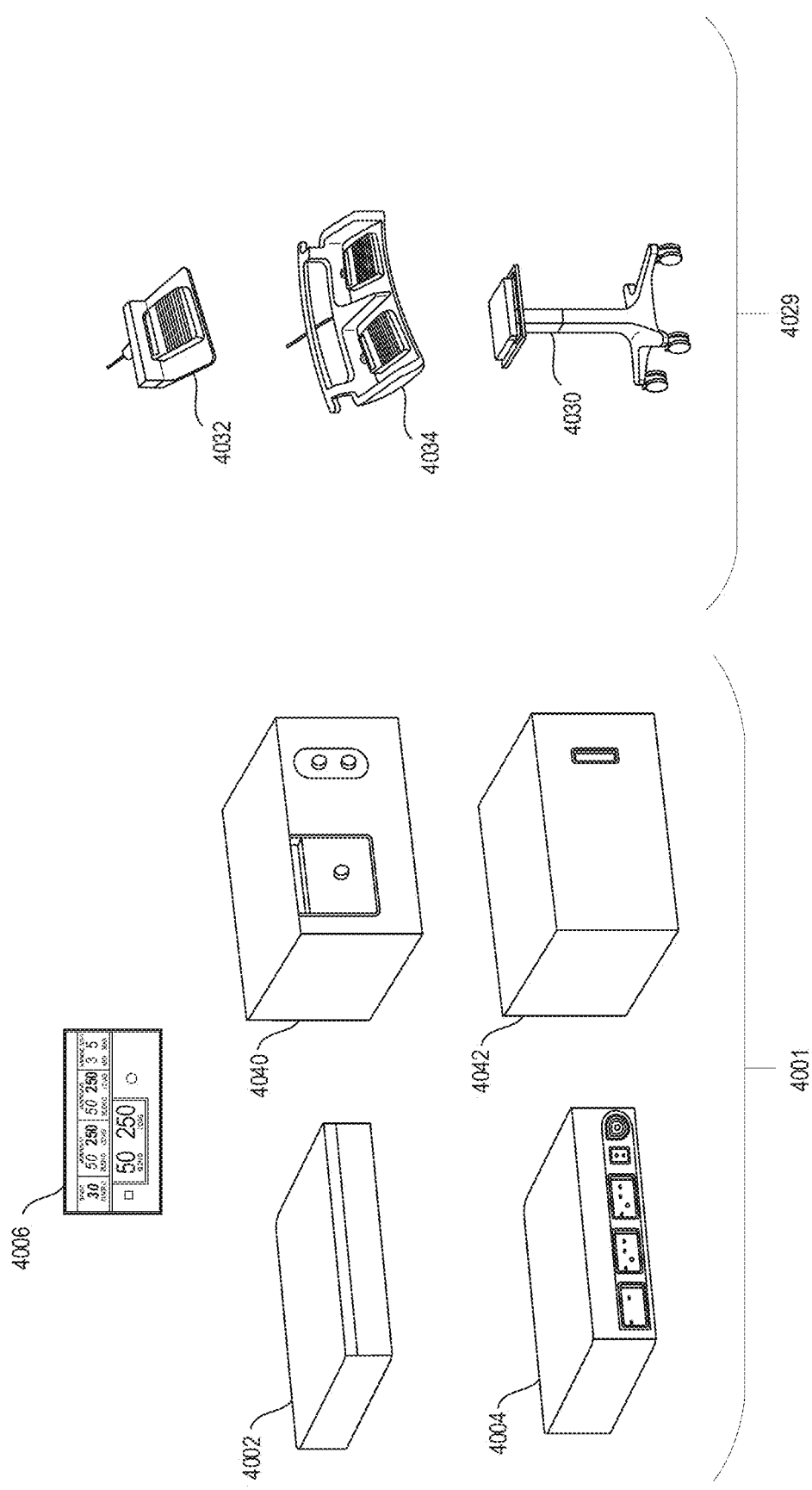

FIG. 24 is a diagram of various modules and other components that are combinable to customize modular energy systems, in accordance with at least one aspect of the present disclosure.

Figure 25B:
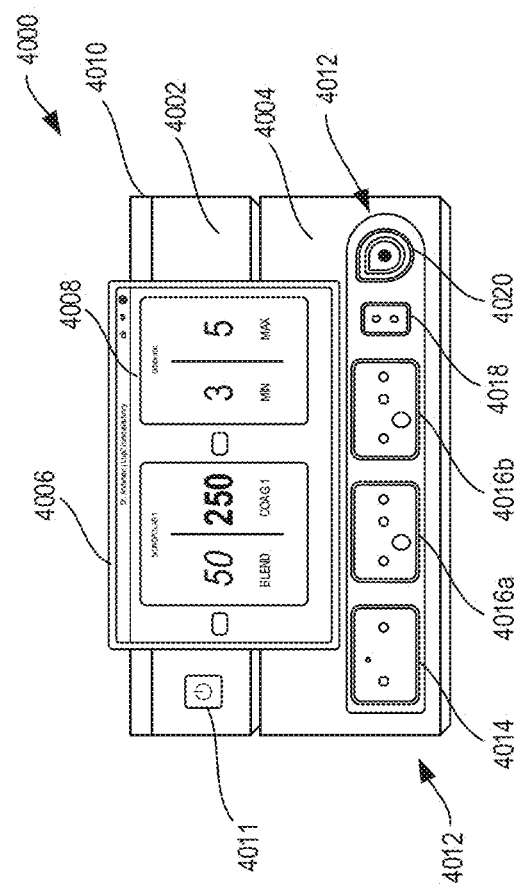
Figure 25A:
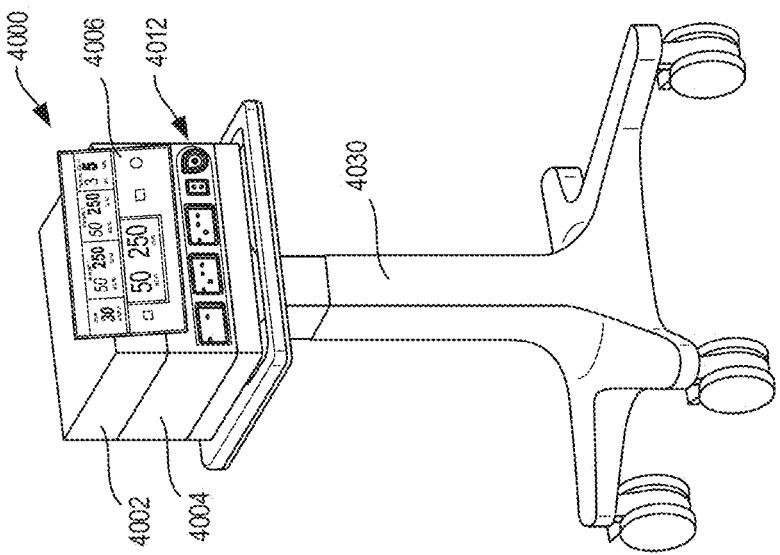

FIG. 25A is a first illustrative modular energy system configuration including a header module and a display screen that renders a graphical user interface (GUI) for relaying information regarding modules connected to the header module, in accordance with at least one aspect of the present disclosure.

FIG. 25B is the modular energy system shown in FIG. 25A mounted to a cart, in accordance with at least one aspect of the present disclosure.

Figure 26:
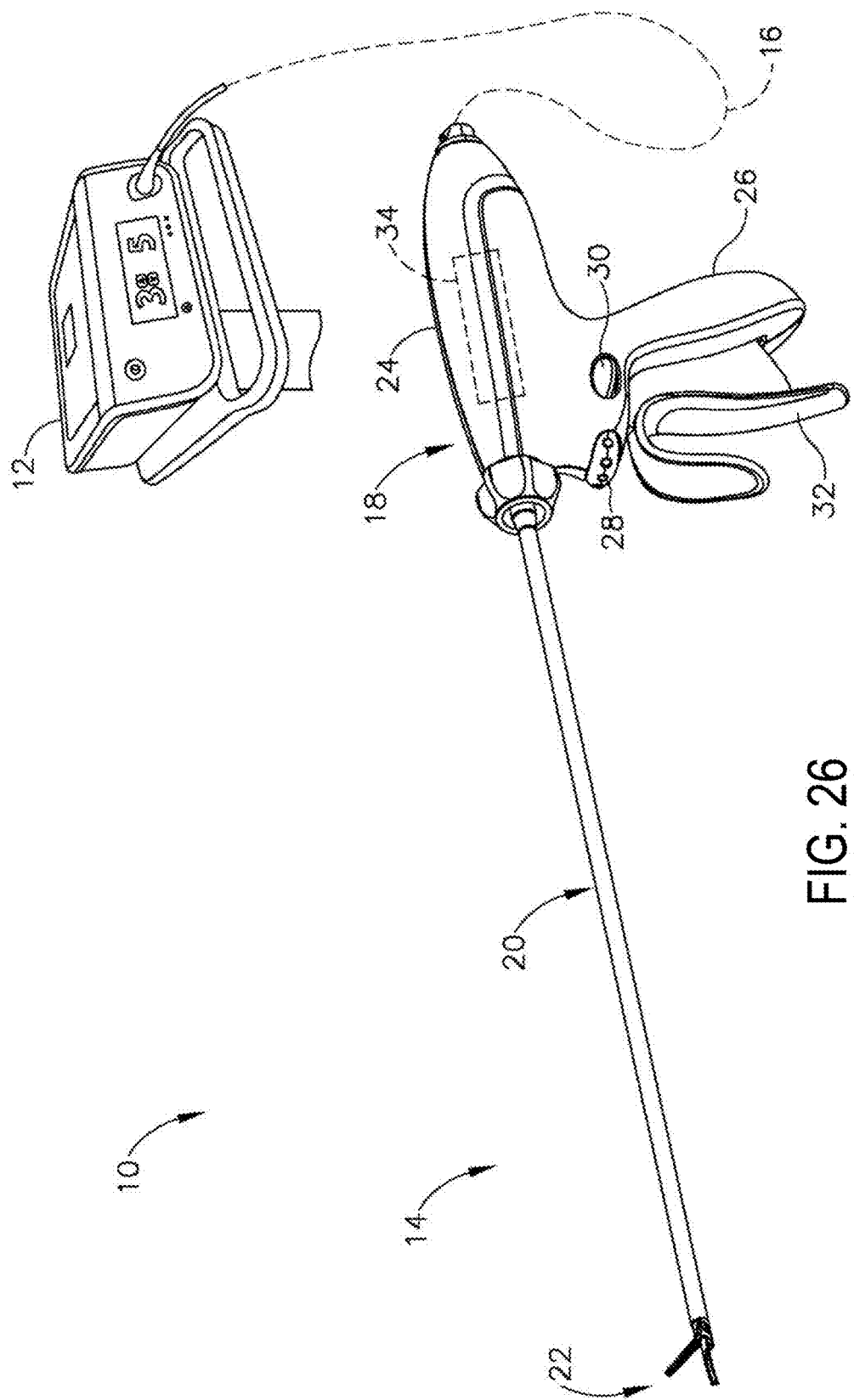

FIG. 26 depicts a perspective view of an exemplary surgical system having a generator and a surgical instrument operable to treat tissue with ultrasonic energy and bipolar RF energy, in accordance with at least one aspect of the present disclosure.

Figure 27:
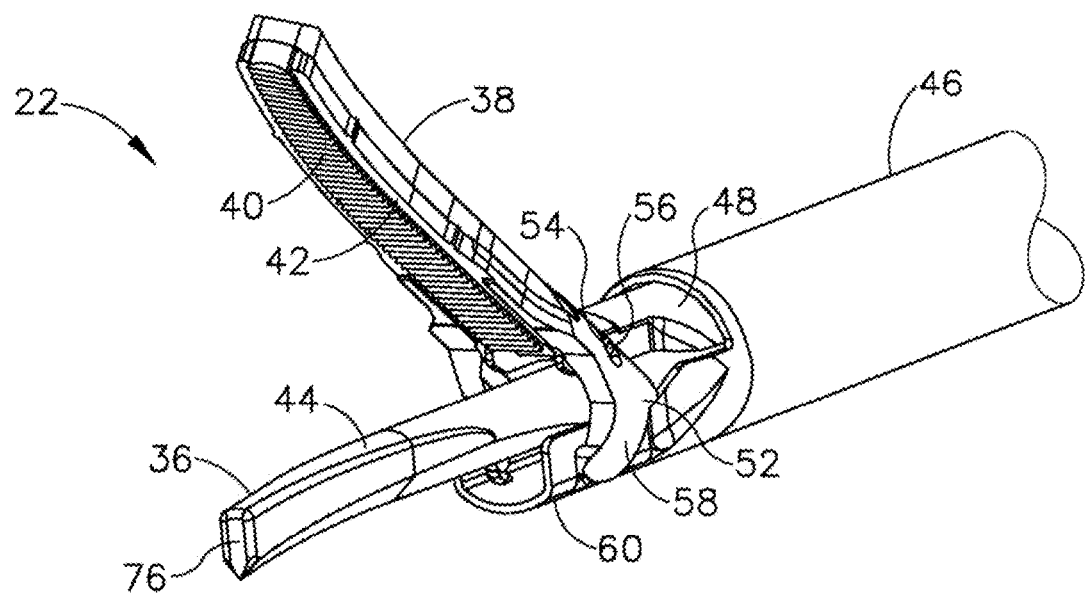

FIG. 27 depicts a top perspective view of an end effector of the surgical instrument of FIG. 26, having a clamp arm that provides a first electrode and an ultrasonic blade that provides a second electrode, in accordance with at least one aspect of the present disclosure.

Figure 28:
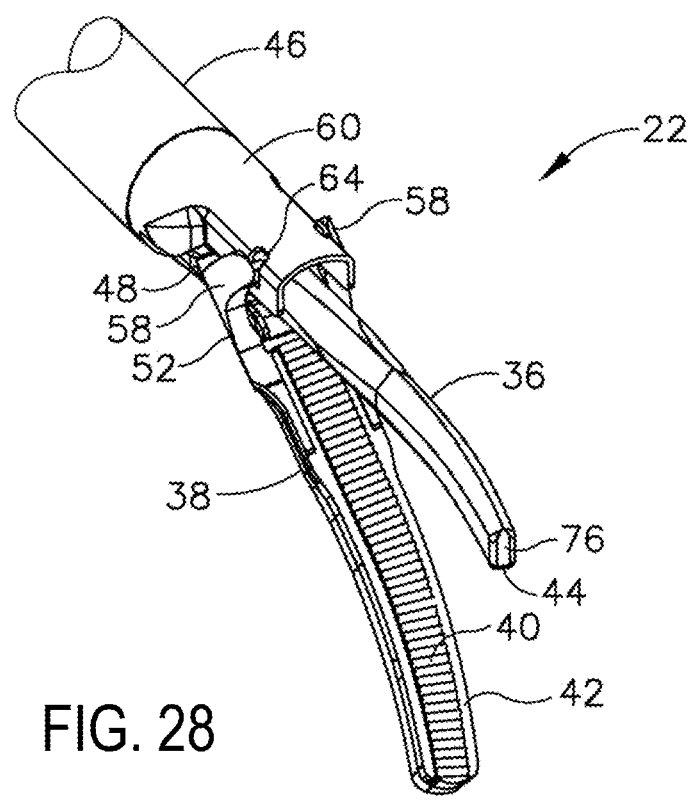

FIG. 28 depicts a bottom perspective view of the end effector of FIG. 27, in accordance with at least one aspect of the present disclosure.

Figure 29:
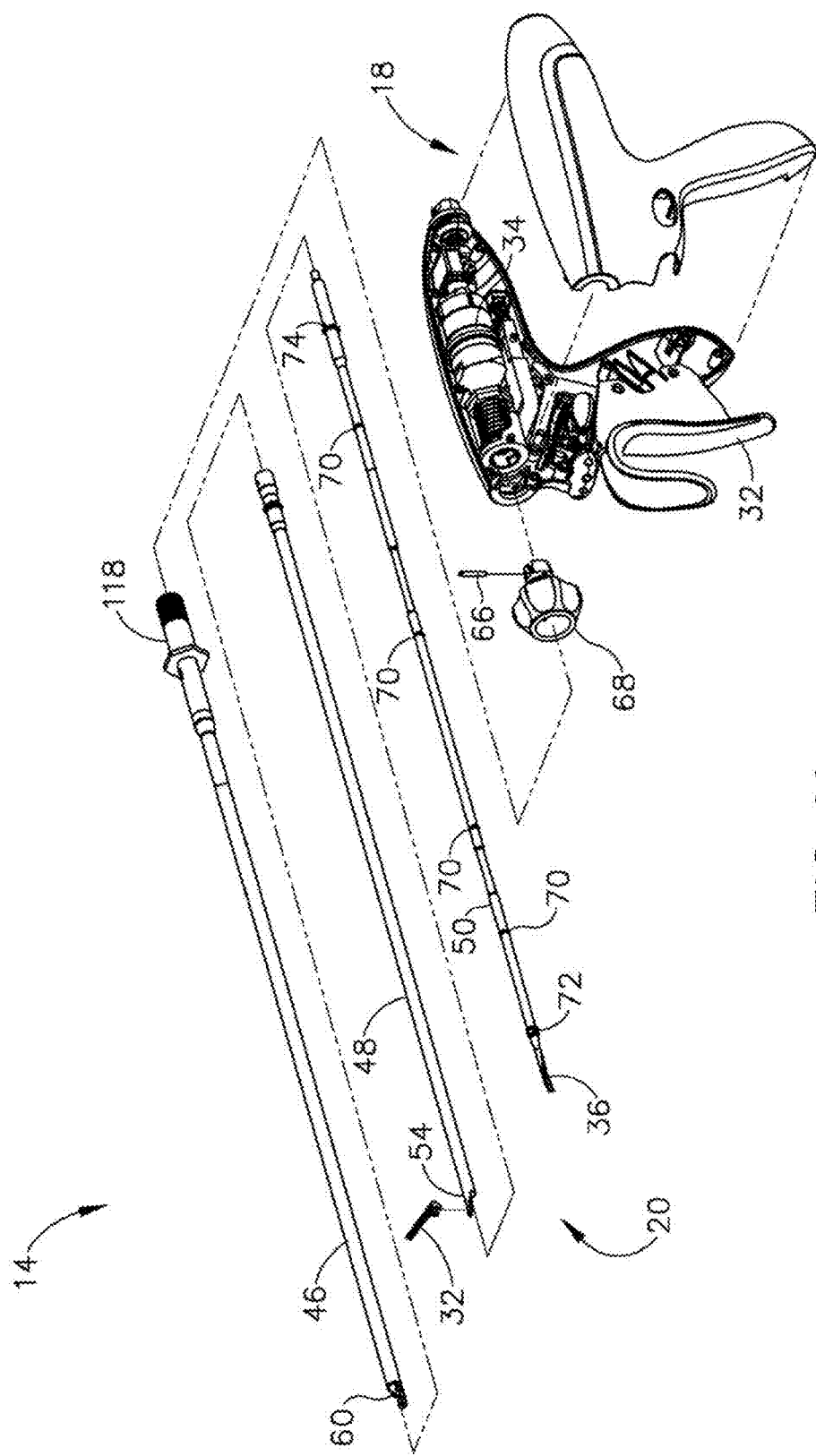

FIG. 29 depicts a partially exploded perspective view of the surgical instrument of FIG. 26, in accordance with at least one aspect of the present disclosure.

Figure 30:
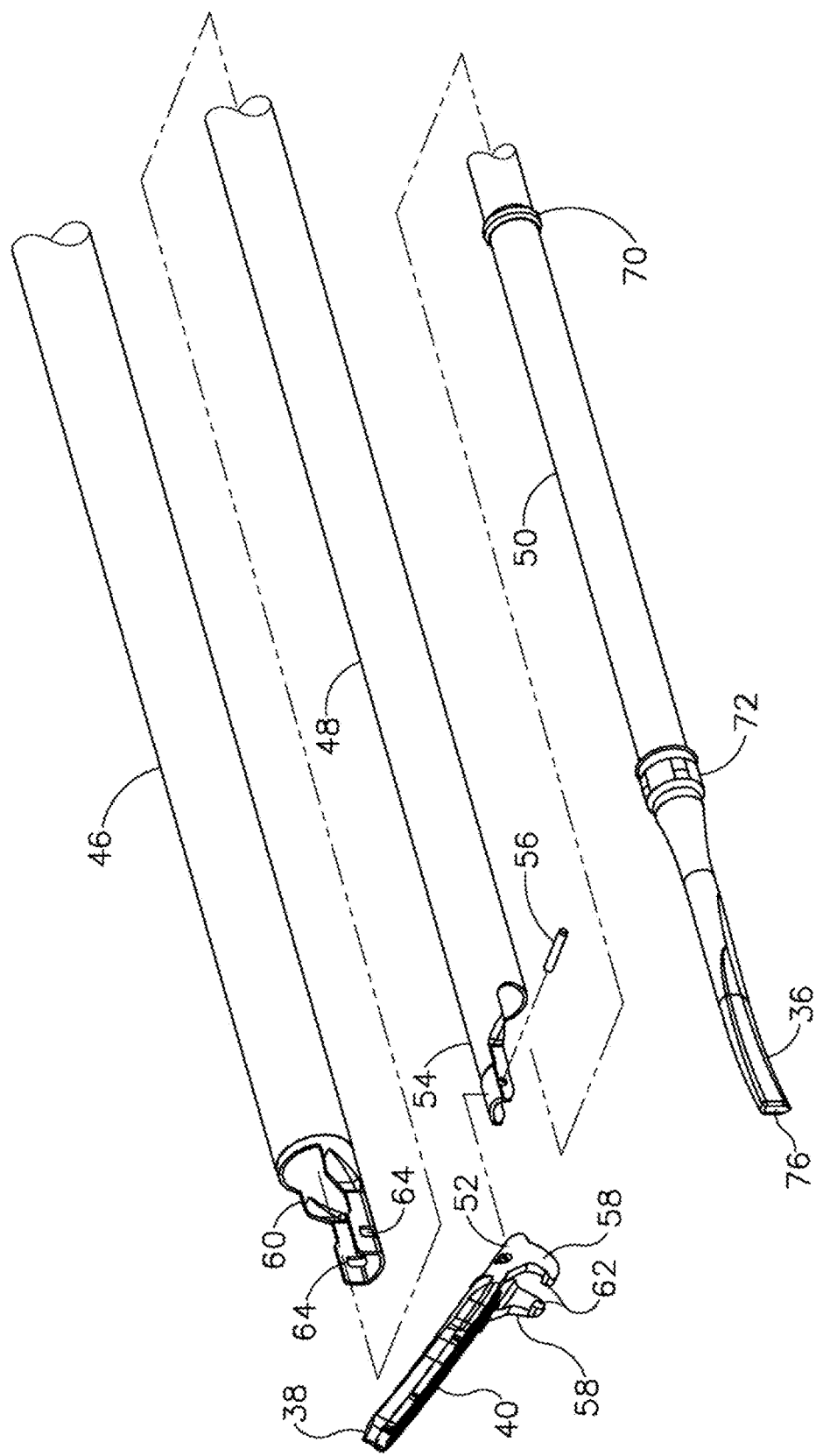

FIG. 30 depicts an enlarged exploded perspective view of a distal portion of the shaft assembly and the end effector of the surgical instrument of FIG. 26, in accordance with at least one aspect of the present disclosure.

DESCRIPTION

Applicant of the present application owns the following U.S. Patent Applications that were filed on May 29, 2020, and which are each herein incorporated by reference in their respective entireties:

U.S. patent application Ser. No. 16/887,493, entitled METHOD OF OPERATING A COMBINATION ULTRASONIC/BIPOLAR RF SURGICAL DEVICE WITH A COMBINATION ENERGY MODALITY END-EFFECTOR, now U.S. Patent Application Publication No. 2021/0196334;

U.S. patent application Ser. No. 16/887,506, entitled DEFLECTABLE SUPPORT OF RF ENERGY ELECTRODE WITH RESPECT TO OPPOSING ULTRASONIC BLADE, now U.S. Pat. No. 11,786,291;

U.S. patent application Ser. No. 16/887.515, entitled NON-BIASED DEFLECTABLE ELECTRODE TO MINIMIZE CONTACT BETWEEN ULTRASONIC BLADE AND ELECTRODE, now U.S. Patent Application Publication No. 2021/0196306;

U.S. patent application Ser. No. 16/887,519, entitled DEFLECTABLE ELECTRODE WITH HIGHER DISTAL BIAS RELATIVE TO PROXIMAL BIAS, now U.S. Patent Application Publication No. 2021/0196307;

U.S patent application Ser. No. 16/887,532, entitled DEFLECTABLE ELECTRODE WITH VARIABLE COMPRESSION BIAS ALONG THE LENGTH OF THE DEFLECTABLE ELECTRODE, now U.S. Patent Application Publication No. 2021/0196335;

U.S. patent application Ser. No. 16/887,554, entitled ASYMMETRIC SEGMENTED ULTRASONIC SUPPORT PAD FOR COOPERATIVE ENGAGEMENT WITH A MOVABLE RF ELECTRODE, now U.S. Patent Application Publication No. 2021/0196336;

U.S. patent application Ser. No. 16/887,561, entitled VARIATION IN ELECTRODE PARAMETERS AND DEFLECTABLE ELECTRODE TO MODIFY ENERGY DENSITY AND TISSUE INTERACTION, now U.S. Patent Application Publication No. 2021/0196346;

U.S. patent application Ser. No. 16/887,568, entitled TECHNIQUES FOR DETECTING ULTRASONIC BLADE TO ELECTRODE CONTACT AND REDUCING POWER TO ULTRASONIC BLADE, now U.S. Patent Application Publication No. 2021/0196305;

U.S. patent application Ser. No. 16/887,576, entitled CLAMP ARM JAW TO MINIMIZE TISSUE STICKING AND IMPROVE TISSUE CONTROL, now U.S. Pat. No. 11,779,387; and U.S. patent application Ser. No. 16/887,579, entitled PARTIALLY CONDUCTIVE CLAMP ARM PAD TO ENABLE ELECTRODE WEAR THROUGH AND MINIMIZE SHORT CIRCUITING, now U.S. Patent Application Publication No. 2021/0196352.

Applicant of the present application owns the following U.S. Patent Applications that were filed on May 28, 2020, and which are each herein incorporated by reference in their respective entireties:

U.S. patent application Ser. No. 16/885,813, entitled METHOD FOR AN ELECTROSURGICAL PROCEDURE;

U.S. patent application Ser. No. 16/885,820, entitled ARTICULATABLE SURGICAL INSTRUMENT;

U.S. patent application Ser. No. 16/885,823, entitled SURGICAL INSTRUMENT WITH JAW ALIGNMENT FEATURES;

U.S. patent application Ser. No. 16/885,826, entitled SURGICAL INSTRUMENT WITH ROTATABLE AND ARTICULATABLE SURGICAL END EFFECTOR;

U.S. patent application Ser. No. 16/885,838, entitled ELECTROSURGICAL INSTRUMENT WITH ASYNCHRONOUS ENERGIZING ELECTRODES;

U.S. patent application Ser. No. 16/885,851, entitled ELECTROSURGICAL INSTRUMENT WITH ELECTRODES BIASING SUPPORT;

U.S. patent application Ser. No. 16/885,860, entitled ELECTROSURGICAL INSTRUMENT WITH FLEXIBLE WIRING ASSEMBLIES;

U.S. patent application Ser. No. 16/885,866, entitled ELECTROSURGICAL INSTRUMENT WITH VARIABLE CONTROL MECHANISMS;

U.S. patent application Ser. No. 16/885,870, entitled ELECTROSURGICAL SYSTEMS WITH INTEGRATED AND EXTERNAL POWER SOURCES;

U.S. patent application Ser. No. 16/885,873, entitled ELECTROSURGICAL INSTRUMENTS WITH ELECTRODES HAVING ENERGY FOCUSING FEATURES;

U.S. patent application Ser. No. 16/885,879, entitled ELECTROSURGICAL INSTRUMENTS WITH ELECTRODES HAVING VARIABLE ENERGY DENSITIES;

U.S. patent application Ser. No. 16/885,881, entitled ELECTROSURGICAL INSTRUMENT WITH MONOPOLAR AND BIPOLAR ENERGY CAPABILITIES;

U.S. patent application Ser. No. 16/885,888, entitled ELECTROSURGICAL END EFFECTORS WITH THERMALLY INSULATIVE AND THERMALLY CONDUCTIVE PORTIONS;

U.S. patent application Ser. No. 16/885,893, entitled ELECTROSURGICAL INSTRUMENT WITH ELECTRODES OPERABLE IN BIPOLAR AND MONOPOLAR MODES;

U.S. patent application Ser. No. 16/885,900, entitled ELECTROSURGICAL INSTRUMENT FOR DELIVERING BLENDED ENERGY MODALITIES TO TISSUE;

U.S. patent application Ser. No. 16/885,917, entitled CONTROL PROGRAM ADAPTATION BASED ON DEVICE STATUS AND USER INPUT;

U.S. patent application Ser. No. 16/885,923, entitled CONTROL PROGRAM FOR MODULAR COMBINATION ENERGY DEVICE; and U.S. patent application Ser. No. 16/885,931, entitled SURGICAL SYSTEM COMMUNICATION PATHWAYS.

Before explaining various forms of surgical instruments in detail, it should be noted that the illustrative forms are not limited in application or use to the details of construction and arrangement of parts illustrated in the accompanying drawings and description. The illustrative forms may be implemented or incorporated in other forms, variations and modifications, and may be practiced or carried out in various ways. Further, unless otherwise indicated, the terms and expressions utilized herein have been chosen for the purpose of describing the illustrative forms for the convenience of the reader and are not for the purpose of limitation thereof.

Further, it is understood that any one or more of the following-described forms, expressions of forms, examples, can be combined with any one or more of the other following-described forms, expressions of forms, and examples.

Various forms are directed to user interfaces for surgical instruments with ultrasonic and/or electrosurgical (RF) end-effectors configured for effecting tissue treating, dissecting, cutting, and/or coagulation during surgical procedures. In one form, a user interface is provided for a combined ultrasonic and electrosurgical instrument that may be configured for use in open surgical procedures, but has applications in other types of surgery, such as minimally invasive laparoscopic procedures, for example, non-invasive endoscopic procedures, either in hand held or and robotic-assisted procedures. Versatility is achieved by selective application of multiple energy modalities simultaneously, independently, sequentially, or combinations thereof. For example, versatility may be achieved by selective use of ultrasonic and electrosurgical energy (e.g., monopolar or bipolar RF energy, microwave, IRE) either simultaneously, independently, sequentially, or combinations thereof.

In one aspect, the present disclosure provides a user interface for an apparatus comprising an ultrasonic blade and clamp arm with a deflectable RF electrode such that the ultrasonic blade and deflectable RF electrode cooperate to effect sealing, cutting, and clamping of tissue by cooperation of a clamping mechanism of the apparatus comprising the RF electrode with an associated ultrasonic blade. The clamping mechanism includes a pivotal clamp arm which cooperates with the ultrasonic blade for gripping tissue therebetween. The clamp arm is preferably provided with a clamp tissue pad (also known as "clamp arm pad") having a plurality of axially spaced gripping teeth, segments, elements, or individual units which cooperate with the ultrasonic blade of the end-effector to achieve the desired sealing and cutting effects on tissue, while facilitating grasping and gripping of tissue during surgical procedures.

In one aspect, the end-effectors described herein comprise an electrode. In other aspects, the end-effectors described herein comprise alternatives to the electrode to provide a compliant coupling of RF energy to tissue, accommodate pad wear/thinning, minimize generation of excess heat (low coefficient of friction, pressure), minimize generation of sparks, minimize interruptions due to electrical shorting, or combinations thereof. The electrode is fixed to the clamp jaw at the proximal end and is free to deflect at the distal end. Accordingly, the electrode may be referred to throughout this disclosure as a cantilever beam electrode or as a deflectable electrode.

In other aspects, the end-effectors described herein comprise a clamp arm mechanism configured to high pressure between a pad and an ultrasonic blade to grasp and seal tissue, maximize probability that the clamp arm electrode contacts tissue in limiting or difficult scenarios, such as, for example, thin tissue, tissue under lateral tension, tissue tenting/vertical tension especially tenting tissue away from clamp arm.

In other aspects, the end-effectors described herein are configured to balance match of surface area/current densities between electrodes, balance and minimize thermal conduction from tissue interface, such as , for example, impacts lesion formation and symmetry, cycle time, residual thermal energy.

In other aspects, the end-effectors described herein are configured to minimize sticking, tissue adherence (minimize anchor points) and may comprise small polyimide pads.

In various aspects, the present disclosure provides a surgical device configured to deliver at least two energy types (e.g., ultrasonic, monopolar, bipolar RF, microwave, or irreversible electroporation [IRE]) to tissue. The surgical device includes a first activation button switch for activating energy, a second button switch for selecting an energy mode for the activation button switch. The second button switch is connected to a circuit that uses at least one input parameter to define the energy mode. The input parameter can be modified remotely through connection to a generator or through a software update.

In one aspect, at least one of the energy modes is a simultaneous blend of RF and ultrasonic energy, and the input parameter represents a duty cycle of the RF and ultrasonic energy.

In one aspect, the second button switch is configurable to select from a list of predefined modes and the number of modes in the list is defined by a second input parameter defined by a user.

In one aspect, the input parameter is either duty cycle, voltage, frequency, pulse width, or current.

In one aspect, the device also includes a visual indicator of the selected energy mode within the portion of device in the surgical field In one aspect, the second button switch is a separate control from the end effector closure trigger.

In one aspect, the second button switch is configured to be activated second stage of the closure trigger. The first stage of the closure trigger in the closing direction is to actuate the end effector.

In one aspect, at least one of the energy modes is selected from ultrasonic, RF bipolar, RF monopolar, microwave, or IRE.

In one aspect, at least one of the energy modes is selected from ultrasonic, RF bipolar, RF monopolar, microwave, or IRE and is configured to be applied in a predefined duty cycle or pulsed algorithm.

In one aspect, at least one of the energy modes is selected from a sequential application of two or more of the following types of energy: ultrasonic, RF bipolar, RF monopolar, microwave, or IRE.

In one aspect, at least one of the energy modes is a simultaneous blend of two or more of the following types of energy: ultrasonic, RF bipolar, RF monopolar, microwave, and IRE.

In one aspect, at least one of the energy modes is a simultaneous blend of two or more of the following types of energy: ultrasonic, RF bipolar, RF monopolar, microwave, and IRE followed sequentially by one or more of the aforementioned energies.

In one aspect, at least one of the energy modes is one off the following types of energy: Ultrasonic, RF bipolar, RF monopolar, microwave, and IRE followed sequentially by a simultaneous blend of two or more of the aforementioned energies.

In one aspect, at least one of the energy modes is procedure or tissue specific predefined algorithm.

In one aspect, at least one of the energy modes is compiled from learned surgical behaviors or activities.

In one aspect, the input parameter is at least one of: energy type, duty cycle, voltage, frequency, pulse width, current, impedance limit, activation time, or blend of energy.

In one aspect, the second button switch is configurable to select from a list of predefined modes and the number of modes in the list is either predefined or defined by a second input parameter defined by a user.

In one aspect, the aforementioned energy modes are made available to the user through software updates to the generator.

In one aspect, the aforementioned energy modes are made available to the user through software updates to the device.

In one aspect, the preferred selections by the user are made available to multiple generators through either networking, the cloud, or manual transfer.

In one aspect, the device also includes a visual indicator of the selected energy mode within the portion of device in the surgical field.

As used herein a button switch can be a manually, mechanically, or electrically operated electromechanical device with one or more sets of electrical contacts, which are connected to external circuits. Each set of electrical contacts can be in one of two states: either "closed" meaning the contacts are touching and electricity can flow between them, or "open", meaning the contacts are separated and the switch is electrically non-conducting. The mechanism actuating the transition between these two states (open or closed) can be either an "alternate action" (flip the switch for continuous "on" or "off") or "momentary" (push for "on" and release for "off") type.

As surgical devices evolve and become more capable, the number of specialized modes in which they can be operated increases. Adding extra button switches on a device to accommodate these new additional modes would complicate the user interface and make the device more difficult to use. Accordingly, the present disclosure provides techniques for assigning different modes to a single physical button switch, which enables a wider selection of modes without adding complexity to the housing design (e.g., adding more and more button switches). In one aspect the housing is in the form of a handle or pistol grip.

As more specialized modes become available, there is a need to provide multiple modes to a surgeon using the surgical device without creating a complex user interface. Surgeons want to be able to control the mode selection from the sterile field rather than relying on a circulating nurse at the generator. Surgeon want real time feedback so they are confident they know which mode is selected.

Figure 1:
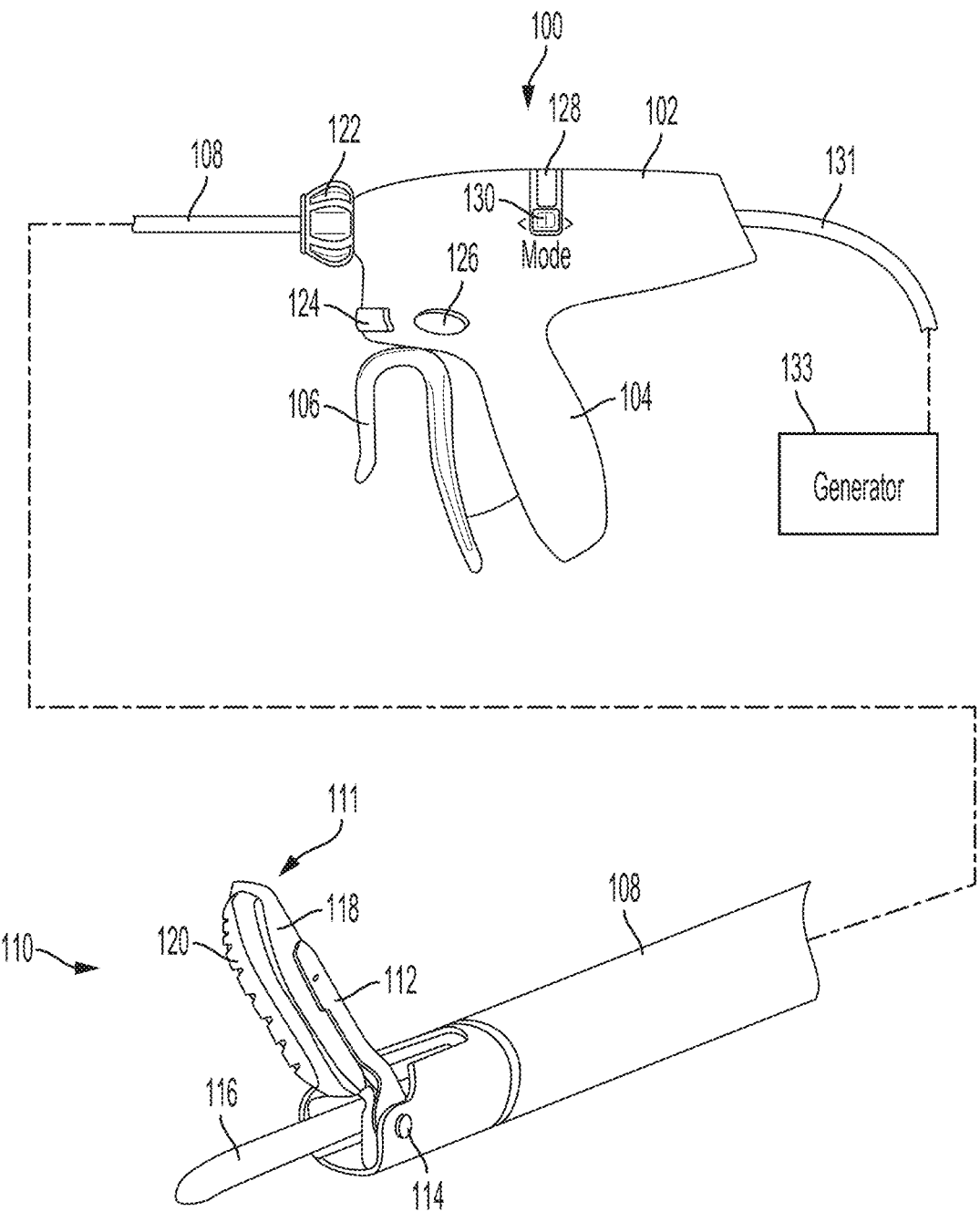
FIG. 1 illustrates a surgical device comprising a mode selection button switch on the device, according to at least one aspect of the present disclosure.

FIG. 1 illustrates a surgical device 100 comprising a mode selection button switch 130 on the device 100, according to at least one aspect of the present disclosure. The surgical device 100 comprises a housing 102 defining a handle 104 in the form of a pistol grip. The housing 102 comprises a trigger 106 which when squeezed is received into the internal space defined by the handle 104. The trigger 106 is used to operate a clamp arm 111 portion of an end-effector 110. A clamp jaw 112 is pivotally movable about pivot point 114. The housing 102 is coupled to the end-effector 110 through a shaft 108, which is rotatable by a knob 122.

The end-effector 110 comprises a clamp arm 111 and an ultrasonic blade 116. The clamp arm 111 comprises a clamp jaw 112, an electrode 118, and a clamp arm pad 120. In one aspect, the clamp arm pad 120 is made of a non-stick lubricious material such as polytetrafluoroethylene (PTFE) or similar synthetic fluoropolymers of tetrafluoroethylene. PTFE is a hydrophobic, non-wetting, high density and resistant to high temperatures, and versatile material and non-stick properties. The clamp arm pad 120 is electrically non-conductive. In contrast, the electrode 118 is made of an electrically conductive material to deliver electrical energy such as monopolar RF, bipolar RF, microwave, or irreversible electroporation (IRE), for example. The electrode 118 may comprises gap setting pads made of a polyimide material, and in one aspect, is made of a durable high-performance polyimide-based plastic known under the tradename VESPEL and manufactured by DuPont or other suitable polyimide, polyimide polymer alloy, or PET (Polyethylene Terephthalate), PEEK (Polyether Ether Ketone), PEKK (Poly Ether Ketone Ketone) polymer alloy, for example. Unless otherwise noted hereinbelow, the clamp arm pads and gap pads described hereinbelow are made of the materials described in this paragraph.

The electrode 118 and the ultrasonic blade 116 are coupled to the generator 133. The generator 133 is configured to drive RF, microwave, or IRE energy to the electrode 118. The generator 133 also is configured to drive an ultrasonic transducer acoustically coupled to the ultrasonic blade 116. In certain implementations, the electrode 118 is one pole of an electrical circuit and the ultrasonic blade 116 is the opposite pole of the electrical circuit. The housing 102 includes a switch 124 to activate the ultrasonic blade 116. The circuit may be contained in the housing 102 or may reside in the generator 133. The surgical device 100 is coupled to the generator 133 via a cable 131. The cable 131 conducts signals for the electrosurgical functions and the ultrasonic transducer.

In various aspects, the surgical device 100 is configured to deliver at least two energy types (e.g., ultrasonic, monopolar RF, bipolar RF, microwave, or irreversible electroporation [IRE]) to tissue located in the end-effector 110 between the clam arm 111 and the ultrasonic blade 116. The housing 102 of the surgical device 100 includes a first activation button switch 126 for activating energy and a second "mode" button switch 130 for selecting an energy mode for the activation button switch. The second button switch 130 is connected to a circuit that uses at least one input parameter to define the energy mode. The input parameter can be modified remotely through connection to a generator or through a software update. The energy mode is displayed on a visual indicator 128, such as display, screen, or similar visual feedback device, to provide feedback to the user concerning the mode or other parameters.

In one aspect, the surgical instrument 100 provides mode switching through the on device directional selector "mode" button switch 130. The user can press the mode button switch 130 to toggle through different modes and the colored light on the visual indicator 128 indicates the selected mode.

According to various aspects of the present disclosure, different modes of operation can be assigned to the surgical device by pressing the "mode" button switch 130, where each time the mode button switch 130 is pressed, or pushed and held, the surgical device 100 toggles through the available modes, which are displayed on the visual indicator 128. Once a mode is selected, the generator 133 will provide the appropriate generator tone and the surgical device 100 will have a lighted indicator on the visual indicator 128 to indicate which mode was selected.

In the example illustrated in FIG. 1, the "mode" selection button switch 130 is placed symmetrically on both sides of the housing 102. This enables both a right and left handed surgeon to select/toggle through modes without using a second hand. In this aspect, the "mode" selection button switch 130 can toggle in many different directions, which enables the surgeon to select from a list of options and navigate more complex selections remotely from the sterile field without having to ask a circulator to make adjustments at the generator 133. The lighted indicator on the visual indicator 128 of the surgical device 100, in addition to generator 133 tones, gives the surgeon feedback on which mode is selected.

In various aspects, the surgical instrument 100 comprises a user interface. The user interface of the surgical instrument 100 comprises, alone or in combination, the first activation button switch 126 to activate a first energy source, the second "mode" button switch 130 to select an energy mode for the first activation button switch 126, and the visual indicator 128. The user interface may further comprises the trigger 106 and the switch 124 to activate a second energy source. The user interface may further comprise the rotatable knob 122 to rotate the shaft 108 and the end-effector 110.

FIGS. 2A-2C illustrate three options for selecting the various operating modes of the surgical device 100, according to at least one aspect of the present disclosure. In addition to the colored light visual indicator 128 on the housing 102 of the surgical device 100, feedback for mode selection is audible and/or visible through the generator 133 interface where the generator 133 announces the selected mode verbally and/or shows a description of the selected mode on a screen of the generator 133.

FIG. 2A shows a first mode selection option 132A where the button switch 130 can be pressed forward 136 or backward 134 to cycle the surgical instrument 100 through the various modes.

FIG. 2B sows a second mode selection option 132B where the button switch 130 is pressed up 140 or down 138 to cycle the surgical instrument 100 through the various modes.

FIG. 2C shows a third mode selection option 132C where the button switch 130 is pressed forward 136, backward 134, up 149, or down 138 to cycle the surgical instrument 100 through the various modes.

FIG. 3 illustrates a surgical device 150 comprising a mode selection button switch 180 on the back of the device 150, according to at least one aspect of the present disclosure. The surgical device 150 comprises a housing 152 defining a handle 154 in the form of a pistol grip. The housing 152 comprises a trigger 156 which when squeezed is received into the internal space defined by the handle 154. The trigger 156 is used to operate a clamp arm 161 portion of an end-effector 160. A clamp jaw 162 is pivotally movable about pivot point 164. The housing 152 is coupled to the end-effector 160 through a shaft 158, which is rotatable by a knob 172.

The end-effector 160 comprises a clamp arm 161 and an ultrasonic blade 166. The clamp arm 161 comprises a clamp jaw 162, an electrode 168, and a clamp arm pad 170. In one aspect, the clamp arm pad 170 is made of a non-stick lubricious material such as polytetrafluoroethylene (PTFE) or similar synthetic fluoropolymers of tetrafluoroethylene. PTFE is a hydrophobic, non-wetting, high density and resistant to high temperatures, and versatile material and non-stick properties. The clamp arm pad 170 is electrically non-conductive. In contrast, the electrode 168 is made of an electrically conductive material to deliver electrical energy such as monopolar RF, bipolar RF, microwave, or irreversible electroporation (IRE), for example. The electrode 168 may comprises gap setting pads made of a polyimide material, and in one aspect, is made of a durable high-performance polyimide-based plastic known under the tradename VESPEL and manufactured by DuPont or other suitable polyimide, polyimide polymer alloy, or PET (Polyethylene Terephthalate), PEEK (Polyether Ether Ketone), PEKK (Poly Ether Ketone Ketone) polymer alloy, for example. Unless otherwise noted hereinbelow, the clamp arm pads and gap pads described hereinbelow are made of the materials described in this paragraph.

The electrode 168 and the ultrasonic blade 166 are coupled to the generator 133. The generator 133 is configured to drive RF, microwave, or IRE energy to the electrode 168. The generator 133 also is configured to drive an ultrasonic transducer acoustically coupled to the ultrasonic blade 166. In certain implementations, the electrode 168 is one pole of an electrical circuit and the ultrasonic blade 166 is the opposite pole of the electrical circuit. The housing 152 includes a switch 174 to activate the ultrasonic blade 166. The circuit may be contained in the housing 152 or may reside in the generator 133. The surgical device 150 is coupled to the generator 133 via a cable 181. The cable 181 conducts signals for the electrosurgical functions and the ultrasonic transducer.

In various aspects, the surgical device 150 is configured to deliver at least two energy types (e.g., ultrasonic, monopolar RF, bipolar RF, microwave, or irreversible electroporation [IRE]) to tissue located in the end-effector 160 between the clam arm 161 and the ultrasonic blade 166. The housing 152 of the surgical device 150 includes a first activation button switch 176 for activating energy and a second "mode" button switch 180 for selecting an energy mode for the activation button switch. The second button switch 180 is connected to a circuit that uses at least one input parameter to define the energy mode. The input parameter can be modified remotely through connection to a generator 133 or through a software update. The energy mode is displayed on a visual indicator 178 such as a display, screen, or similar visual feedback device.

In one aspect, the surgical instrument 150 provides mode switching through the on device directional selector "mode" button switch 180. The user can press the mode button switch 180 to toggle through different modes and the colored light on the visual indicator 178 indicates the selected mode.

According to various aspects of the present disclosure, different modes of operation can be assigned to the surgical device by pressing the "mode" button switch 180, where each time the mode button switch 180 is pressed, or pushed and held, the surgical device 150 toggles through the available modes, which are displayed on the visual indicator 178. Once a mode is selected, the generator 133 will provide the appropriate generator tone and the surgical device 150 will have a lighted indicator on the visual indicator 178 to indicate which mode was selected.

In the example illustrated in FIG. 3, the "mode" selection button switch 180 is placed on the back of the surgical device 150. The location of the "mode" selection button switch 180 is out of the reach of the surgeon's hand holding the surgical device 150 so a second hand is required to change modes. This is intended to prevent inadvertent activation. In order to change modes, a surgeon must use her second hand to intentionally press the mode button switch 180. The lighted indicator on the visual indicator 178 of the surgical device 150, in addition to generator tones gives the surgeon feedback on which mode is selected.

In various aspects, the surgical instrument 150 comprises a user interface. The user interface of the surgical instrument 150 comprises, alone or in combination, the first activation button switch 176 to activate a first energy source, the second "mode" button switch 180 to select an energy mode for the first activation button switch 176, and the visual indicator 178. The user interface may further comprises the trigger 156 and the switch 174 to activate a second energy source. The user interface may further comprise the rotatable knob 172 to rotate the shaft 158 and the end-effector 160.

FIG. 4A shows a first mode selection option where as the mode button switch 180 is pressed to toggle through various modes, a visual indicator 178, such as colored light, indicates the selected mode.

FIG. 4B shows a second mode selection option where as the mode button switch 180 is pressed to toggle through various modes, a visual indicator 182 such as display, screen, or similar visual feedback device, indicates the selected mode (e.g., LCD, e-ink).

FIG. 4C shows a third mode selection option where as the mode button switch 180 is pressed to toggle through various modes, a visual indicator 184 such as labelled lights, indicates the selected mode.

FIG. 4D shows a fourth mode selection option where as a visual indicator in the form of labeled button switches 186 is pressed to select a mode, when the selected labeled button switch form of the visual indicator 180 is selected, it is illuminated to indicate mode selected As more functionality is added to advanced energy surgical devices additional button switches or controls are added to the surgical devices. The additional button switches or controls make these advanced energy surgical devices complicated and difficult to use. Additionally, when using an advanced energy surgical device to control bleeding, difficult to use user interfaces or difficult to access capability will cost critical time and attention during a surgical procedure.

According to the present disclosure, monopolar RF energy or advanced bipolar RF energy is activated by closing the trigger by squeezing the trigger past a first closure click to a second activation click and holding closed until energy delivery is ceased by the power source in the generator. Energy also can be immediately reapplied by slightly releasing and re-squeezing the trigger as many times as desired.

FIG. 5 illustrates a surgical device 190 comprising a trigger 196 activation mechanism, according to at least one aspect of the present disclosure. The surgical device 190 comprises a housing 192 defining a handle 194 in the form of a pistol grip. The housing 192 comprises a trigger 196 which when squeezed is received into the internal space defined by the handle 194. The housing 192 is coupled to an end-effector through a shaft 198, which is rotatable by a knob 202. The surgical device 190 is coupled to a generator 206 via a cable 204. The cable 204 conducts signals for the electrosurgical functions and the ultrasonic transducer.

The trigger 196 is configured to operate a clamp arm portion of an end-effector and to trigger electrosurgical energy, thus eliminating the activation button switch 126, 176 shown in FIGS. 1 and 3. The trigger 196 closes to a first audible and tactile click to close the jaws for grasping tissue and further closes to a second audible and tactile click to activate electrosurgical energy such as monopolar or bipolar RF. Microwave, or IRE energy. The full sequence is completed by activating the front button switch which cuts using ultrasonic energy.

Procedure for operating the surgical device 190: squeeze the trigger 196 to a first audible and tactile click; verify targeted tissue in jaws; activate RF energy by further squeezing the trigger 196 to a second audible and tactile click until end tone is heard; cut by pressing ultrasonic front switch 200 until tissue divides.

Modified procedure for operating the surgical instrument 190 for additional capability: activate RF energy with the trigger 196 and hold while simultaneously activation the front button switch 200 to activate the ultrasonic transducer, which will result in simultaneous application of electrosurgical and ultrasonic energy modalities being delivered to the tissue at the same time.

In an alternative implementation, the front button switch 200 for activating ultrasonic energy may be toggled to different speeds via a mode selector on the surgical device 190 or on the power source generator 206.

In various aspects, the surgical instrument 190 comprises a user interface. The user interface of the surgical instrument 190 comprises, alone or in combination, the trigger 196 configured to close to a first audible and tactile click to close the jaws for grasping tissue and further close to a second audible and tactile click to activate a first energy source such as monopolar or bipolar RF, microwave, IRE, among others, and a display. The user interface may further comprises the switch 200 to activate a second energy source. The user interface may further comprise the rotatable knob 202 to rotate the shaft 198 and the end-effector. The user interface may further comprise a mode switch button to select an energy mode associated with the second audible and tactile click of the trigger 196.

In various aspects, the present disclosure provides the framework for energy mode selection and switching for a surgical instrument such as the surgical instruments 100, 150, 190 descried in FIGS. 1-5. Specifically, the present disclosure provides the framework for energy mode selection and switching for a surgical instrument capable of delivering multiple forms of energy, including both pre-defined and user-defined algorithms of individual energies, combined energies, sequential energies, duty cycle or pulsed energies, tissue-specific or procedure-specific energies, or any combination of above. Specific more in-depth information on each category addressed in the framework 300 depicted in FIGS. 6A-6B can be found throughout this disclosure. The multiple energies include, without limitation, ultrasonic, monopolar RF, bipolar RF, microwave, IRE, applied either independently or in any combination, to seal, cut, feather, blend, etc.

In various aspects, the present disclosure provides mode switching algorithms for a surgical instrument capable of delivering multiple energy options, including both pre-defined algorithms and user-defined algorithms. Pre-defined algorithms include (but not limited to) individual energies, combined energies, sequential energies, duty cycle or pulsed energies, tissue-specific or procedure-specific energies, or any combination of the above.

User-defined algorithms include, without limitation, any selection of pre-defined algorithms or a user-defined sequence of varied electrical outputs.

In various aspects, the present disclosure provides a framework for energy mode selection and switching for a surgical instrument including options for loading different modes to a generator, making modes available to a surgical device, user interface options, and confirmation of selected mode and input parameters, either on the generator or the surgical device, or other user interface option.

FIGS. 6A-6B illustrates a framework 300 for energy mode selection and switching for a surgical device, according to at least one aspect of the present disclosure. The framework 300 is described in the context of the surgical device 100, 150, 190 in FIGS. 1-5 and the generator 133, 206 in FIGS. 1, 3, 5).

The various modes are loaded 302 onto the generator (e.g., generator 133, 206 in FIGS. 1, 3, and 5). This task can be accomplished in multiple different ways, including but not limited to a software upgrade 304 to the generator, a software upgrade 306 to the surgical device (e.g., surgical device 100, 150, 190 in FIGS. 1-5 that is then plugged into the generator with available modes "read" by the generator), a transfer 308 of modes from generator to generator (e.g., via the cloud or other storage solution), or modes could be "learned" 310 by the generator (e.g., via a "User Profile", or learned surgical behaviors or activities).

The modes are made available 312 to the surgical device. This task can be accomplished in multiple different ways, including but not limited to the user selecting 314 from a pre-defined list of modes at the generator or selecting/defining 316 "User-Defined" modes at the generator.

Whether the user selects 314 from a pre-defined list of modes at the generator or selects/defines 316 "User-Defined" modes at the generator, the user selects 318 the desired mode using several user interface options. The user can interact with, switch between, and select different modes via a mode-switching button switch 338 (e.g., mode button switch 130, 180 in FIGS. 1-4D) on the surgical device via a foot pedal 336, or via the user interface on the generator 340.

Both the generator and the device confirm the mode selected by the user. Example of device confirmation are described herein at sections 278280 and 278282. The surgical device confirms 320 the mode selected by the user. The confirmation 320 of the mode selection can be made by visual 324, audible 326 or tactile 328 feedback. The generator will display 322 the appropriate input parameters based on the mode selected by the user. These input parameters will be defined either by pre-defined algorithms 342 (defined by the manufacturer) or by user-defined algorithms 344 (defined by the user).

Once user selection and confirmation is complete, the user activates 332 the surgical device. The user will be able to activate the selected energy mode (i.e., selected algorithm) in at least one of the following ways from the surgical device: (1) via a foot pedal 346, (2) via the activation button switch 348 (FIGS. 1-4D), (3) via a second activation button switch 350 (i.e., a "Seal Only" button switch), or (4) via a second position of the closure trigger 352 as described in section 279011 (FIG. 5).

Once the device is activated 332, the generator supplies 334 energy output defined by the input parameters. The process continues to monitor the user selection 318 of desired modes and user set 330 input parameters on the generator for any changes and implements the changes as described above.

The pre-defined algorithms 342 may include, for example, individual energies algorithm 354, combined energies algorithm 356, sequential energies algorithm 358, duty cycled/pulsed energies algorithm 360, an algorithm comprising any combination of the above algorithm 354, 356, 358, 360, or tissue/procedure specific algorithm 364. The individual energies algorithm 354 includes, without limitation, RF monopolar 366, RF bipolar 368, ultrasonic 370, microwave 372, and IRE 374 energy modalities.

The user-defined algorithms 344 may include, for example, any selection 376 of pre-defined. Alternatively, the user-defined algorithms 344 may include, for example, vary 378 at least one of the following: type of energy, duty cycle, voltage, frequency, impedance limit, pulse width, or current.

During a surgical procedure, surgeons desire to know what mode the surgical device 100, 150, 190 (FIGS. 1-5) is in at any given point in time without taking their eyes off the surgical laparoscopic field of view. For this reason, a mode indicator would be best placed close to the end-effector such that it is in the line of sight at all times. It is difficult to place LEDs or other physical, dynamic visual indicators on the distal end of the surgical device shaft 108, 158, 198 (FIGS. 1-5) due to manufacturing complexity and limited space in the shaft 108, 158, 198 assembly. Accordingly, it is desirable to provide a surgical device with the functionality to clearly communicate dynamic mode feedback without relying on audible/tone feedback alone.

FIG. 7 illustrates various shaft light indicators with optional digital overlay disposed on a distal end of the shaft 108, 158, 198 (FIGS. 1-5) near the end-effector 110, 160 (FIGS. 1-4D) to indicate the operating mode the surgical device 100, 150, 190 (FIGS. 1-5), according to at least one aspect of the present disclosure. A vision system incorporated in a laparoscopic camera may be employed to interpret a static pattern (printed, etched, lasered, etc.) on the distal end of the shaft 108, 158, 198 and digitally overlays a dynamic, visual indicator on the laparoscopic view. Because this is a digital overlay, minimal cost or complexity is added to the surgical device 100, 150, 190. The digital overlay enables many different types of visual indicators and enables them to be customized or dynamically change. Unlike other heads-up display indicators, the present indicator tracks to the pattern on the shaft 108, 158, 198 and enables the mode indicator to follow the surgical device 100, 150, 190 around the surgical field.

The mode switching shaft light indicators with augmented digital overlay are shown in FIG. 7. An un-augmented view 380 shows a physical printed pattern visible on the shaft. A first augmented view 382 shows a physical printed pattern digitally removed in laparoscopic view. A second augmented view 384 shows a mode color indicator digitally overlaid on the shaft. A third augmented view 386 shows mode color indicator adaptability on the shaft. Variables that could be digitally modified include, without limitation, include indicator style/shape, size, color, brightness, or gross positioning (distal/proximal). A fourth augmented view 388 shows a mode described in language on the shaft.

When using a surgical device with mode assignable button switches as disclosed herein in FIGS. 1-6B, it may difficult at times to tell which mode is selected. Although the generator provides audio feedback on mode selected, providing a visual indicator in the line of sight can assist to communicate more clearly when a new mode is assigned.

Surgeons desire to know what mode the surgical device is in at any given point without taking their eyes off the surgical task at hand. For this reason, a visual mode indicator in the line of sight of the surgical task at hand would be best placed close to the end-effector such that the it is in the line of sight of the surgeon at all times.

FIGS. 8-17 illustrate various options of physical shaft light indicators placed on the distal end of the shaft 108, 158, 198 (FIGS. 1-5) near the end-effector 110, 160 (FIGS. 1-4D) to indicate the operating mode of the surgical device 100, 150, 190 (FIGS. 1-5), according to at least one aspect of the present disclosure. This placement is visible directly in the laparoscopic camera field of view or, for open procedures, at the surgical site. A lighted indicator could be achieved through a micro-LED placed physically on the distal end of the shaft or remotely through the use of light pipes to transmit colored mode indication to the distal end.

FIG. 8 illustrates a surgical device 400 comprising a physical shaft light indicator 410 (e.g., a visual indicator) disposed on a distal end of a shaft 402 coupled to an end-effector 404, according to at least one aspect of the present disclosure. The end-effector 404 comprises a clamp arm 406 and an ultrasonic blade 408. The physical shaft light indicator 410 disposed on the distal end of the shaft 402 near the end-effector 404 indicates the operating mode of the surgical device 400. In FIG. 8, the surgical device 400 is in default mode and the physical shaft light indicator 410 shows no color. This can be indicated by illuminating a white LED or simply turning off the LED to indicate the default mode of the surgical device 400.

FIG. 9 illustrates a surgical device 420 comprising a physical shaft light indicator 430 (e.g., a visual indicator) disposed on a distal end of a shaft 422 coupled to an end-effector 424, according to at least one aspect of the present disclosure. The end-effector 424 comprises a clamp arm 426 and an ultrasonic blade 428. The physical shaft light indicator 430 disposed on the distal end of the shaft 422 near the end-effector 424 indicates the operating mode of the surgical device 420. In FIG. 8, the surgical device 420 is in a selected mode and the physical shaft light indicator 430 LED is illuminated in color to indicate the selected mode of the surgical device 420.

FIG. 10 is a cross sectional schematic layout view of four LED physical shaft light indicators 444, 446, 448, 450 (e.g., visual indicators) disposed at the distal end of a shaft 442 of a surgical device 440, according to at least one aspect of the present disclosure.

FIG. 11 is a flexible circuit 452 with four embedded LED physical shaft light indicators 444, 446, 448, 450 (e.g., visual indicators) attached thereto, according to at least one aspect of the present disclosure. The flexible circuit 452 may be employed in the surgical device 440 shown in FIG. 10.

FIG. 12 is a cross sectional schematic layout view of two LEDs physical shaft light indicators 464, 466 with a light pipe 468 (e.g., a visual indicator) or tube with a co-molded light pipe 468 disposed at the distal end of a shaft 462 of a surgical device 460, according to at least one aspect of the present disclosure.

FIG. 13 is a light pipe 468 or tube with co-molded light pipe 468 (e.g., a visual indicator) for use with the surgical device 460 shown in FIG. 12, according to at least one aspect of the present disclosure.

FIGS. 14-15 illustrate a surgical device 470 comprising a single physical shaft light indicator 480, 482 (e.g., visual indicators) comprising multi-color LEDS disposed on a distal end of a shaft 472 coupled to an end-effector 474, according to at least one aspect of the present disclosure. The end-effector 474 comprises a clamp arm 476 and an ultrasonic blade 478. The physical shaft light indicator 480, 482 disposed on the distal end of the shaft 472 indicates the operating mode of the surgical device 470. In FIG. 14, the surgical device 470 is in a first mode and the physical shaft light indicator 480 multi-color LED is illuminated in a first color to indicate the first mode of the surgical device 470. In FIG. 15, the surgical device 470 is in a second mode and the physical shaft light indicator 480 multi-color LED is illuminated in a second color to indicate the second mode of the surgical device 470.

FIGS. 16-17 illustrate a surgical device 490 comprising physical shaft light indicators 500, 502 (e.g., visual indicators) comprising multiple staggered single color LEDS disposed on a distal end of a shaft 492 coupled to an end-effector 494, according to at least one aspect of the present disclosure. The end-effector 494 comprises a clamp arm 496 and an ultrasonic blade 498. The physical shaft light indicators 500, 502 disposed on the distal end of the shaft 492 indicate the operating mode of the surgical device 490. In FIG. 16, the surgical device 490 is in a first mode and the first physical shaft light indicator 500 LED is illuminated in a first color to indicate the first mode of the surgical device 490. In FIG. 17, the surgical device 490 is in a second mode and the second physical shaft light indicator 502 LED is illuminated in a second color to indicate the second mode of the surgical device 490.

The following disclosure provides examples of pre-defined algorithms 342 for mode switching on a combination energy surgical device such as the surgical device 100, 150, 190 described in FIGS. 1-5.

FIG. 18 is diagram of a pre-defined algorithm 342, according to at least one aspect of the present disclosure. With reference to FIGS. 1-6B and as shown in FIG. 18, from a mode switching user interface, the user is able to select from a pre-defined set of algorithms 342. The pre-defined set of algorithms 342 each enable a different type of energy delivery. Energy modalities include, but are not limited to, RF monopolar 366, RF bipolar 368, ultrasonic 370, microwave 372, IRE 374, among others.

A combined energy algorithm 356 enables simultaneous delivery of two or more of the energy modalities 366, 368, 370, 372, 374 listed above. As an example, the combined energy algorithm 356 may deliver power to both RF bipolar electrodes and an ultrasonic transducer that drives an ultrasonic waveguide and an end-effector at the same time to seal and cut a target vessel.

A sequential energy algorithm 358 enables delivery of two or more of the energy modalities listed above in a sequential manner. As an example, the sequential energy algorithm 358 may deliver power to RF bipolar electrodes to seal a target vessel before triggering power to an ultrasonic transducer that drives an ultrasonic waveguide and an end-effector to cut through the sealed target vessel.

A duty cycle/pulsed energy algorithm 360 enables delivery of two or more of the energy modalities 366, 368, 370, 372, 374 listed above in a particular, pre-set order. As an example, the duty cycle/pulsed energy algorithm 360 may cycle quickly between delivering power to RF bipolar electrodes and to an ultrasonic transducer that drives an ultrasonic waveguide and an end-effector to seal but not cut a target vessel, and then pulse power to an ultrasonic transducer to cut through the sealed vessel.

FIG. 19 is a graphical illustration of impedance, power, and cumulative energy for combined (simultaneous) application of ultrasonic and RF energy versus normalized time, according to at least one aspect of the present disclosure. The top graph 600 illustrates the behavior of RF impedance 602, RF power 604, and cumulative RF energy 606 over normalized time during the simultaneous application of RF and ultrasonic energy. The bottom graph 610 illustrates the behavior of ultrasonic (US) impedance 612, US power 614, and cumulative US energy 616 over normalized time during the simultaneous application of RF and ultrasonic energy. With reference to the top and bottom graphs 600, 610, while the cumulative US energy 616 rises in an approximately steady linear manner, the cumulative RF energy 606 rises non-linearly in a rapid exponential manner and then plateaus asymptotically to a maximum cumulative RF energy 606. The illustrated simultaneous application of cumulative RF energy 606 and cumulative US energy achieves sealing and cutting functions.

FIG. 20 is a graphical illustration of impedance, power, and cumulative energy for sequential application of ultrasonic and RF energy versus normalized time, according to at least one aspect of the present disclosure. The top graph 620 illustrates the initial application of RF energy with no ultrasonic (US) energy applied. The top graph 620 illustrates the behavior of RF impedance 622, RF power 624, and cumulative RF energy 626 over normalized time during the sole application of RF energy. The bottom graph 630 illustrates the subsequent application of US energy with no RF energy applied. The bottom graph 630 illustrates the behavior of US impedance 632, US power 634, and cumulative US energy 636 over normalized time during the sole application of US energy. With reference to the top and bottom graphs 620, 630, while the cumulative RF energy 626 rises exponentially until it reaches a maximum, the cumulative US energy 632 is zero. When the cumulative RF energy 626 reaches a maximum indicating that a seal has been made, the RF energy is shut off the cumulative RF energy 626 drops to zero. The US energy is then turned on for cutting the sealed tissue. The cumulative US energy 632 rises in steady linear manner sharply to a maximum until the cut is completed.

The following disclosure provides examples of user-defined algorithms 344 for mode switching on a combination energy surgical device such as the surgical device 100, 150, 190 described in FIGS. 1-5.

FIG. 21 is diagram of a user-defined algorithm 344, according to at least one aspect of the present disclosure. With reference to FIGS. 1-6B, 18, and as shown in FIG. 21, from a mode switching user Interface, the user is able to either select from a pre-defined set of algorithms 376 or to create/select a user-defined algorithm 378, which could vary at least one of the following properties: type of energy, duty cycle, voltage, frequency, impedance limit, pulse width, current. The various types of energy or energy modalities include, but are not limited to, RF monopolar 366, RF bipolar 368, ultrasonic 370, microwave 372, IRE 374 as shown in FIGS. 6B and 18. Some examples of different types of user defined algorithms 344 are given below.

A user may decide to create a user-defined algorithm 344 by selecting any of the pre-defined algorithms 376, especially for defining an algorithm with sequenced energy modalities (e.g., sequential energy algorithm 358 in FIGS. 6B and 18) that reduces the number of button switch activations and/or mode switching that the user has to perform to complete a desired task. A user-defined algorithm 344 is particularly useful for customization from user to user by varying the properties 378 discussed above. Each user has its own preferences and its own strategy for completing a surgical procedure. For tasks that may be repetitive and may occur several times during a surgery, a user-defined algorithm 344 can be established to reduce the number of actions that the user has to perform during the surgical procedure to complete their target task. Two examples of this are given below.

By way of a first example, a user-defined algorithm 344 may be defined to execute instructions for double cycle RF bipolar sealing and ultrasonic cutting. Accordingly, for extra confidence in a seal on a vessel or for extra debulking of tissue prior to a cut, the user may desire two cycles of RF bipolar energy before a cut sequence (i.e., ultrasonic activation). The user could create a user-defined algorithm 344 that cycles through two RF bipolar activations and an ultrasonic activation with a single button switch press. For the user-defined algorithm 344, the user could have the option to pre-set target energy parameters (e.g., ultrasonic power level or voltage driving the ultrasonic transducer) when the user-defined algorithm 344 is defined, or could elect to change the input parameters at the user Interface during the surgical procedure before activating the user-defined algorithm 344.

By way of a second example, a user-defined algorithm 344 may be defined to execute instructions for RF bipolar sealing and RF monopolar cutting. Accordingly, a user may desire an RF bipolar seal cycle prior to an RF monopolar cut, and may decide to create a user-defined algorithm 344 to reduce the number of button switch activations or mode-switching required to complete this sequence, especially if there are multiple occasions within a surgical procedure that the User would want to complete this given sequence of outputs.

By way of a third example, a user-defined algorithm 344 may be defined to execute instructions for tissue-specific RF bipolar activation and ultrasonic cutting. In a liver-specific surgical procedure, a user may desire to activate a seal-only cycle (i.e., RF bipolar) at low power over an extended period of time under a light clamp on the target tissue in order to debulk the target tissue and achieve more confidence in sealing of very small vessels running through the target tissue. The cut then could be completed with ultrasonic activation. A user-defined algorithm 344 in this scenario would enable the user to pre-set parameters such as target power output and time of activation for the sealing cycle before switching to an ultrasonic cutting cycle. This user-defined algorithm 344 is particularly useful for repetitive activations on sensitive tissues during a surgical procedure.

The surgical instruments 100, 150, 190 and associated algorithms described above in connection with FIGS. 1-21 may be implemented in the following surgical hub system in conjunction with the following generator and modular energy system, for example.

FIG. 22 is a surgical system 3102 comprising a surgical hub 3106 paired with a visualization system 3108, a robotic system 3110, and an intelligent instrument 3112, in accordance with at least one aspect of the present disclosure. Referring now to FIG. 22, the hub 3106 is depicted in communication with a visualization system 3108, a robotic system 3110, and a handheld intelligent surgical instrument 3112 configured in a similar manner to the surgical instruments 100, 150, 190 as described in FIGS. 1-5. The hub 3106 includes a hub display 3135, an imaging module 3138, a generator module 3140, a communication module 3130, a processor module 3132, and a storage array 3134. In certain aspects, as illustrated in FIG. 22, the hub 3106 further includes a smoke evacuation module 3126 and/or a suction/irrigation module 3128.

During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure 3136 offers a unified environment for managing the power, data, and fluid lines, which reduces the frequency of entanglement between such lines.

Aspects of the present disclosure present a surgical hub for use in a surgical procedure that involves energy application to tissue at a surgical site. The surgical hub includes a hub enclosure and a combo generator module slidably receivable in a docking station of the hub enclosure. The docking station includes data and power contacts. The combo generator module includes two or more of an ultrasonic energy generator component, a bipolar RF energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component.

In one aspect, the fluid line is a first fluid line and a second fluid line extends from the remote surgical site to a suction and irrigation module slidably received in the hub enclosure. In one aspect, the hub enclosure comprises a fluid interface.

Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 136 is configured to accommodate different generators, and facilitate an interactive communication therebetween. One of the advantages of the hub modular enclosure 136 is enabling the quick removal and/or replacement of various modules.

Aspects of the present disclosure present a modular surgical enclosure for use in a surgical procedure that involves energy application to tissue. The modular surgical enclosure includes a first energy-generator module, configured to generate a first energy for application to the tissue, and a first docking station comprising a first docking port that includes first data and power contacts, wherein the first energy-generator module is slidably movable into an electrical engagement with the power and data contacts and wherein the first energy-generator module is slidably movable out of the electrical engagement with the first power and data contacts, Further to the above, the modular surgical enclosure also includes a second energy-generator module configured to generate a second energy, different than the first energy, for application to the tissue, and a second docking station comprising a second docking port that includes second data and power contacts, wherein the second energy-generator module is slidably movable into an electrical engagement with the power and data contacts, and wherein the second energy-generator module is slidably movable out of the electrical engagement with the second power and data contacts.

In addition, the modular surgical enclosure also includes a communication bus between the first docking port and the second docking port, configured to facilitate communication between the first energy-generator module and the second energy-generator module.

FIG. 23 illustrates an example of a generator 3900, in accordance with at least one aspect of the present disclosure. As shown in FIG. 23, the generator 3900 is one form of a generator configured to couple to a surgical instrument 100, 150, 190 as described in FIGS. 1-5, and further configured to execute adaptive ultrasonic and electrosurgical control algorithms in a surgical data network comprising a modular communication hub as shown in FIG. 22. The generator 3900 is configured to deliver multiple energy modalities to a surgical instrument. The generator 3900 provides RF and ultrasonic signals for delivering energy to a surgical instrument either independently or simultaneously. The RF and ultrasonic signals may be provided alone or in combination and may be provided simultaneously. As noted above, at least one generator output can deliver multiple energy modalities (e.g., ultrasonic, bipolar or monopolar RF, irreversible and/or reversible electroporation, and/or microwave energy, among others) through a single port, and these signals can be delivered separately or simultaneously to the end effector to treat tissue.

The generator 3900 comprises a processor 3902 coupled to a waveform generator 3904. The processor 3902 and waveform generator 3904 are configured to generate a variety of signal waveforms based on information stored in a memory coupled to the processor 3902, not shown for clarity of disclosure. The digital information associated with a waveform is provided to the waveform generator 3904 which includes one or more DAC circuits to convert the digital input into an analog output. The analog output is fed to an amplifier 3906 for signal conditioning and amplification. The conditioned and amplified output of the amplifier 3906 is coupled to a power transformer 3908. The signals are coupled across the power transformer 3908 to the secondary side, which is in the patient isolation side. A first signal of a first energy modality is provided to the surgical instrument between the terminals labeled ENERGY1 and RETURN. A second signal of a second energy modality is coupled across a capacitor 3910 and is provided to the surgical instrument between the terminals labeled ENERGY2 and RETURN. It will be appreciated that more than two energy modalities may be output and thus the subscript "n" may be used to designate that up to n ENERGYn terminals may be provided, where n is a positive integer greater than 1. It also will be appreciated that up to "n" return paths RETURNn may be provided without departing from the scope of the present disclosure.

A first voltage sensing circuit 3912 is coupled across the terminals labeled ENERGY1 and the RETURN path to measure the output voltage therebetween. A second voltage sensing circuit 3924 is coupled across the terminals labeled ENERGY2 and the RETURN path to measure the output voltage therebetween. A current sensing circuit 3914 is disposed in series with the RETURN leg of the secondary side of the power transformer 3908 as shown to measure the output current for either energy modality. If different return paths are provided for each energy modality, then a separate current sensing circuit should be provided in each return leg. The outputs of the first and second voltage sensing circuits 3912, 3924 are provided to respective isolation transformers 3916, 3922 and the output of the current sensing circuit 3914 is provided to another isolation transformer 3918. The outputs of the isolation transformers 3916, 3928, 3922 in the on the primary side of the power transformer 3908 (non-patient isolated side) are provided to a one or more ADC circuit 3926. The digitized output of the ADC circuit 3926 is provided to the processor 3902 for further processing and computation. The output voltages and output current feedback information can be employed to adjust the output voltage and current provided to the surgical instrument and to compute output impedance, among other parameters. Input/output communications between the processor 3902 and patient isolated circuits is provided through an interface circuit 3920. Sensors also may be in electrical communication with the processor 3902 by way of the interface circuit 3920.

In one aspect, the impedance may be determined by the processor 3902 by dividing the output of either the first voltage sensing circuit 3912 coupled across the terminals labeled ENERGY1/RETURN or the second voltage sensing circuit 3924 coupled across the terminals labeled ENERGY2/RETURN by the output of the current sensing circuit 3914 disposed in series with the RETURN leg of the secondary side of the power transformer 3908. The outputs of the first and second voltage sensing circuits 3912, 3924 are provided to separate isolations transformers 3916, 3922 and the output of the current sensing circuit 3914 is provided to another isolation transformer 3916. The digitized voltage and current sensing measurements from the ADC circuit 3926 are provided the processor 3902 for computing impedance. As an example, the first energy modality ENERGY1 may be ultrasonic energy and the second energy modality ENERGY2 may be RF energy. Nevertheless, in addition to ultrasonic and bipolar or monopolar RF energy modalities, other energy modalities include irreversible and/or reversible electroporation and/or microwave energy, among others. Also, although the example illustrated in FIG. 23 shows a single return path RETURN may be provided for two or more energy modalities, in other aspects, multiple return paths RETURNn may be provided for each energy modality ENERGYn. Thus, as described herein, the ultrasonic transducer impedance may be measured by dividing the output of the first voltage sensing circuit 3912 by the current sensing circuit 3914 and the tissue impedance may be measured by dividing the output of the second voltage sensing circuit 3924 by the current sensing circuit 3914.

As shown in FIG. 23, the generator 3900 comprising at least one output port can include a power transformer 3908 with a single output and with multiple taps to provide power in the form of one or more energy modalities, such as ultrasonic, bipolar or monopolar RF, irreversible and/or reversible electroporation, and/or microwave energy, among others, for example, to the end effector depending on the type of treatment of tissue being performed. For example, the generator 3900 can deliver energy with higher voltage and lower current to drive an ultrasonic transducer, with lower voltage and higher current to drive RF electrodes for sealing tissue, or with a coagulation waveform for spot coagulation using either monopolar or bipolar RF electrosurgical electrodes. The output waveform from the generator 3900 can be steered, switched, or filtered to provide the frequency to the end effector of the surgical instrument. The connection of an ultrasonic transducer to the generator 3900 output would be preferably located between the output labeled ENERGY1 and RETURN as shown in FIG. 23. In one example, a connection of RF bipolar electrodes to the generator 3900 output would be preferably located between the output labeled ENERGY2 and RETURN. In the case of monopolar output, the preferred connections would be active electrode (e.g., pencil or other probe) to the ENERGY2 output and a suitable return pad connected to the RETURN output.

Additional details are disclosed in U.S. Patent Application Publication No. 2017/0086914, titled TECHNIQUES FOR OPERATING GENERATOR FOR DIGITALLY GENERATING ELECTRICAL SIGNAL WAVEFORMS AND SURGICAL INSTRUMENTS, which published on Mar. 30, 2017, which is herein incorporated by reference in its entirety.

FIG. 24 is a diagram of various modules and other components that are combinable to customize modular energy systems, in accordance with at least one aspect of the present disclosure. FIG. 25A is a first illustrative modular energy system configuration including a header module and a display screen that renders a graphical user interface (GUI) for relaying information regarding modules connected to the header module, in accordance with at least one aspect of the present disclosure. FIG. 25B is the modular energy system shown in FIG. 25A mounted to a cart, in accordance with at least one aspect of the present disclosure.

With reference now to FIGS. 24-25B, ORs everywhere in the world are a tangled web of cords, devices, and people due to the amount of equipment required to perform surgical procedures. Surgical capital equipment tends to be a major contributor to this issue because most surgical capital equipment performs a single, specialized task. Due to their specialized nature and the surgeons' needs to utilize multiple different types of devices during the course of a single surgical procedure, an OR may be forced to be stocked with two or even more pieces of surgical capital equipment, such as energy generators. Each of these pieces of surgical capital equipment must be individually plugged into a power source and may be connected to one or more other devices that are being passed between OR personnel, creating a tangle of cords that must be navigated. Another issue faced in modern ORs is that each of these specialized pieces of surgical capital equipment has its own user interface and must be independently controlled from the other pieces of equipment within the OR. This creates complexity in properly controlling multiple different devices in connection with each other and forces users to be trained on and memorize different types of user interfaces (which may further change based upon the task or surgical procedure being performed, in addition to changing between each piece of capital equipment). This cumbersome, complex process can necessitate the need for even more individuals to be present within the OR and can create danger if multiple devices are not properly controlled in tandem with each other. Therefore, consolidating surgical capital equipment technology into singular systems that are able to flexibly address surgeons' needs to reduce the footprint of surgical capital equipment within ORs would simplify the user experience, reduce the amount of clutter in ORs, and prevent difficulties and dangers associated with simultaneously controlling multiple pieces of capital equipment. Further, making such systems expandable or customizable would allow for new technology to be conveniently incorporated into existing surgical systems, obviating the need to replace entire surgical systems or for OR personnel to learn new user interfaces or equipment controls with each new technology.

A surgical hub can be configured to interchangeably receive a variety of modules, which can in turn interface with surgical devices (e.g., a surgical instrument or a smoke evacuator) or provide various other functions (e.g., communications). In one aspect, a surgical hub can be embodied as a modular energy system 4000, which is illustrated in connection with FIGS. 24-25B. The modular energy system 4000 can include a variety of different modules 4001 that are connectable together in a stacked configuration. In one aspect, the modules 4001 can be both physically and communicably coupled together when stacked or otherwise connected together into a singular assembly. Further, the modules 4001 can be interchangeably connectable together in different combinations or arrangements. In one aspect, each of the modules 4001 can include a consistent or universal array of connectors disposed along their upper and lower surfaces, thereby allowing any module 4001 to be connected to another module 4001 in any arrangement (except that, in some aspects, a particular module type, such as the header module 4002, can be configured to serve as the uppermost module within the stack, for example). In an alternative aspect, the modular energy system 4000 can include a housing that is configured to receive and retain the modules 4001, as is shown in FIG. 22. The modular energy system 4000 can also include a variety of different components or accessories that are also connectable to or otherwise associatable with the modules 4001. In another aspect, the modular energy system 4000 can be embodied as a generator module 3140, 3900 (FIGS. 22-23) of a surgical hub 3106. In yet another aspect, the modular energy system 4000 can be a distinct system from a surgical hub 3106. In such aspects, the modular energy system 4000 can be communicably couplable to a surgical hub 3106 for transmitting and/or receiving data therebetween.

The modular energy system 4000 can be assembled from a variety of different modules 4001, some examples of which are illustrated in FIG. 24. Each of the different types of modules 4001 can provide different functionality, thereby allowing the modular energy system 4000 to be assembled into different configurations to customize the functions and capabilities of the modular energy system 4000 by customizing the modules 4001 that are included in each modular energy system 4000. The modules 4001 of the modular energy system 4000 can include, for example, a header module 4002 (which can include a display screen 4006), an energy module 4004, a technology module 4040, and a visualization module 4042. In the depicted aspect, the header module 4002 is configured to serve as the top or uppermost module within the modular energy system stack and can thus lack connectors along its top surface. In another aspect, the header module 4002 can be configured to be positioned at the bottom or the lowermost module within the modular energy system stack and can thus lack connectors along its bottom surface. In yet another aspect, the header module 4002 can be configured to be positioned at an intermediate position within the modular energy system stack and can thus include connectors along both its bottom and top surfaces.

The header module 4002 can be configured to control the system-wide settings of each module 4001 and component connected thereto through physical controls 4011 thereon and/or a graphical user interface (GUI) 4008 rendered on the display screen 4006. Such settings could include the activation of the modular energy system 4000, the volume of alerts, the footswitch settings, the settings icons, the appearance or configuration of the user interface, the surgeon profile logged into the modular energy system 4000, and/or the type of surgical procedure being performed. The header module 4002 can also be configured to provide communications, processing, and/or power for the modules 4001 that are connected to the header module 4002. The energy module 4004, which can also be referred to as a generator module 3140, 3900 (FIGS. 22-23), can be configured to generate one or multiple energy modalities for driving electrosurgical and/or ultrasonic surgical instruments connected thereto, such as is described above in connection with the generator 3900 illustrated in FIG. 23. The technology module 4040 can be configured to provide additional or expanded control algorithms (e.g., electrosurgical or ultrasonic control algorithms for controlling the energy output of the energy module 4004). The visualization module 4042 can be configured to interface with visualization devices (i.e., scopes) and accordingly provide increased visualization capabilities.

The modular energy system 4000 can further include a variety of accessories 4029 that are connectable to the modules 4001 for controlling the functions thereof or that are otherwise configured to work on conjunction with the modular energy system 4000. The accessories 4029 can include, for example, a single-pedal footswitch 4032, a dual-pedal footswitch 4034, and a cart 4030 for supporting the modular energy system 4000 thereon. The footswitches 4032, 4034 can be configured to control the activation or function of particular energy modalities output by the energy module 4004, for example.

By utilizing modular components, the depicted modular energy system 4000 provides a surgical platform that grows with the availability of technology and is customizable to the needs of the facility and/or surgeons. Further, the modular energy system 4000 supports combo devices (e.g., dual electrosurgical and ultrasonic energy generators) and supports software-driven algorithms for customized tissue effects. Still further, the surgical system architecture reduces the capital footprint by combining multiple technologies critical for surgery into a single system.

The various modular components utilizable in connection with the modular energy system 4000 can include monopolar energy generators, bipolar energy generators, dual electrosurgical/ultrasonic energy generators, display screens, and various other modules and/or other components, some of which are also described above in connection with FIGS. 1-21.

Referring now to FIG. 25A, the header module 4002 can, in some aspects, include a display screen 4006 that renders a GUI 4008 for relaying information regarding the modules 4001 connected to the header module 4002. In some aspects, the GUI 4008 of the display screen 4006 can provide a consolidated point of control of all of the modules 4001 making up the particular configuration of the modular energy system 4000. In alternative aspects, the header module 4002 can lack the display screen 4006 or the display screen 4006 can be detachably connected to the housing 4010 of the header module 4002. In such aspects, the header module 4002 can be communicably couplable to an external system that is configured to display the information generated by the modules 4001 of the modular energy system 4000. For example, in robotic surgical applications, the modular energy system 4000 can be communicably couplable to a robotic cart or robotic control console, which is configured to display the information generated by the modular energy system 4000 to the operator of the robotic surgical system. As another example, the modular energy system 4000 can be communicably couplable to a mobile display that can be carried or secured to a surgical staff member for viewing thereby. In yet another example, the modular energy system 4000 can be communicably couplable to a surgical hub 4100 or another computer system that can include a display 4104. In aspects utilizing a user interface that is separate from or otherwise distinct from the modular energy system 4000, the user interface can be wirelessly connectable with the modular energy system 4000 as a whole or one or more modules 4001 thereof such that the user interface can display information from the connected modules 4001 thereon.

Referring still to FIG. 25A, the energy module 4004 can include a port assembly 4012 including a number of different ports configured to deliver different energy modalities to corresponding surgical instruments that are connectable thereto. In the particular aspect illustrated in FIGS. 24-25B, the port assembly 4012 includes a bipolar port 4014, a first monopolar port 4016a, a second monopolar port 4018b, a neutral electrode port 4018 (to which a monopolar return pad is connectable), and a combination energy port 4020. However, this particular combination of ports is simply provided for illustrative purposes and alternative combinations of ports and/or energy modalities may be possible for the port assembly 4012.

As noted above, the modular energy system 4000 can be assembled into different configurations. Further, the different configurations of the modular energy system 4000 can also be utilizable for different surgical procedure types and/or different tasks. For example, FIGS. 25A and 25B illustrate a first illustrative configuration of the modular energy system 4000 including a header module 4002 (including a display screen 4006) and an energy module 4004 connected together. Such a configuration can be suitable for laparoscopic and open surgical procedures, for example.

FIGS. 26-30 illustrate an example surgical system 10 with ultrasonic and electrosurgical features including any one of the end-effectors, surgical instruments, and generators described herein. FIG. 26 depicts a surgical system 10 including a generator 12 and a surgical instrument 14. The surgical instrument 14 is operatively coupled with the generator 12 via a power cable 16. The generator 12 is operable to power the surgical instrument 14 to deliver ultrasonic energy for cutting tissue, and electrosurgical bipolar RF energy (i.e., therapeutic levels of RF energy) for sealing tissue. In one aspect, the generator 12 is configured to power the surgical instrument 14 to deliver ultrasonic energy and electrosurgical bipolar RF energy simultaneously or independently.

The surgical instrument 14 of the present example comprises a handle assembly 18, a shaft assembly 20 extending distally from the handle assembly 18, and an end effector 22 arranged at a distal end of the shaft assembly 20. The handle assembly 18 comprises a body 24 including a pistol grip 26 and energy control buttons 28, 30 configured to be manipulated by a surgeon. A trigger 32 is coupled to a lower portion of the body 24 and is pivotable toward and away from the pistol grip 26 to selectively actuate the end effector 22, as described in greater detail below. In other suitable variations of the surgical instrument 14, the handle assembly 18 may comprise a scissor grip configuration, for example. An ultrasonic transducer 34 is housed internally within and supported by the body 24. In other configurations, the ultrasonic transducer 34 may be provided externally of the body 24.

As shown in FIGS. 27 and 28, the end effector 22 includes an ultrasonic blade 36 and a clamp arm 38 configured to selectively pivot toward and away from the ultrasonic blade 36, for clamping tissue therebetween. The ultrasonic blade 36 is acoustically coupled with the ultrasonic transducer 34, which is configured to drive (i.e., vibrate) the ultrasonic blade 36 at ultrasonic frequencies for cutting and/or sealing tissue positioned in contact with the ultrasonic blade 36. The clamp arm 38 is operatively coupled with the trigger 32 such that the clamp arm 38 is configured to pivot toward the ultrasonic blade 36, to a closed position, in response to pivoting of the trigger 32 toward the pistol grip 26. Further, the clamp arm 38 is configured to pivot away from the ultrasonic blade 36, to an open position (see e.g., FIGS. 26-28), in response to pivoting of the trigger 32 away from the pistol grip 26. Various suitable ways in which the clamp arm 38 may be coupled with the trigger 32 will be apparent to those of ordinary skill in the art in view of the teachings provided herein. In some versions, one or more resilient members may be incorporated to bias the clamp arm 38 and/or the trigger 32 toward the open position.

A clamp pad 40 is secured to and extends distally along a clamping side of the clamp arm 38, facing the ultrasonic blade 36. The clamp pad 40 is configured to engage and clamp tissue against a corresponding tissue treatment portion of the ultrasonic blade 36 when the clamp arm 38 is actuated to its closed position. At least a clamping-side of the clamp arm 38 provides a first electrode 42, referred to herein as clamp arm electrode 42. Additionally, at least a clamping-side of the ultrasonic blade 36 provides a second electrode 44, referred to herein as a blade electrode 44. The electrodes 42, 44 are configured to apply electrosurgical bipolar RF energy, provided by the generator 12, to tissue electrically coupled with the electrodes 42, 44. The clamp arm electrode 42 may serve as an active electrode while the blade electrode 44 serves as a return electrode, or vice-versa. The surgical instrument 14 may be configured to apply the electrosurgical bipolar RF energy through the electrodes 42, 44 while vibrating the ultrasonic blade 36 at an ultrasonic frequency, before vibrating the ultrasonic blade 36 at an ultrasonic frequency, and/or after vibrating the ultrasonic blade 36 at an ultrasonic frequency.

As shown in FIGS. 26-30, the shaft assembly 20 extends along a longitudinal axis and includes an outer tube 46, an inner tube 48 received within the outer tube 46, and an ultrasonic waveguide 50 supported within the inner tube 48. As seen best in FIGS. 27-30, the clamp arm 38 is coupled to distal ends of the inner and outer tubes 46, 48. In particular, the clamp arm 38 includes a pair of proximally extending clevis arms 52 that receive therebetween and pivotably couple to a distal end 54 of the inner tube 48 with a pivot pin 56 received through bores formed in the clevis arms 52 and the distal end 54 of the inner tube 48. The first and second clevis fingers 58 depend downwardly from the clevis arms 52 and pivotably couple to a distal end 60 of the outer tube 46. Specifically, each clevis finger 58 includes a protrusion 62 that is rotatably received within a corresponding opening 64 formed in a sidewall of the distal end 60 of the outer tube 46.

In the present example, the inner tube 48 is longitudinally fixed relative to the handle assembly 18, and the outer tube 46 is configured to translate relative to the inner tube 48 and the handle assembly 18, along the longitudinal axis of the shaft assembly 20. As the outer tube 46 translates distally, the clamp arm 38 pivots about the pivot pin 56 toward its open position. As the outer tube 46 translates proximally, the clamp arm 38 pivots in an opposite direction toward its closed position. A proximal end of the outer tube 46 is operatively coupled with the trigger 32, for example via a linkage assembly, such that actuation of the trigger 32 causes translation of the outer tube 46 relative to the inner tube 48, thereby opening or closing the clamp arm 38. In other suitable configurations not shown herein, the outer tube 46 may be longitudinally fixed and the inner tube 48 may be configured to translate for moving the clamp arm 38 between its open and closed positions.

The shaft assembly 20 and the end effector 22 are configured to rotate together about the longitudinal axis, relative to the handle assembly 18. A retaining pin 66, shown in FIG. 29, extends transversely through the proximal portions of the outer tube 46, the inner tube 48, and the waveguide 50 to thereby couple these components rotationally relative to one another. In the present example, a rotation knob 68 is provided at a proximal end portion of the shaft assembly 20 to facilitate rotation of the shaft assembly 20, and the end effector 22, relative to the handle assembly 18. The rotation knob 68 is secured rotationally to the shaft assembly 20 with the retaining pin 66, which extends through a proximal collar of the rotation knob 68. It will be appreciated that in other suitable configurations, the rotation knob 6) may be omitted or substituted with alternative rotational actuation structures.

The ultrasonic waveguide 50 is acoustically coupled at its proximal end with the ultrasonic transducer 34, for example by a threaded connection, and at its distal end with the ultrasonic blade 36, as shown in FIG. 30. The ultrasonic blade 36 is shown formed integrally with the waveguide 50 such that the blade 36 extends distally, directly from the distal end of the waveguide 50. In this manner, the waveguide 50 acoustically couples the ultrasonic transducer 34 with the ultrasonic blade 36, and functions to communicate ultrasonic mechanical vibrations from the transducer 34 to the blade 36. Accordingly, the ultrasonic transducer 34, the waveguide 50, and the ultrasonic blade 36 together define an acoustic assembly. During use, the ultrasonic blade 36 may be positioned in direct contact with tissue, with or without assistive clamping force provided by the clamp arm 38, to impart ultrasonic vibrational energy to the tissue and thereby cut and/or seal the tissue. For example, the blade 36 may cut through tissue clamped between the clamp arm 38 and a first treatment side of the blade 36, or the blade 36 may cut through tissue positioned in contact with an oppositely disposed second treatment side of the blade 36, for example during a "back-cutting" movement. In some variations, the waveguide 50 may amplify the ultrasonic vibrations delivered to the blade 36. Further, the waveguide 50 may include various features operable to control the gain of the vibrations, and/or features suitable to tune the waveguide 50 to a selected resonant frequency. Additional features of the ultrasonic blade 36 and the waveguide 50 are described in greater detail below.

The waveguide 50 is supported within the inner tube 48 by a plurality of nodal support elements 70 positioned along a length of the waveguide 50, as shown in FIGS. 29-30. Specifically, the nodal support elements 70 are positioned longitudinally along the waveguide 50 at locations corresponding to acoustic nodes defined by the resonant ultrasonic vibrations communicated through the waveguide 50. The nodal support elements 70 may provide structural support to the waveguide 50, and acoustic isolation between the waveguide 50 and the inner and outer tubes 46, 48 of the shaft assembly 20. In variations, the nodal support elements 70 may comprise o-rings. The waveguide 50 is supported at its distal-most acoustic node by a nodal support element in the form of an overmold member 72, shown in FIG. 30. The waveguide 50 is secured longitudinally and rotationally within the shaft assembly 20 by the retaining pin 66, which passes through a transverse through-bore 74 formed at a proximally arranged acoustic node of the waveguide 50, such as the proximal-most acoustic node, for example.

In the present example, a distal tip 76 of the ultrasonic blade 36 is located at a position corresponding to an antinode associated with the resonant ultrasonic vibrations communicated through the waveguide 50. Such a configuration enables the acoustic assembly of the instrument 14 to be tuned to a preferred resonant frequency $f_o$ when the ultrasonic blade 36 is not loaded by tissue. When the ultrasonic transducer 34 is energized by the generator 12 to transmit mechanical vibrations through the waveguide 50 to the blade 36, the distal tip 76 of the blade 36 is caused to oscillate longitudinally in the range of approximately 20 to 120 microns peak-to-peak, for example, and in some instances in the range of approximately 20 to 50 microns, at a predetermined vibratory frequency $f_o$ of approximately 50 kHz, for example. When the ultrasonic blade 36 is positioned in contact with tissue, the ultrasonic oscillation of the blade 36 may simultaneously sever the tissue and denature the proteins in adjacent tissue cells, thereby providing a coagulative effect with minimal thermal spread.

EXAMPLES

Examples of the method according to various aspects of the present disclosure are provided below. An aspect of the method may include any one or more than one, and any combination of, the examples described below.

Example 1

The present disclosure provides a surgical instrument. The surgical instrument comprises a housing, an end-effector, and a user interface. The end-effector comprises a clamp arm and an ultrasonic blade configured to couple to an ultrasonic transducer and to a pole of an electrical generator. The clamp arm comprises a clamp jaw pivotally movable about a pivot point and an electrode defining a surface configured to contact tissue and apply electrical energy to the tissue in contact therewith. The electrode is configured to couple to an opposite pole of the electrical generator. The user interface comprises a first activation button switch to activate a first energy source and a second button switch to select an energy mode for the activation button switch.

Example 2

The surgical instrument of Example 1, wherein the user interface further comprises a closure trigger to operate the end-effector; and a switch to activate a second energy source.

Example 3

The surgical instrument of any one of Examples 1-2, wherein the second button switch is a separate control from the end effector closure trigger.

Example 4

The surgical instrument of any one of Examples 1-3, wherein the closure trigger comprises a two stage activation, wherein the second button switch is configured to activate in a second stage of the closure trigger.

Example 5

The surgical instrument of any one of Examples 1-4, wherein a first stage of the closure trigger is configured to activate in the closing direction to actuate the end-effector.

Example 6

The surgical instrument of any one of Examples 1-5, wherein the user interface further comprises a rotatable knob to rotate a shaft and the end-effector coupled to the shaft.

Example 7

The surgical instrument of any one of Examples 1-6, wherein the second button switch is coupled to a circuit comprising at least one input parameter to define the energy mode.

Example 8

The surgical instrument of any one of Examples 1-7, wherein the input parameter is remotely configured through connection to a generator or through a software update.

Example 9

The surgical instrument of any one of Examples 1-8, wherein the input parameter is either duty cycle, voltage, frequency, pulse width, or current, or any combination thereof.

Example 10

The surgical instrument of any one of Examples 1-9, wherein the input parameter is at least one of energy type, duty cycle, voltage, frequency, pulse width, current, impedance limit, activation time, or blend of energy, or any combination thereof.

Example 11

The surgical instrument of any one of Examples 1-10, wherein the second button switch is configured to select from a list of predefined modes and the number of modes in the list is either predefined or defined by a second input parameter defined by a user.

Example 12

The surgical instrument of any one of Examples 1-11, wherein at least one of the energy modes is a simultaneous blend of RF and ultrasonic energy, and the input parameter represents a duty cycle of the RF and ultrasonic energy.

Example 13

The surgical instrument of any one of Examples 1-12, wherein the second button switch is configured to select from a list of predefined modes and the number of modes in the list is defined by a second input parameter defined by a user.

Example 14

The surgical instrument of any one of Examples 1-13, wherein the input parameter is either duty cycle, voltage, frequency, pulse width, or current, or any combination thereof.

Example 15

The surgical instrument of any one of Examples 1-14, wherein the user interface further comprises a visual indicator of the selected energy mode disposed on the housing.

Example 16

The surgical instrument of any one of Examples 1-15, wherein the user interface further comprises a visual indicator of the selected energy mode disposed on a portion of a shaft coupling the housing and the end-effector, wherein the visual indicator is located in a surgical field of view.

Example 17

The surgical instrument of any one of Examples 1-16, wherein at least one of the energy modes is selected from ultrasonic, RF bipolar, RF monopolar, microwave, or IRE, or any combination thereof.

Example 18

The surgical instrument of any one of Examples 1-17, wherein at least one of the energy modes is configured apply energy based on a predefined duty cycle or pulsed algorithm.

Example 19

The surgical instrument of any one of Examples 1-18, wherein at least one of the energy modes is selected from a sequential application of two or more of ultrasonic, RF bipolar, RF monopolar, microwave, or IRE energy types, or any combination thereof.

Example 20

The surgical instrument of any one of Examples 1-19, wherein at least one of the energy modes is a simultaneous blend of two or more of ultrasonic, RF bipolar, RF monopolar, microwave, or IRE energy types.

Example 21

The surgical instrument of any one of Examples 1-20, wherein at least one of the energy modes is a simultaneous blend of two or more of ultrasonic, RF bipolar, RF monopolar, microwave, or IRE energy types followed by sequential application of one or more of the ultrasonic, RF bipolar, RF monopolar, microwave, or IRE energy types, or any combination thereof.

Example 22

The surgical instrument of any one of Examples 1-21, wherein at least one of the energy modes is ultrasonic, RF bipolar, RF monopolar, microwave, or IRE energy types followed by a sequential application of a simultaneous blend of two or more of the ultrasonic, RF bipolar, RF monopolar, microwave, or IRE energy types, or any combination thereof.

Example 23

The surgical instrument of any one of Examples 1-22, wherein at least one of the energy modes delivers energy based on a tissue specific predefined algorithm.

Example 24

The surgical instrument of any one of Examples 1-23, wherein at least one of the energy modes is compiled from learned surgical behaviors or activities.

Example 25

The surgical instrument of any one of Examples 1-24, wherein the energy mode comprises ultrasonic, RF bipolar, RF monopolar, microwave, or IRE energy types and are made available to the user through software updates to a generator coupled to the surgical instrument, or any combination thereof.

Example 26

The surgical instrument of any one of Examples 1-25, wherein the energy mode comprises ultrasonic, RF bipolar, RF monopolar, microwave, or IRE energy types and are made available to the user through software updates to the surgical instrument, or any combination thereof.

Example 27

The surgical instrument of any one of Examples 1-26, wherein preferred selections by the user are made available to multiple generators through either networking, the cloud, or manual transfer, or any combination thereof.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

The invention claimed is:

1. A surgical instrument, comprising:
   a housing;
   an end-effector, comprising:
      an ultrasonic blade configured to couple to an ultrasonic transducer and to a pole of an electrical generator; and
      a clamp arm, comprising:
         a clamp jaw pivotally movable about a pivot point; and
         an electrode defining a surface configured to contact tissue and apply electrical energy to the tissue, wherein the electrode is configured to couple to an opposite pole of the electrical generator;
   a user interface, comprising:
      an indicator to display a list of the plurality of energy modes, wherein, for each of the plurality of energy modes, the electrical generator stores corresponding instructions for delivering energy to the surgical instrument according to a predefined algorithm;
      a mode selection button switch actuatable to toggle through the list of the plurality of energy modes displayed by the indicator and select an energy mode from the list of the plurality of energy modes; and
      a first activation button switch actuatable to cause the electrical generator to deliver energy to the surgical instrument according to the selected energy mode, wherein selecting a first energy mode of the plurality of energy modes and actuating the first activation button switch causes the electrical generator to sequentially deliver two or more energy sources to the surgical instrument; and
   a circuit couplable to the electrical generator and the user interface, wherein the circuit is to:
      receive the list of the plurality of energy modes from the electrical generator;
      cause the indicator to display the list of the plurality of energy modes;
      receive a mode selection signal from the user interface based on actuating the mode selection button switch to the selected energy mode; and
      transmit a parameter adjustment signal to the generator based on receiving the mode selection signal, wherein transmitting the parameter adjustment signal causes the electrical generator to adjust parameters for delivering energy according to the selected energy mode.

2. The surgical instrument of claim 1, wherein the two or more energy sources sequentially delivered to the surgical instrument by selecting the first energy mode and actuating the first activation button switch comprises a first energy source and a second energy source, and wherein the user interface further comprises:
- a closure trigger to operate the end-effector; and
- a second activation button switch to separately activate the second energy source.

3. The surgical instrument of claim 2, wherein the second activation button switch is a separate control from the closure trigger.

4. The surgical instrument of claim 2, wherein the closure trigger comprises a two stage activation, wherein the second activation button switch is configured to activate in a second stage of the closure trigger.

5. The surgical instrument of claim 4, wherein a first stage of the closure trigger is configured to actuate the clamp jaw.

6. The surgical instrument of claim 1, further comprising a shaft coupling the end effector to the housing, wherein the user interface further comprises a rotatable knob to rotate the shaft and the end-effector coupled to the shaft.

7. The surgical instrument of claim 2, wherein, for each of the plurality of energy modes, the predefined algorithm comprises an input parameter to define the corresponding energy mode.

8. The surgical instrument of claim 7, wherein, for each of the plurality of energy modes, the input parameter is remotely configured through connection to the electrical generator or through a software update.

9. The surgical instrument of claim 7, wherein, for a second energy mode of the plurality of energy modes, the input parameter comprises at least one of an energy type, a duty cycle, a voltage, a frequency, a pulse width, a current, an impedance limit, an activation time, or a blend of energy, or any combination thereof.

10. The surgical instrument of claim 1, wherein the list of the plurality of energy modes from the electrical generator is selectable by a user via interaction with the electrical generator.

11. The surgical instrument of claim 7, wherein selecting a second energy mode of the plurality of energy modes and actuating the first activation button switch causes the electrical generator to cause activation of a simultaneous blend of RF and ultrasonic energy, and wherein the input parameter comprises a duty cycle of the RF and ultrasonic energy.

12. The surgical instrument of claim 10, wherein the number of the energy modes in the list is selectable by the user via interaction with the electrical generator.

13. The surgical instrument of claim 1, wherein the indicator comprises a display screen disposed on the housing.

14. The surgical instrument of claim 1, further comprising a shaft coupling the end effector to the housing, and wherein the indicator is disposed on a portion of the shaft.

15. The surgical instrument of claim 2, wherein the first energy source comprises at least one of an ultrasonic energy source, a bipolar radio frequency (RF) energy source, a monopolar RF energy source, a microwave energy source, or an irreversible electroporation (IRE) energy source, or any combination thereof.

16. The surgical instrument of claim 1, wherein selecting the first energy mode and actuating the first activation button switch causes the electrical generator to sequentially deliver the two or more energy sources to the surgical instrument based on a predefined duty cycle or a pulsed algorithm.

17. The surgical instrument of claim 2, wherein the two or more energy sources are selected from the group consisting of an ultrasonic energy source, a bipolar radio frequency (RF) energy source, a monopolar RF energy source, a microwave energy source, and an irreversible electroporation (IRE) energy source.

18. The surgical instrument of claim 2, wherein selecting a second energy mode of the plurality of energy modes and actuating the first activation button switch causes the electrical generator to simultaneously deliver a blend of the two or more energy sources, wherein the two or more energy sources are selected from the group consisting of an ultrasonic energy source, a bipolar radio frequency (RF) energy source, a monopolar RF energy source, a microwave energy source, and an irreversible electroporation (IRE) energy source.

19. The surgical instrument of claim 1, wherein selecting a second energy mode of the plurality of energy modes and actuating the first activation button switch causes the electrical generator to simultaneously deliver a blend of the two or more energy sources followed by sequential activation of one or more of the two or more energy sources.

20. The surgical instrument of claim 2, wherein selecting a second energy mode of the plurality of energy modes and actuating the first activation button switch causes the electrical generator to activate the first energy source followed by a sequential activation of a simultaneous blend of the two or more energy sources, wherein both the first energy source and the two or more energy sources are selected from the group consisting of an ultrasonic energy source, a bipolar radio frequency (RF) energy source, a monopolar RF energy source, a microwave energy source, and an irreversible electroporation (IRE) energy source.

21. The surgical instrument of claim 2, wherein selecting a second energy mode of the plurality of energy modes and actuating the first activation button switch causes the electrical generator to activate the first energy source based on a tissue-specific predefined algorithm.

22. The surgical instrument of claim 1, wherein the selected energy mode is configured based on learned surgical behaviors or activities.

23. The surgical instrument of claim 1, wherein the plurality of energy modes are made available for selection through software updates to the electrical generator.

24. A surgical instrument, comprising:
- an end effector, comprising:
  - an ultrasonic blade configured to deliver an ultrasonic energy modality for treating tissue; and
  - a clamp arm comprising an electrode, wherein the electrode is configured to deliver a radio frequency (RF) energy modality for treating tissue, and wherein the ultrasonic blade and the electrode are couplable to a generator configured to drive the ultrasonic energy modality and the RF energy modality;
- a housing, comprising:
  - a first activation switch that is actuatable to deliver the ultrasonic energy modality;
  - a second activation switch that is actuatable to cause the electrode to deliver the RF energy modality;
  - an indicator to display a list of plurality of operating modes associated with the RF energy modality, wherein, for each of the plurality of operating modes, the electrical generator stores corresponding instructions for delivering the RF energy to the surgical instrument according to a predefined algorithm; and
  - a mode selection switch that is actuatable to toggle through the list of the plurality of operating modes displayed by the indicator and select an operating mode from the list of the plurality of operating modes, wherein actuating the second activation switch causes the generator to deliver to the electrode the RF energy modality according to the selected operating mode, and wherein selecting a first operating mode from the plurality of operating modes and activating the second activation switch causes the generator to sequentially deliver the ultrasonic energy modality to the ultrasonic blade and the RF energy modality to the electrode;

a circuit couplable to the generator, wherein the circuit is to:

receive the list of the plurality of operating modes from the generator;

cause the indicator to display the list of the plurality of operating modes;

receive a mode selection signal based on actuating the mode selection switch to select the selected operating mode; and transmit a parameter adjustment signal to the generator based on receiving the mode selection signal, wherein transmitting the parameter adjustment signal causes the generator to adjust parameters for delivering RF energy according to the selected operating mode; and a shaft operably coupling the end effector to the housing.

* * * * *